United States Patent
Ahn

(10) Patent No.: US 10,529,933 B2
(45) Date of Patent: Jan. 7, 2020

(54) ORGANIC ELECTROLUMINESCENT COMPOUNDS AND ORGANIC ELECTROLUMINESCENT DEVICE COMPRISING THE SAME

(71) Applicant: Rohm and Haas Electronic Materials Korea Ltd., Cheonan (KR)

(72) Inventor: Hee-Choon Ahn, Seoul (KR)

(73) Assignee: Rohm and Haas Electronic Materials Korea Ltd., Cheonan (KR)

( * ) Notice: Subject to any disclaimer, the term of this patent is extended or adjusted under 35 U.S.C. 154(b) by 0 days.

(21) Appl. No.: 15/757,725

(22) PCT Filed: Sep. 20, 2016

(86) PCT No.: PCT/KR2016/010462
§ 371 (c)(1),
(2) Date: Mar. 6, 2018

(87) PCT Pub. No.: WO2017/065419
PCT Pub. Date: Apr. 20, 2017

(65) Prior Publication Data
US 2018/0351113 A1    Dec. 6, 2018

(30) Foreign Application Priority Data

Oct. 13, 2015 (KR) .................... 10-2015-0143015
Aug. 17, 2016 (KR) .................... 10-2016-0104280

(51) Int. Cl.
*H01L 51/00* (2006.01)
*C07D 409/10* (2006.01)
*C07D 409/14* (2006.01)
*C09K 11/02* (2006.01)
*H01L 51/50* (2006.01)

(52) U.S. Cl.
CPC ........ *H01L 51/0074* (2013.01); *C07D 409/10* (2013.01); *C07D 409/14* (2013.01); *C09K 11/025* (2013.01); *H01L 51/0067* (2013.01); *H01L 51/0072* (2013.01); *H01L 51/5008* (2013.01); *H01L 51/5016* (2013.01); *H01L 51/5072* (2013.01); *H01L 2251/5384* (2013.01)

(58) Field of Classification Search
CPC ............. H01L 51/0074; H01L 51/0067; H01L 51/0072; C07D 409/10; C07D 409/14; C09K 11/025
See application file for complete search history.

(56) References Cited

U.S. PATENT DOCUMENTS

| | | |
|---|---|---|
| 8,968,887 B2 | 3/2015 | Ma et al. |
| 2013/0099208 A1 | 4/2013 | Lee et al. |
| 2014/0117331 A1 | 5/2014 | Kim et al. |
| 2015/0041770 A1 | 2/2015 | Lee |
| 2017/0256719 A1 | 9/2017 | Jang et al. |

FOREIGN PATENT DOCUMENTS

KR    10-2016-0107669 A    9/2016

*Primary Examiner* — Victor A Mandala
*Assistant Examiner* — Colleen E Snow
(74) *Attorney, Agent, or Firm* — S. Matthew Cairns

(57) ABSTRACT

The present disclosure relates to organic electroluminescent compounds, and a host material, an electron buffer material, an electron transport material and an organic electroluminescent device comprising the same. By using the organic electroluminescent compounds of the present disclosure, the organic electroluminescent device secures fast electron current properties by intermolecular stacking and interaction, and thus, it is possible to provide the organic electroluminescent device having low driving voltage and/or excellent luminous efficiency and/or efficient lifespan properties.

9 Claims, 1 Drawing Sheet

ORGANIC ELECTROLUMINESCENT COMPOUNDS AND ORGANIC ELECTROLUMINESCENT DEVICE COMPRISING THE SAME

TECHNICAL FIELD

The present disclosure relates to organic electroluminescent compounds and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules and aluminum complexes as materials for forming a light-emitting layer [Appl. Phys. Lett. 51, 913, 1987].

An organic electroluminescent device (hereinafter abbreviated as an OLED) is a device changing electrical energy to light by applying electricity to an organic electroluminescent material, and generally has a structure comprising an anode, a cathode, and an organic layer between the anode and the cathode. The organic layer of an OLED, if necessary, may comprise a hole injection layer, a hole transport layer, a hole auxiliary layer, a light-emitting auxiliary layer, an electron blocking layer, a light-emitting layer (which comprises host and dopant materials), an electron buffer layer, a hole blocking layer, an electron transport layer, an electron injection layer, etc. The materials used for the organic layer may be categorized by their functions in hole injection materials, hole transport materials, hole auxiliary materials, light-emitting auxiliary materials, electron blocking materials, light-emitting materials, electron buffer materials, hole blocking materials, electron transport materials, electron injection materials, etc. In the OLED, due to an application of a voltage, holes are injected from the anode to the light-emitting layer, electrons are injected from the cathode to the light-emitting layer, and excitons of high energies are formed by a recombination of the holes and the electrons. By this energy, organic luminescent compounds reach an excited state, and light emission occurs by emitting light from energy due to returning from the excited state of the organic luminescent compounds to a ground state.

The most important factor determining luminous efficiency in an OLED is a light-emitting material. A light-emitting material must have high quantum efficiency, and high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an OLED having high efficiency and long lifespan is an urgent issue. In particular, considering EL characteristic requirements for a middle or large-sized panel of OLED, light-emitting materials showing excellent characteristics compared to conventional ones must be urgently developed. The host material, which acts as a solvent in a solid state and an energy transferer, is desirable to have high purity and an appropriate molecular weight capable for a vacuum deposition. Furthermore, the host material is desirable to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

Also, the electron buffer layer is equipped to improve a problem of light-emitting luminance reduction which may occur due to change of current properties in the device when the device is exposed to a high temperature during a process of producing panels. Thus, the properties of compounds comprised in the electron buffer layer are important. In addition, the compound used in the electron buffer layer is desirable to perform a role of controlling an electron injection by the electron withdrawing characteristics and the electron affinity LUMO (lowest unoccupied molecular orbital) energy level, and thus may perform a role to improve the efficiency and the lifespan of the OLED.

Meanwhile, an organometallic complex having a light-emitting function such as $Alq_3$ was conventionally used as an electron transport material in an OLED due to excellent electron transfer capability. However, $Alq_3$ had a problem moving to another layer, and lowering color purity when used in a blue light-emitting device. Thus, a new electron transport material without the aforementioned problem and having a high electron affinity that can cause an OLED to have a high luminous efficiency due to fast electron transfer properties has been desired.

U.S. Pat. No. 8,968,887 discloses a host material comprising a phenanthrene compound as a substituent, but the host material disclosed therein must comprise a triphenylene as a backbone.

Korean Patent Application Laid-Open No. 10-2013-42901 discloses an OLED comprising a compound of a phenanthro(4,3-b)thiophene, a phenanthro(4,3-b)furan or a phenanthro(4,3-b)pyrrole as a backbone.

Korean Patent Application Laid-Open No. 10-2014-57439 discloses an OLED using a heterocyclic compound of a benzonaphtho(2,3-d)furan structure or a benzonaphtho(2,3-d)thiophene structure as a hole transport material or a host.

DISCLOSURE OF THE INVENTION

Problems to be Solved

The object of the present disclosure is to provide organic electroluminescent compounds being effective to produce an organic electroluminescent device having low driving voltage, and/or excellent current and power efficiencies, and/or significantly improved operative lifespan.

Solution to Problems

The present inventors found that the above objective can be achieved by an organic electroluminescent compound represented by the following formula 1:

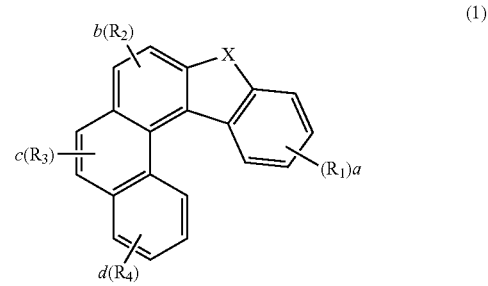

(1)

wherein

X represents O, S, or $CR_{11}R_{12}$;

$R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; wherein, at least one of $R_1$ to $R_4$ represent a substituted or unsubstituted (C6-C30)aryl, a substituted or unsubstituted (3- to 30-membered)heteroaryl, or a substituted or unsubstituted mono- or di-(C6-C30)arylamino, with the proviso that at least one of $R_1$ to $R_4$ does not represent a triphenylenyl;

$R_{11}$ and $R_{12}$, each independently, represent a substituted or unsubstituted (C1-C30)alkyl, a substituted or unsubstituted (C6-C30)aryl, or a substituted or unsubstituted (3- to 30-membered)heteroaryl; or are linked to each other to form a substituted or unsubstituted, mono- or polycyclic, (C3-C30) alicyclic or aromatic ring, whose carbon atom(s) may be replaced with at least one heteroatom selected from nitrogen, oxygen, and sulfur;

a and d, each independently, represent an integer of 1 to 4; b and c, each independently, represent an integer of 1 or 2; and the heteroaryl contains at least one heteroatom selected from B, N, O, S, Si, and P.

The compound of the present disclosure can be utilized at a hole transport layer (HTL), a light-emitting layer (EML), an electron buffer layer (compound deposited between an electron transport layer and a light-emitting layer in a deposited device), and an electron transport layer by bonding with various substituents due to its unique fusing positions. Among the layers, inventors of the present disclosure found that the compound shows excellent device performance when it is used at a light-emitting layer, an electron transport layer, an electron buffer layer, or both an electron transport layer and an electron buffer layer.

Meanwhile, during the charge transport in an OLED, there is a possibility for unexpected degradation due to weak bonds within the charge transport material. One solution for overcoming such degradation is to rigidify molecular framework (see Adv. Mater. 2013, 25, 2114-2129). The core structure of the compound of the present disclosure has a rigid aromatic network which does not have rotational freedom. The present inventors found that this feature would result in excellent performance in an OLED.

Effects of the Invention

By using the organic electroluminescent compound of the present disclosure as a host material, an electron buffer material, or an electron transport material, the organic electroluminescent device may secure fast electron current properties by intermolecular stacking and interaction, and thus, it is possible to provide the organic electroluminescent device having low driving voltage and/or excellent luminous efficiency and/or efficient lifespan properties.

EMBODIMENTS OF THE INVENTION

Figure 1:
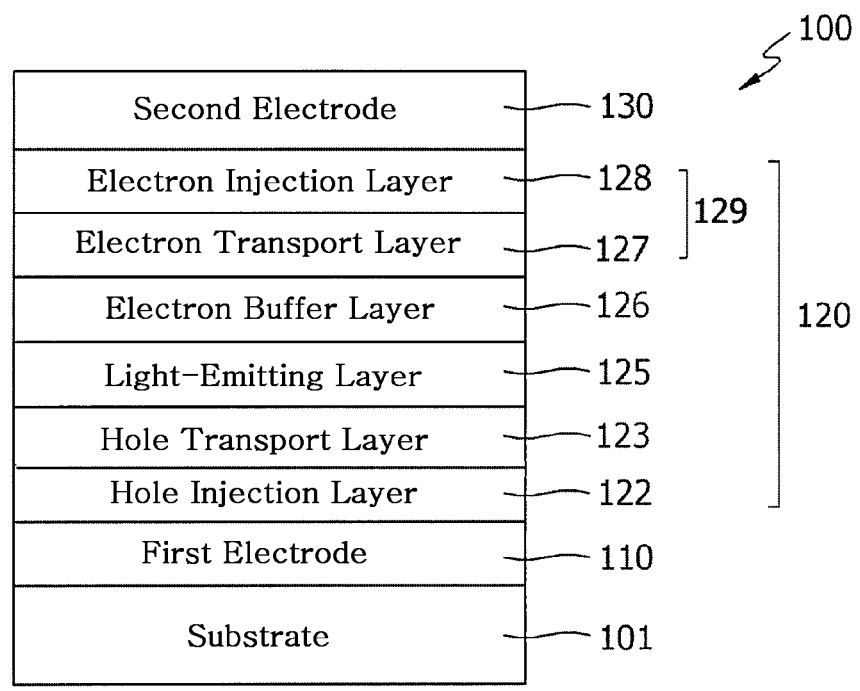
FIG. 1 illustrates a schematic view representing the structure of an OLED according to an embodiment of the present disclosure.

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an OLED, and may be comprised in any layers consisting of an OLED, if necessary.

The organic electroluminescent compound represented by formula 1 will be described in detail as follows.

In formula 1, X represents O, S, or $CR_{11}R_{12}$. Herein, $R_{11}$ and $R_{12}$, each independently, represent a substituted or unsubstituted (C1-C30)alkyl, a substituted or unsubstituted (C6-C30)aryl, or a substituted or unsubstituted (3- to 30-membered)heteroaryl; or are linked to each other to form a substituted or unsubstituted, mono- or polycyclic, (C3-C30) alicyclic or aromatic ring, whose carbon atom(s) may be replaced with at least one heteroatom selected from nitrogen, oxygen, and sulfur. $R_{11}$ and $R_{12}$, each independently, represent preferably a substituted or unsubstituted (C1-C20)alkyl, more preferably, a substituted or unsubstituted (C1-C10)alkyl, and for example, a methyl.

In formula 1, $R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino. Herein, at least one of $R_1$ to $R_4$ represents a substituted or unsubstituted (C6-C30)aryl, a substituted or unsubstituted (3- to 30-membered)heteroaryl, or a substituted or unsubstituted mono- or di-(C6-C30)arylamino, with the proviso that at least one of $R_1$ to $R_4$ does not represent a triphenylenyl. $R_1$ to $R_4$, each independently, represents preferably hydrogen, a substituted or unsubstituted (C6-C25)aryl, a substituted or unsubstituted (5- to 25-membered)heteroaryl, or a substituted or unsubstituted mono- or di-(C6-C25)arylamino, more preferably, hydrogen, a substituted (C6-C18)aryl, a substituted (5- to 18-membered)heteroaryl, or a substituted or unsubstituted di-(C6-C18)arylamino, and for example, hydrogen, a substituted triazinyl, a substituted phenyl, a substituted naphthyl, a substituted fluorenyl, a substituted carbazolyl, a substituted phenoxazinyl, a substituted phenothiazinyl, or a substituted or unsubstituted di(C6-C15)arylamino.

In formula 1, a and d, each independently, represent an integer of 1 to 4; b and c, each independently, represent an integer of 1 or 2. Preferably, a to d, each independently, represent 1.

In formula 1, the heteroaryl contains at least one heteroatom selected from B, N, O, S, Si, and P, and preferably, one heteroatom selected from N, O, and S.

The compound represented by formula 1 may be represented by any one of the following formulas 2 to 4:

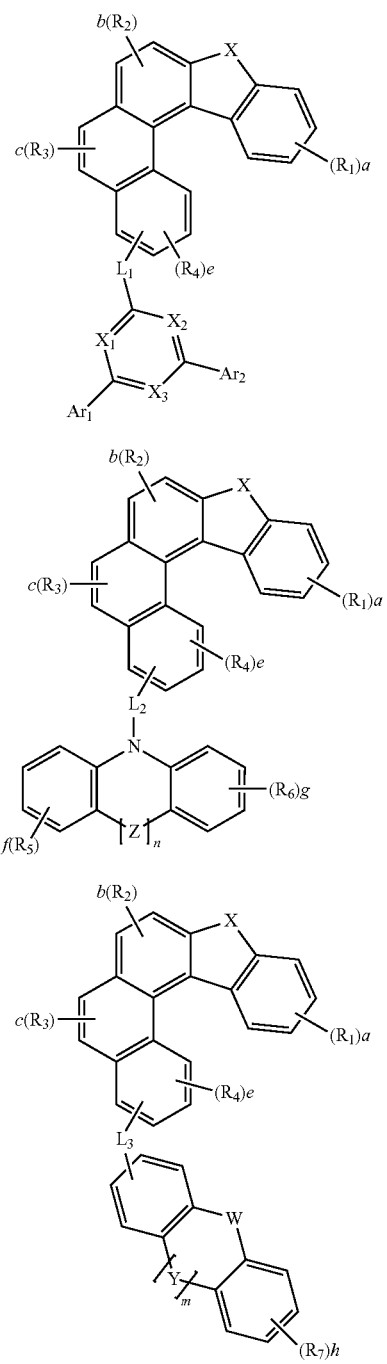

(2)

(3)

(4)

In formulas 2 to 4, X, $R_1$ to $R_4$, a, b and c are as defined in formula 1.

In formulas 2 to 4, $L_1$ to $L_3$, each independently, represent a single bond, a substituted or unsubstituted (C6-C30) arylene, or a substituted or unsubstituted (3- to 30-membered)heteroarylene; preferably, a single bond, a substituted or unsubstituted (C6-C25)arylene, or a substituted or unsub- stituted (5- to 25-membered)heteroarylene; and more preferably, a single bond, a substituted or unsubstituted (C6-C18)arylene, or an unsubstituted (5- to 18-membered) heteroarylene. For example, $L_1$ may be a single bond, an unsubstituted phenylene, an unsubstituted naphthylene, or a substituted fluorenylene; $L_2$ may be a single bond, or an unsubstituted phenylene; and $L_3$ may be an unsubstituted carbazolylene.

In formula 2, $X_1$ to $X_3$, each independently, represent N or CH; with the proviso that at least one of $X_1$ to $X_3$ represents N, and preferably at least two of $X_1$ to $X_3$ represent N.

In formula 2, $Ar_1$ and $Ar_2$, each independently, represent a substituted or unsubstituted (C6-C30)aryl, or a substituted or unsubstituted (3- to 30-membered)heteroaryl; preferably, a substituted or unsubstituted (C6-C25)aryl, or a substituted or unsubstituted (5- to 25-membered)heteroaryl; more preferably, a substituted or unsubstituted (C6-C18)aryl, or a substituted or unsubstituted (5- to 18-membered)heteroaryl; and for example, a substituted or unsubstituted phenyl, an unsubstituted biphenyl, an unsubstituted naphthyl, a substituted fluorenyl, a substituted carbazolyl, or an unsubstituted dibenzofuranyl.

In formulas 3 and 4, W, Y and Z, each independently, represent a single bond, O, S, $NR_{13}$, or $CR_{14}R_{15}$, preferably, a single bond, O, S, or $NR_{13}$. For example, W may represent $NR_{13}$; Y may represent a single bond; and Z may represent a single bond, O, or S.

Herein, $R_{13}$ to $R_{15}$, each independently, represent a substituted or unsubstituted (C1-C30)alkyl, a substituted or unsubstituted (C6-C30)aryl, or a substituted or unsubstituted (3- to 30-membered)heteroaryl; or $R_{14}$ and $R_{15}$ may be linked to each other to form a substituted or unsubstituted, mono- or polycyclic, (C3-C30) alicyclic or aromatic ring, whose carbon atom(s) may be replaced with at least one heteroatom selected from nitrogen, oxygen, and sulfur. $R_{13}$ to $R_{15}$, each independently, represent preferably, a substituted or unsubstituted (C6-C18)aryl, or a substituted or unsubstituted (5- to 18-membered)heteroaryl; more preferably, an unsubstituted (C6-C12)aryl; and for example, an unsubstituted phenyl.

In formulas 3 and 4, n and m, each independently, represent an integer of 0 or 1.

In formulas 2 to 4, e represents an integer of 1 to 3, and preferably, 1.

In formulas 3 and 4, f, g and h, each independently represent an integer of 1 to 4, and preferably, an integer of 1 or 2.

In formulas 3 and 4, $R_5$ to $R_7$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or are linked to an adjacent substituent(s) to form a substituted or unsubstituted, mono- or polycyclic, (C3-C30) alicyclic or aromatic ring, whose carbon atom(s) may be replaced with at least one heteroatom selected from nitrogen, oxygen, and sulfur. Preferably, $R_5$ to $R_7$, each independently, represent hydrogen, a substituted or unsubstituted (C6-C25)aryl, or a substituted or unsubstituted (5- to 25-membered)heteroaryl, or are linked to an adjacent substituent(s) to form a substituted, mono- or polycyclic, (C3-C25) aromatic ring. More preferably, $R_5$ to $R_7$, each independently, represent hydrogen, a substituted or unsubstituted (C6-C18)aryl, or a substituted or unsubstituted (5- to 20-membered)heteroaryl, or are linked to an adjacent substituent(s) to form a substituted polycyclic (C5-C18) aromatic ring. For example, $R_5$ to $R_7$, each independently, represent hydrogen, a substituted or unsubstituted phenyl, or a substituted or unsubstituted carbazolyl, or are linked to an adjacent substituent(s) and the backbone to form a fluorenyl substituted with at least one methyl.

Herein, the term "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. The term "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. The term "(3- to 7-membered) heterocycloalkyl" is a cycloalkyl having 3 to 7, preferably 5 to 7, ring backbone atoms, including at least one heteroatom selected from B, N, O, S, Si, and P, preferably O, S, and N, and includes tetrahydrofuran, pyrrolidine, thiolan, tetrahydropyran, etc. The term "(C6-C30)aryl(ene)" is a monocyclic or fused ring radical derived from an aromatic hydrocarbon having 6 to 30 ring backbone carbon atoms, in which the number of carbon atoms is preferably 6 to 20, more preferably 6 to 15, and may comprise a spiro structure. The above aryl(ene) may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered) heteroaryl(ene)" is an aryl having 3 to 30 ring backbone atoms, including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); may comprise a spiro structure; and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring in $R_1$ to $R_7$, $R_{11}$ to $R_{15}$, $Ar_1$, $Ar_2$, and $L_1$ to $L_3$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C1-C30)alkyl and/or a (C6-C30)aryl; a (C6-C30)aryl unsubstituted or substituted with a (C6-C30)aryl, a (5- to 30-membered) heteroaryl, and/or mono- or di-(C6-C30)arylamino; a tri(C1-C30)alkylsilyl; a tri(C6-C30)arylsilyl; a di(C1-C30)alkyl (C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30) arylcarbonyl; a di(C6-C30)arylboronyl; a di(C1-C30)alkylboronyl; a (C1-C30)alkyl(C6-C30)arylboronyl; a (C6-C30) aryl(C1-C30)alkyl; and a (C1-C30)alkyl(C6-C30)aryl; preferably, are at least one selected from the group consisting of a (C1-C20)alkyl; a (5- to 25-membered)heteroaryl unsubstituted or substituted with (C1-C20)alkyl and/or (C6-C25)aryl; a (C6-C25)aryl unsubstituted or substituted with a (C6-C30)aryl, (5- to 25-membered)heteroaryl and/or di(C6-C30)arylamino; a di(C6-C25)arylamino unsubstituted or substituted with a (C1-C20)alkyl; and a (C1-C20)alkyl(C6-C25)aryl; more preferably, at least one selected from the group consisting of a (C1-C10)alkyl; a (6- to 25-membered) heteroaryl unsubstituted or substituted with (C1-C10)alkyl and/or (C6-C25)aryl; a (C6-C20)aryl unsubstituted or substituted with a (C6-C25)aryl, (6- to 25-membered)heteroaryl and/or di(C6-C18)arylamino; a di(C6-C18)arylamino unsubstituted or substituted with a (C1-C10)alkyl; and a (C1-C10)alkyl(C6-C20)aryl; and for example, may be at least one selected from the group consisting of a methyl; a phenyl unsubstituted or substituted with a diphenylfluorenyl, a carbazolyl and/or a diphenylamino; an unsubstituted biphenyl; an unsubstituted naphthyl, a fluorenyl substituted with a methyl and/or a phenyl; a carbazolyl unsubstituted or substituted with a phenyl; an unsubstituted dibenzofuranyl; a triazinyl substituted with a (C6-C25)aryl and/or a (6- to 18-membered)heteroaryl; a pyrimidinyl substituted with a naphthyl; and a di(C6-C18)arylamino unsubstituted or substituted with a methyl.

The compound represented by formula 1 includes the following compounds, but is not limited thereto:

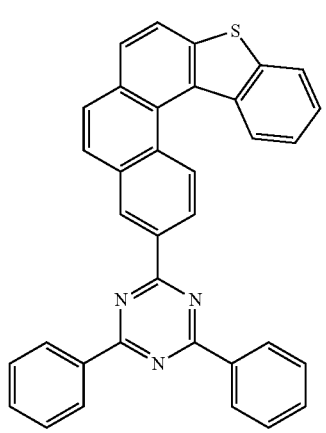

C-1

-continued
C-2
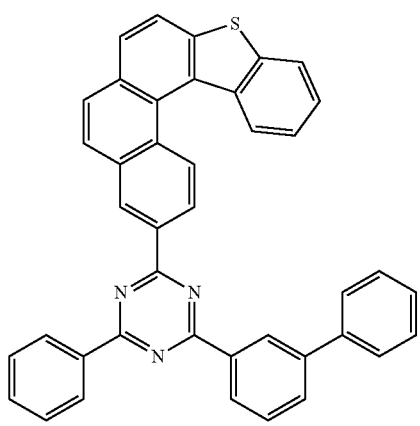
C-3
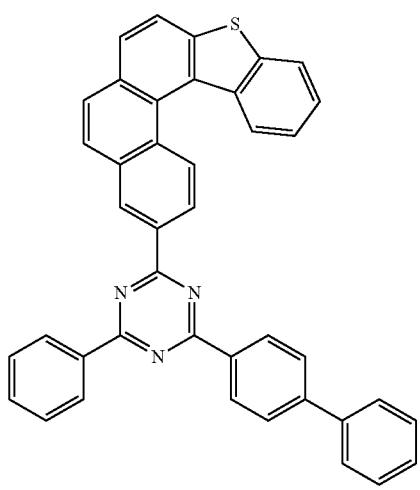
C-4
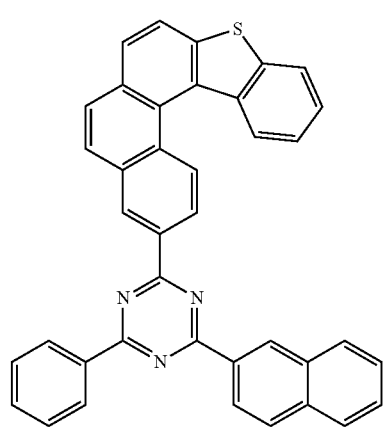
-continued
C-5
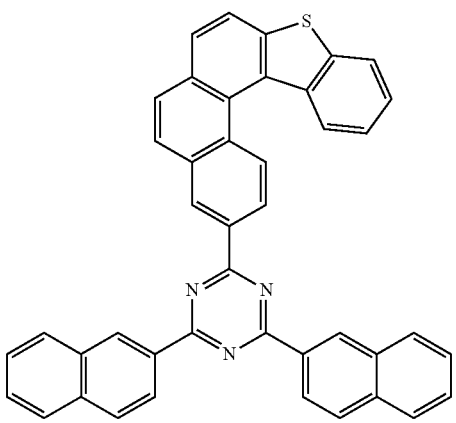
C-6
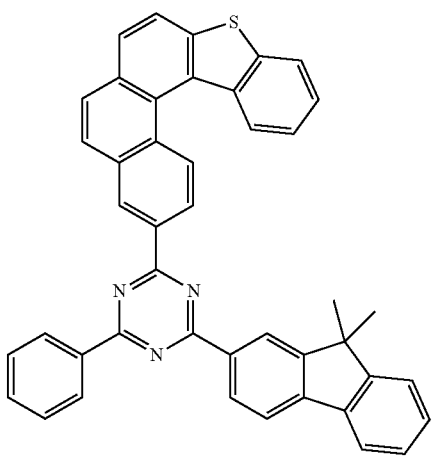
C-7
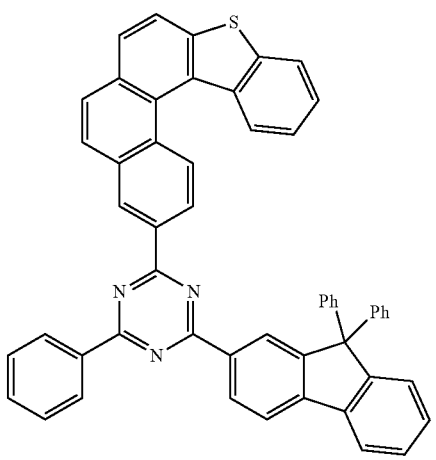

-continued
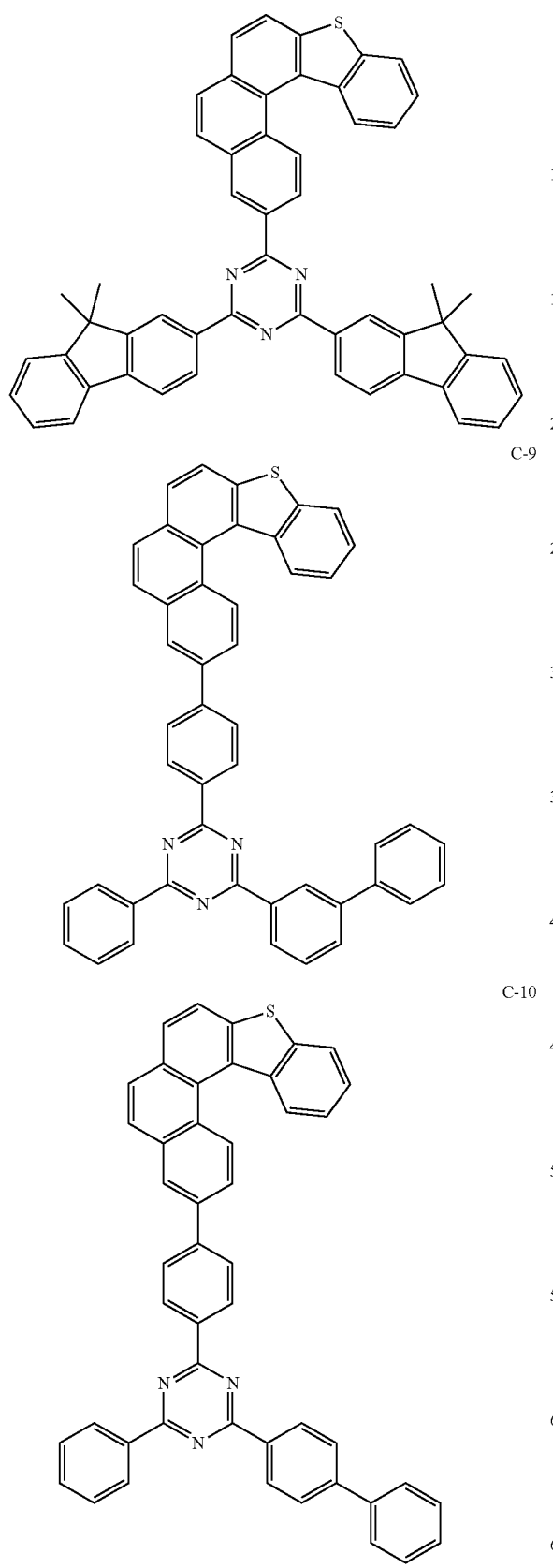
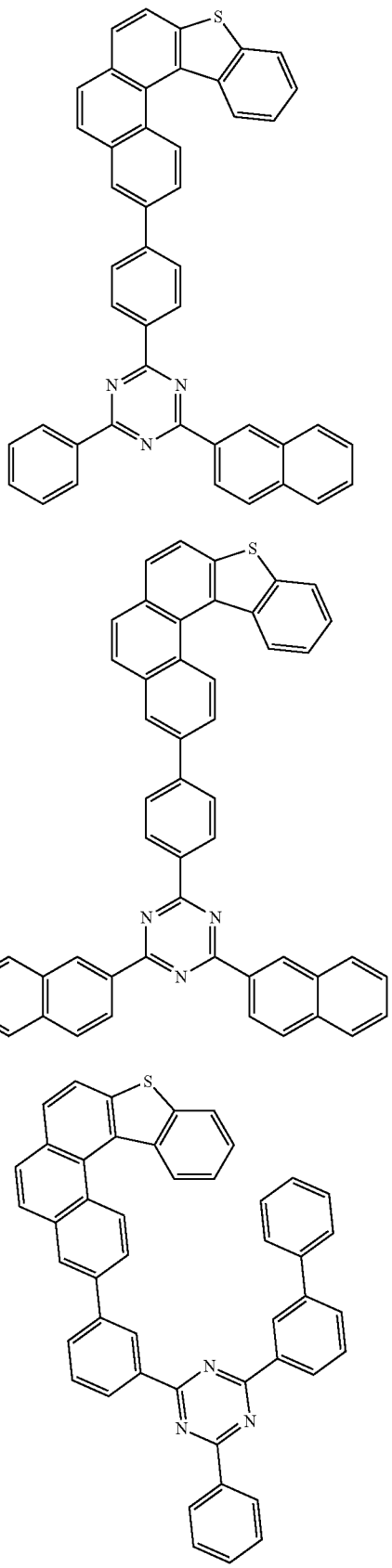

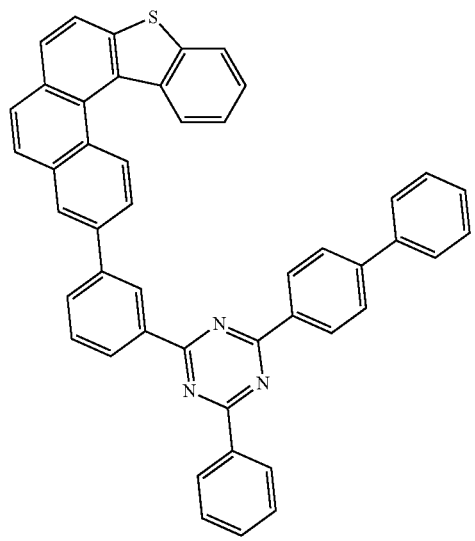
C-14
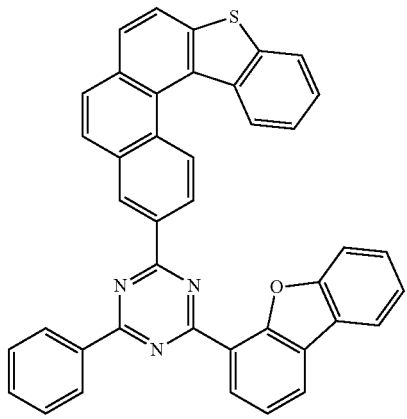
C-17
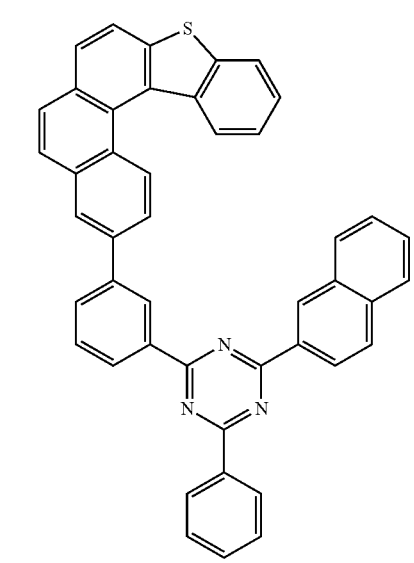
C-15
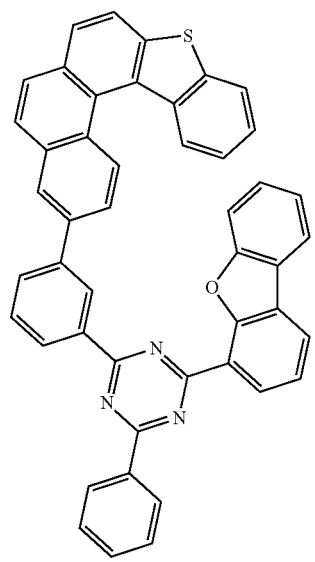
C-18
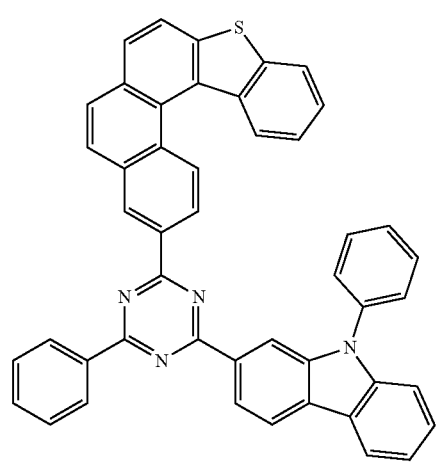
C-16
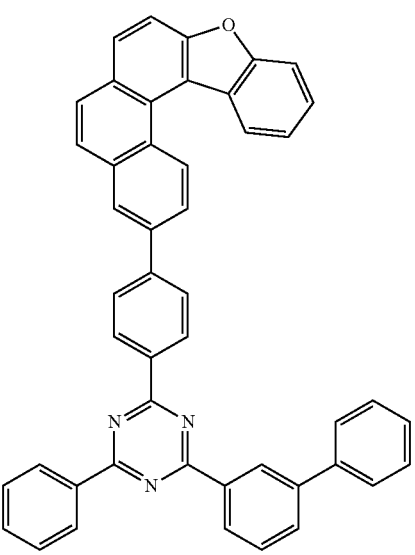
C-19

C-20
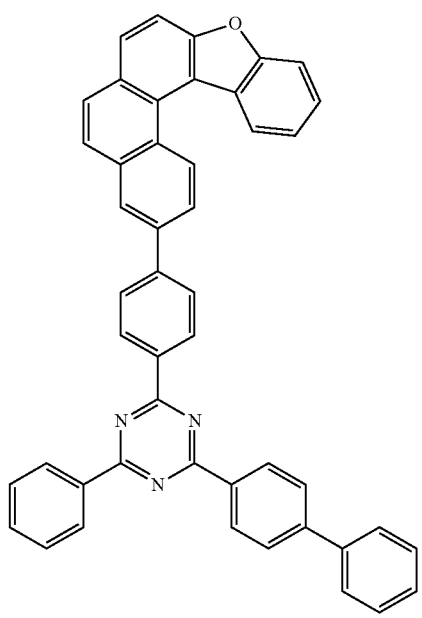
C-22
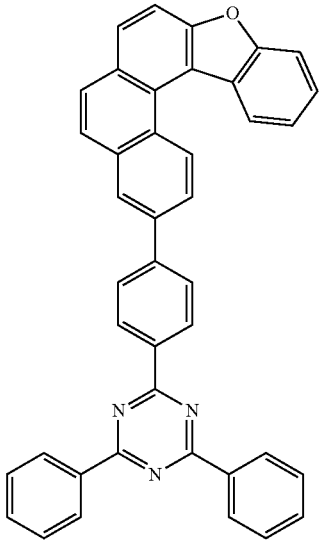
C-21
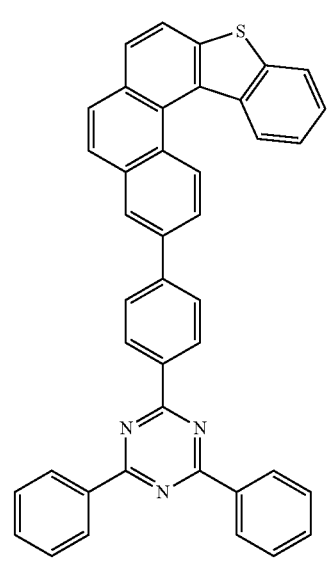
C-23
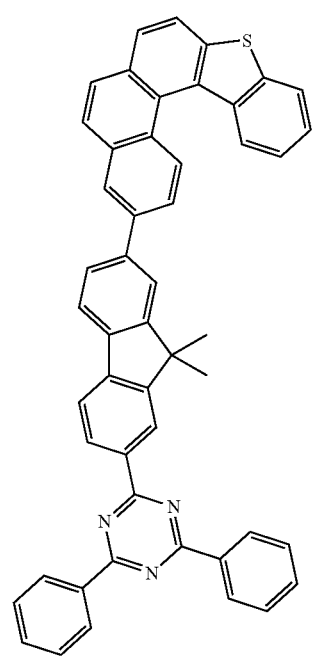

-continued
C-24
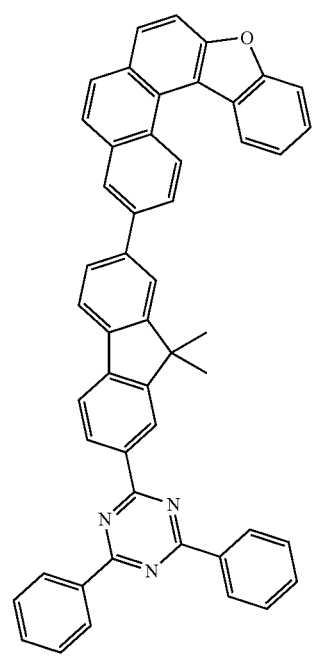
C-25
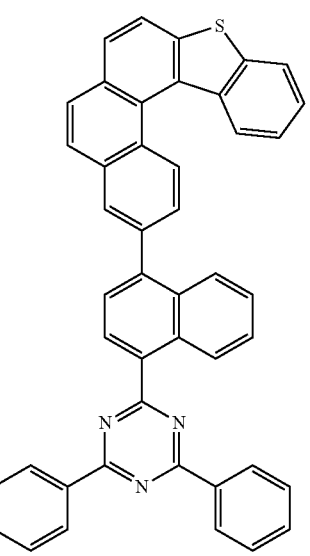
-continued
C-26
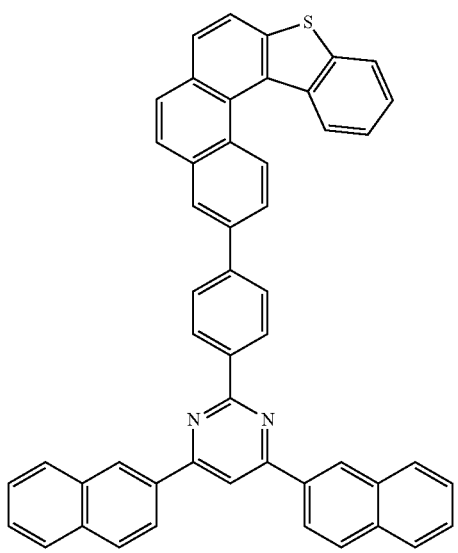
C-27
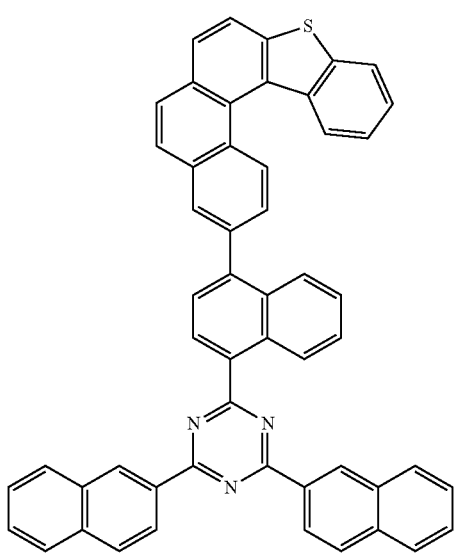
C-28
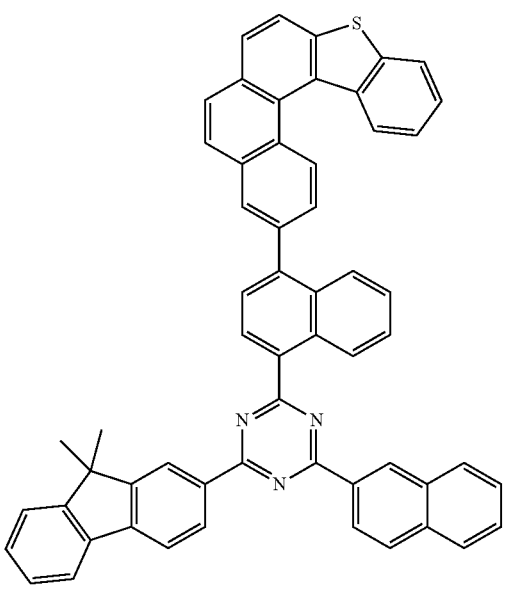

C-29
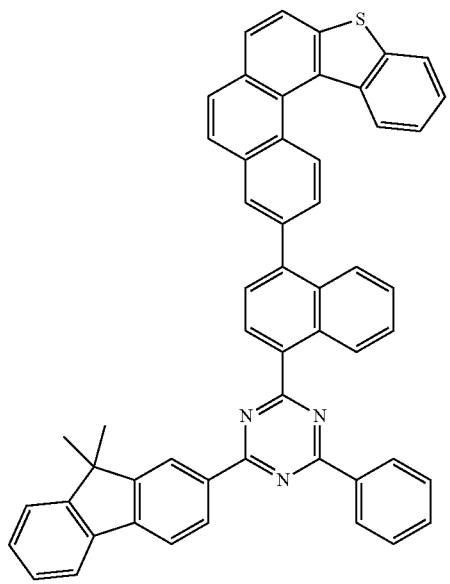
C-30
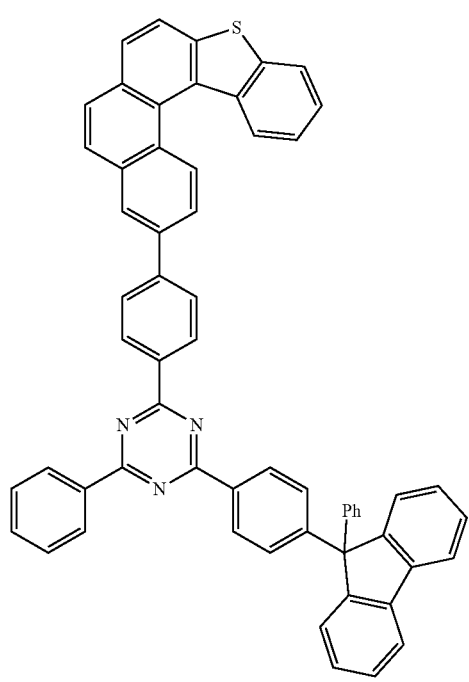
C-31
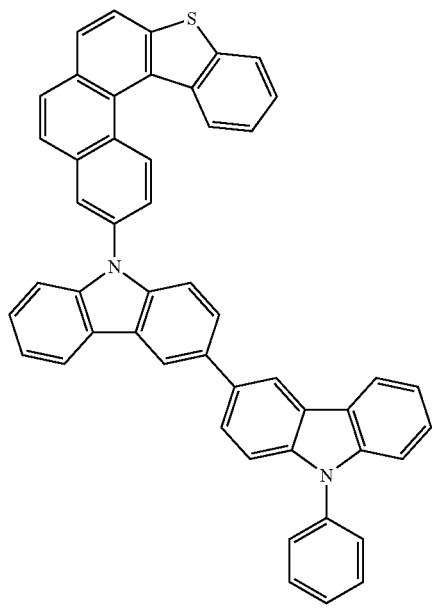
C-32
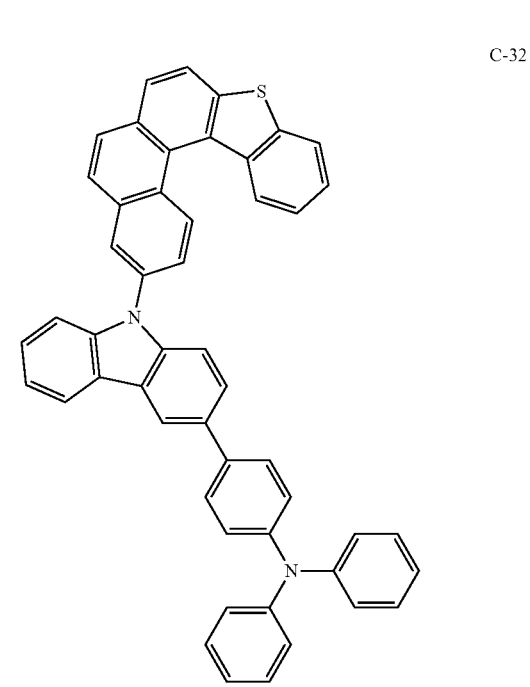

C-33
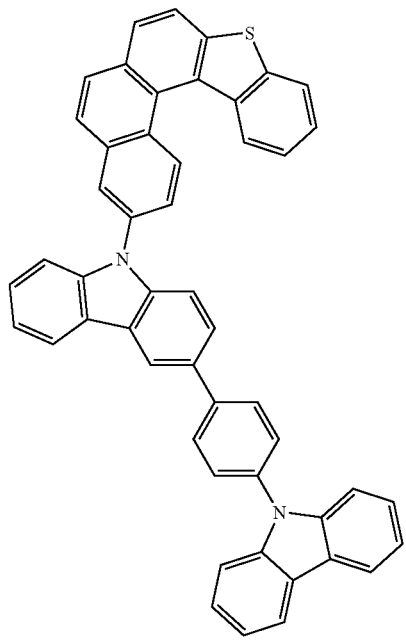
C-34
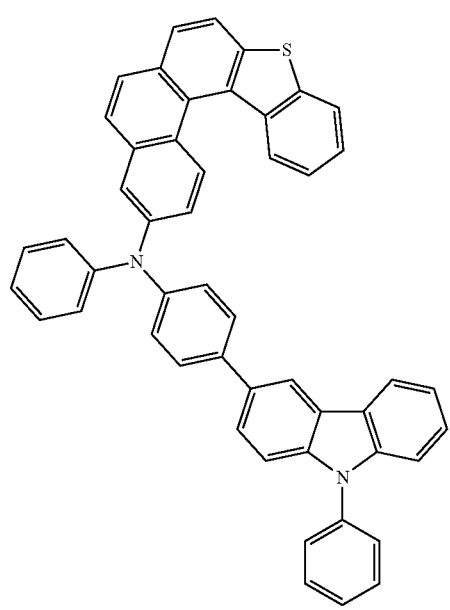
C-35
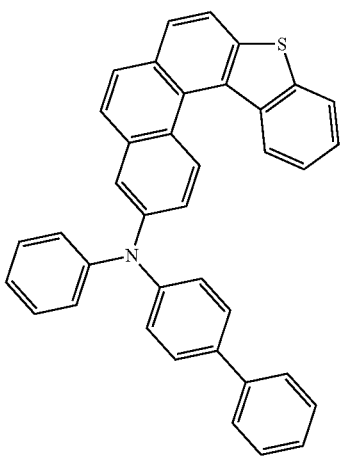
C-36
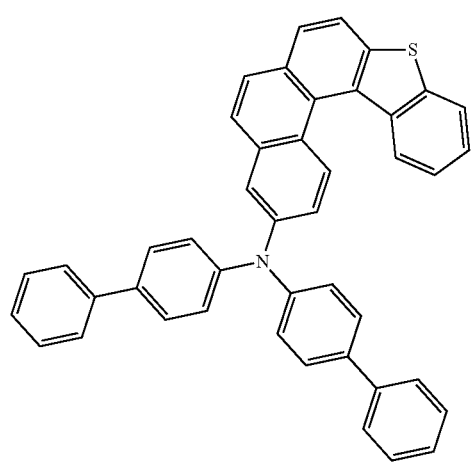
C-37
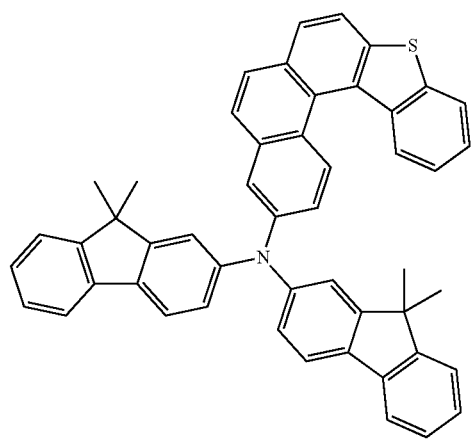

C-38
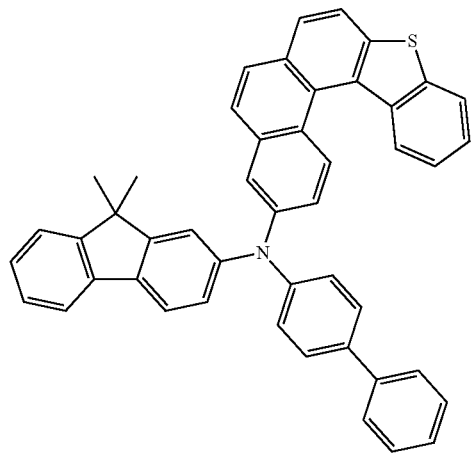
C-39
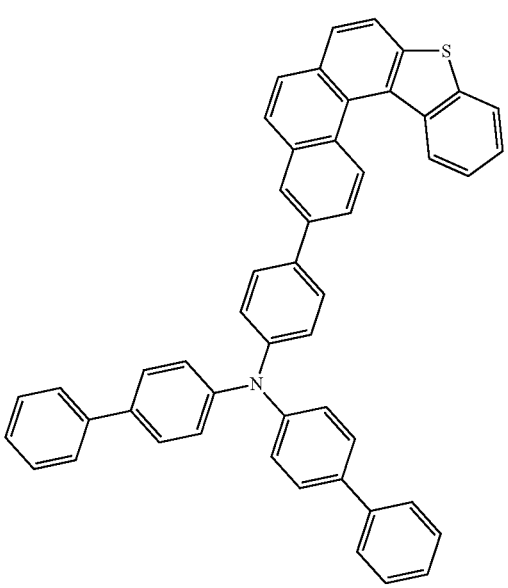
C-40
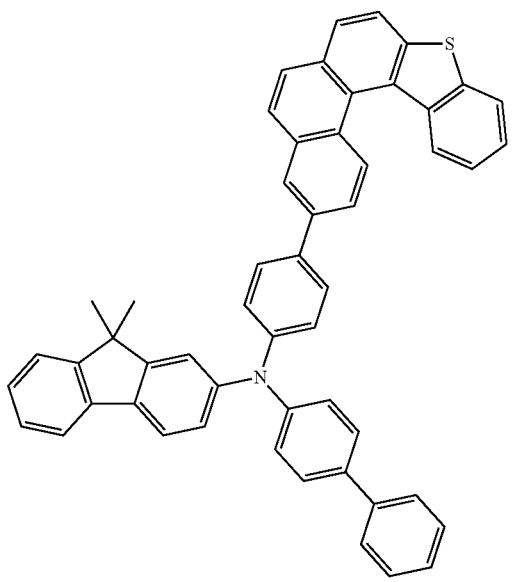
C-41
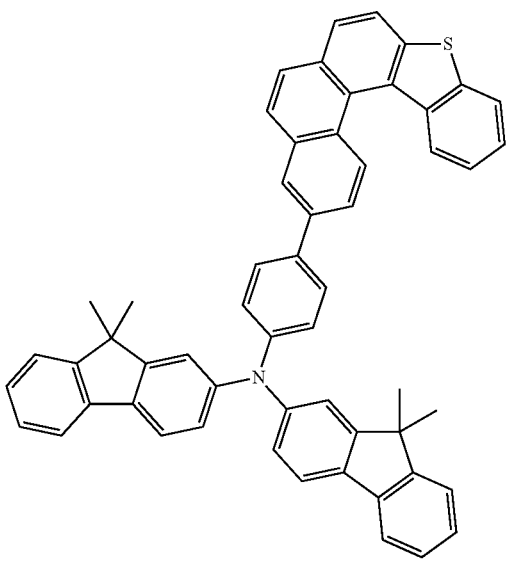
C-42
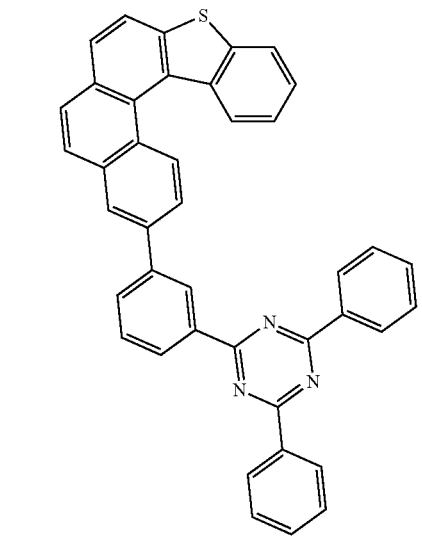
C-43
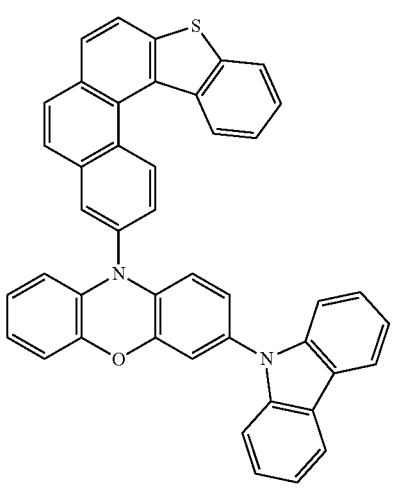

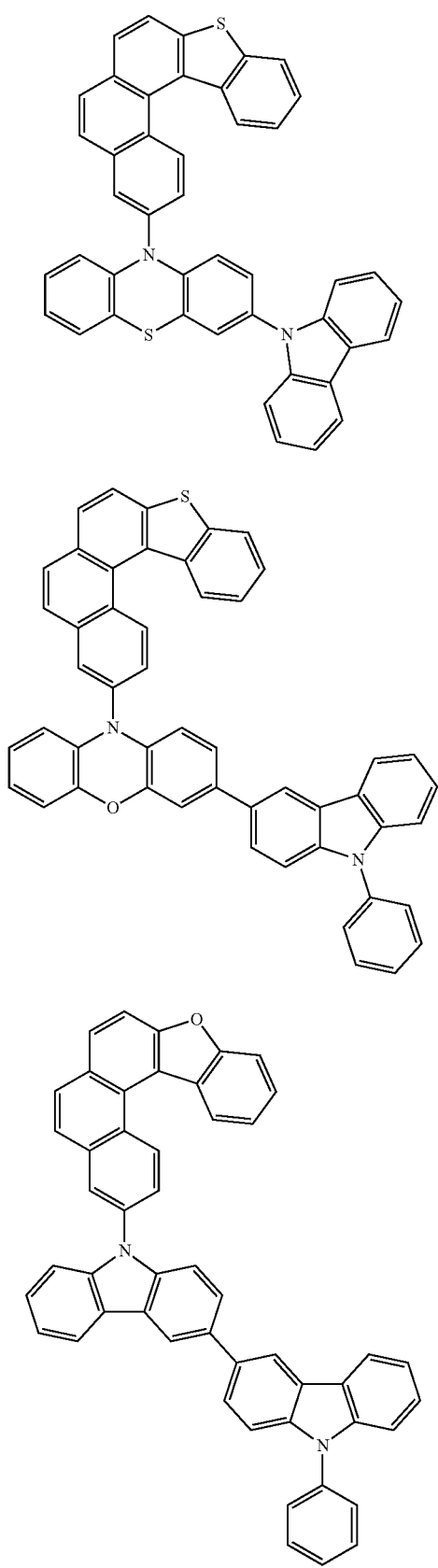
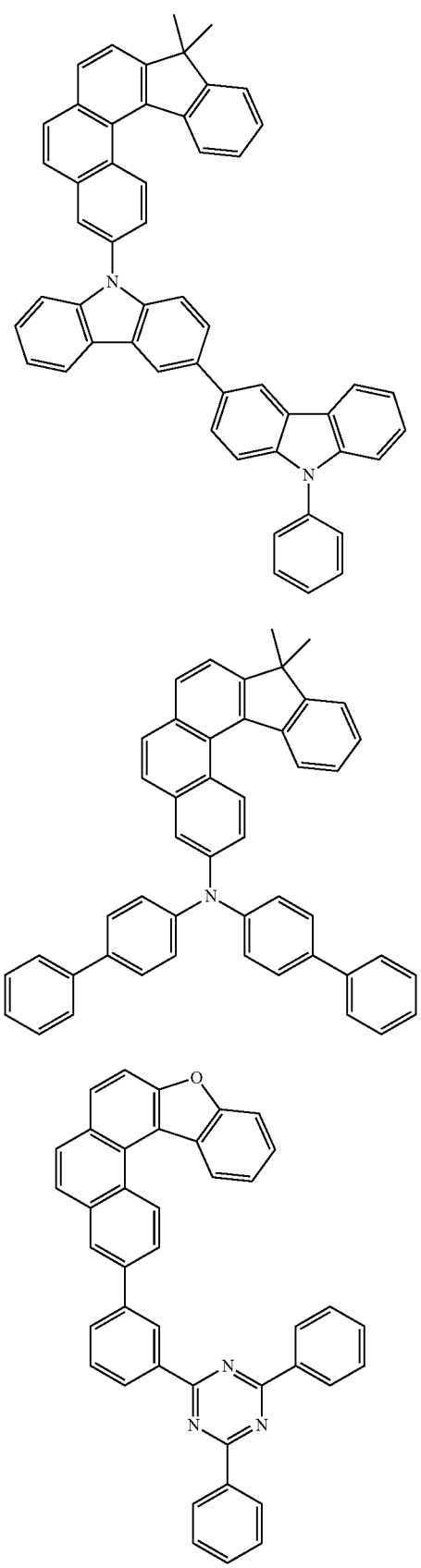

C-50

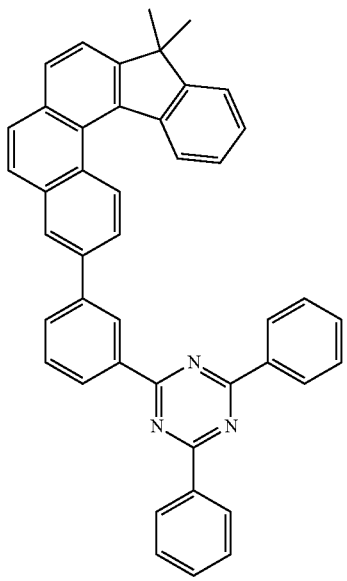

The present disclosure also discloses an organic electroluminescent compound comprising the compound of formula 1, and an OLED comprising the same.

The organic electroluminescent compound may consist of the organic electroluminescent compound of the present disclosure as a sole compound, or may be a mixture or a composition comprising the organic electroluminescent compound of the present disclosure and further comprising conventional materials generally used in organic electroluminescent materials.

The OLED of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

Herein, the hole auxiliary layer or the light-emitting auxiliary layer may be placed between the hole transport layer and the light-emitting layer, which may control a transport rate of a hole. The hole auxiliary layer or the light-emitting auxiliary layer may be effective to produce an OLED having excellent efficiencies and/or improved lifespan.

According to one embodiment of the present disclosure, the compound represented by formula 1 may be comprised in an OLED as at least one of a host material, an electron buffer material and an electron transport material.

According to one embodiment of the present disclosure, the compound represented by formula 1 may be comprised in the light-emitting layer as a host material. Preferably, the light-emitting layer may comprise at least one dopant. If necessary, another compound besides the organic electroluminescent compound of formula 1 may be comprised as a second host material. Herein, the weight ratio of the first host material to the second host material is in the range of 1:99 to 99:1. The doping concentration of a dopant compound to a host compound in the light-emitting layer is preferable to be less than 20 wt %.

The second host material can use any of the known phosphorescent hosts. Preferably, the second host material may comprise the compound represented by the following formula 5:

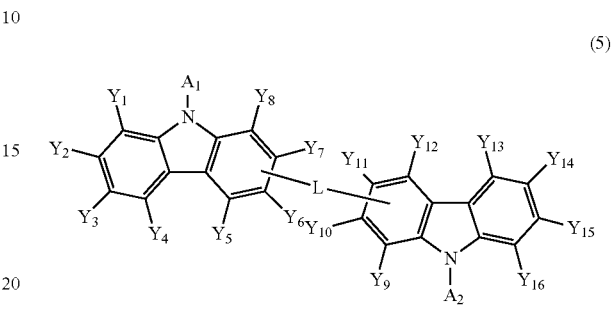

(5)

wherein $A_1$ and $A_2$, each independently, represent a substituted or unsubstituted (C6-C30)aryl; with the proviso that a substituent for neither $A_1$ nor $A_2$ is a nitrogen-containing heteroaryl;

L represents a single bond, or a substituted or unsubstituted (C6-C30)arylene; and $Y_1$ to $Y_{16}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered) heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one heteroatom selected from nitrogen, oxygen, and sulfur.

The compound of formula 5 may be represented by any one of the following formulas 6 to 9.

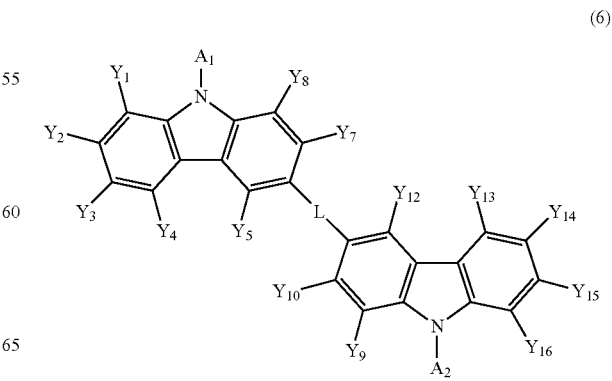

(6)

-continued

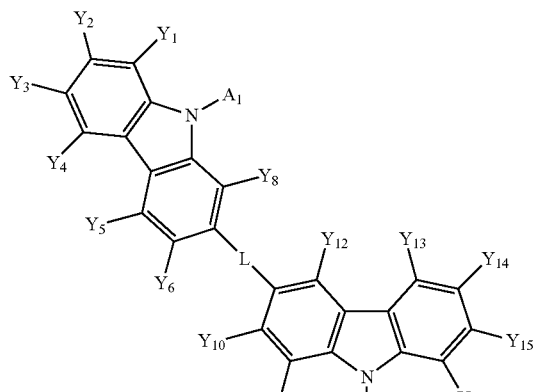

(7)

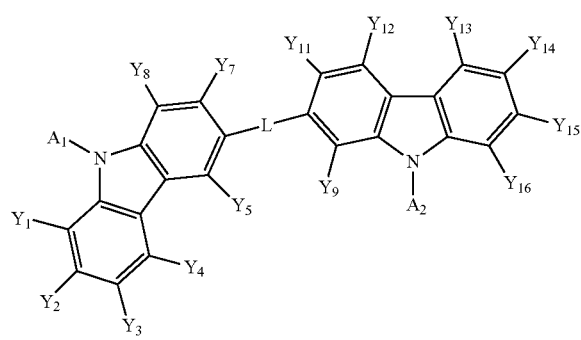

(8)

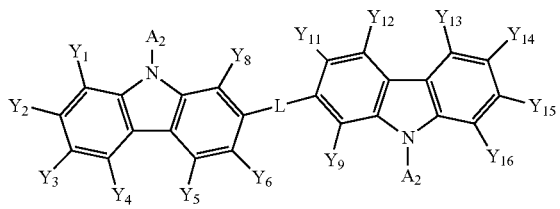

(9)

In formulas 6 to 9, $A_1$, $A_2$, L, and $Y_1$ to $Y_{16}$ are as defined in formula 5.

In formulas 5 to 9, $A_1$ and $A_2$, each independently, represent preferably, a substituted or unsubstituted (C6-C20) aryl, and more preferably, a (C6-C20)aryl unsubstituted or substituted with a cyano, a halogen, a (C1-C6)alkyl, a (C6-C12)aryl or tri(C6-C12)arylsilyl. For example, $A_1$ and $A_2$, each independently, may be selected from the group consisting of a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, and a substituted or unsubstituted fluoranthenyl. The substituent of the substituted group such as the substituted phenyl may be a cyano, a halogen, a (C1-C6)alkyl, a (C6-C12)aryl, or a tri(C6-C12)arylsilyl.

In formulas 5 to 9, $Y_1$ to $Y_{16}$, each independently, represent preferably, hydrogen; a cyano; a substituted or unsubstituted (C1-C10)alkyl; a substituted or unsubstituted (C6-C20)aryl; a substituted or unsubstituted (5- to 20-membered) heteroaryl; or a substituted or unsubstituted tri(C6-C12) arylsilyl; more preferably, hydrogen; a cyano; a (C1-C10) alkyl; a (C6-C20)aryl unsubstituted or substituted with a cyano, a (C1-C10)alkyl or a tri(C6-C12)arylsilyl; a (5- to 20-membered) heteroaryl unsubstituted or substituted with a (C1-C10)alkyl, a (C6-C15)aryl or a tri(C6-C12)arylsilyl; or a tri(C6-C12)arylsilyl unsubstituted or substituted with a (C1-C10)alkyl. For example, $Y_1$ to $Y_{16}$, each independently, represent hydrogen; a cyano; a (C1-C6)alkyl; a phenyl, a biphenyl, a terphenyl, or a naphthyl, unsubstituted or substituted with a cyano, a (C1-C6)alkyl or a triphenylsilyl; a dibenzothiophenyl or a dibenzofuranyl, unsubstituted or substituted with a (C1-C6)alkyl, a phenyl, a biphenyl, a naphthyl or a triphenylsilyl; or a triphenylsilyl unsubstituted or substituted with a (C1-C6)alkyl.

In formulas 5 to 9, L represents a single bond, or a substituted or unsubstituted (C6-C30)arylene; preferably, a single bond, or a substituted or unsubstituted (C6-C15) arylene; more preferably, a single bond, or a (C6-C15) arylene unsubstituted or substituted with a cyano, a (C1-C6)alkyl or a tri(C6-C12)arylsilyl; and for example, a single bond, a substituted or unsubstituted phenylene, a substituted or unsubstituted naphthylene, or a substituted or unsubstituted biphenylene.

Specifically, L may represent a single bond, or any one of the following formulas 10 to 22.

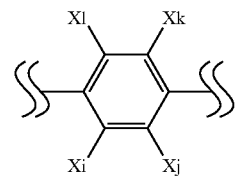

(10)

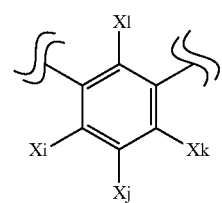

(11)

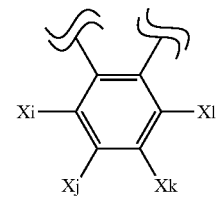

(12)

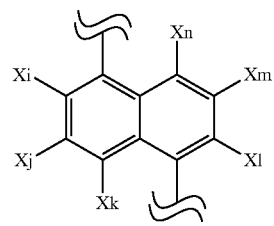

(13)

-continued

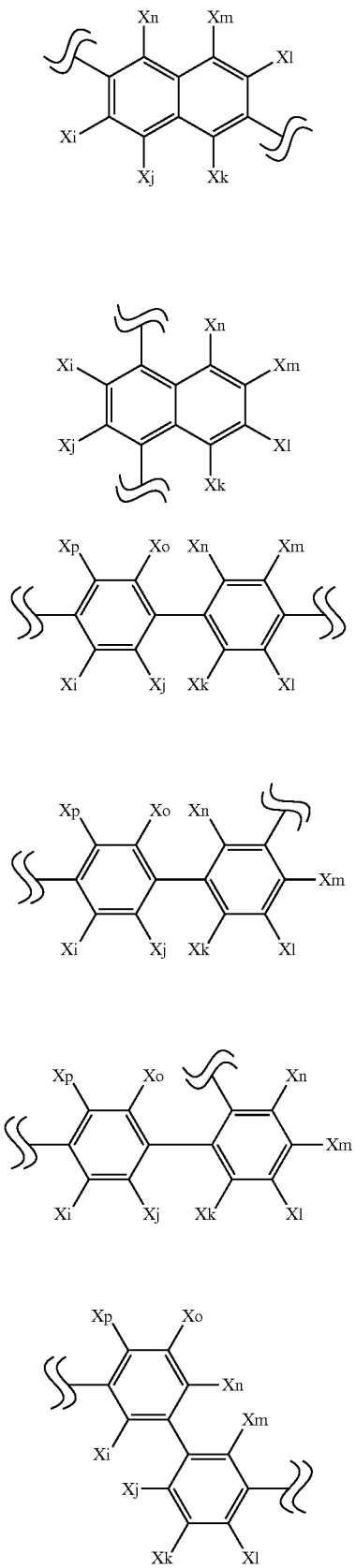

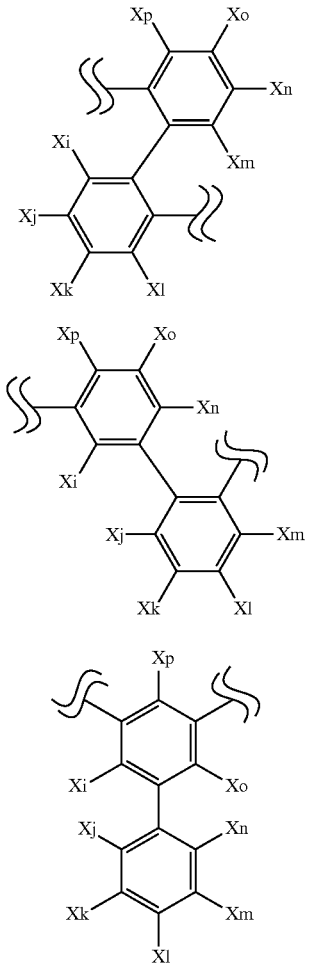

wherein

Xi to Xp, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered) heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one heteroatom selected from the group consisting of nitrogen, oxygen, and sulfur; and represents a bonding site. Xi to Xp, each independently, represent preferably, hydrogen, a halogen, a cyano, a (C1-C10)alkyl, a (C3-C20) cycloalkyl, a (C6-C12)aryl, a (C1-C6)alkyldi(C6-C12)arylsilyl, or a tri(C6-C12)arylsilyl; and more preferably, hydrogen, a cyano, a (C1-C6)alkyl, or a tri(C6-C12)arylsilyl.

The compound represented by formula 5 includes the following compounds, but is not limited thereto:
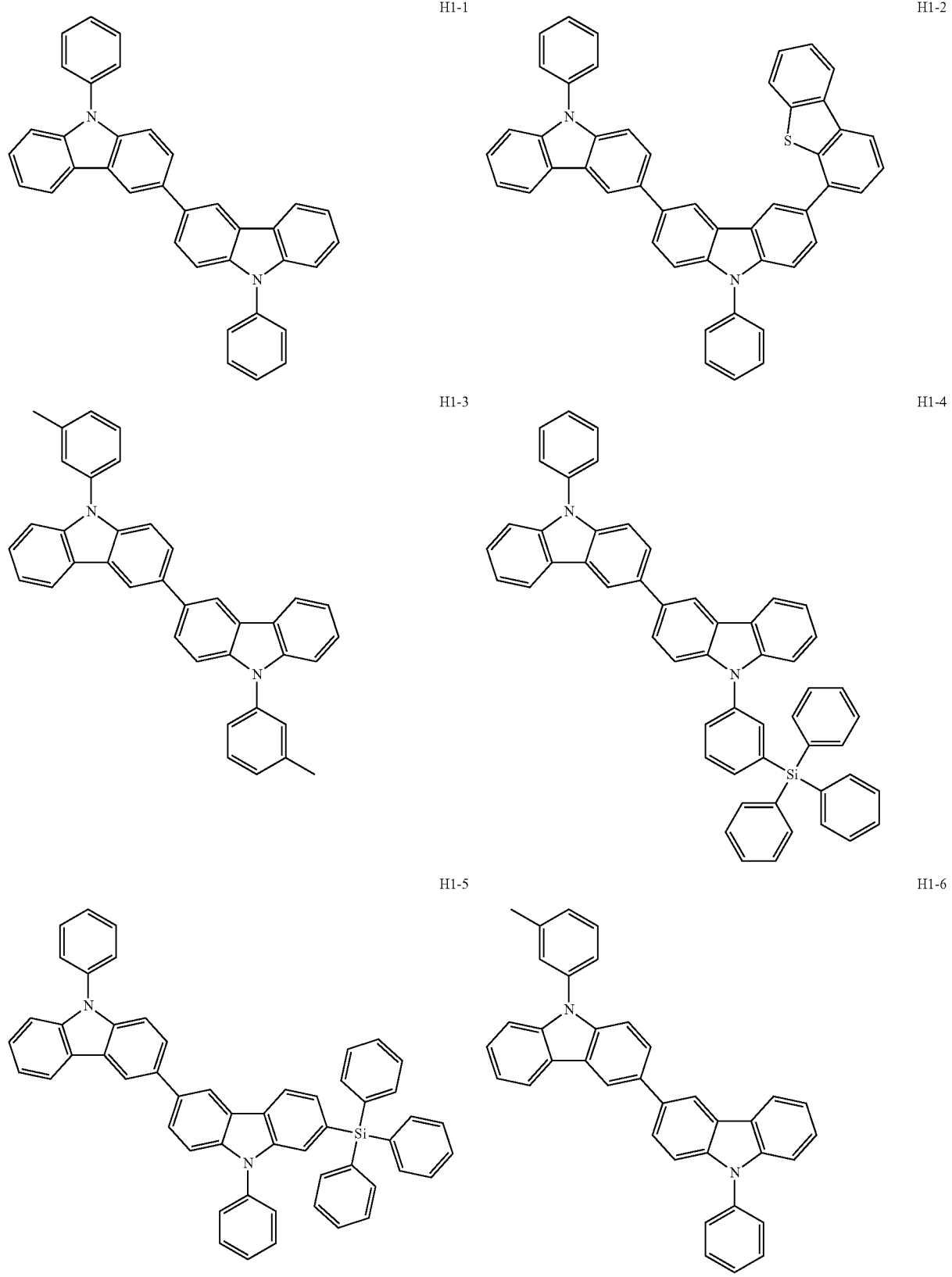

-continued
H1-7
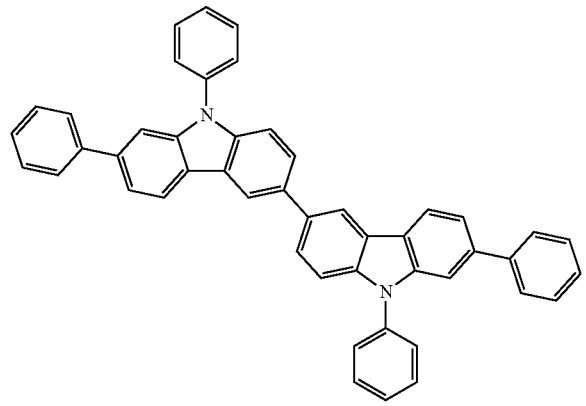
H1-8
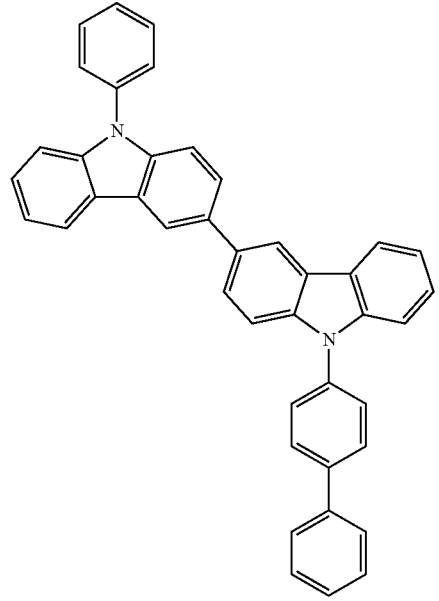
H1-9
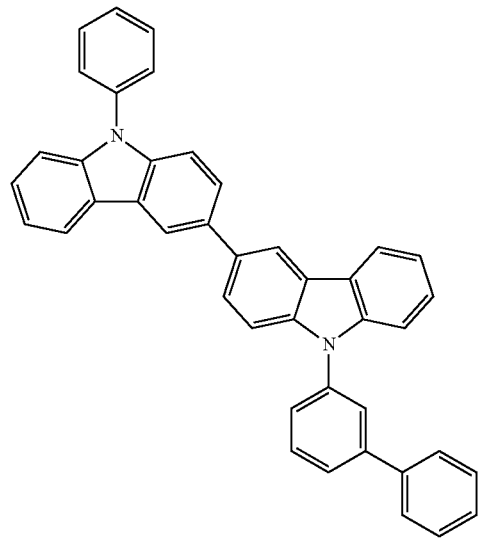
H1-10
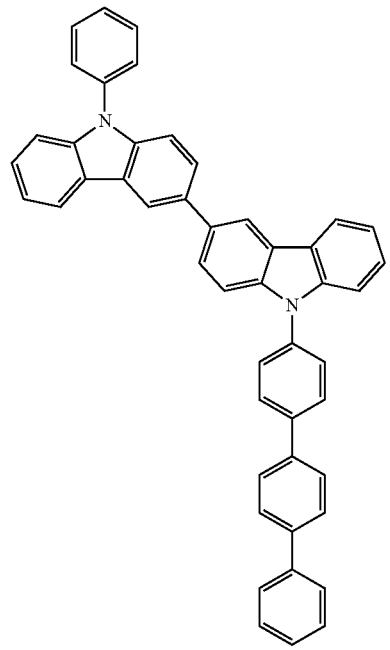

H1-11
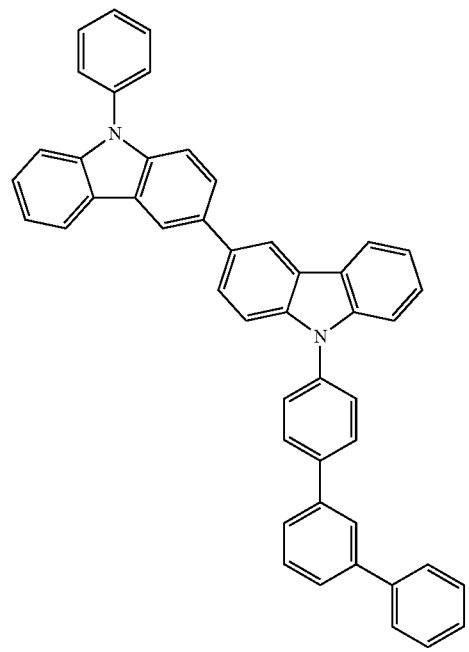
H1-12
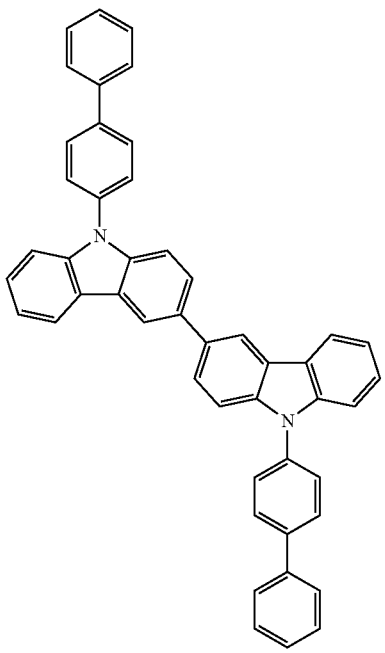
H1-13
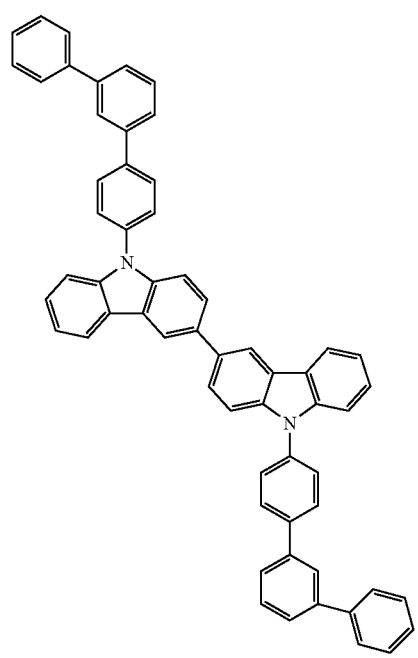
H1-14
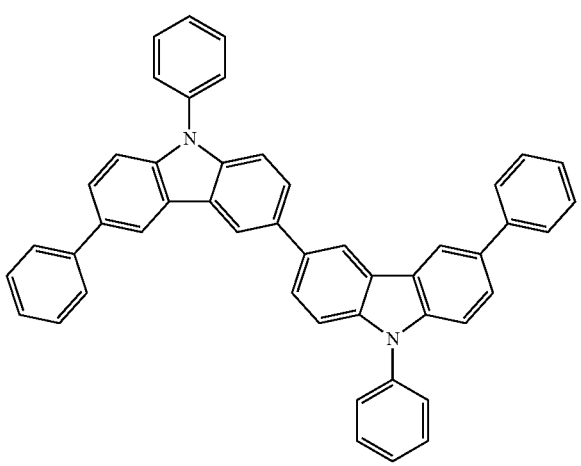

-continued
H1-15
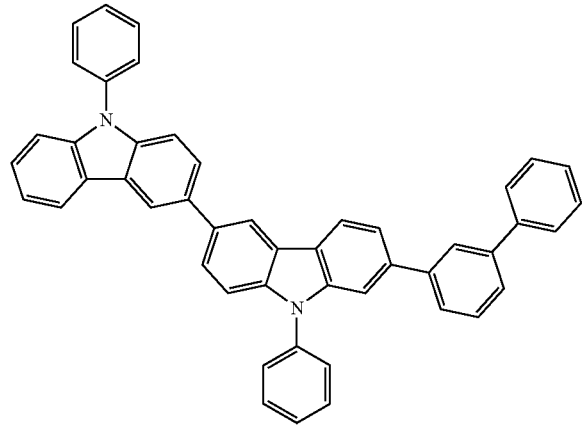
H1-16
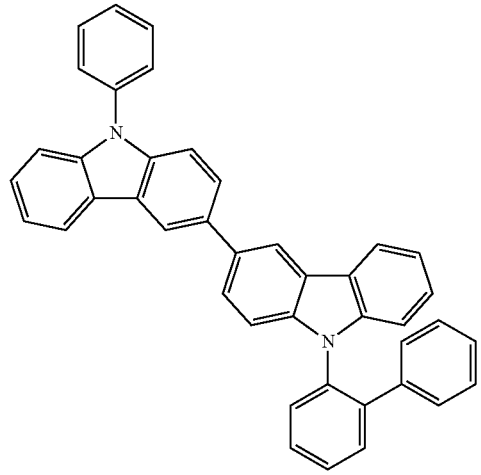
H1-17
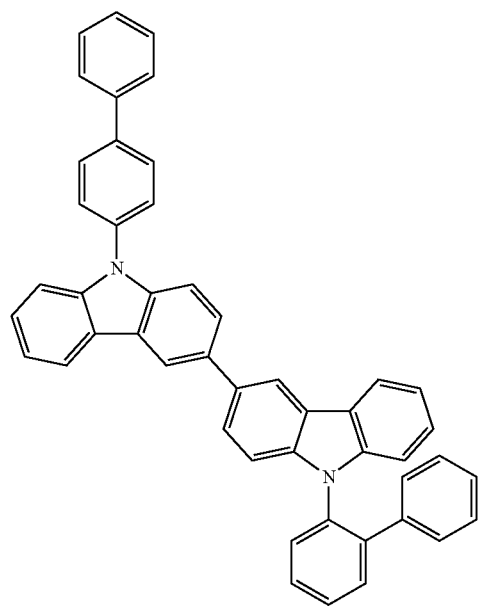
H1-18
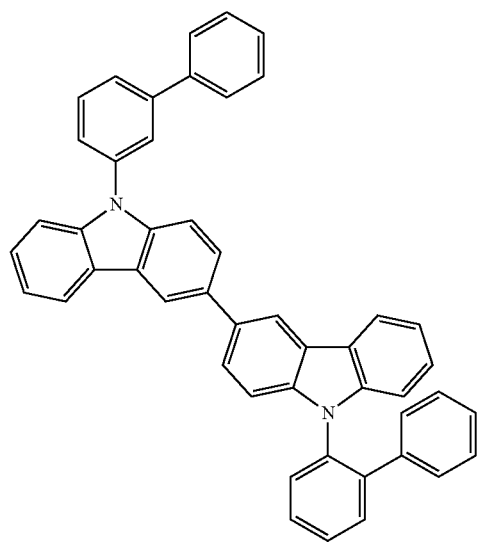

-continued
H1-19
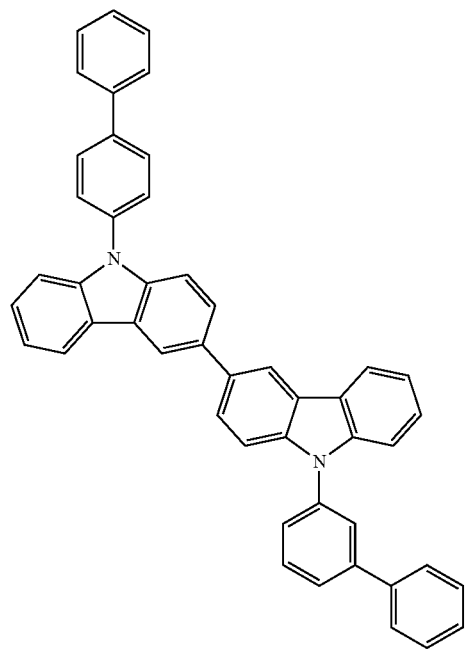
H1-20
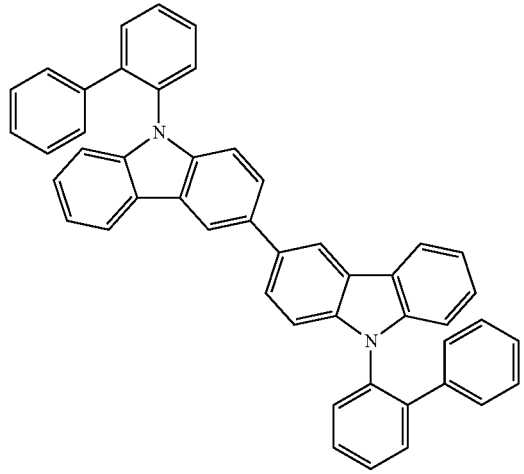
H1-21
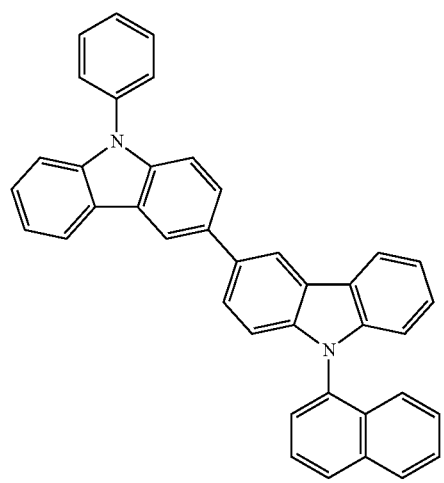
H1-22
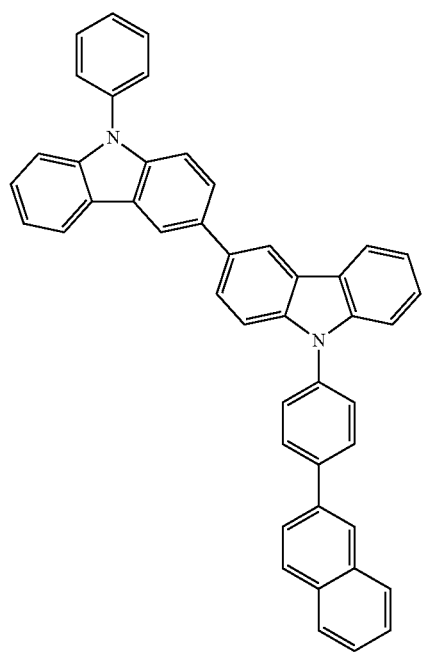

-continued
H1-23
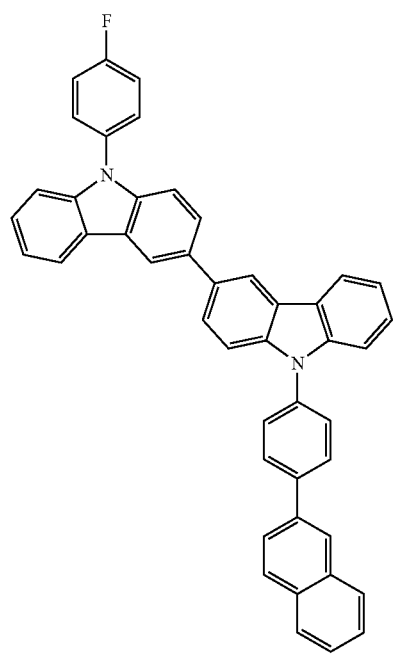
H1-24
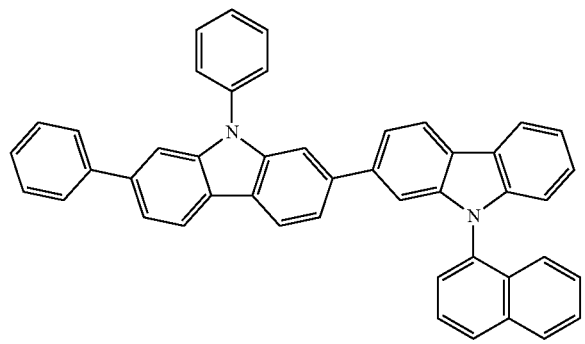
H1-25
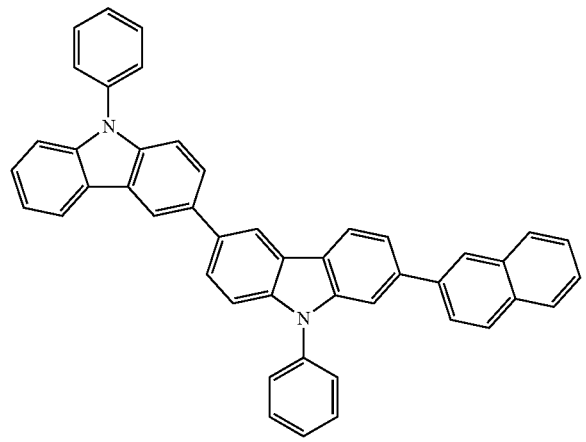
H1-26
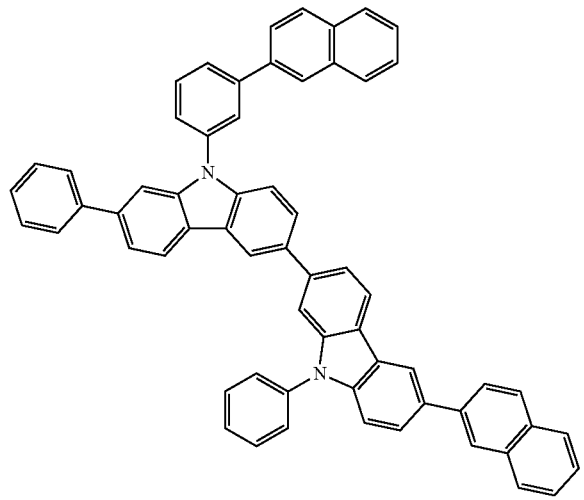

-continued
H1-27
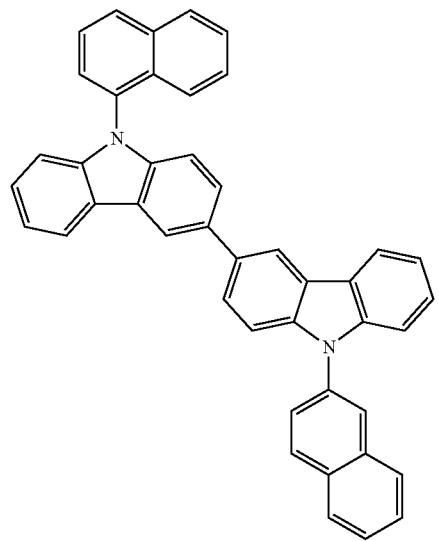
H1-28
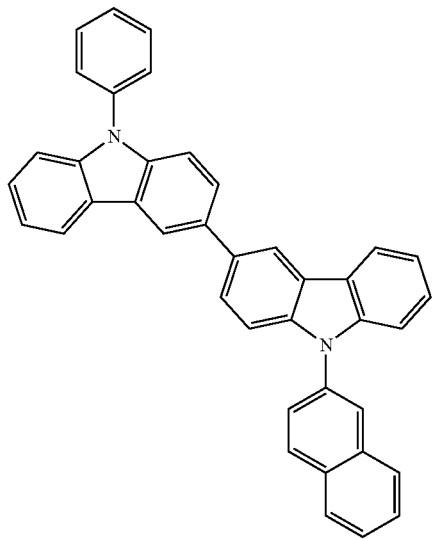
H1-29
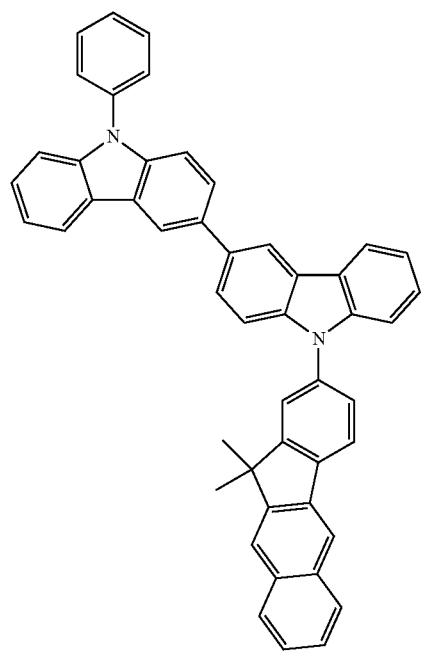
H1-30
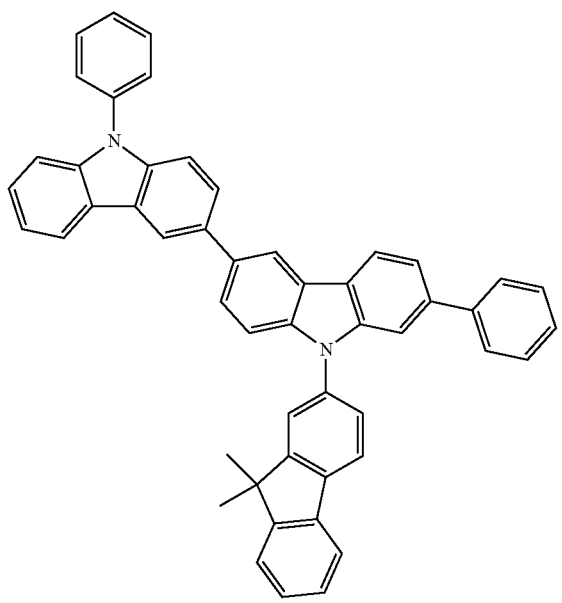

-continued
H1-31
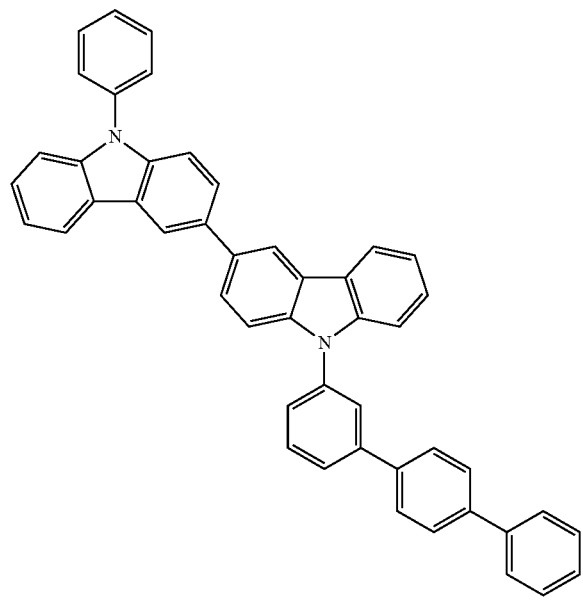
H1-32
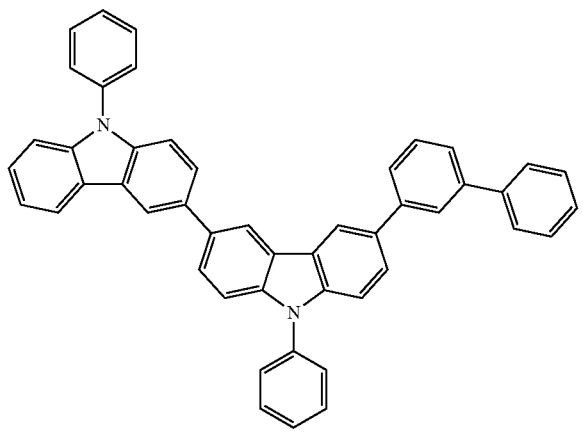
H1-33
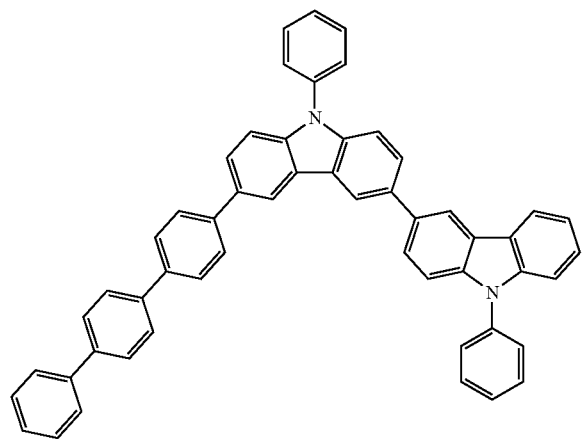
H1-34
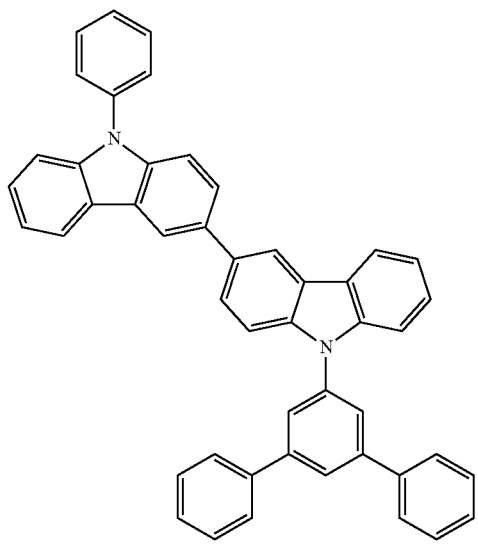

-continued
H1-35
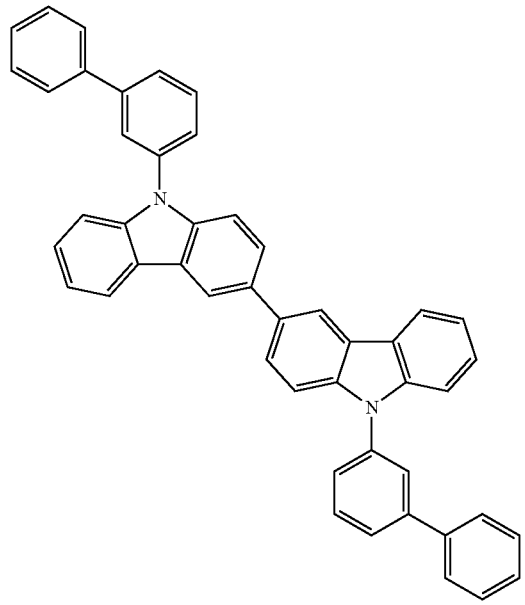
H1-36
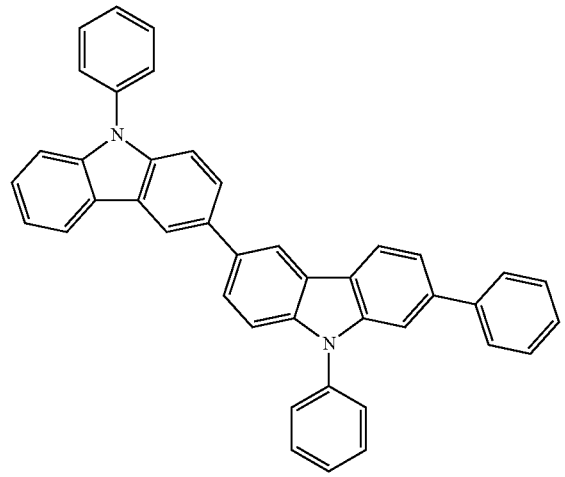
H1-37
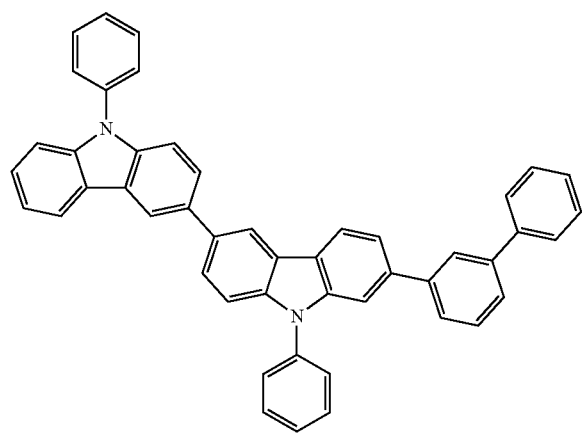
H1-38
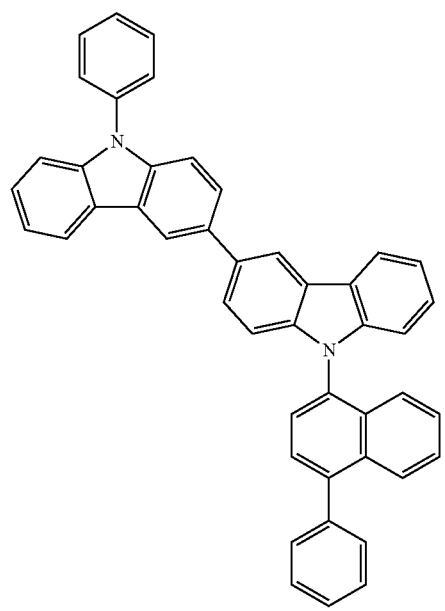

-continued
H1-39
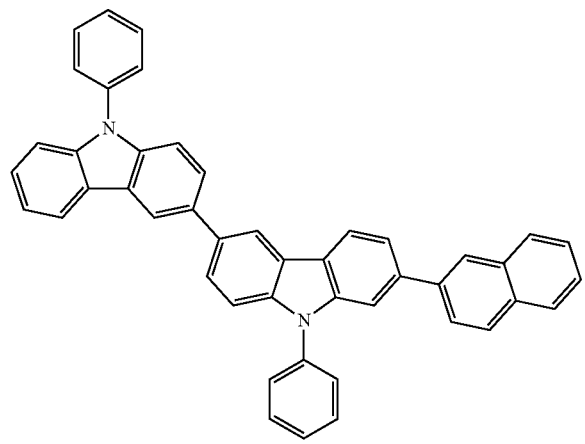
H1-40
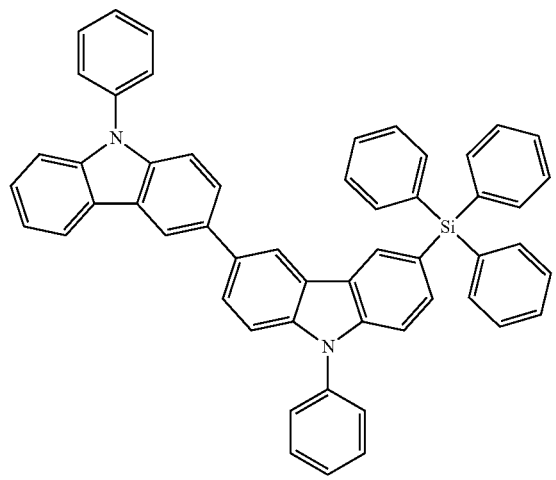
H1-41
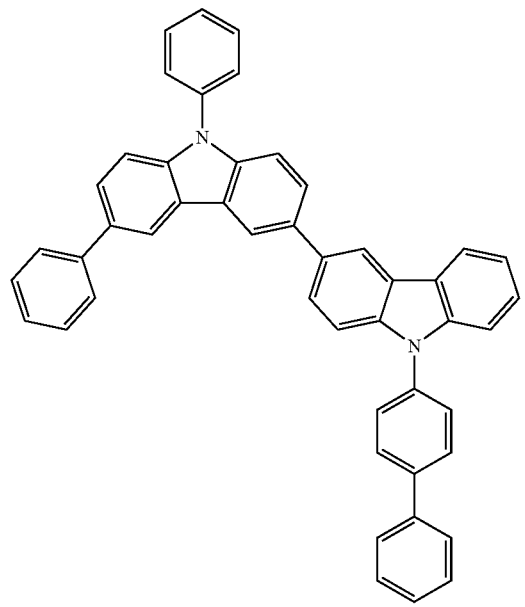
H1-42
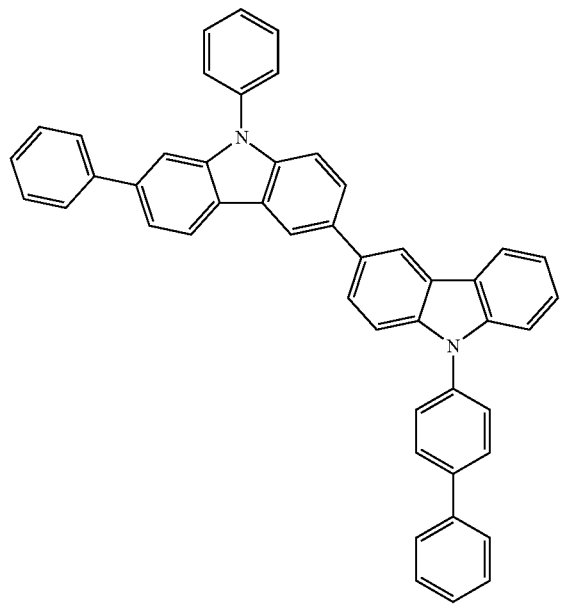

H1-43
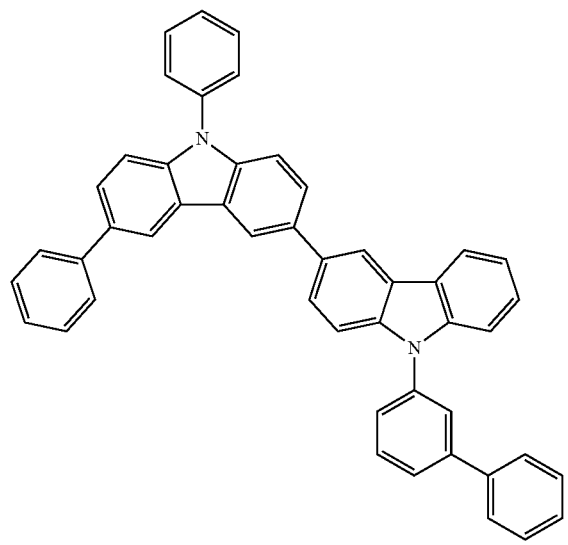
H1-44
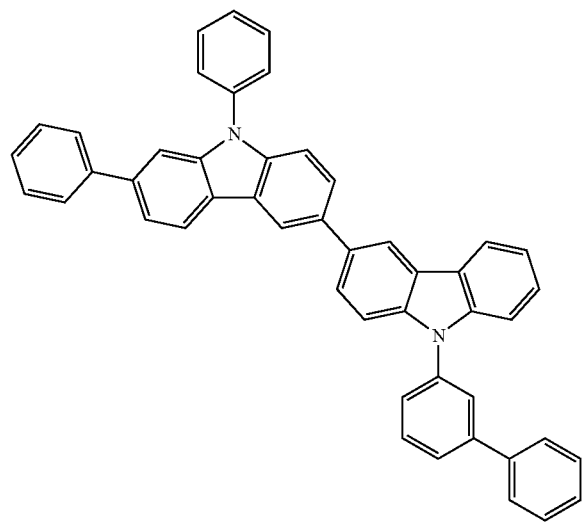
H1-45
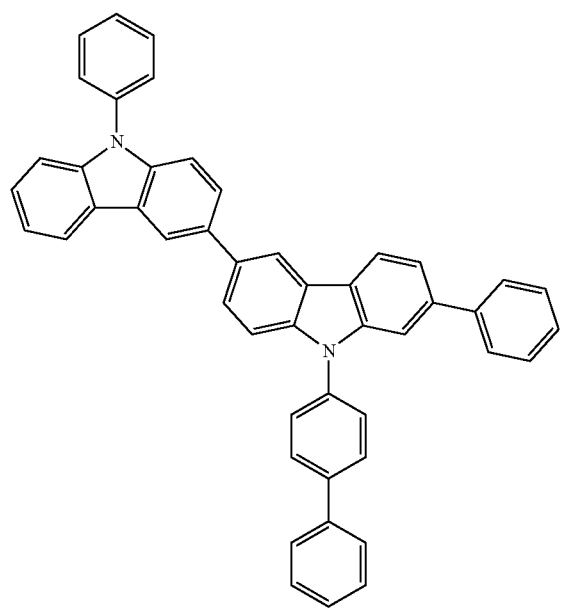
H1-46
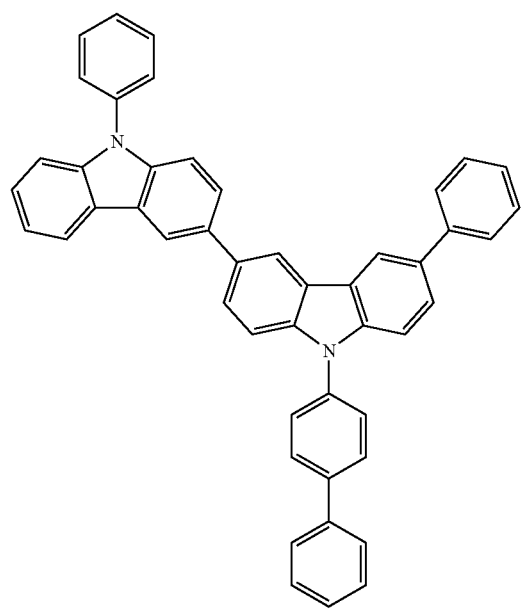

-continued
H1-47
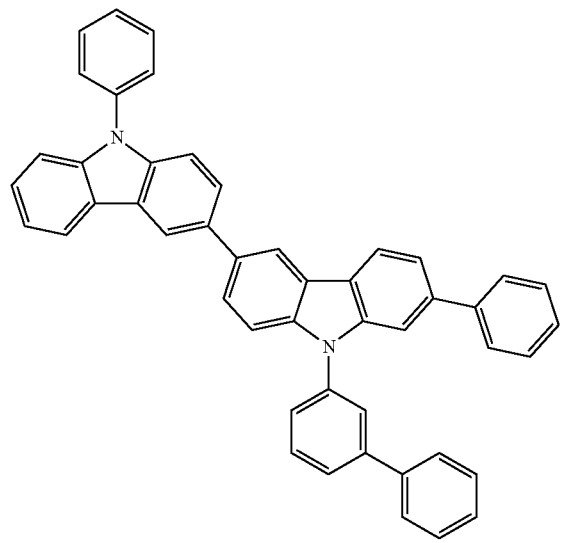
H1-48
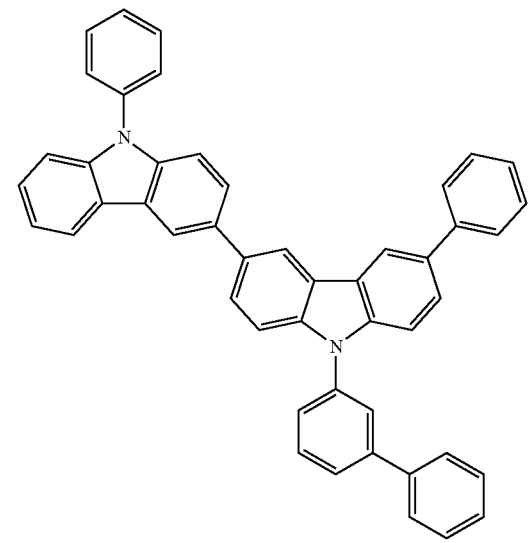
H1-49
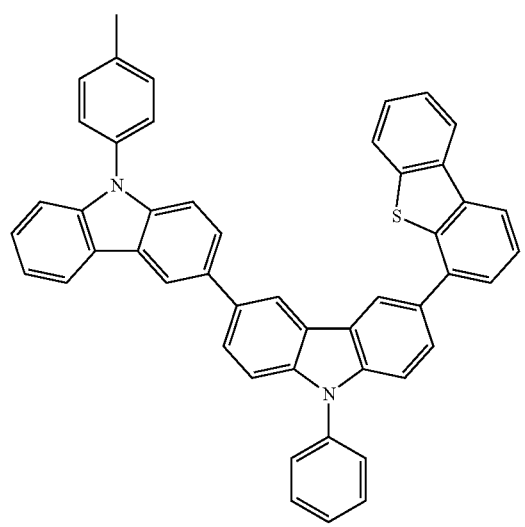
H1-50
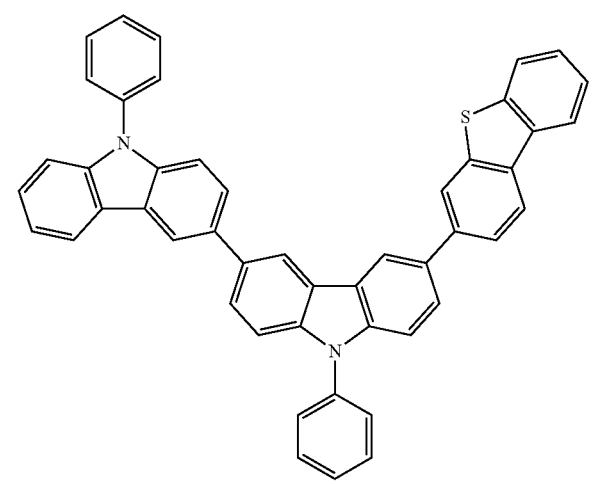
H1-51
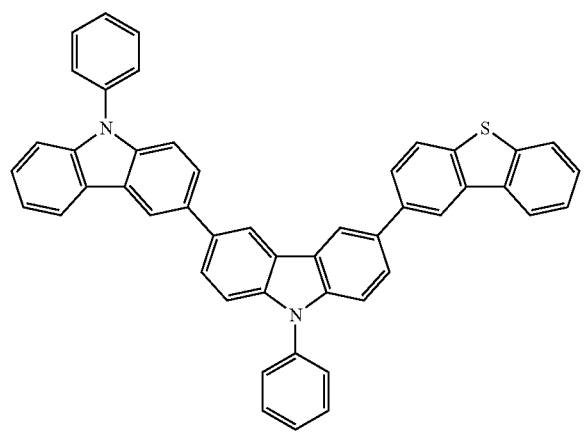
H1-52
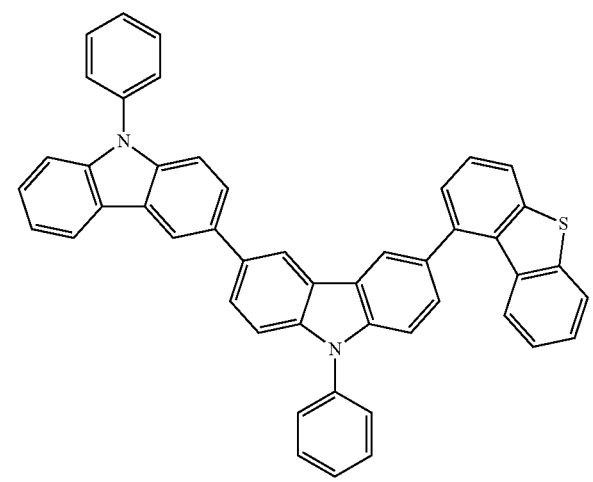

-continued
H1-53
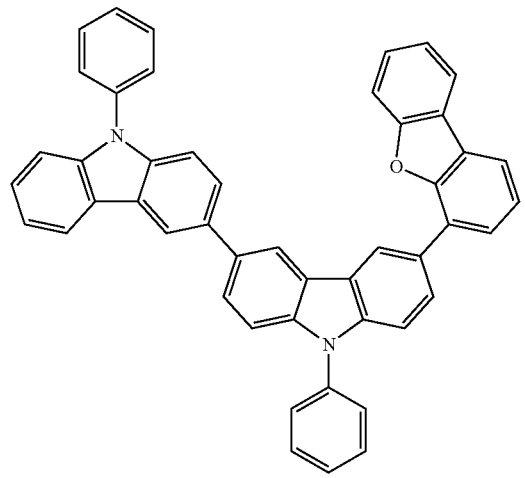
H1-54
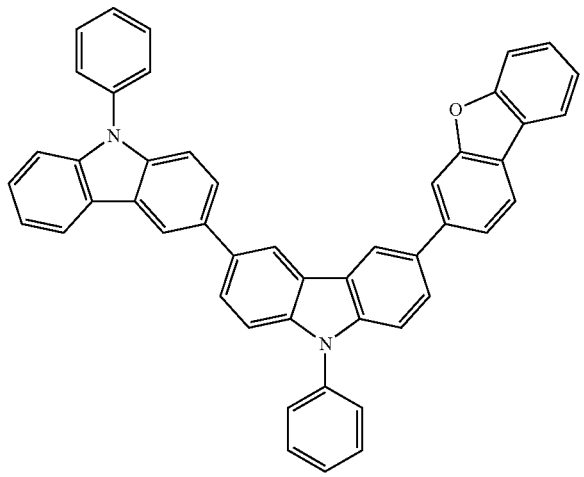
H1-55
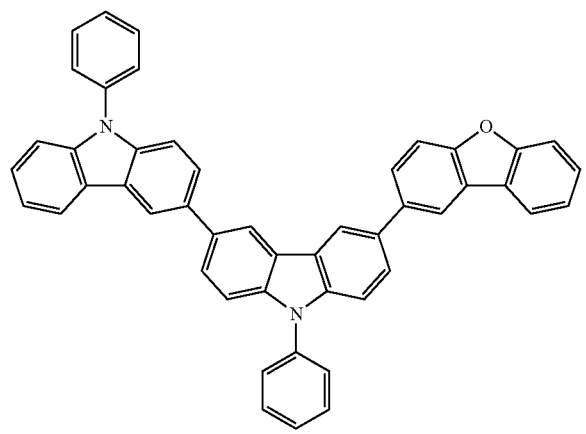
H1-56
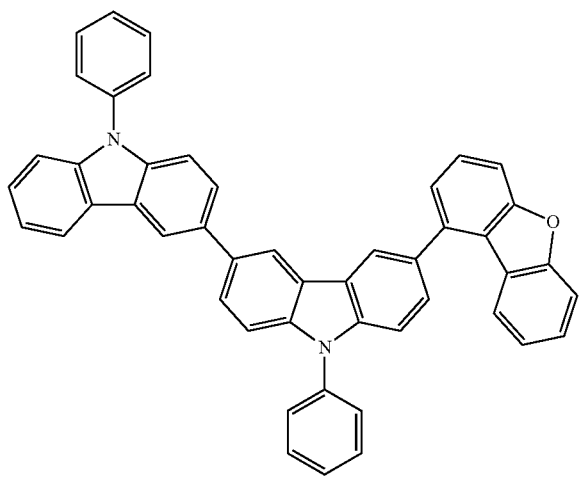
H1-57
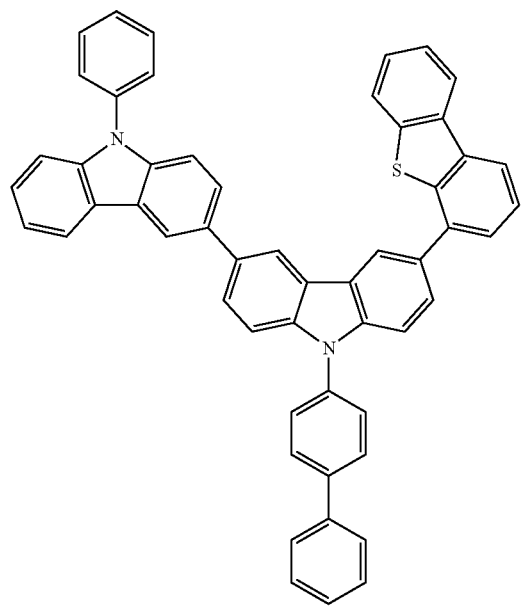
H1-58
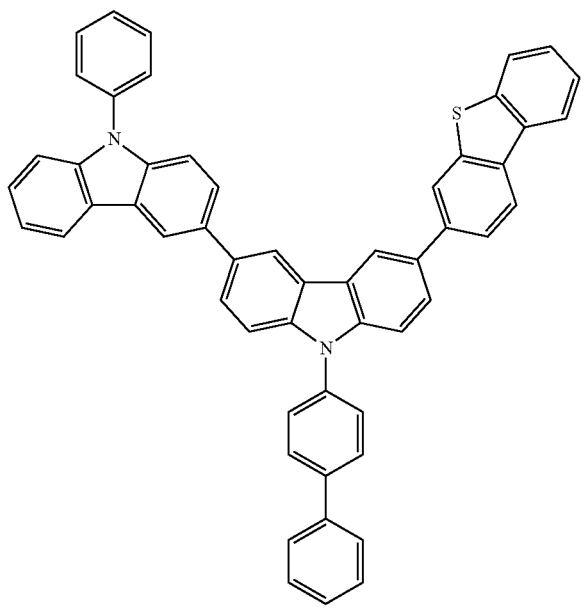

H1-59
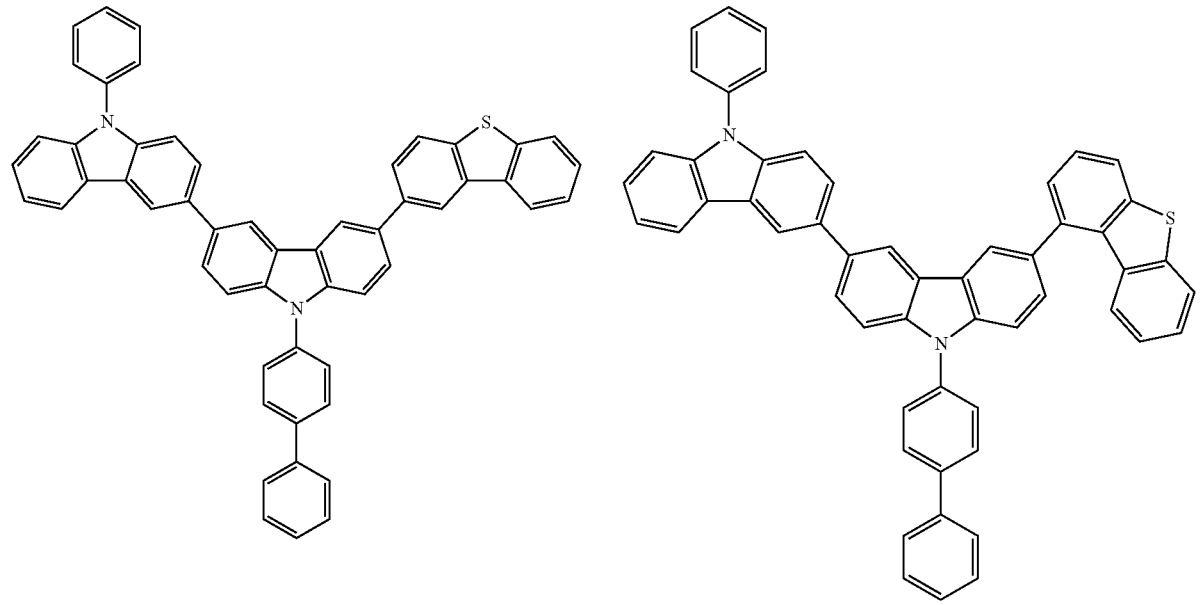
H1-60
H1-61
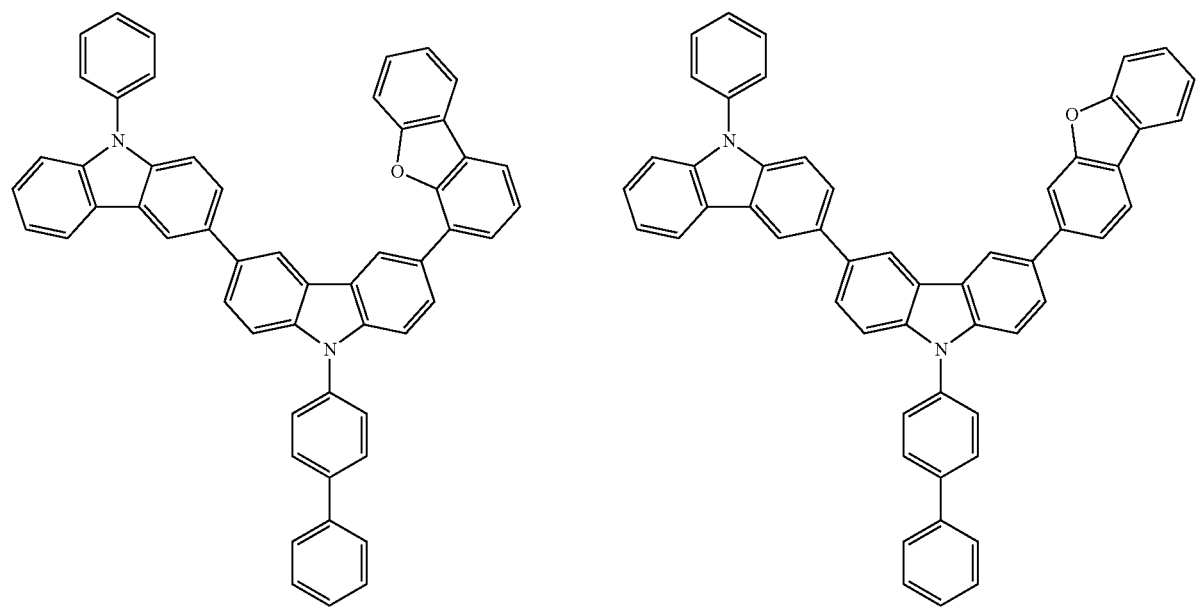
H1-62

-continued
H1-63
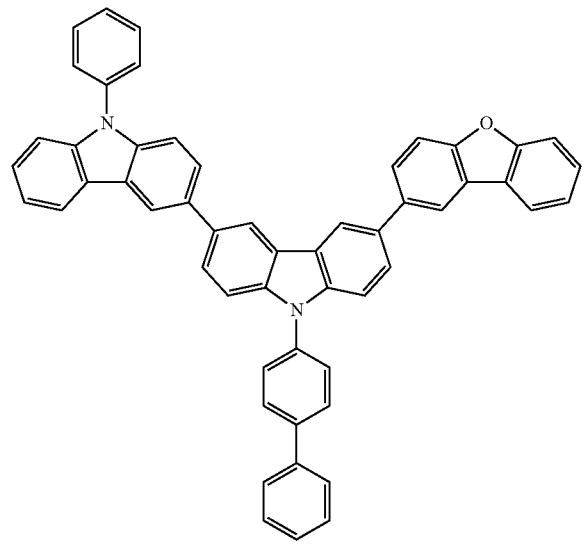
H1-64
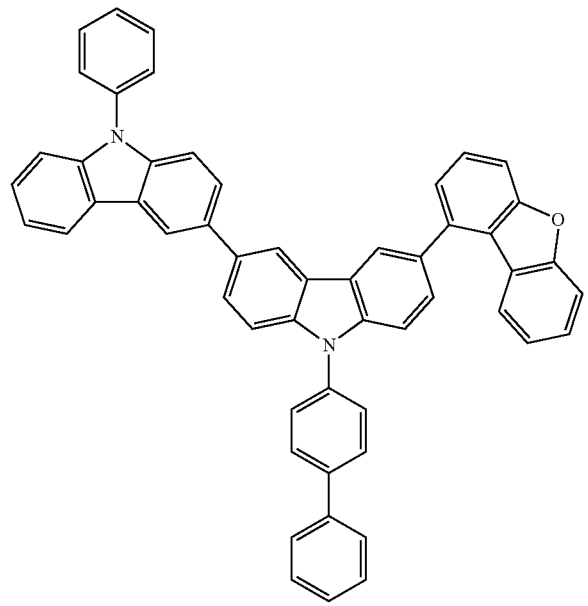
H1-65
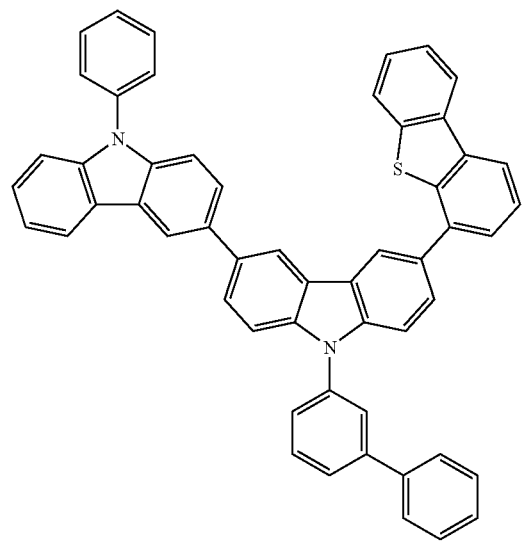
H1-66
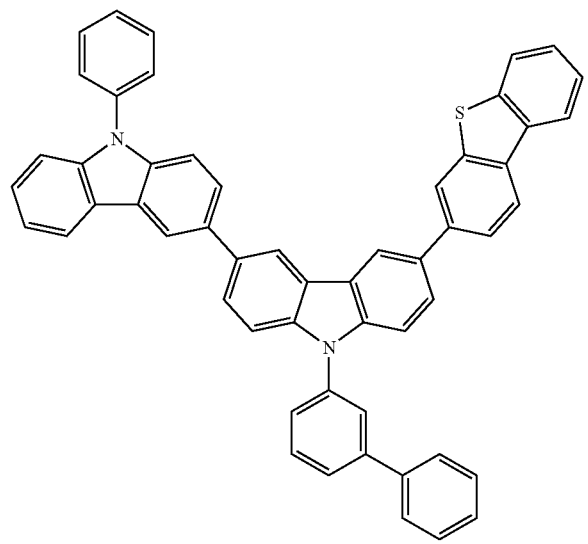

-continued
H1-67
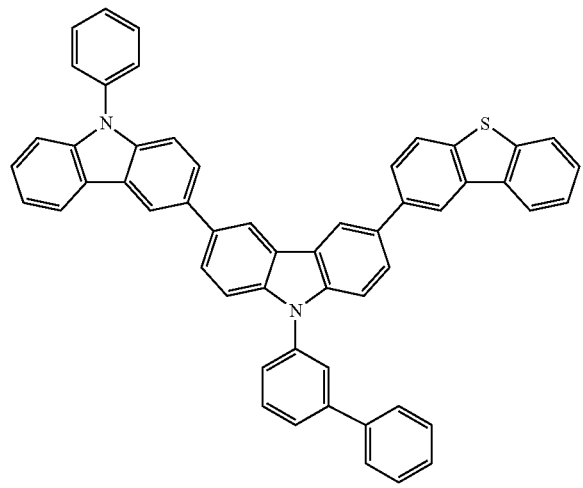
H1-68
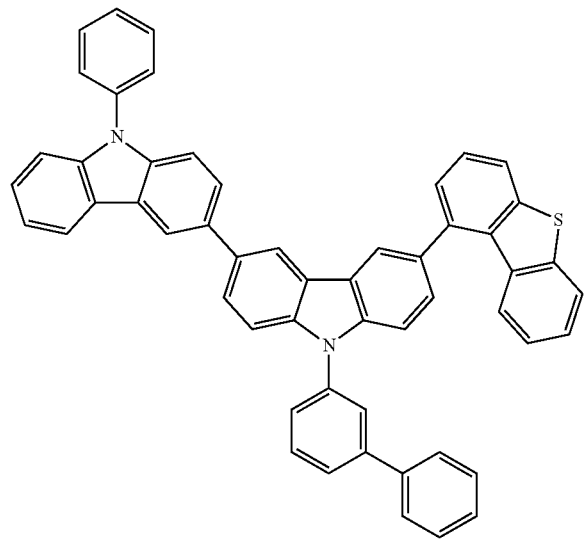
H1-69
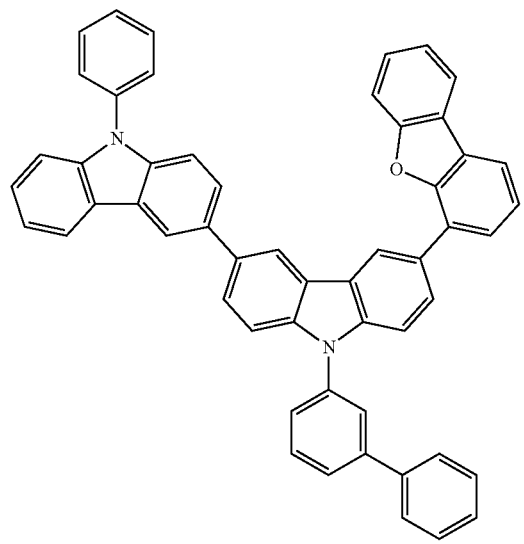
H1-70
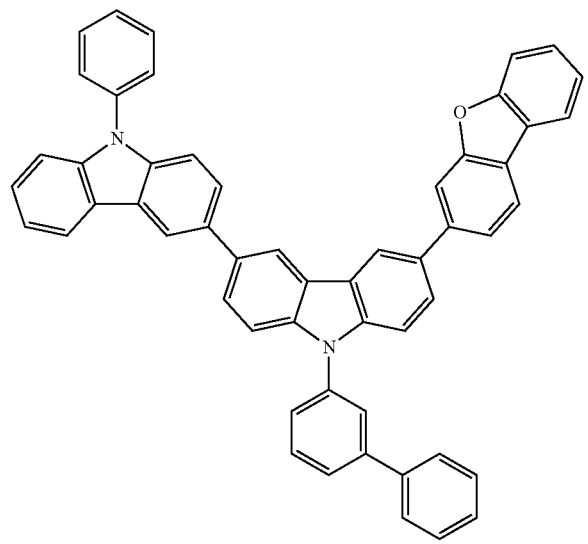

H1-71
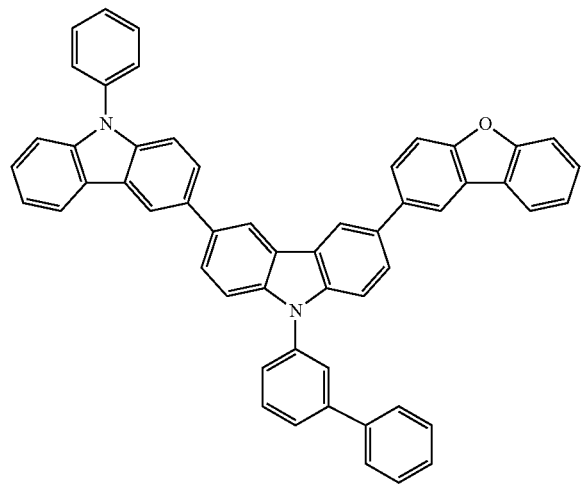
H1-72
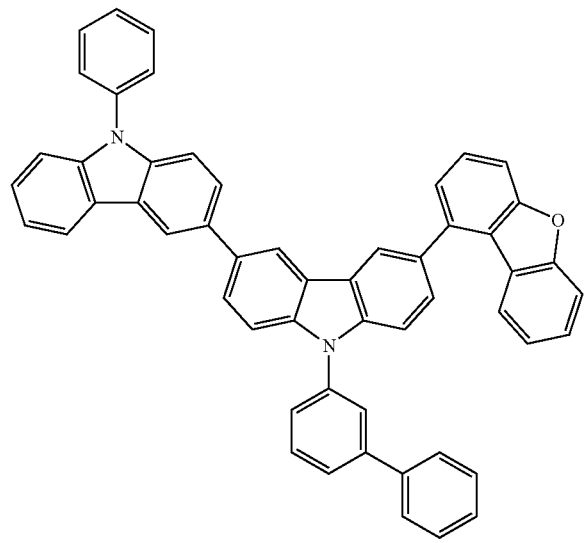
H1-73
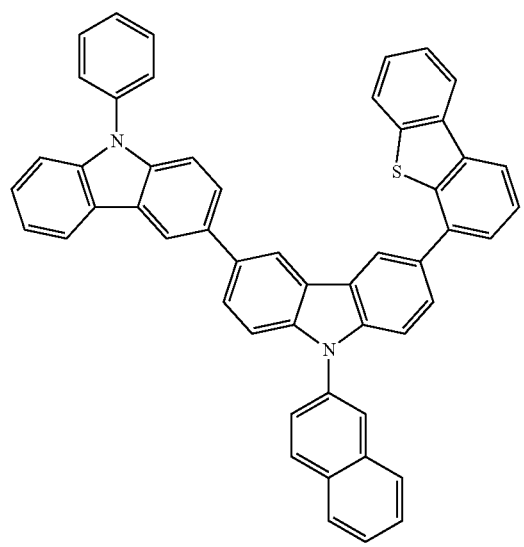
H1-74
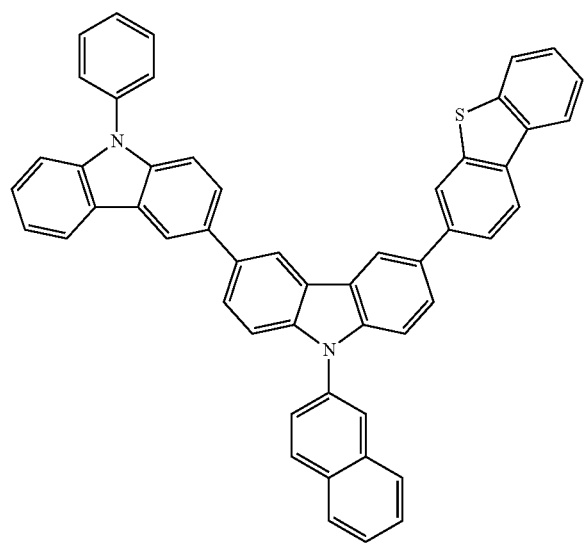

-continued
H1-75
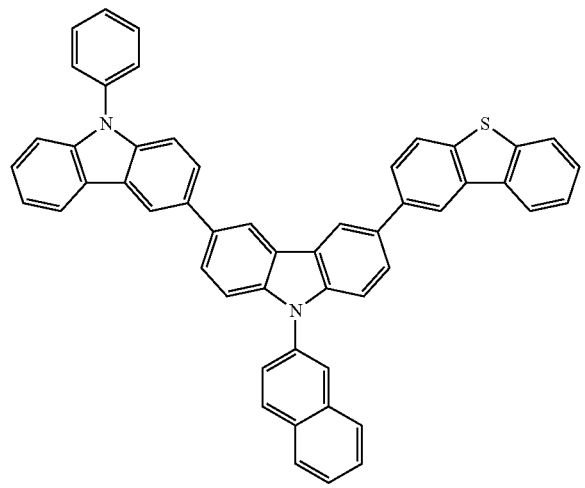
H1-76
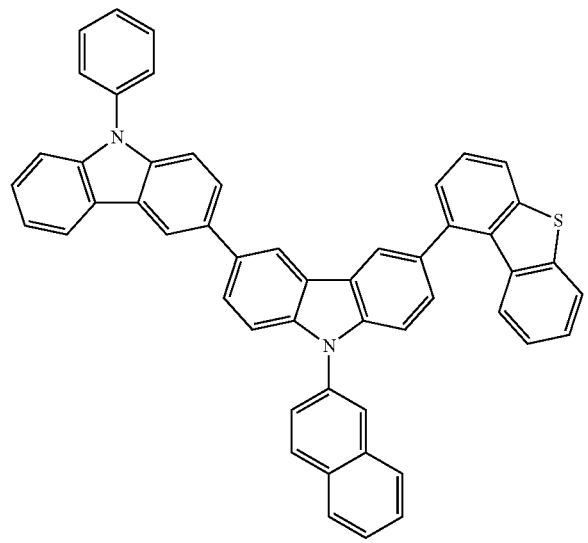
H1-77
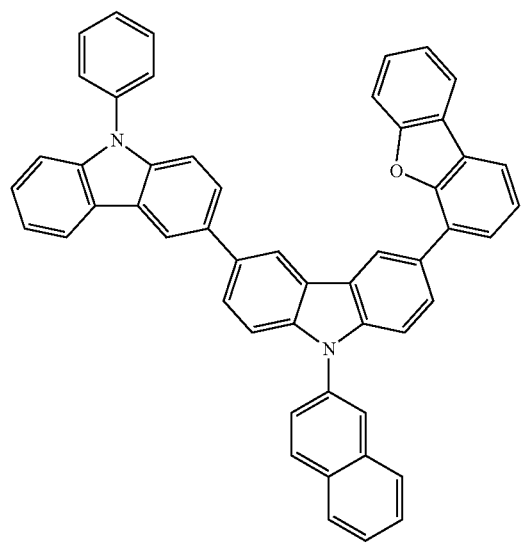
H1-78
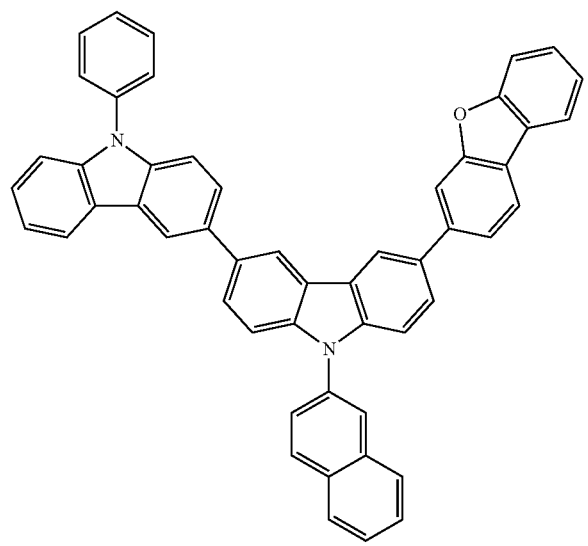

-continued
H1-79
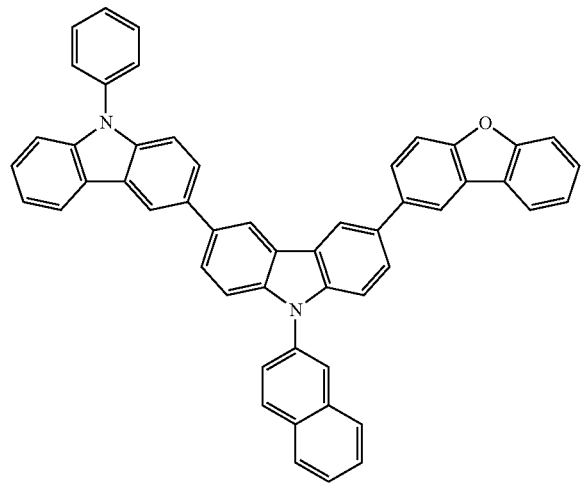
H1-80
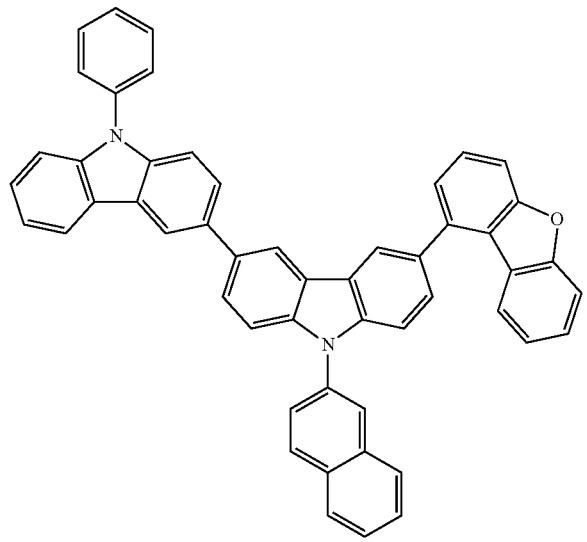
H1-81
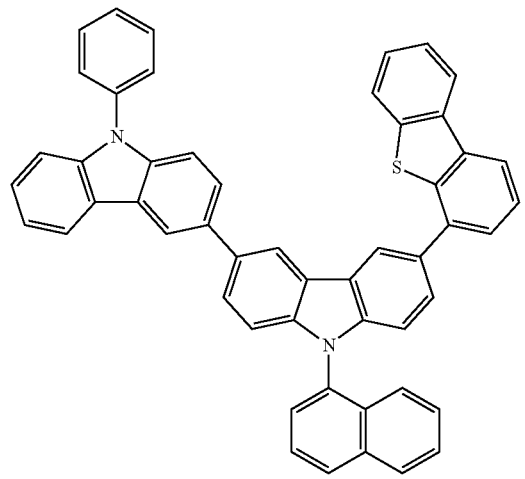
H1-82
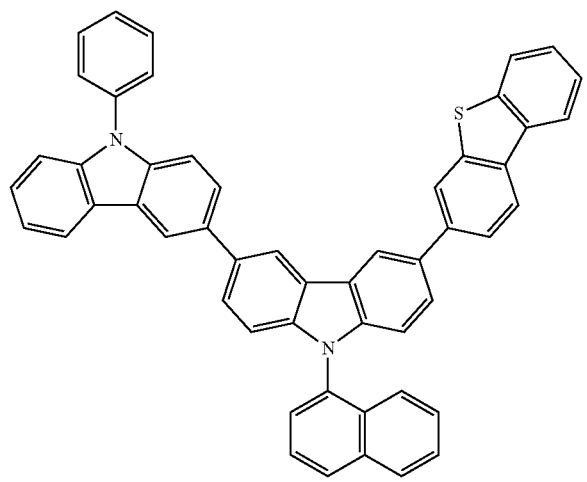
H1-83
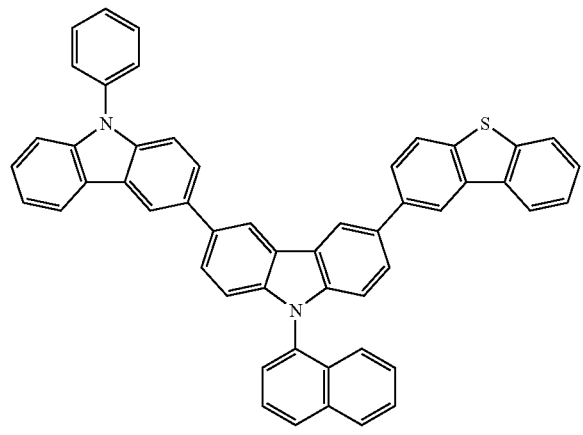
H1-84
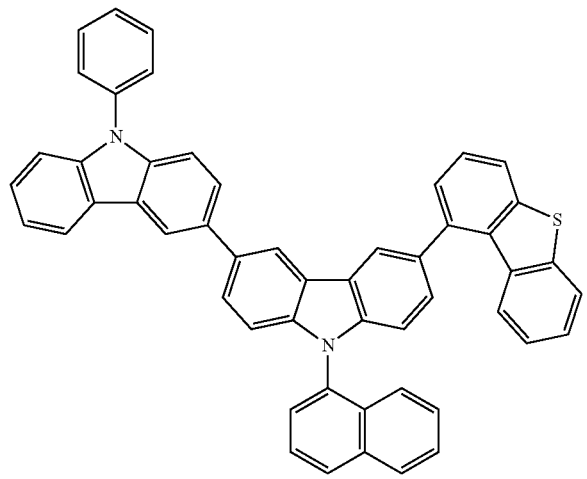

-continued
H1-85
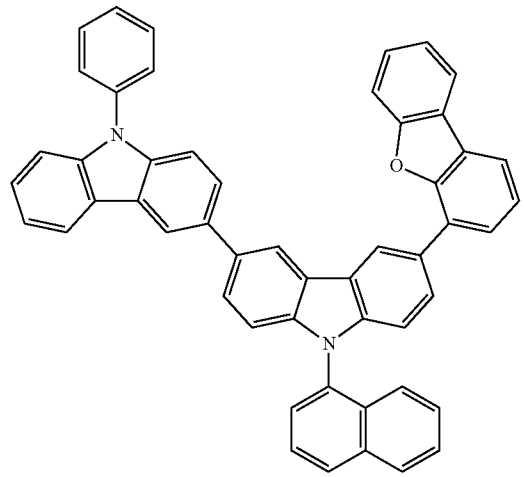
H1-86
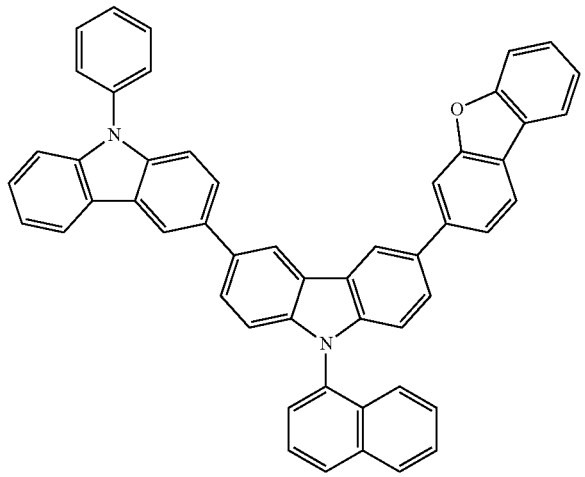
H1-87
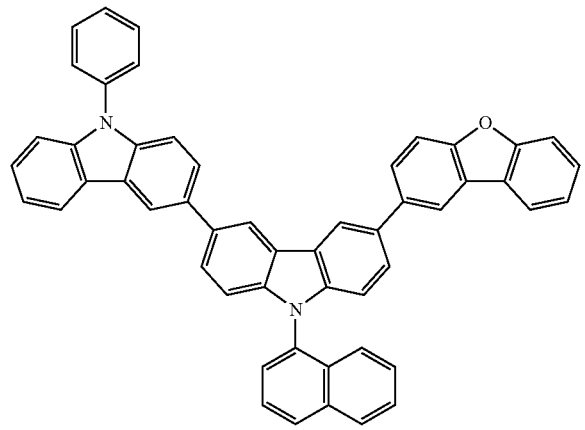
H1-88
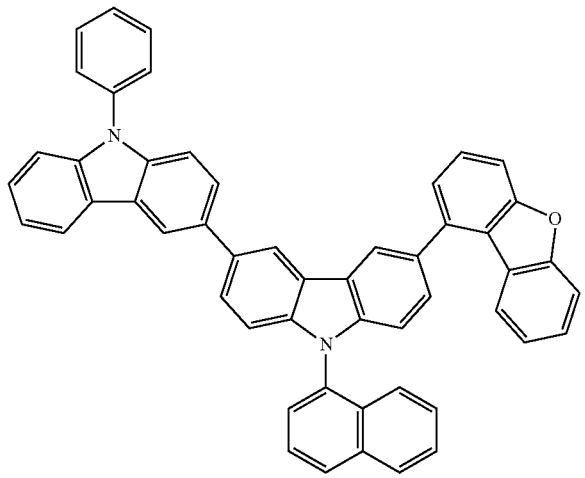
H1-89
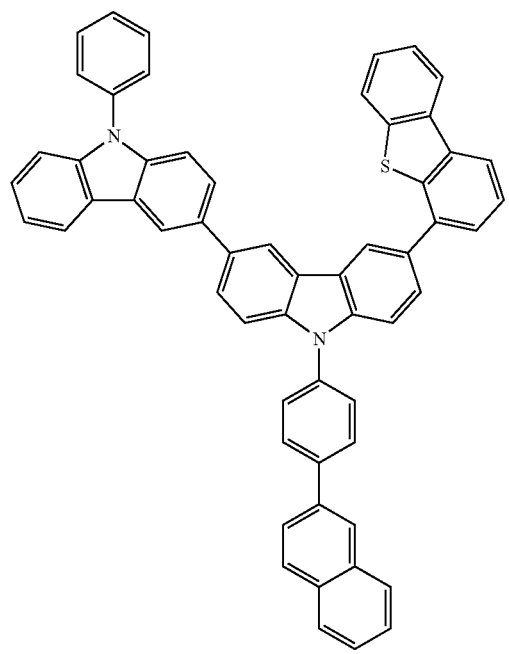
H1-90
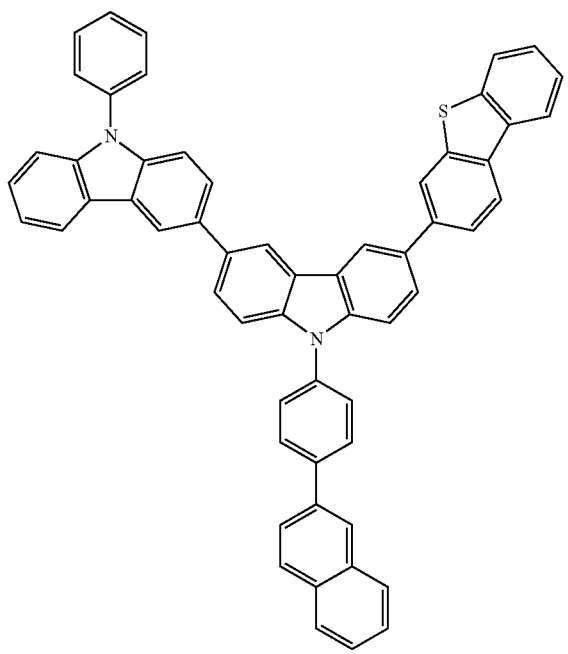

-continued
H1-91
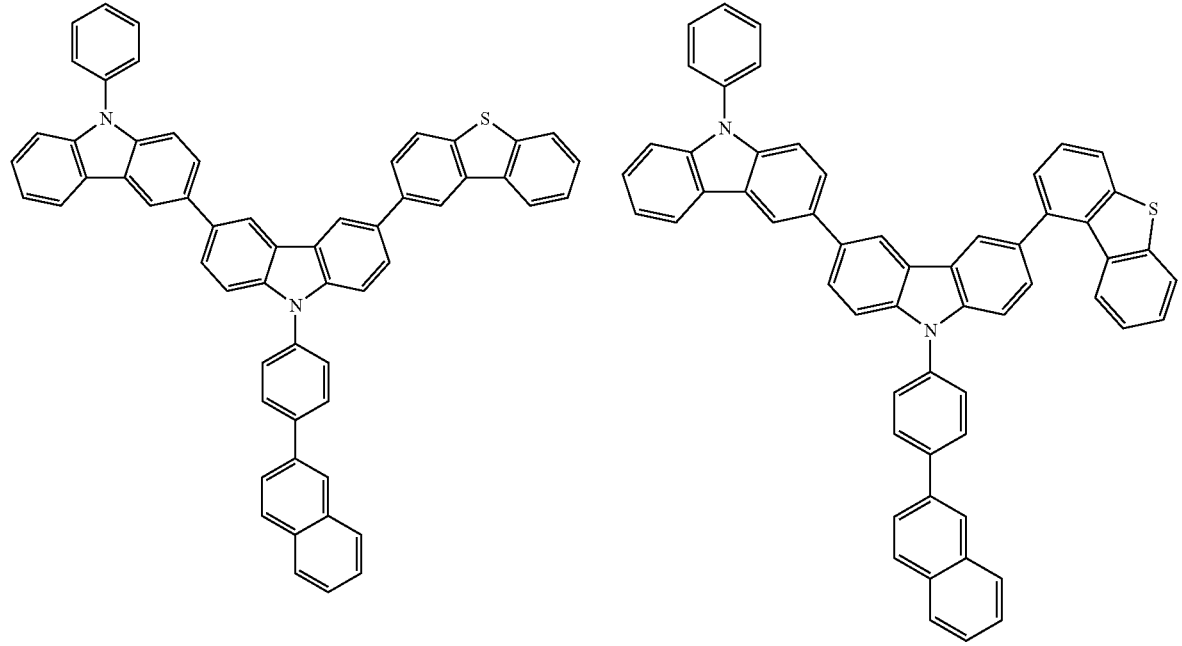
H1-92
H1-93
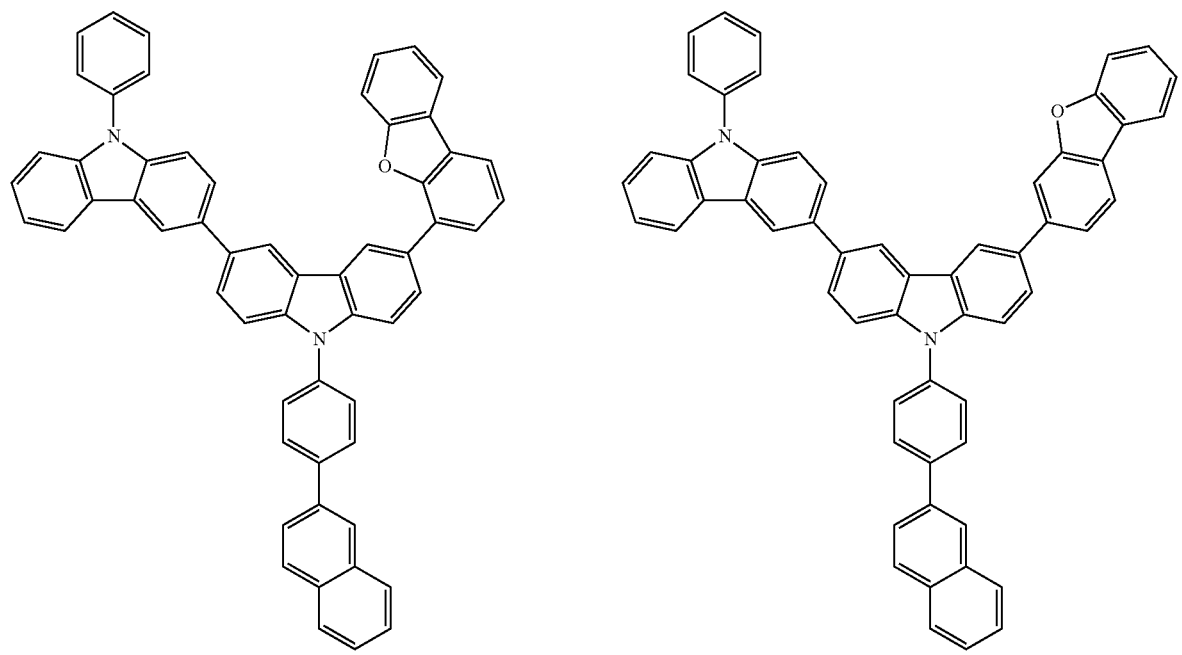
H1-94

-continued
H1-95
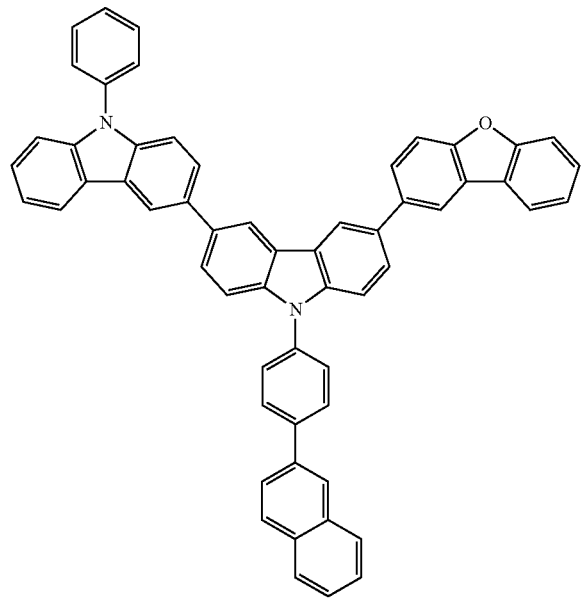
H1-96
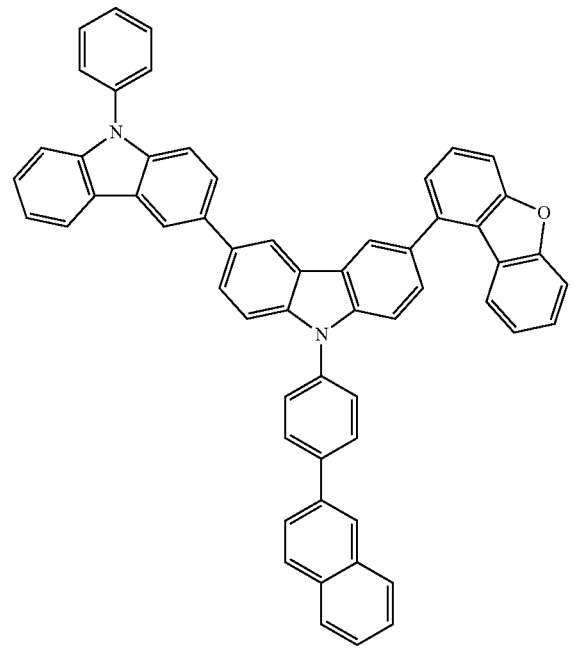
H1-97
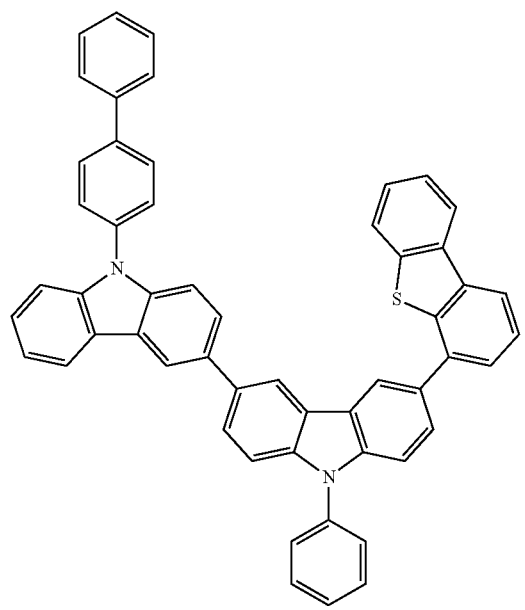
H1-98
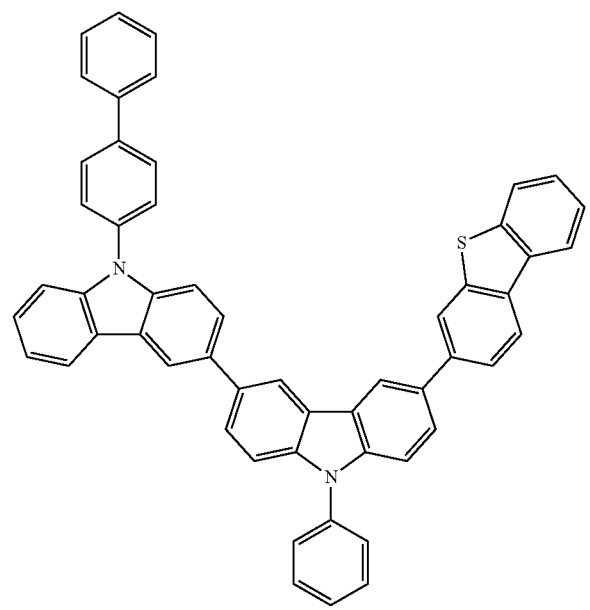

-continued
H1-99
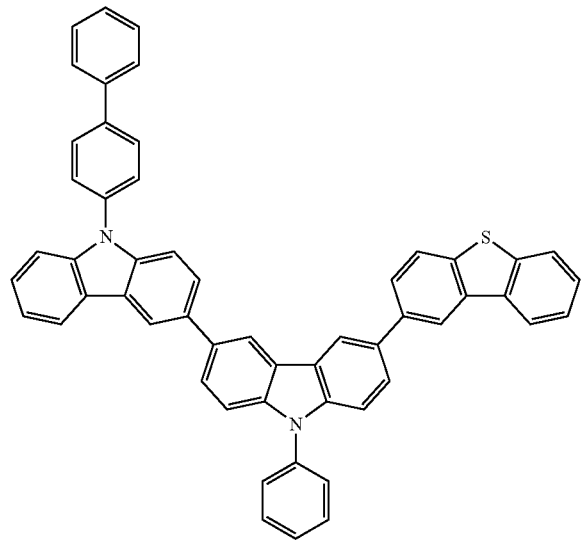
H1-100
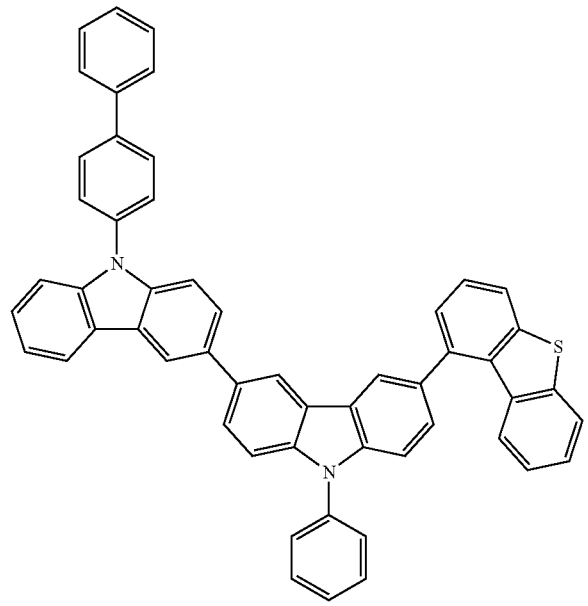
H1-101
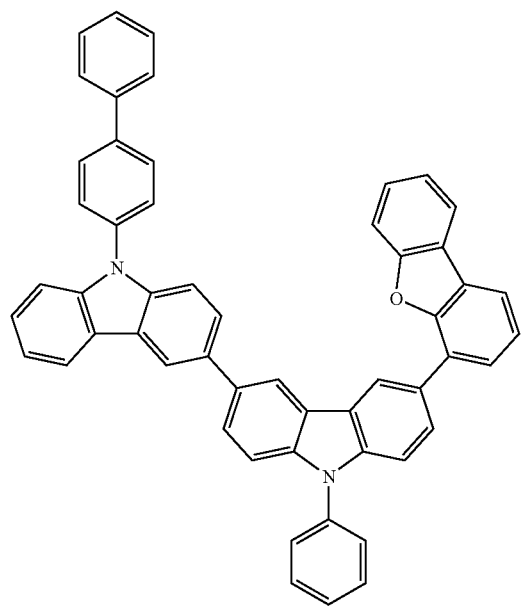
H1-102
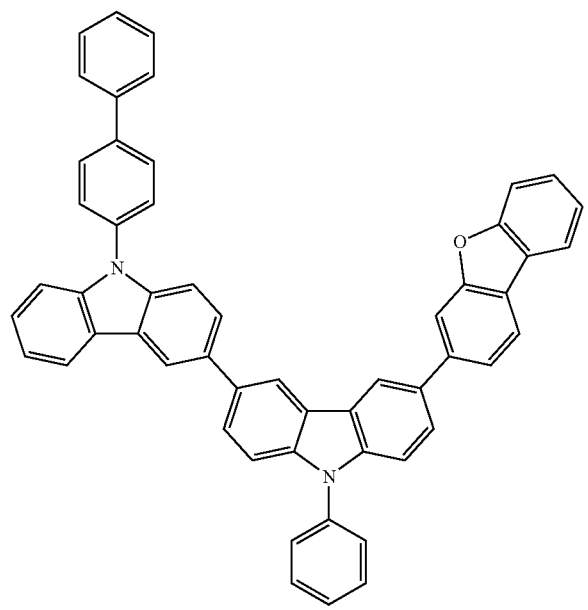

-continued
H1-103
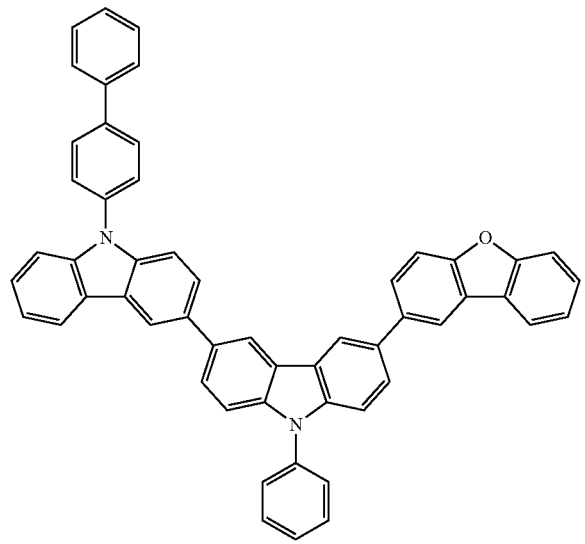
H1-104
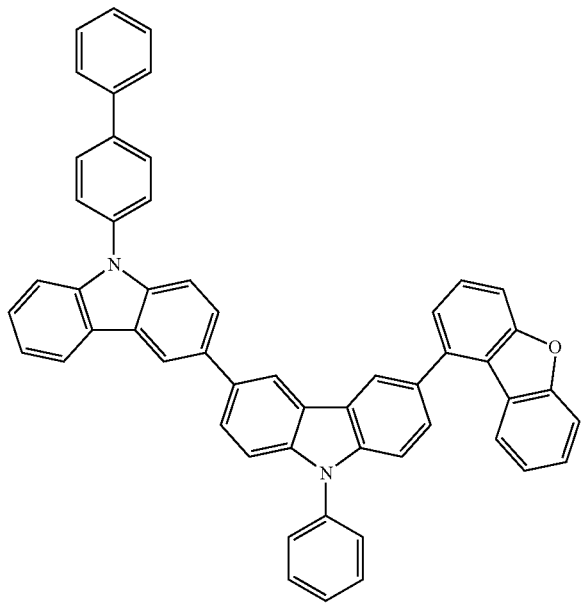
H1-105
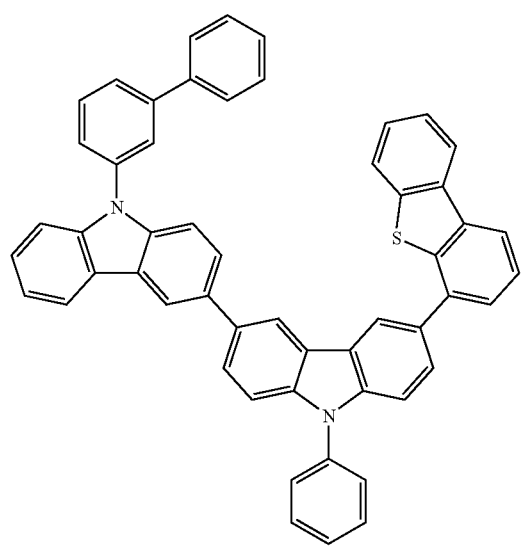
H1-106
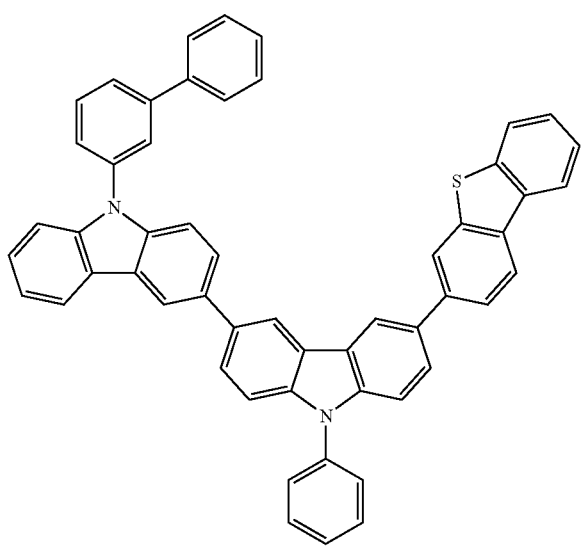

-continued
H1-107
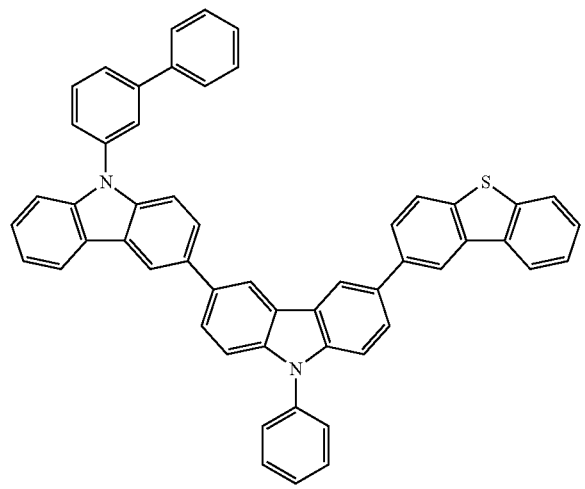
H1-108
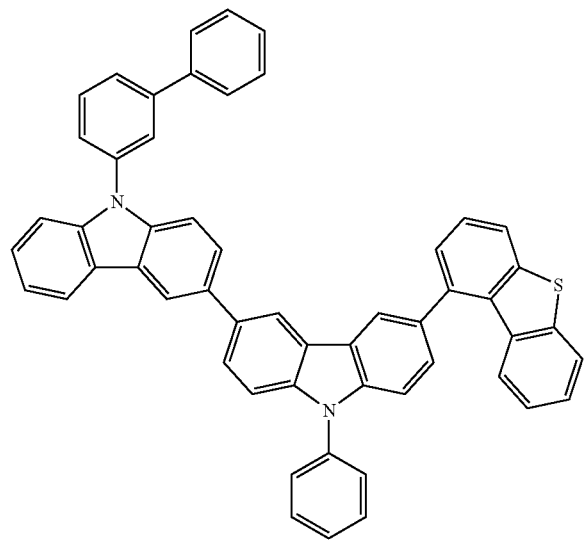
H1-109
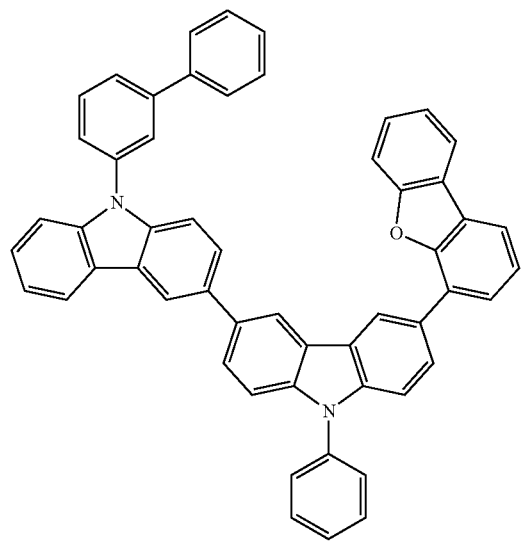
H1-110
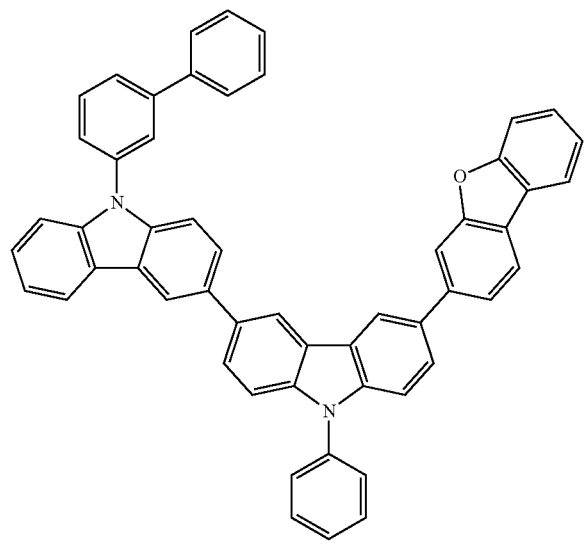

-continued
H1-111
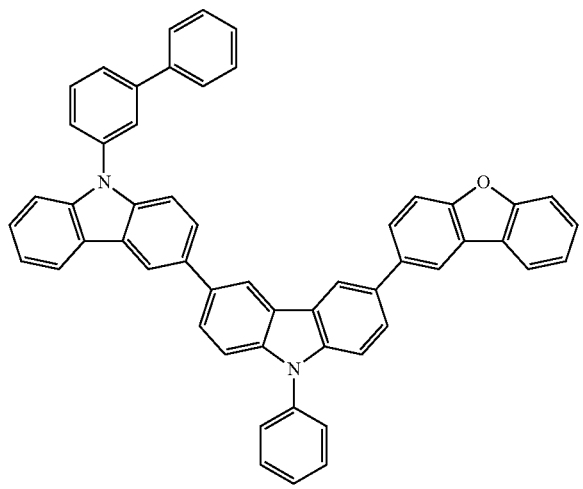
H1-112
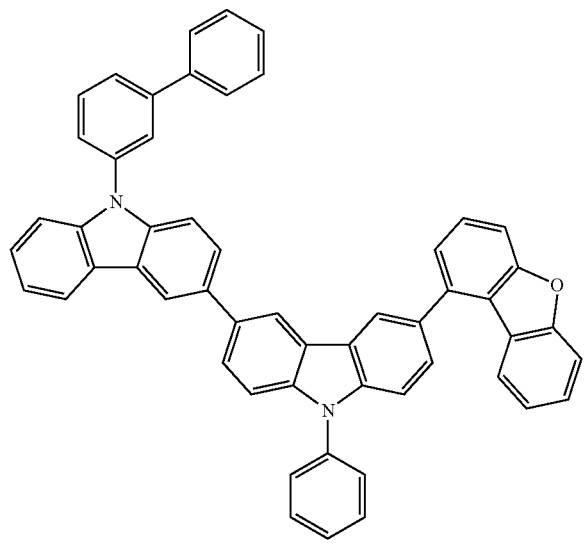
H1-113
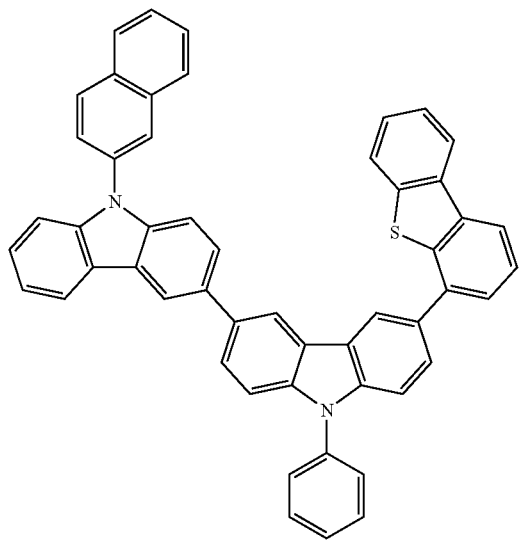
H1-114
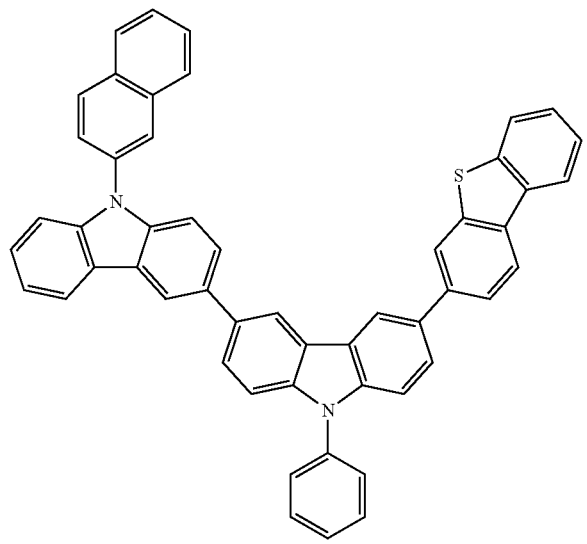

-continued
H1-115
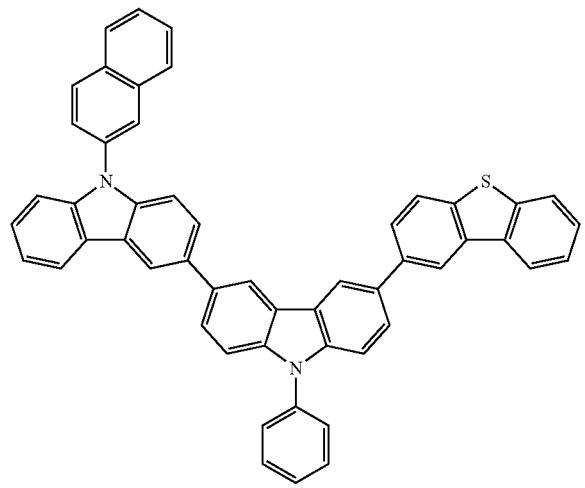
H1-116
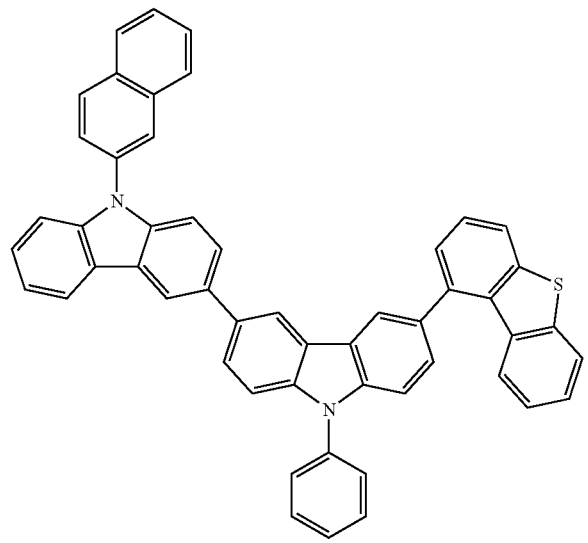
H1-117
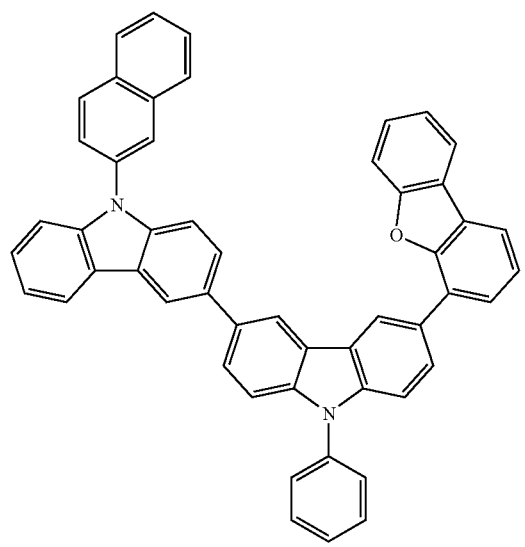
H1-118
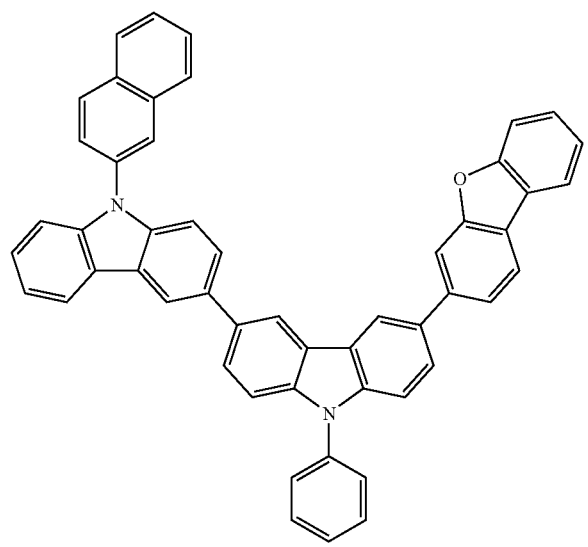

-continued
H1-119
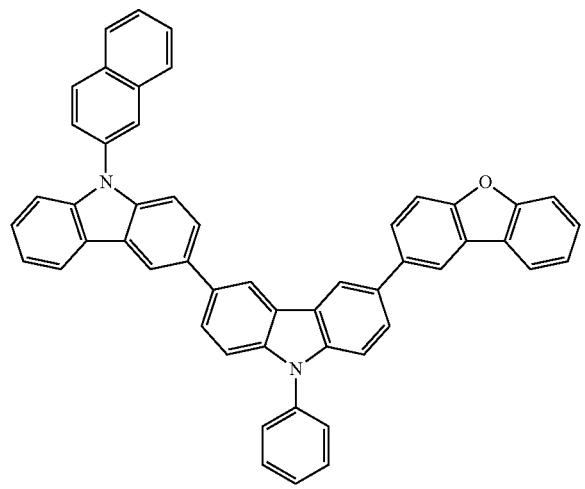
H1-120
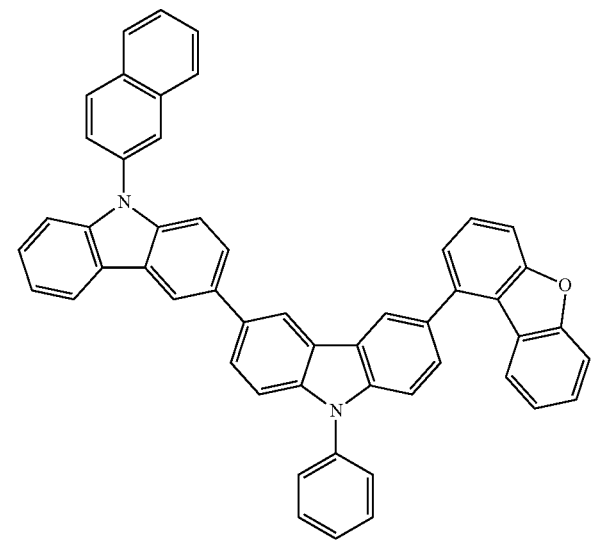
H1-121
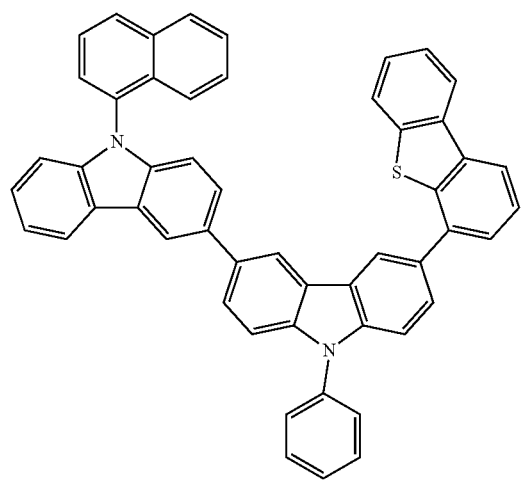
H1-122
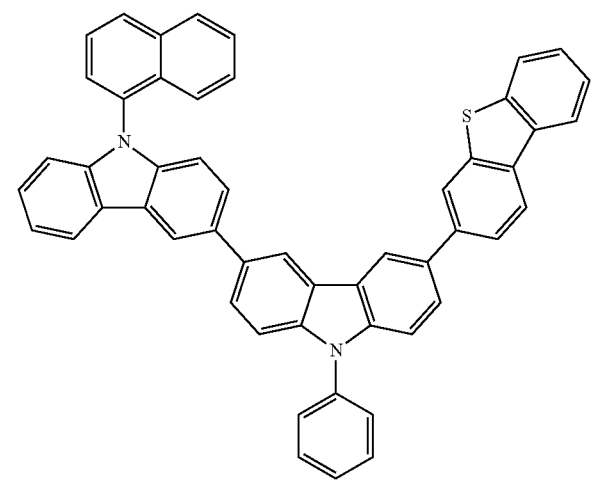
H1-123
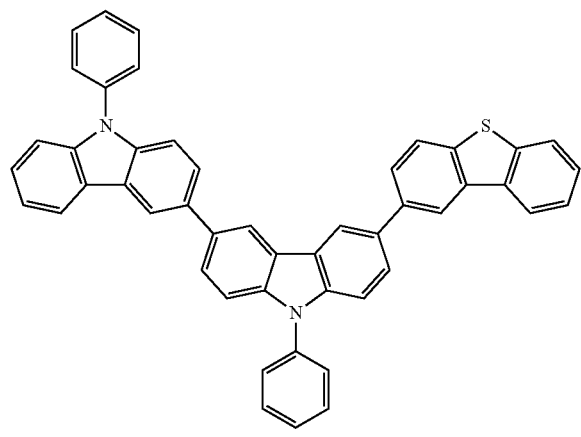
H1-124
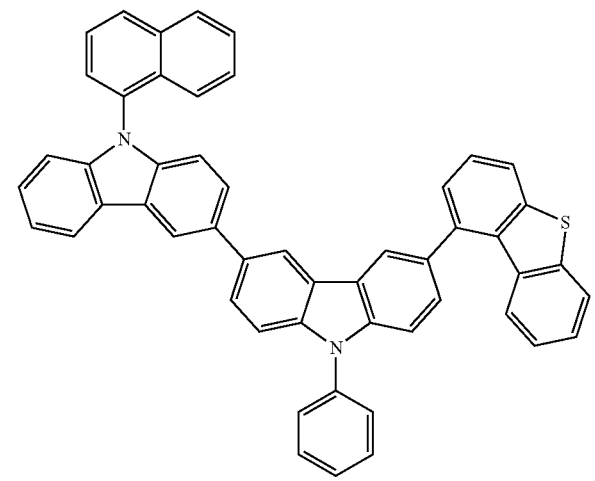

-continued
H1-125
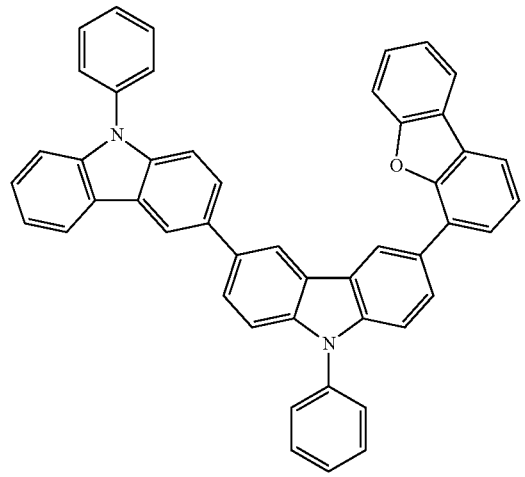
H1-126
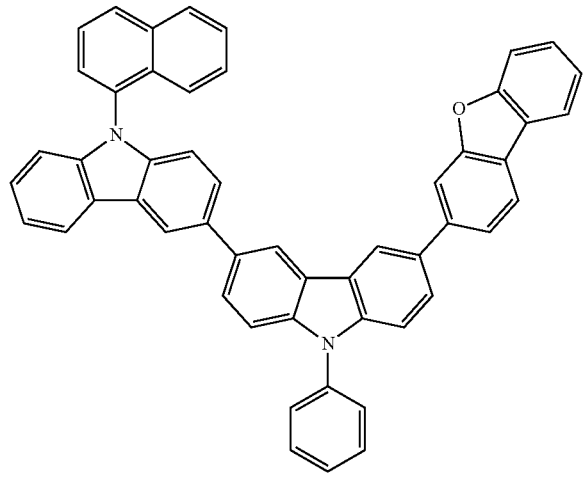
H1-127
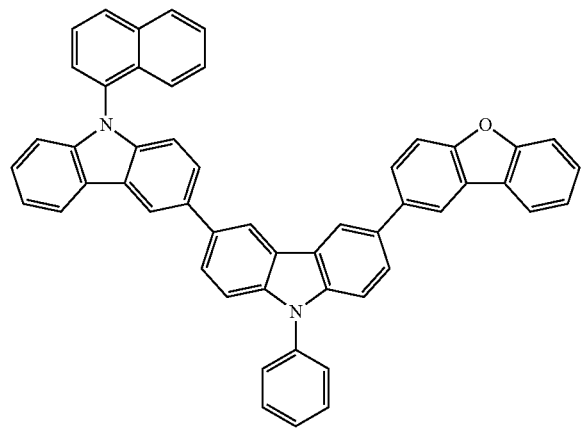
H1-128
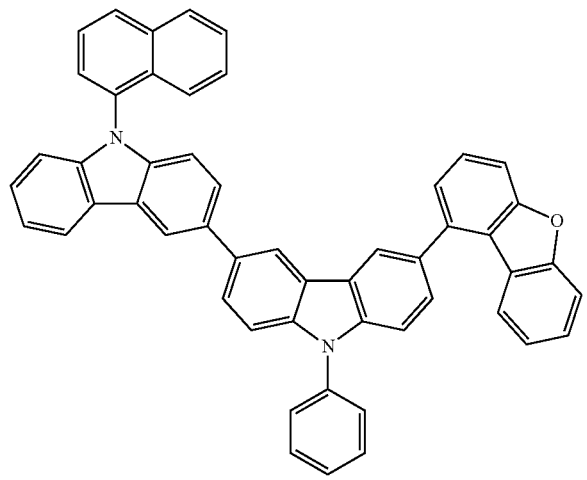
H1-129
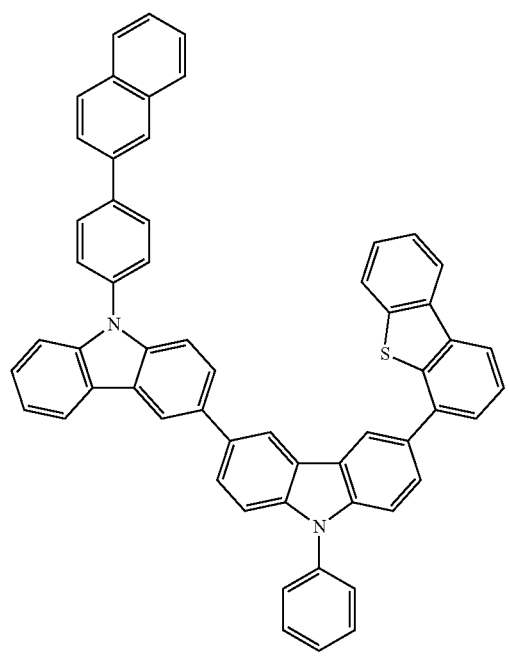
H1-130
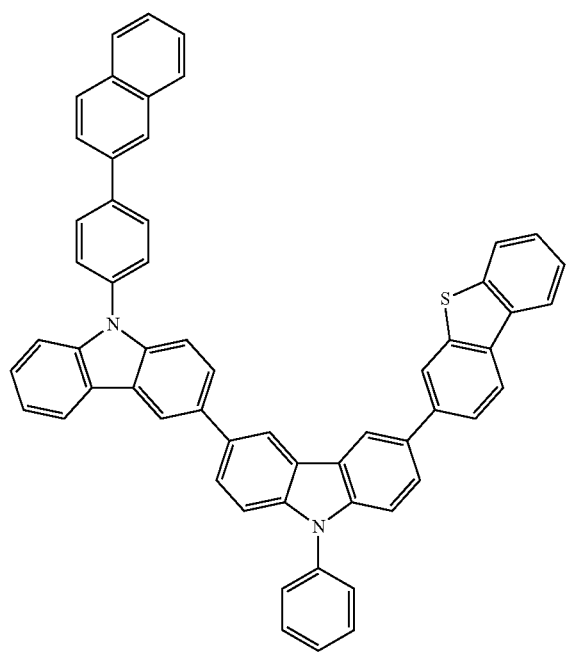

-continued
H1-131
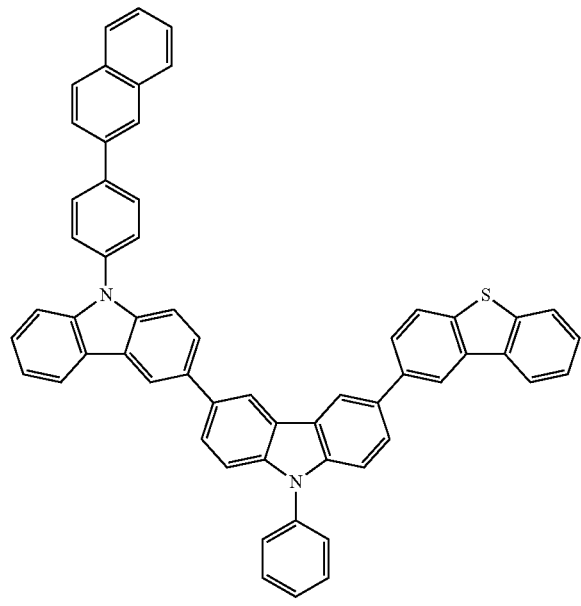
H1-132
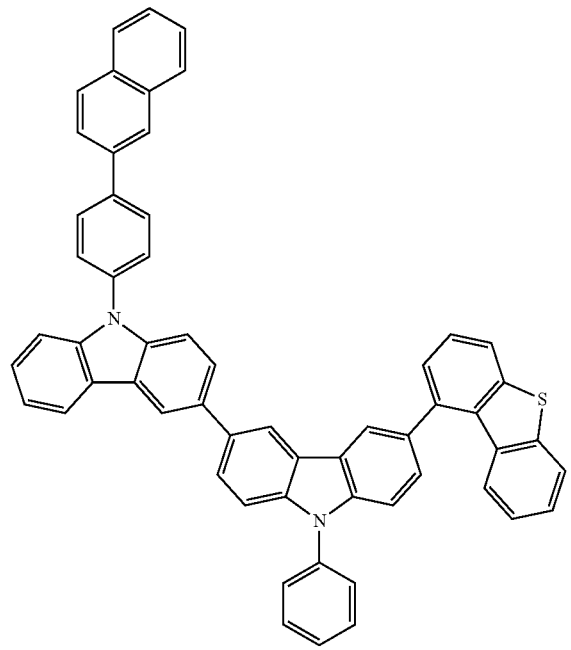
H1-133
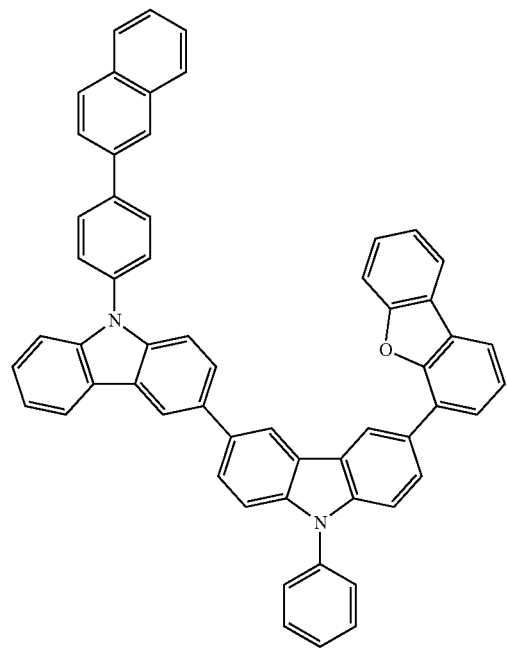
H1-134
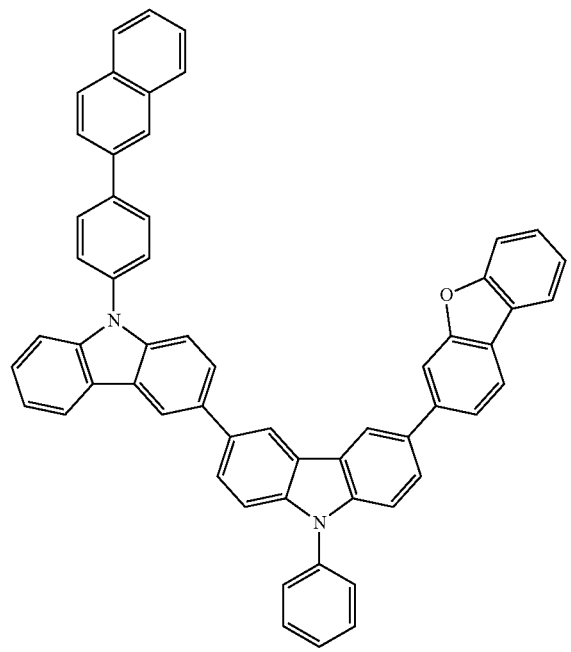

-continued
H1-135
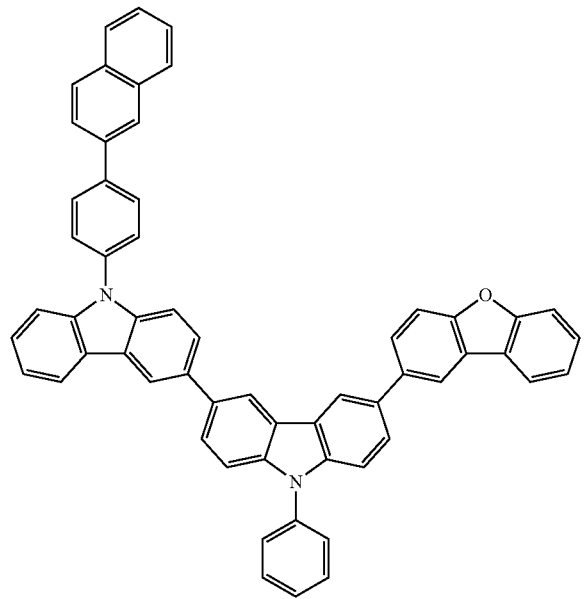
H1-136
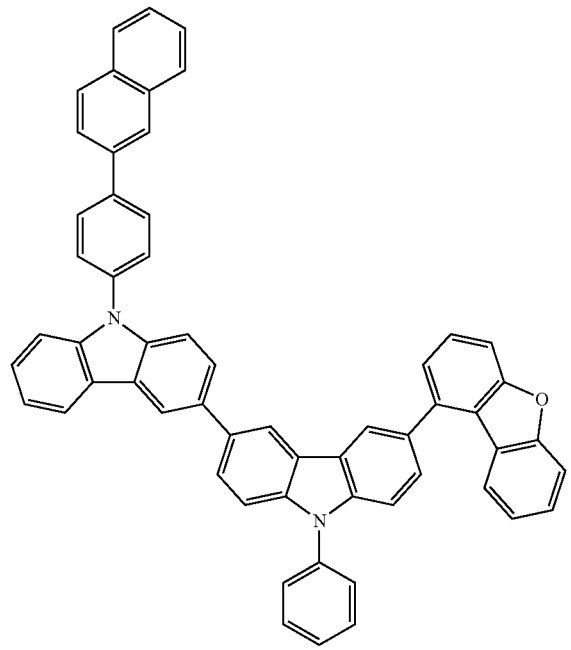
H1-137
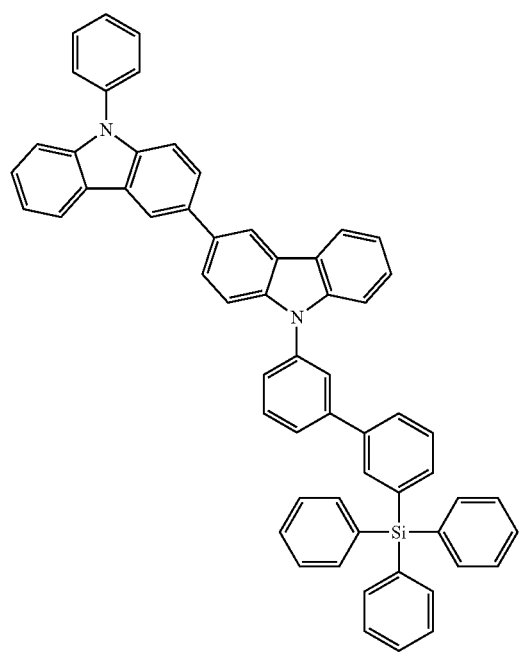
H1-138
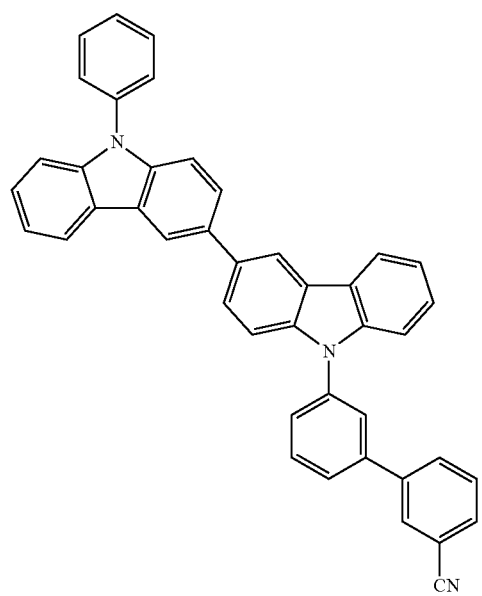

-continued
H1-139
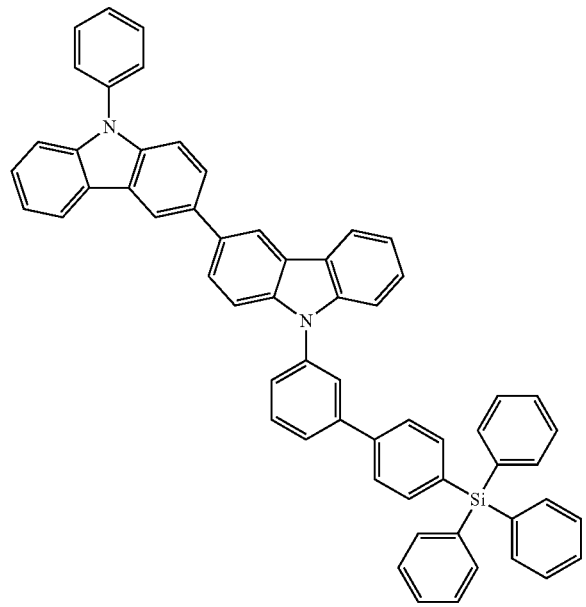
H1-140
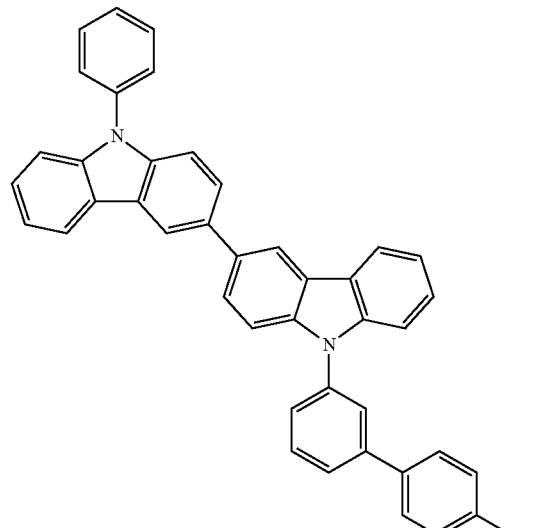
H1-141
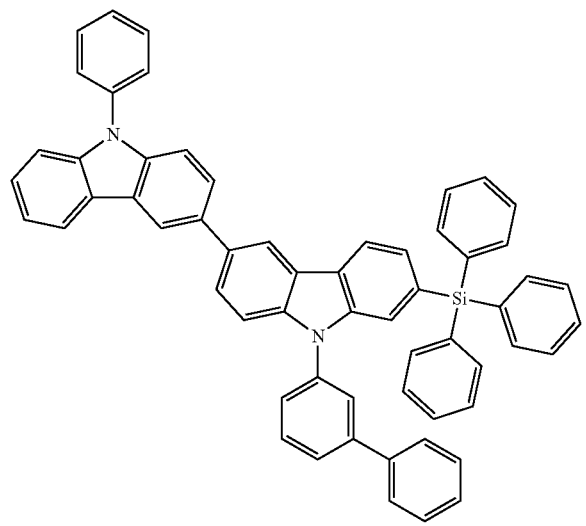
H1-142
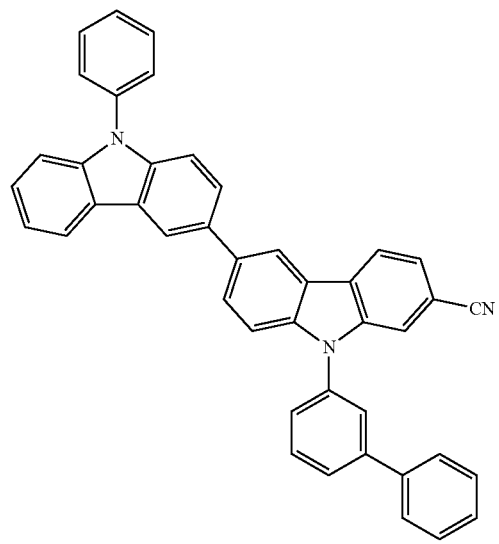

H1-143
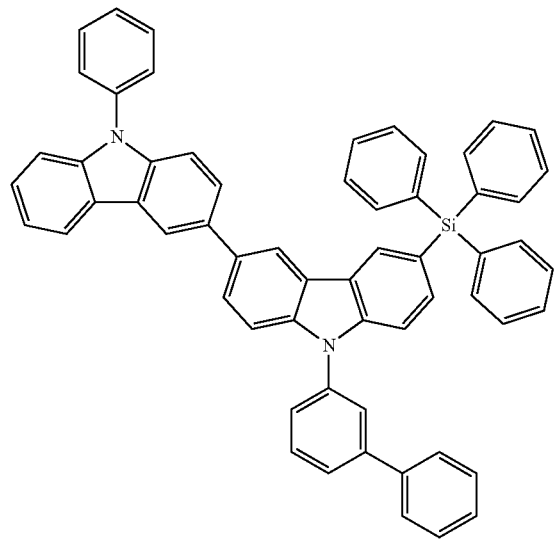
H1-144
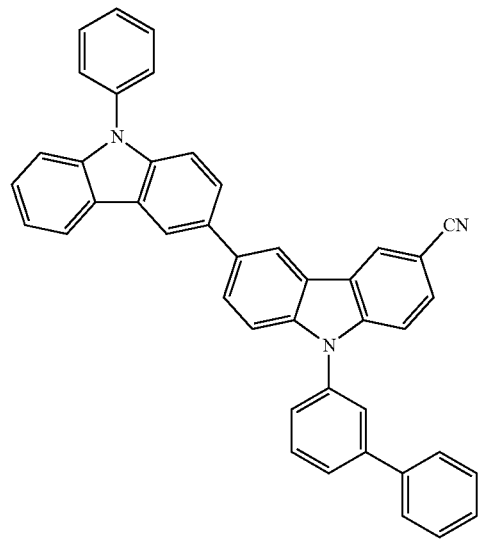
H1-145
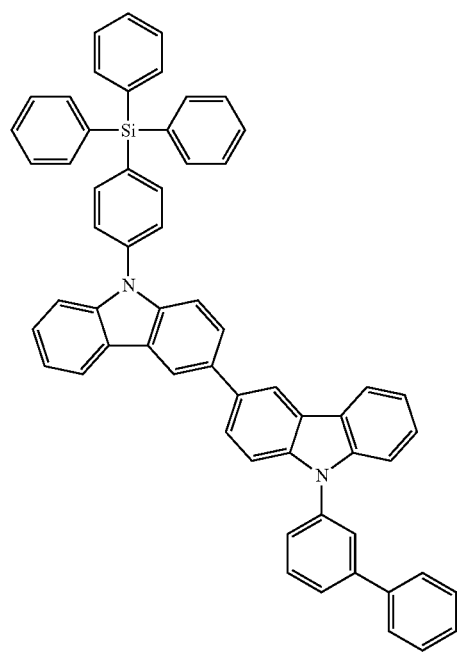
H1-146
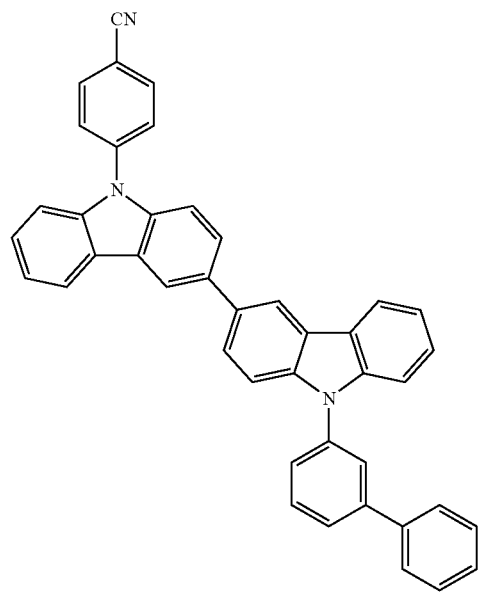

-continued
H1-147
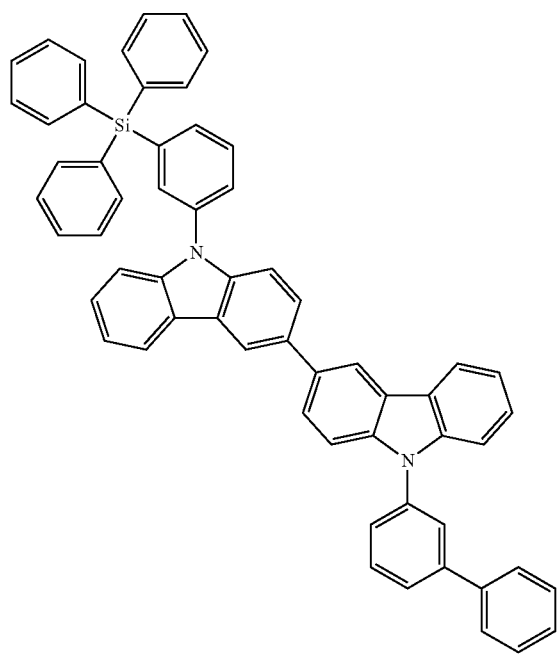
H1-148
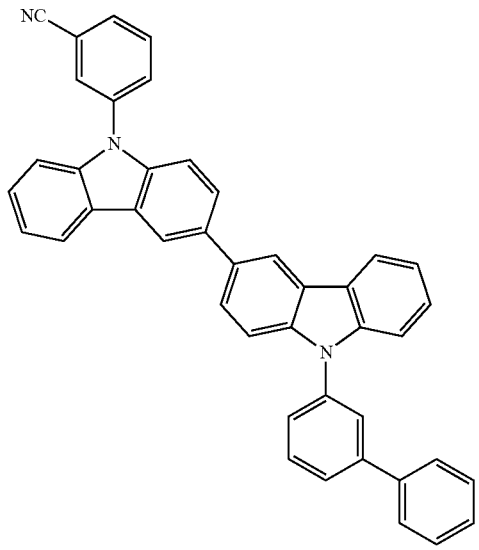
H1-149
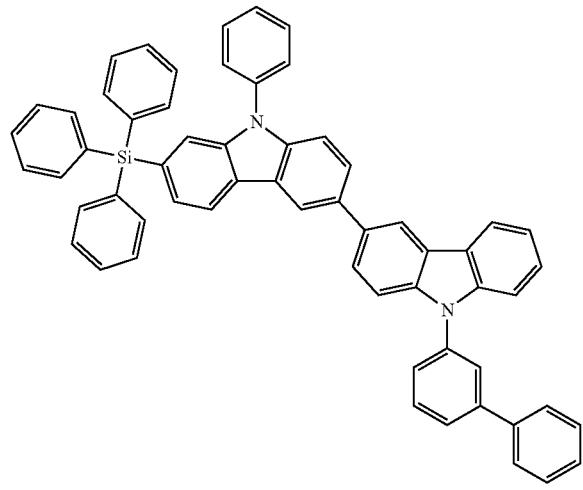
H1-150
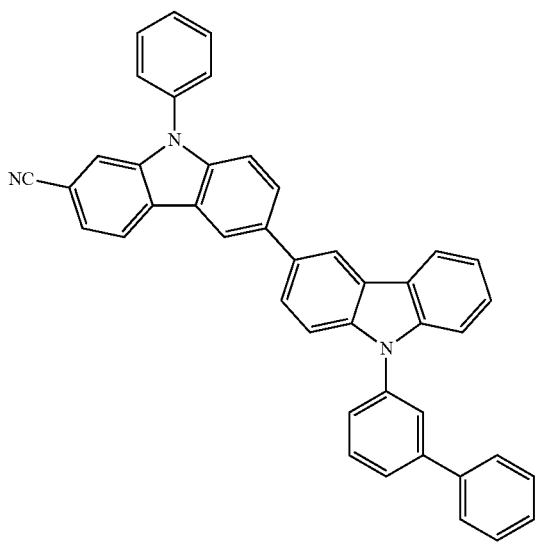

H1-151
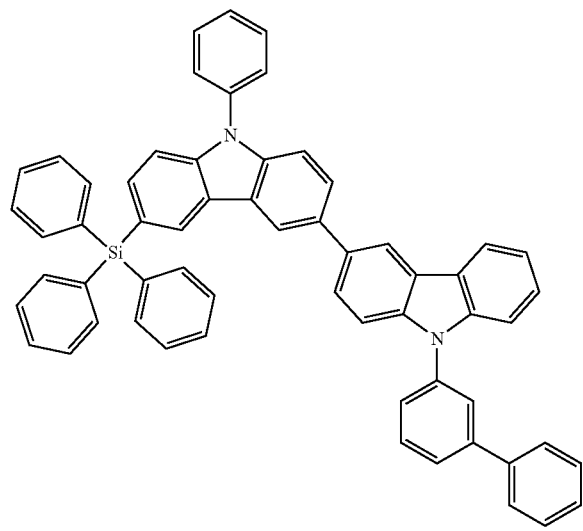
H1-152
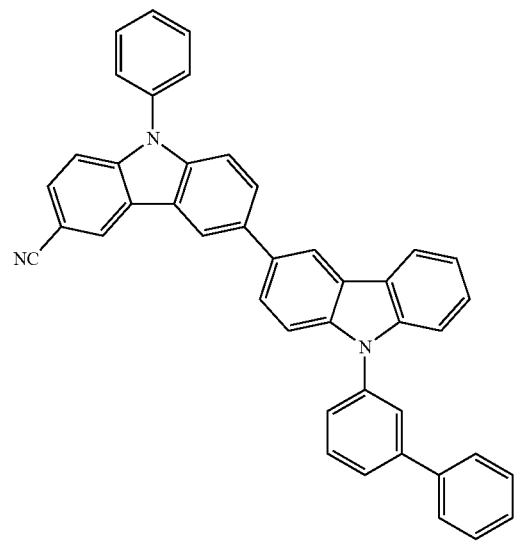
H1-153
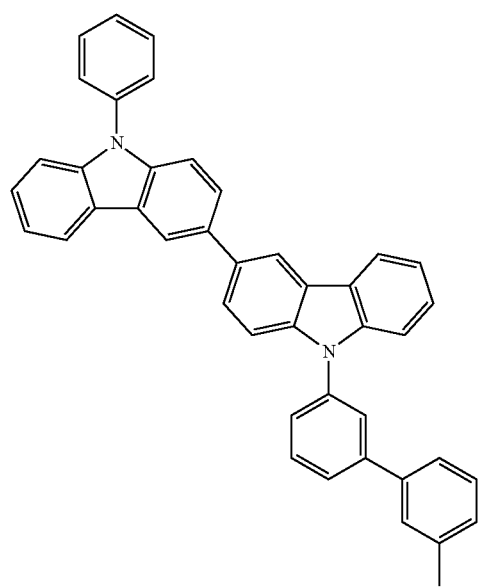
H1-154
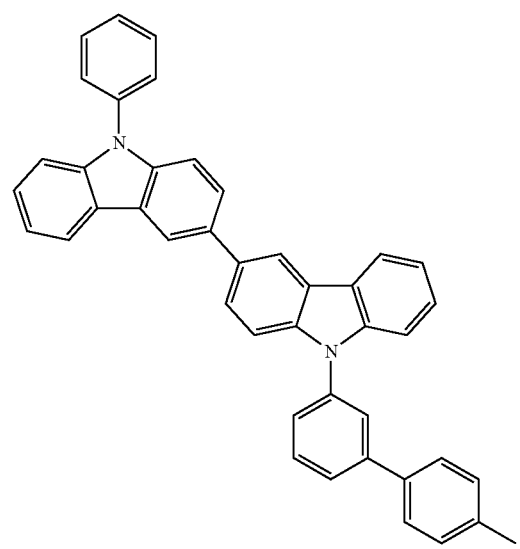

-continued
H1-155
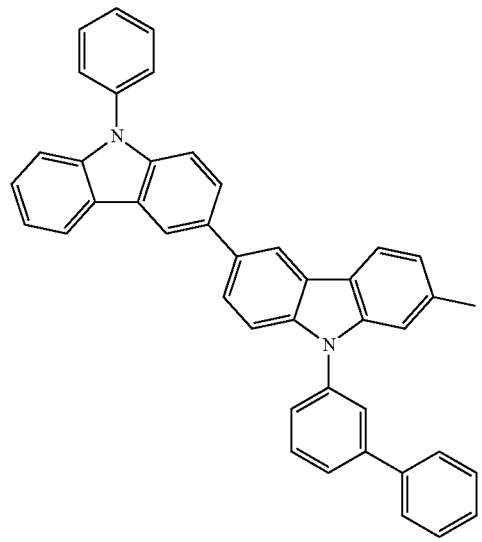
H1-156
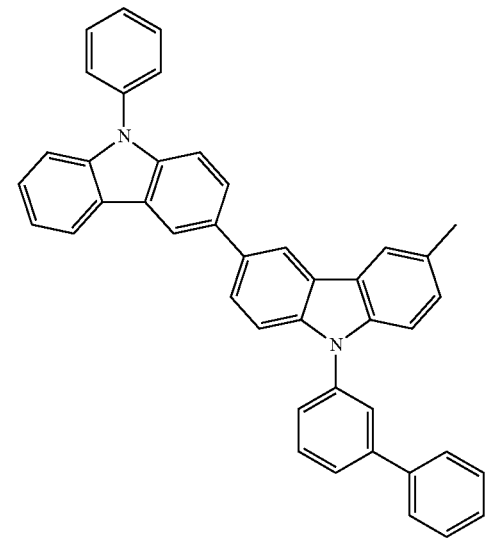
H1-157
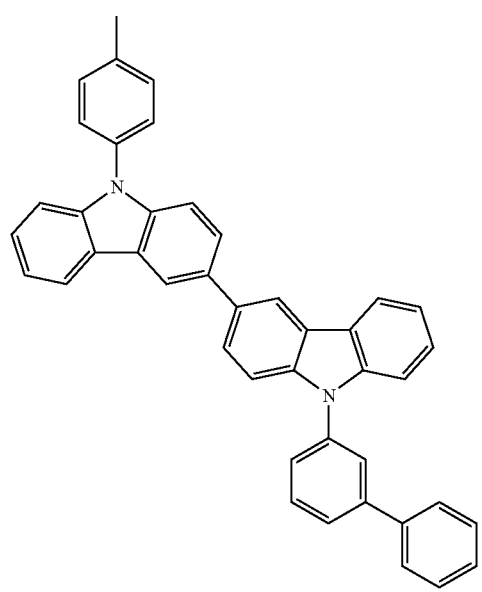
H1-158
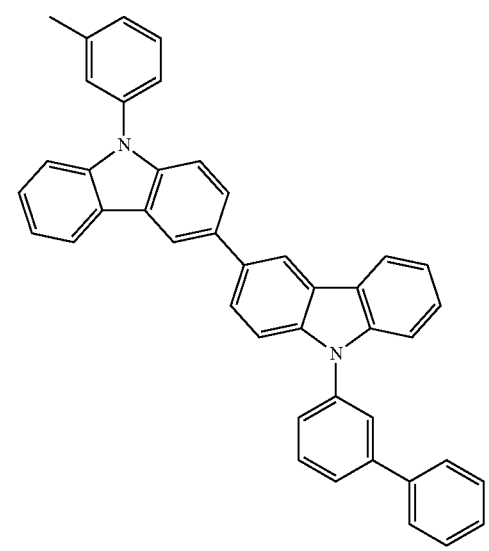
H1-159
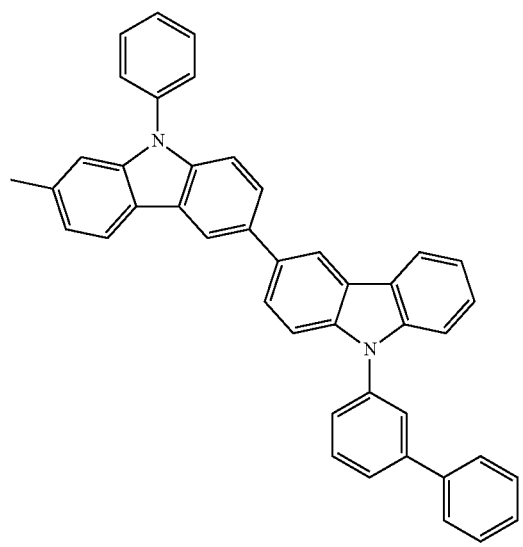
H1-160
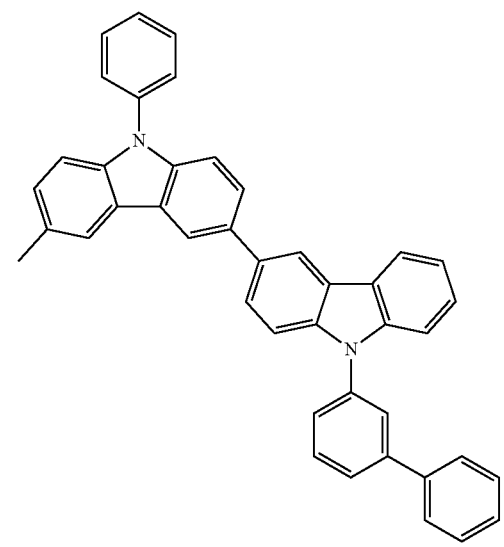

-continued
H1-161
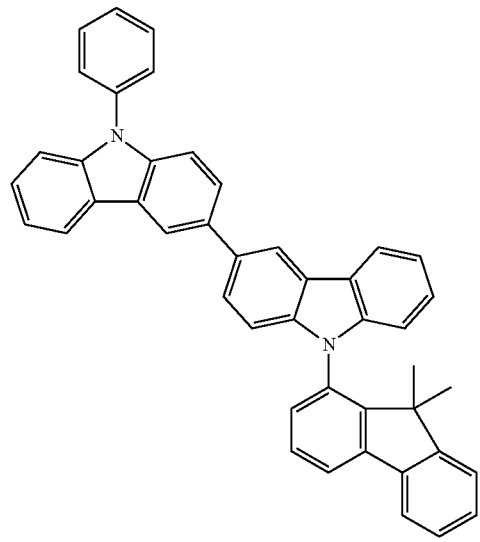
H1-162
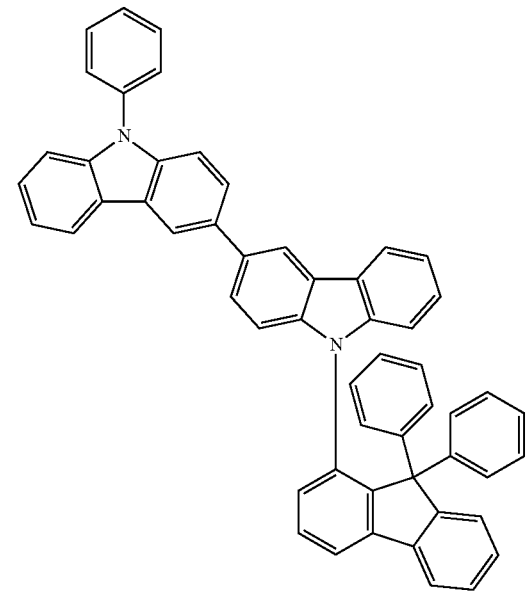
H1-163
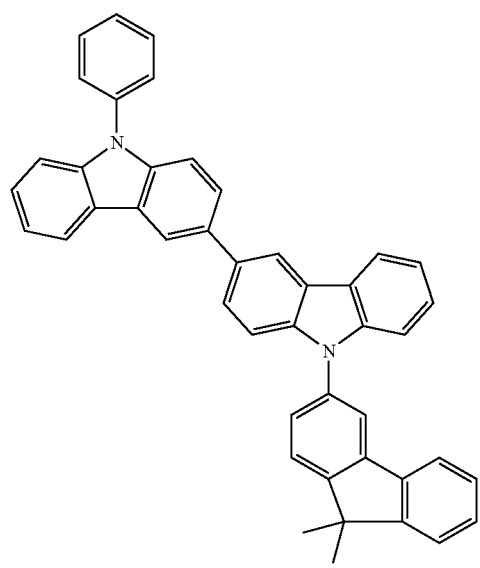
H1-164
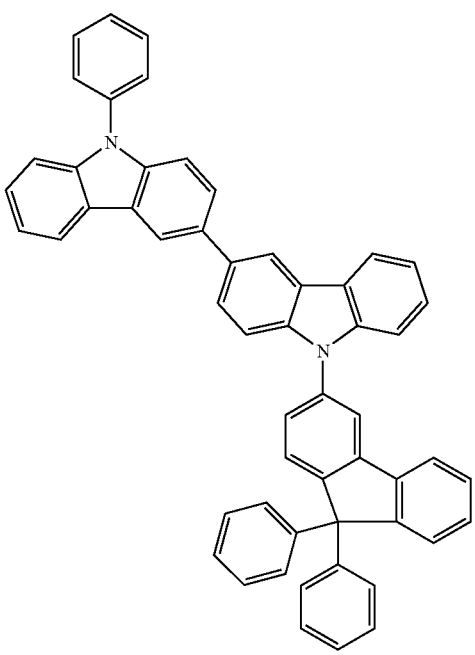

H1-165
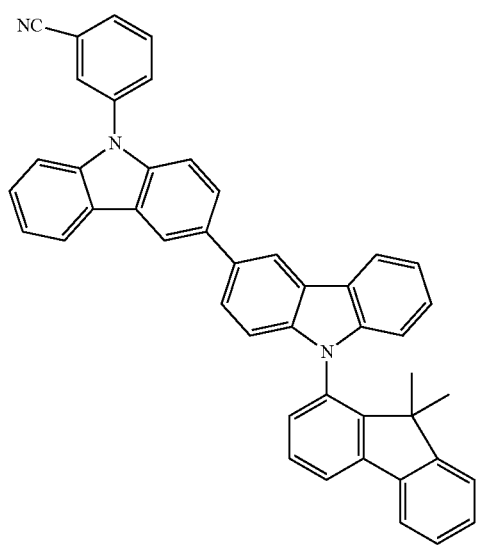
H1-166
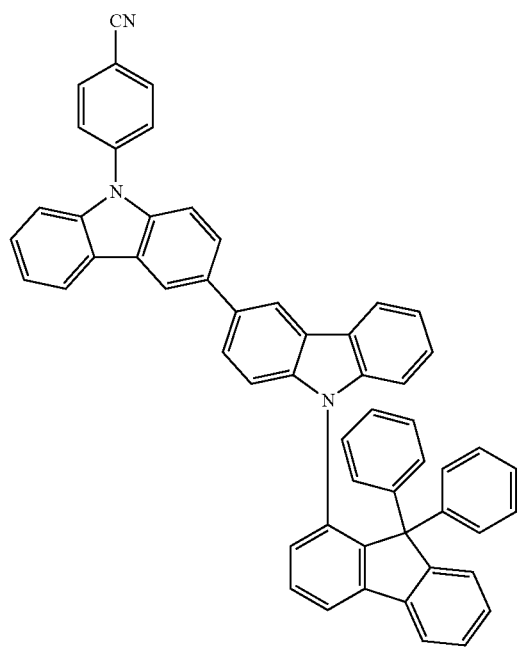
H1-167
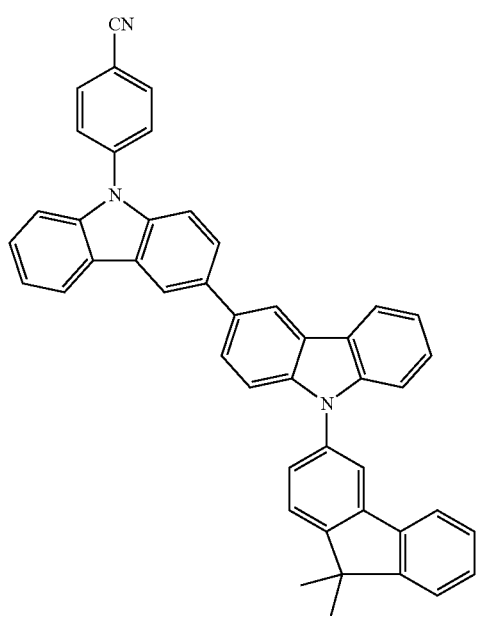
H1-168
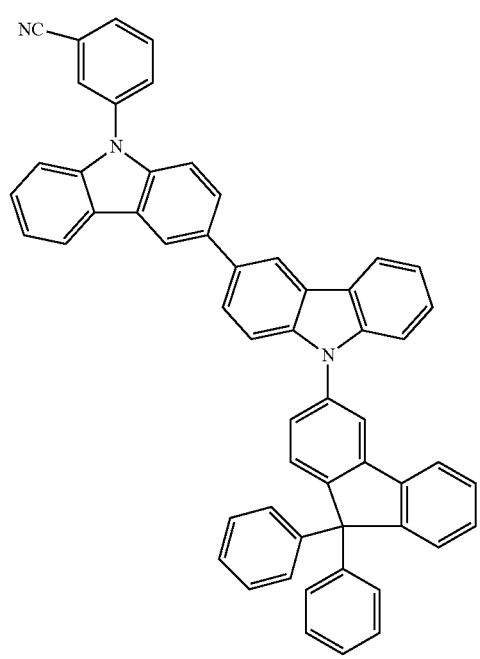

-continued
H1-169
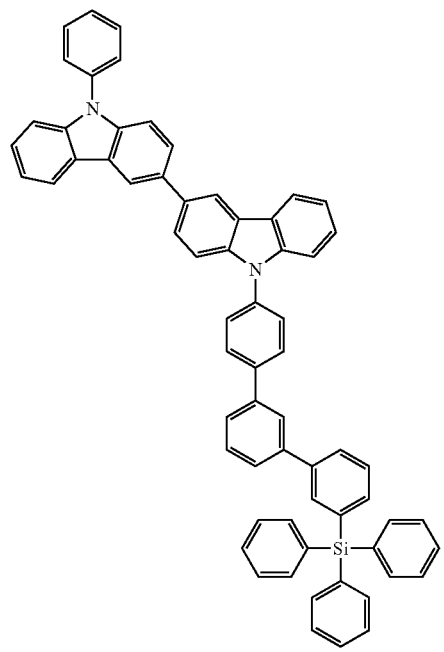
H1-170
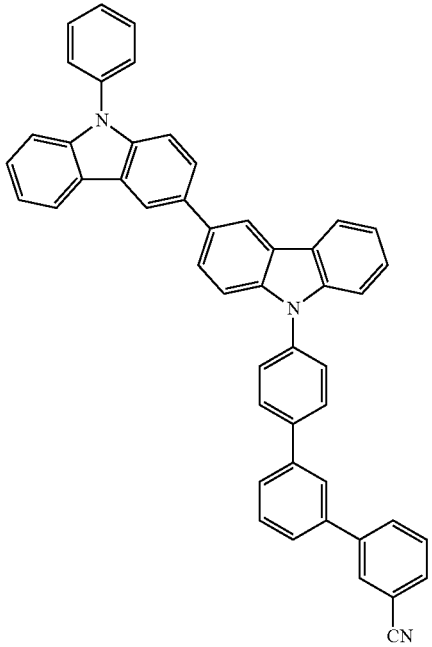
H1-171
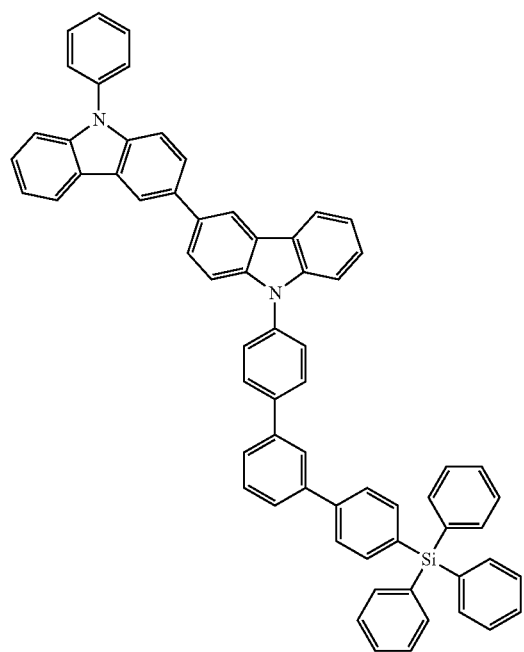
H1-172
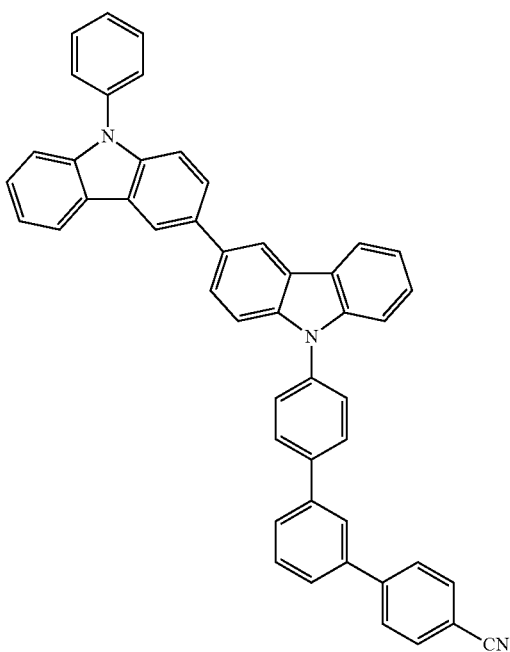

-continued
H1-173
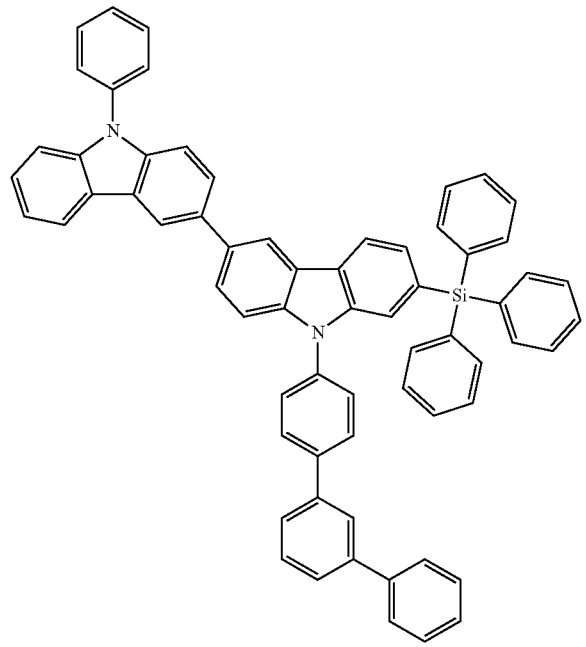
H1-174
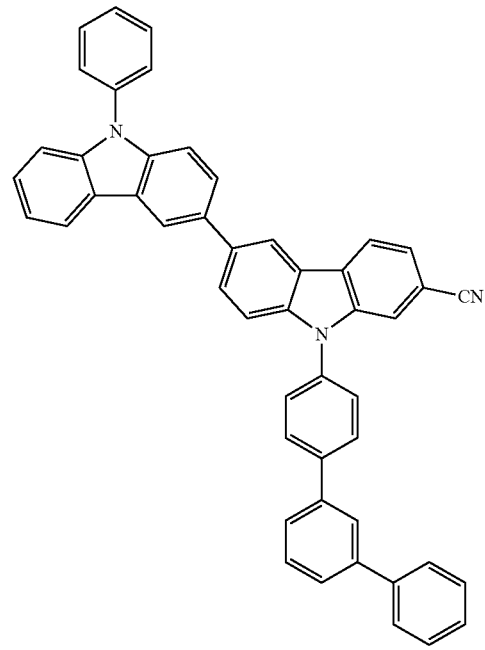
H1-175
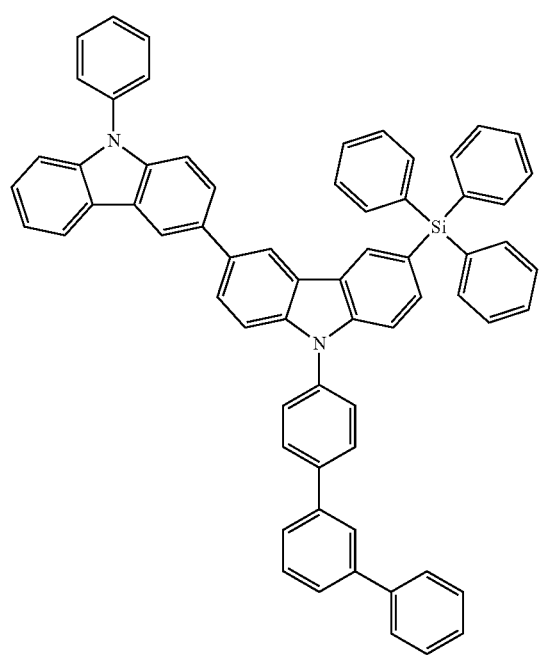
H1-176
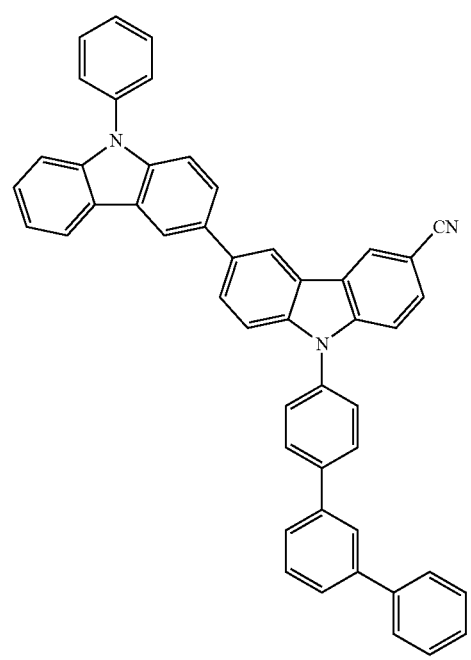

-continued
H1-177
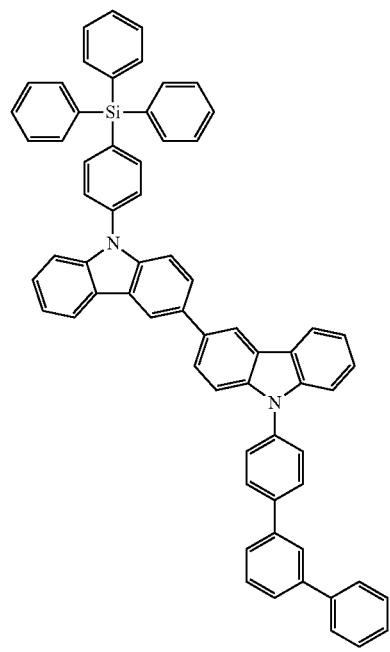
H1-178
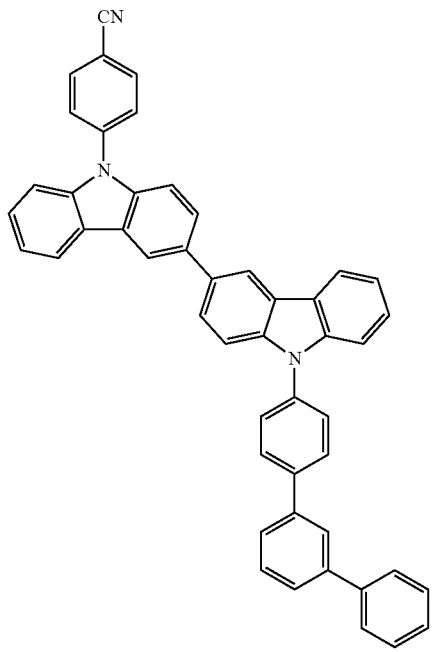
H1-179
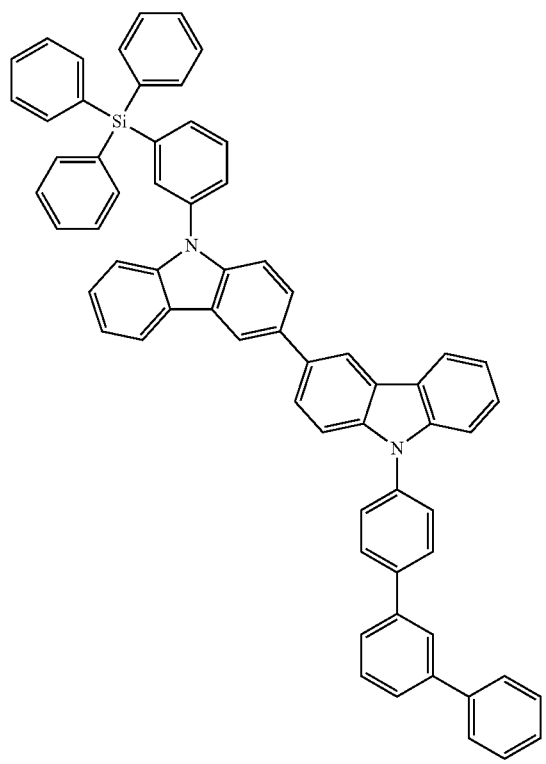
H1-180
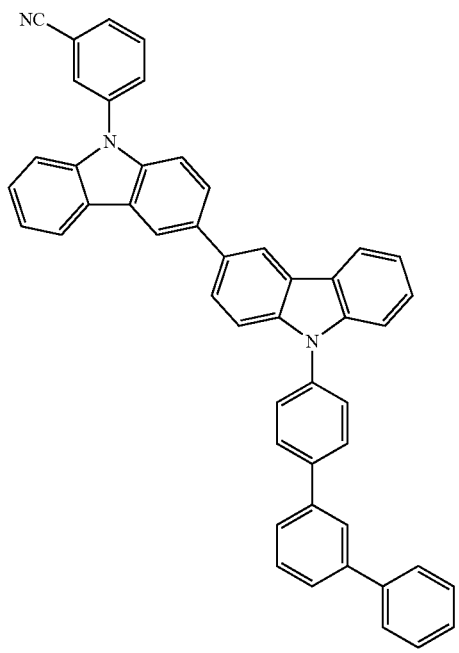

-continued
H1-181
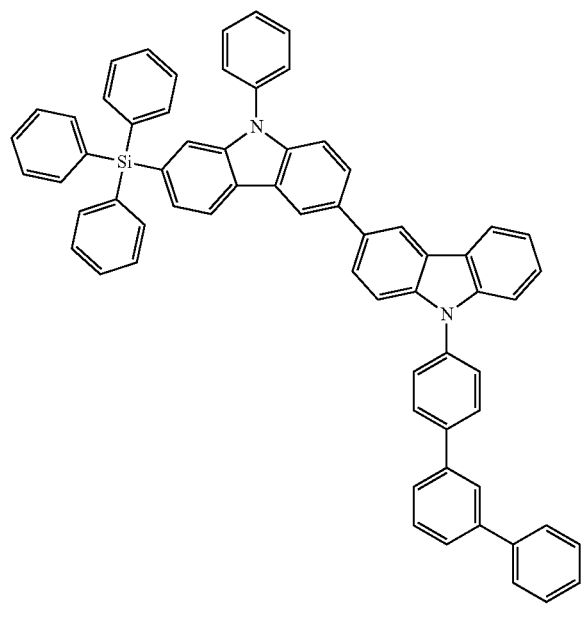
H1-182
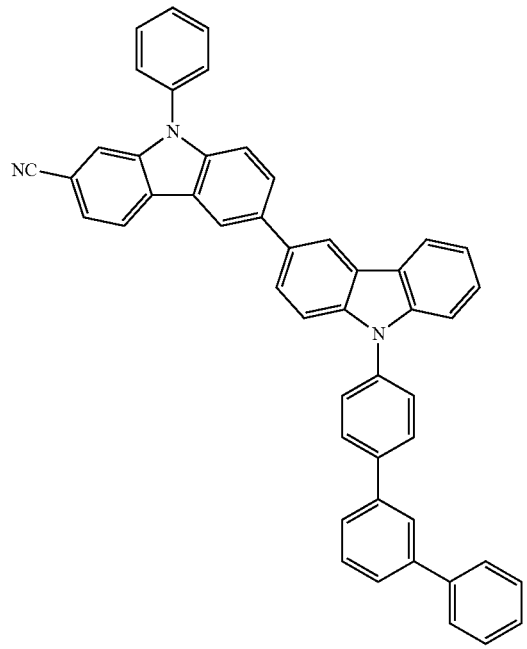
H1-183
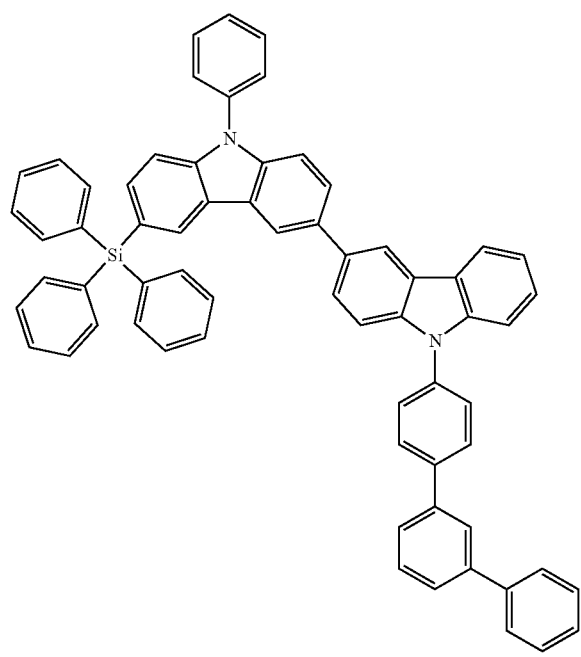
H1-184
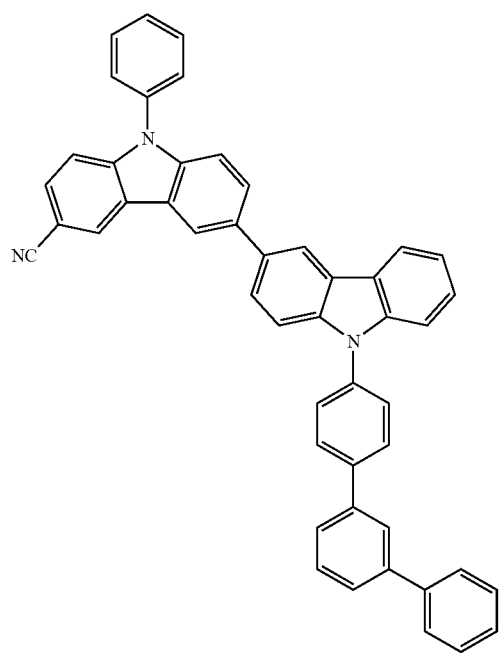

-continued
H1-185
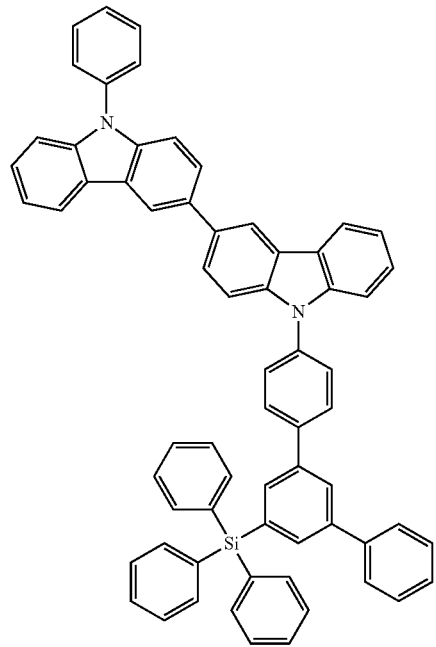
H1-186
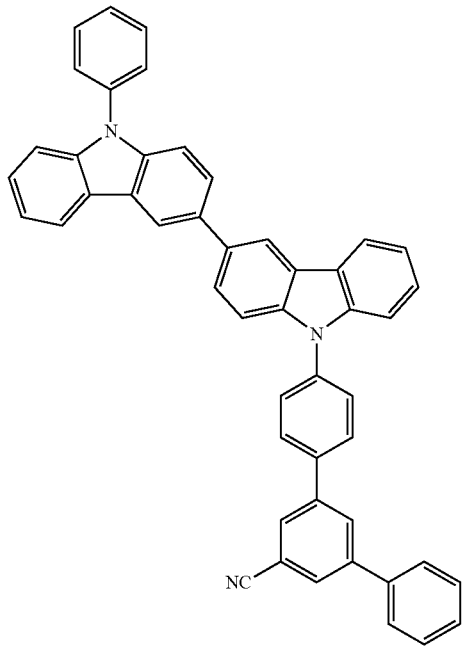
H1-187
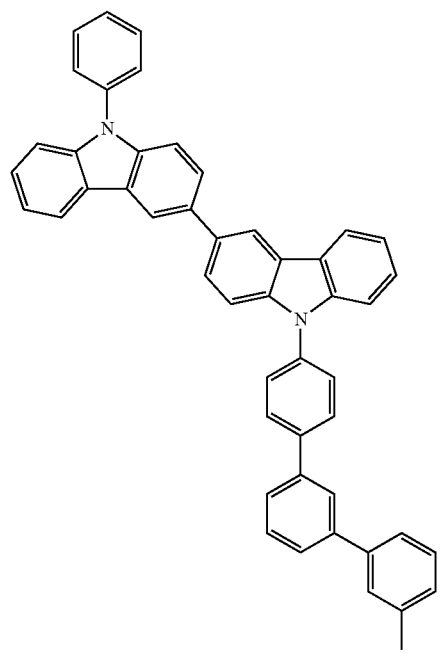
H1-188

-continued
H1-189
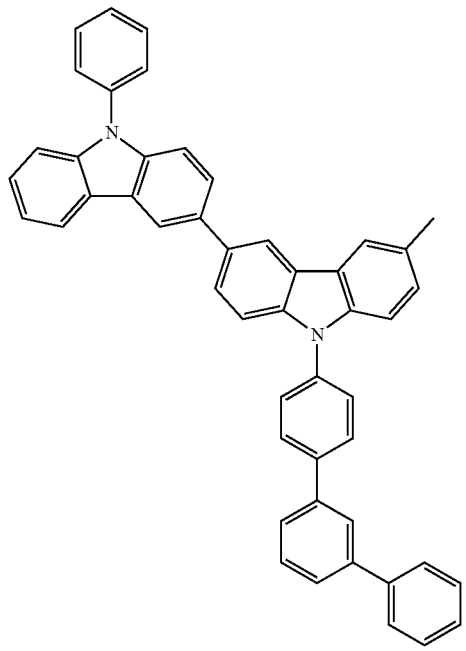
H1-190
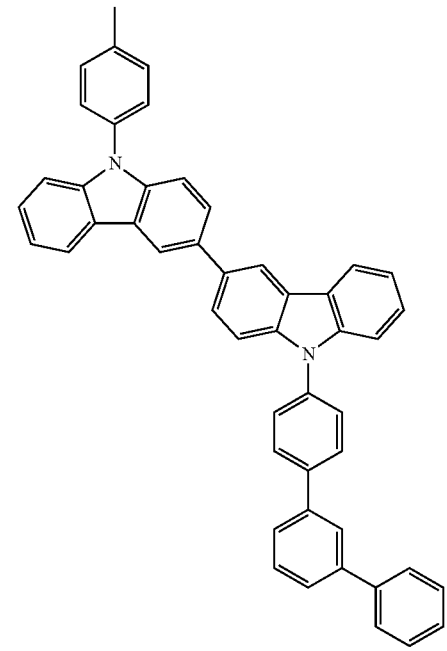
H1-191
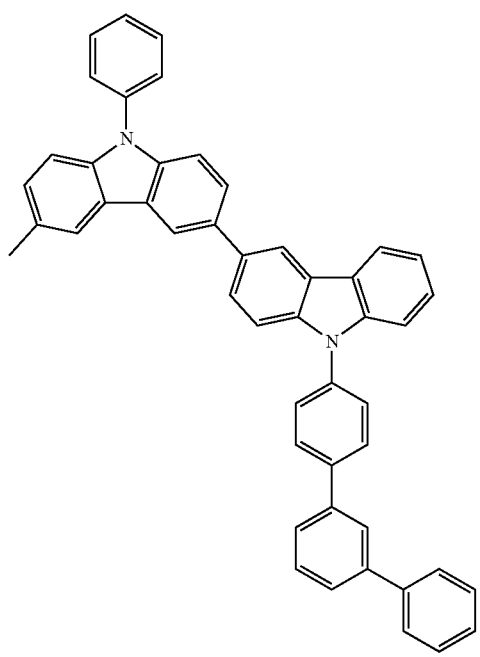
H1-192
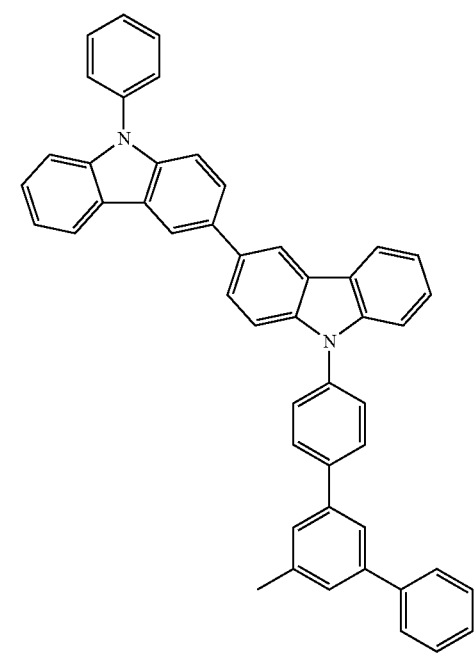

-continued
H1-193
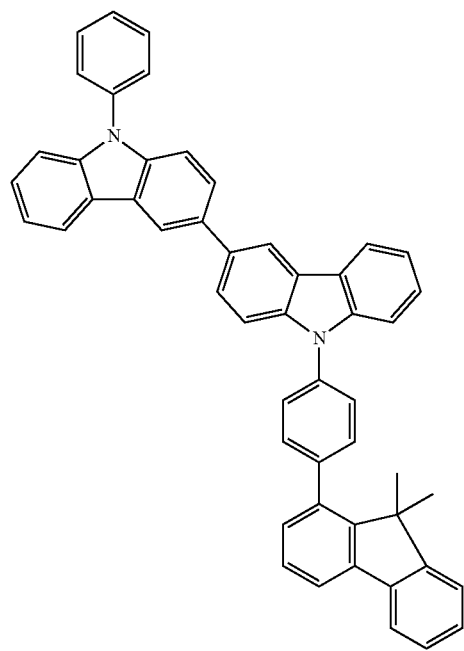
H1-194
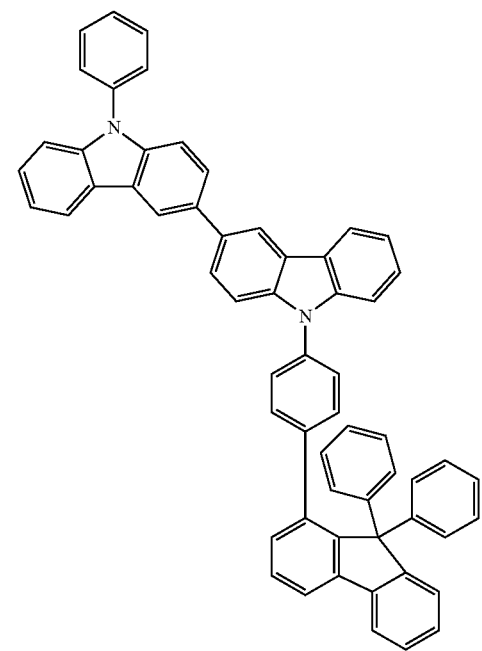
H1-195
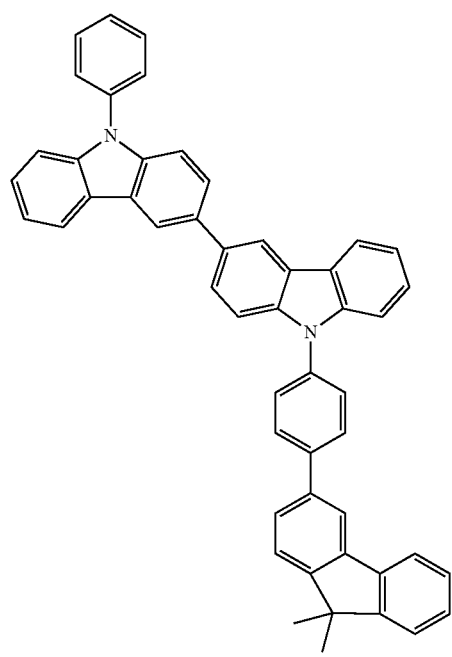
H1-196
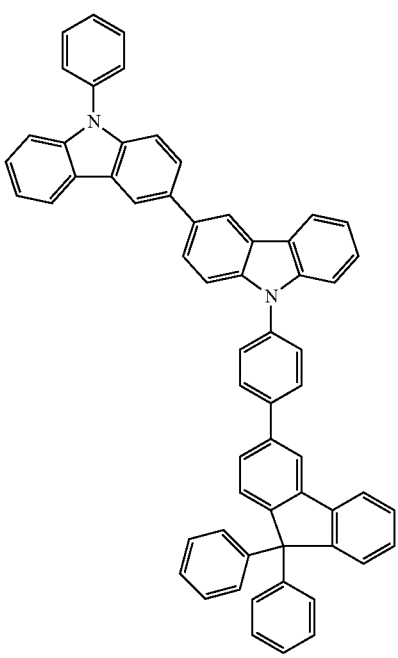

-continued
H1-197
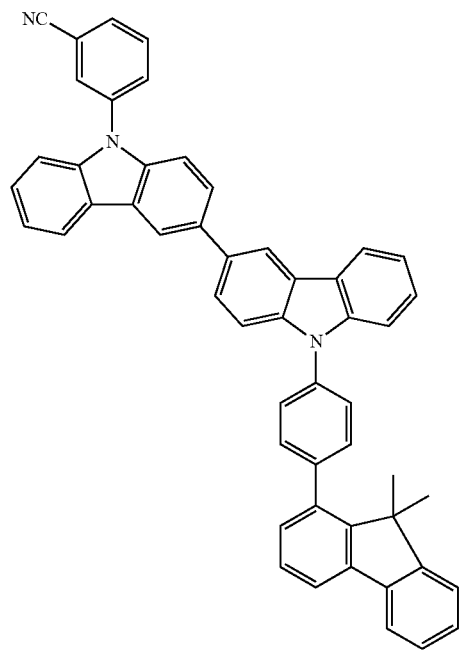
H1-198
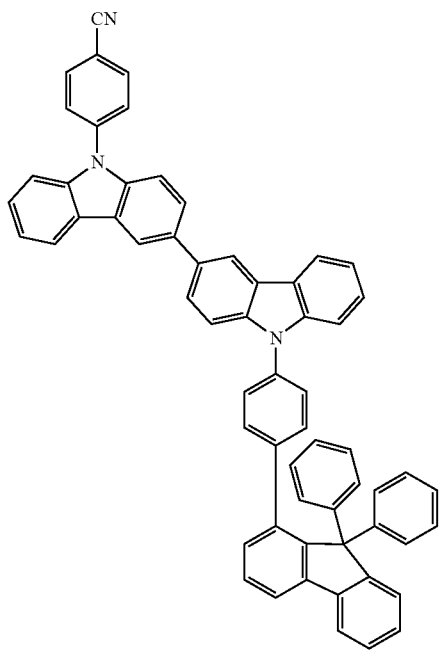
H1-199
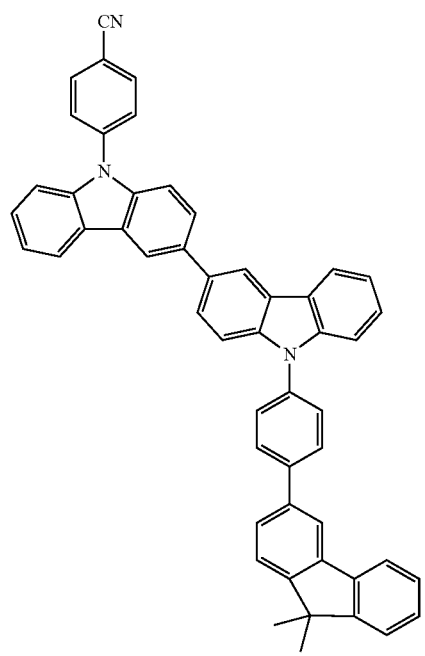
H1-200
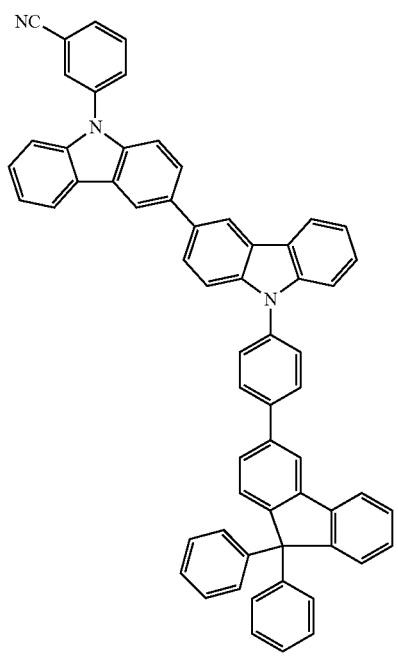

-continued
H1-201
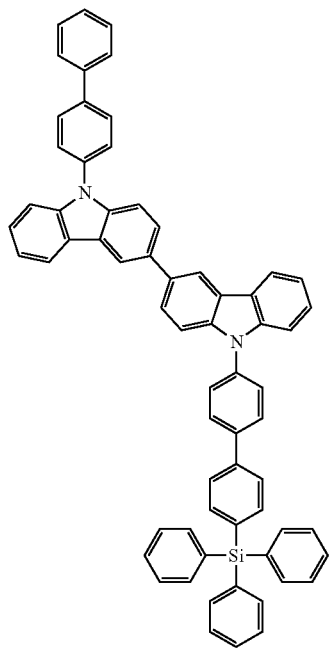
H1-202
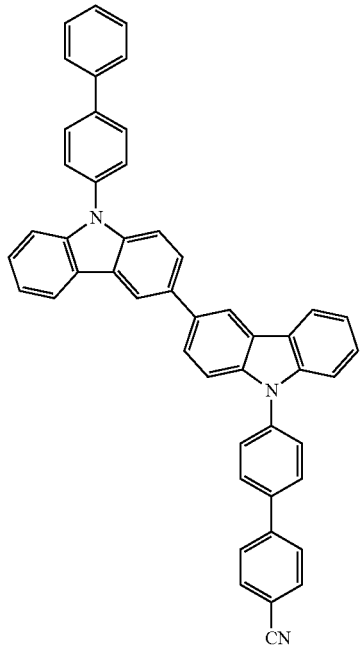
H1-203
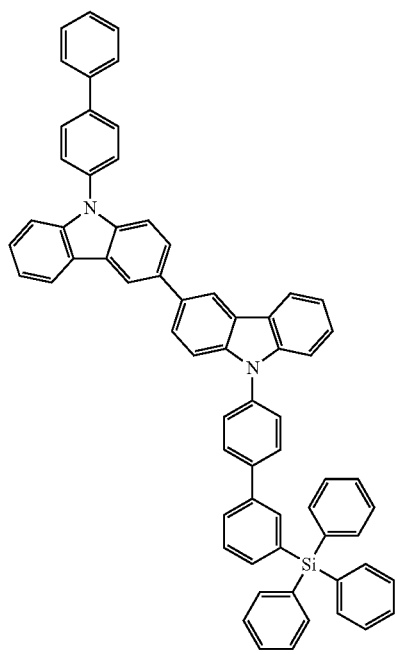
H1-204
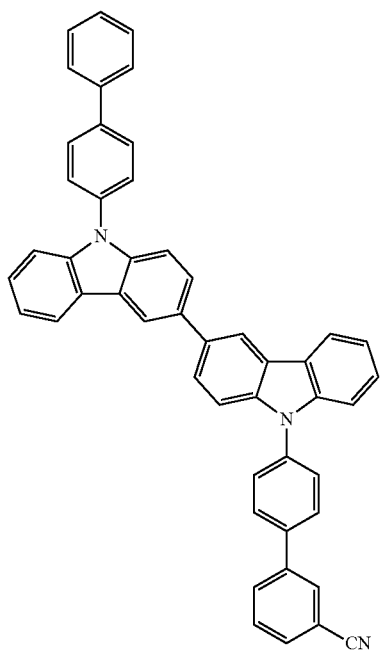

-continued
H1-205
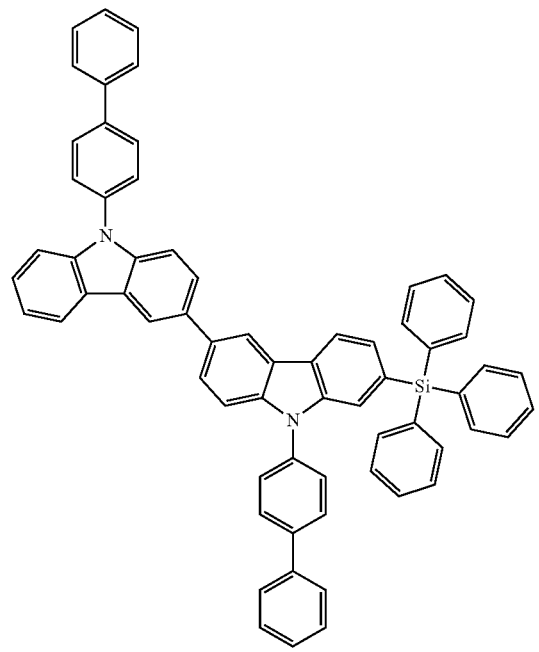
H1-206
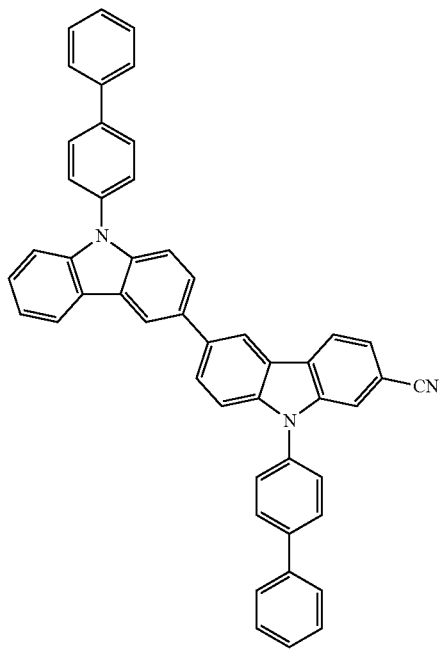
H1-207
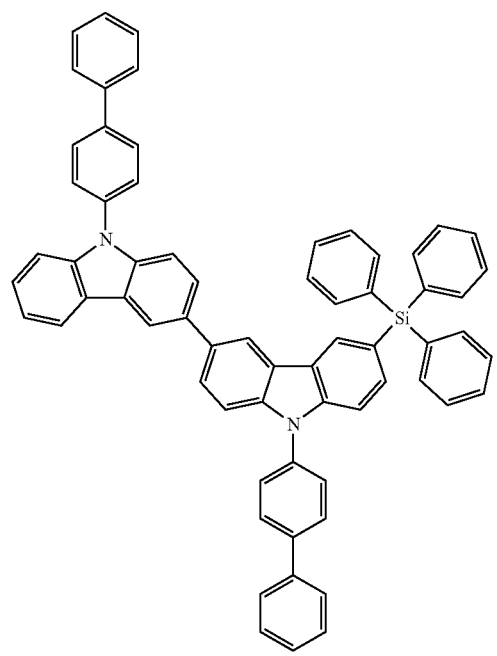
H1-208
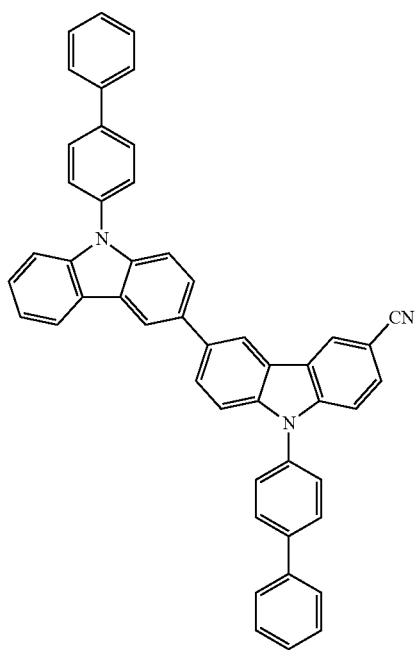

-continued
H1-209
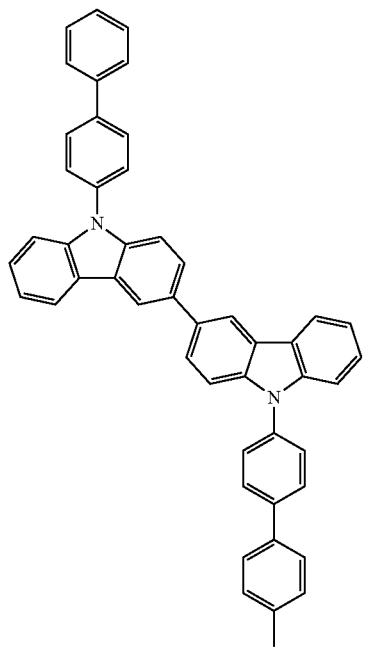
H1-210
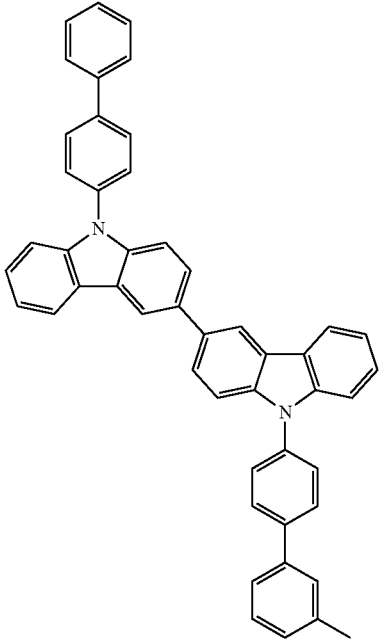
H1-211
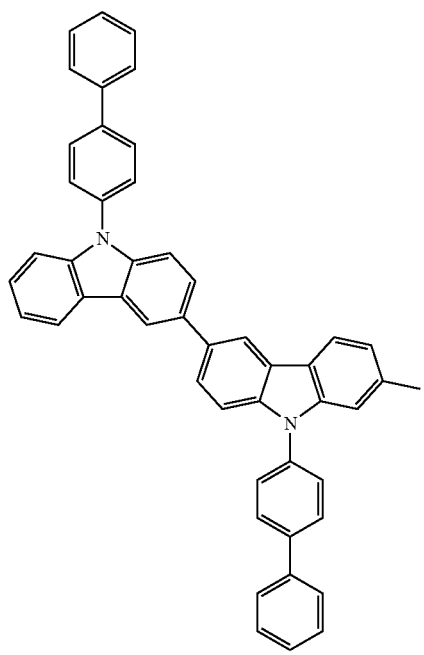
H1-212
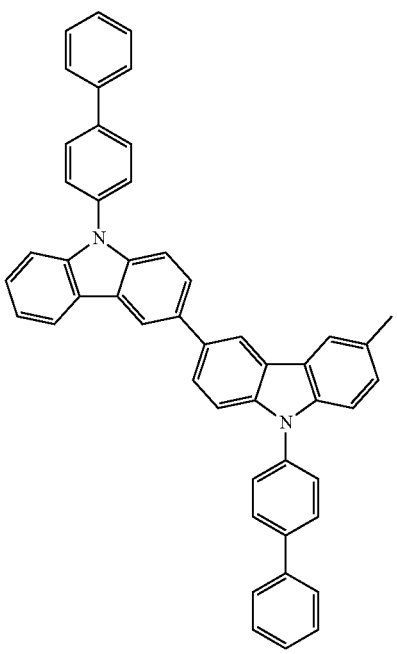

-continued
H1-213
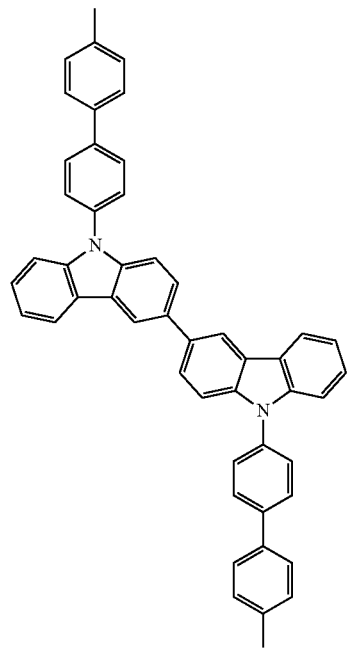
H1-214
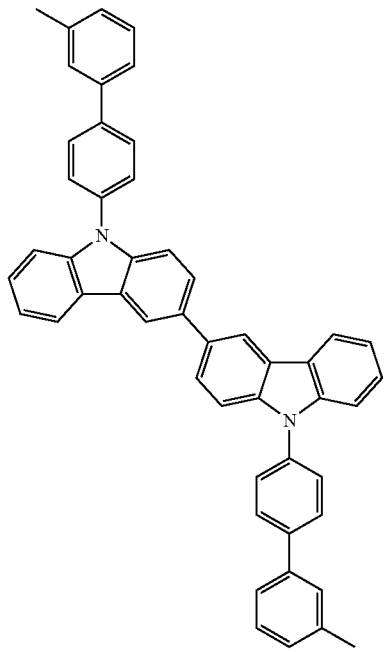
H1-215
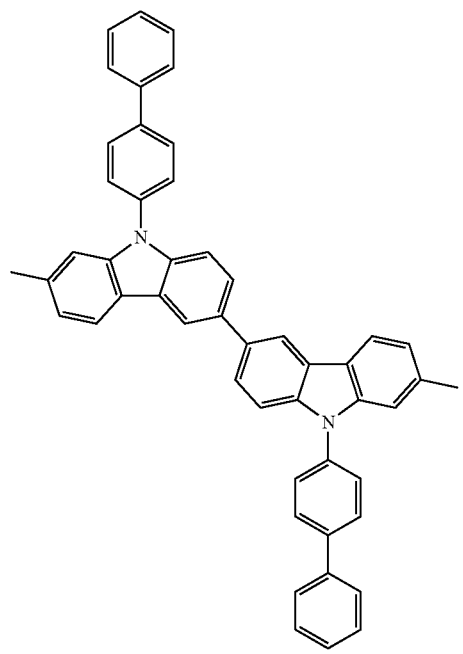
H1-216

-continued
H1-217
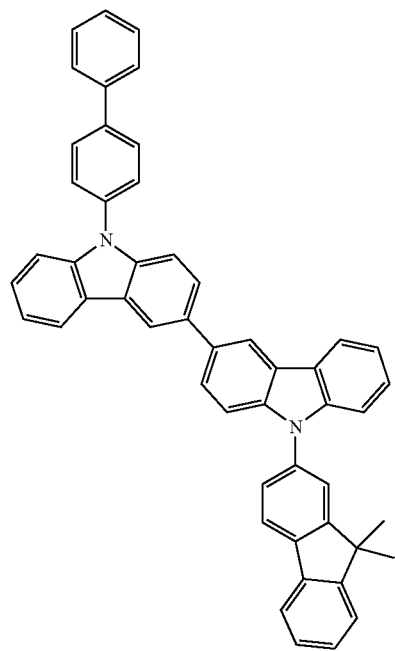
H1-218
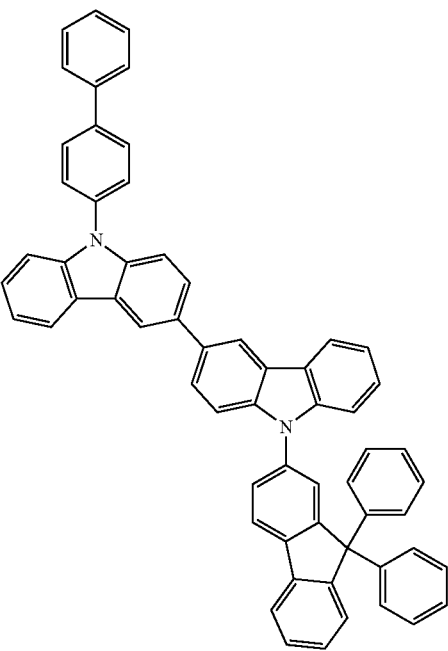
H1-219
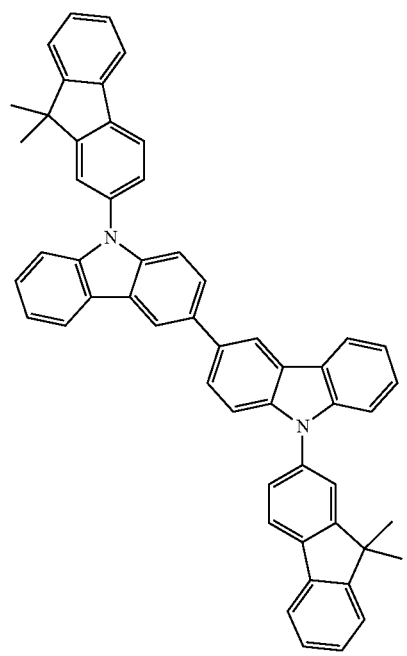
H1-220
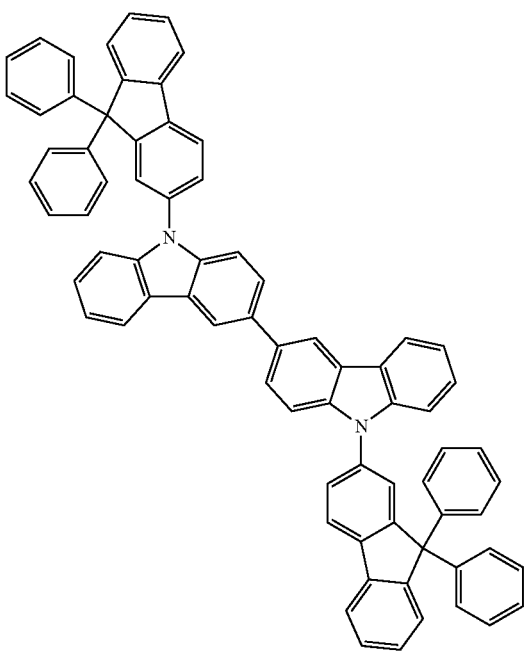

H1-221
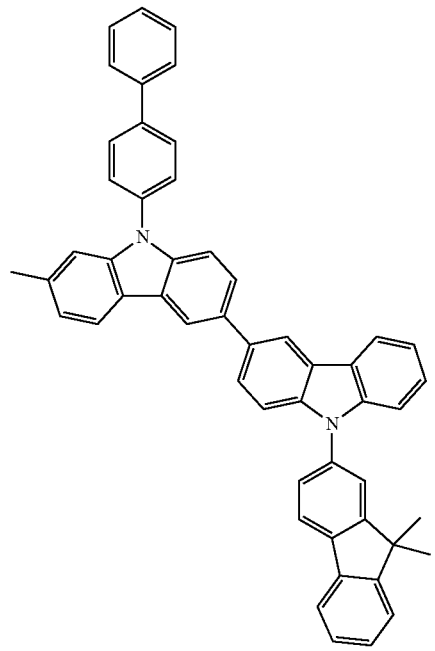
H1-222
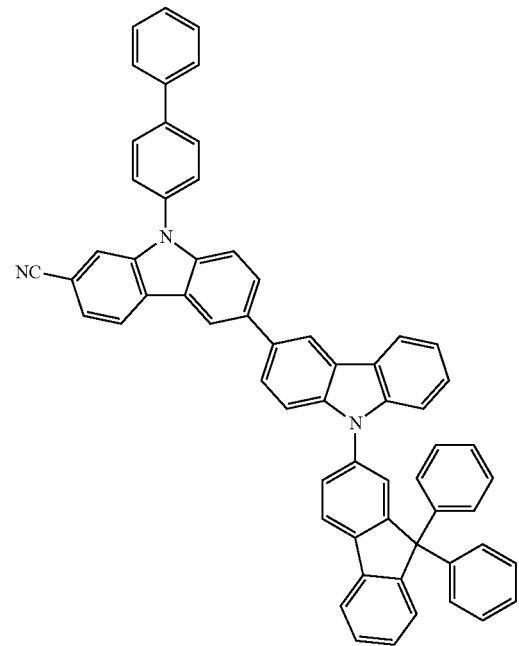
H1-223
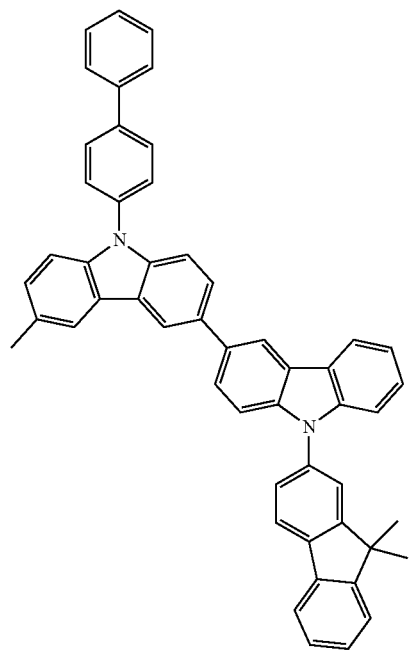
H1-224
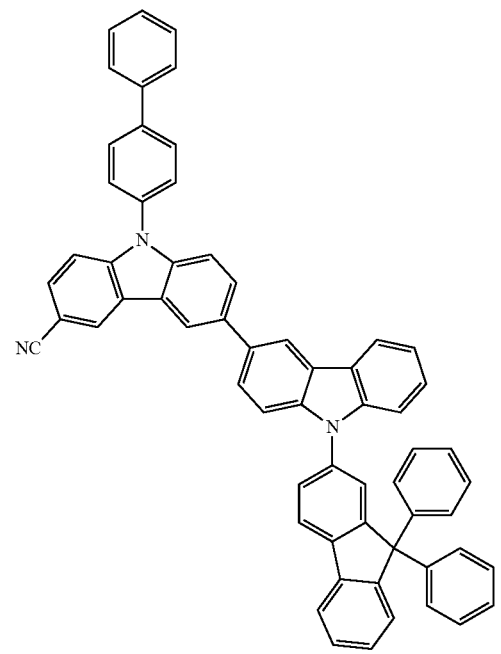

-continued
H1-225
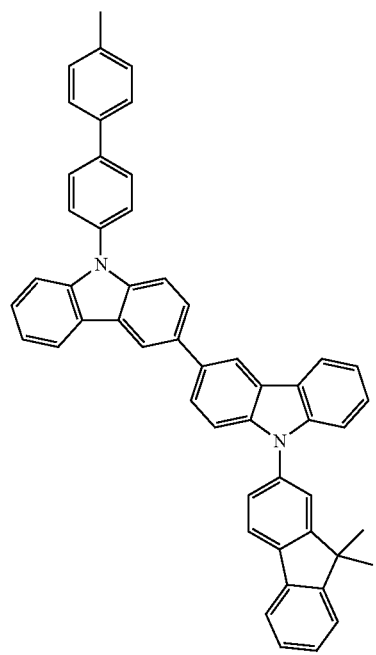
H1-226
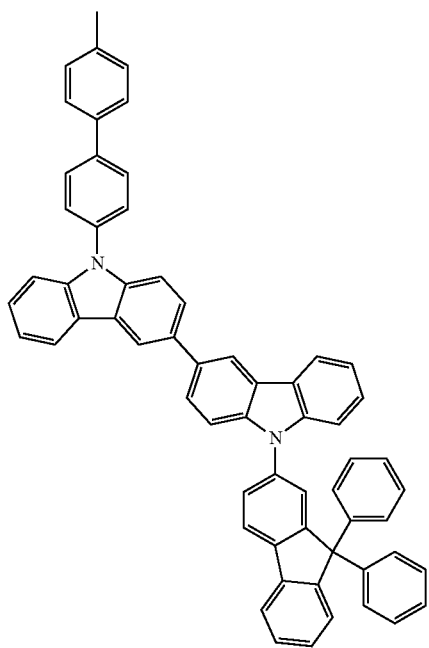
H1-227
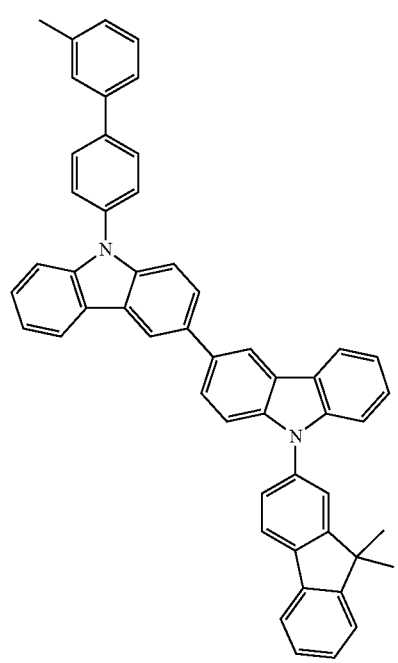
H1-228
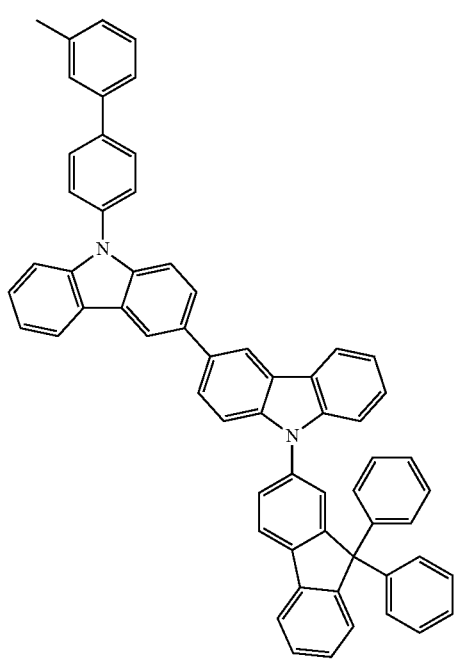

-continued
H1-229
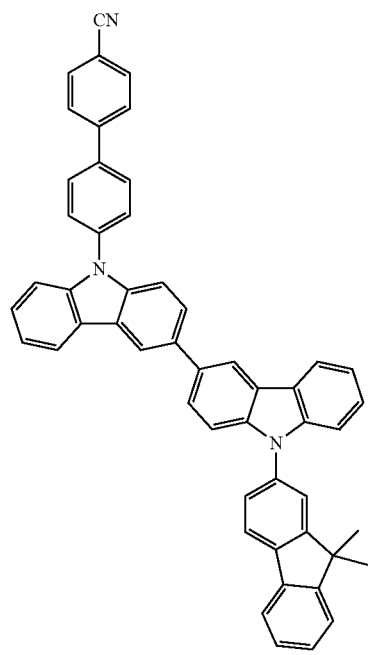
H1-230
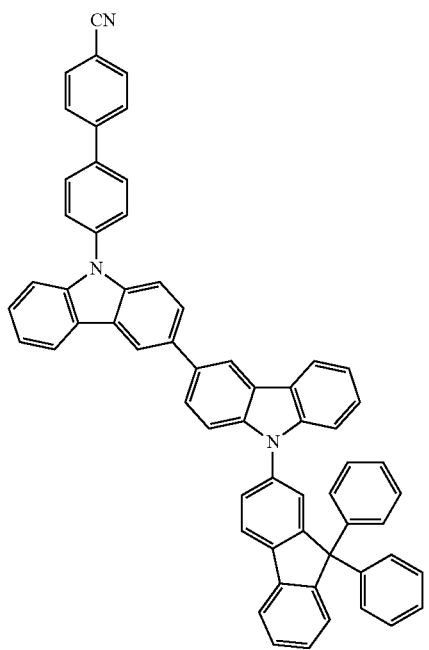
H1-231
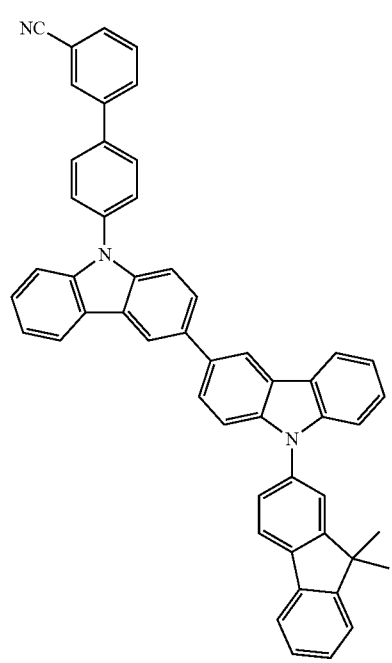
H1-232
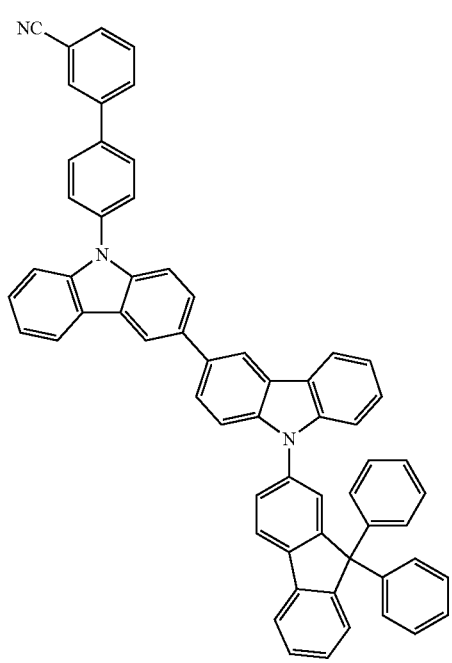

H1-233
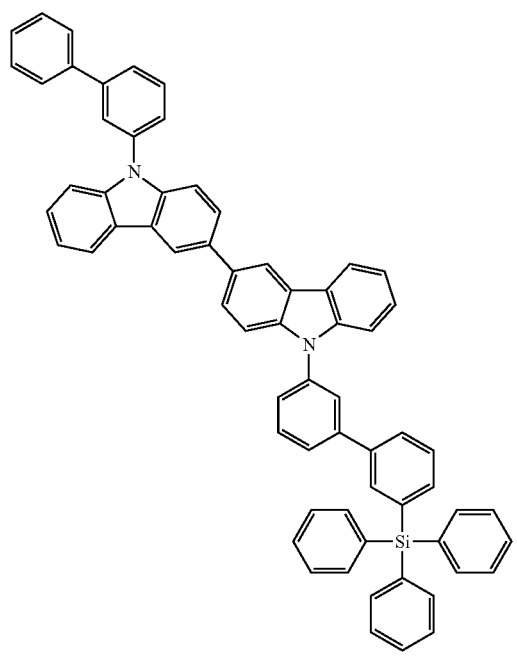
H1-234
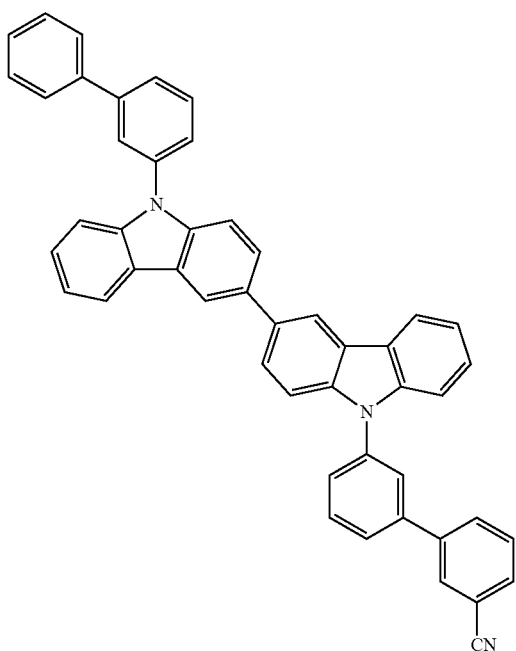
H1-235
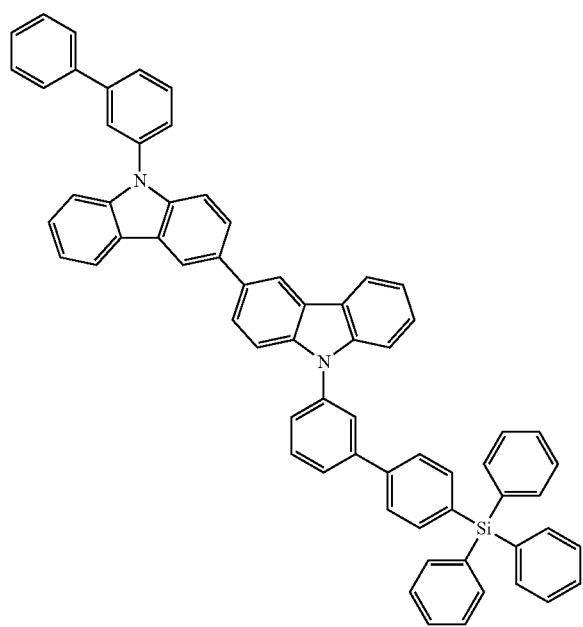
H1-236
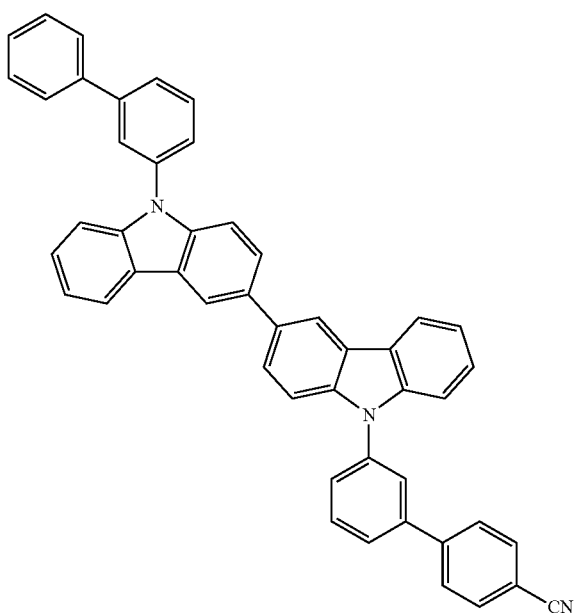

-continued
H1-237
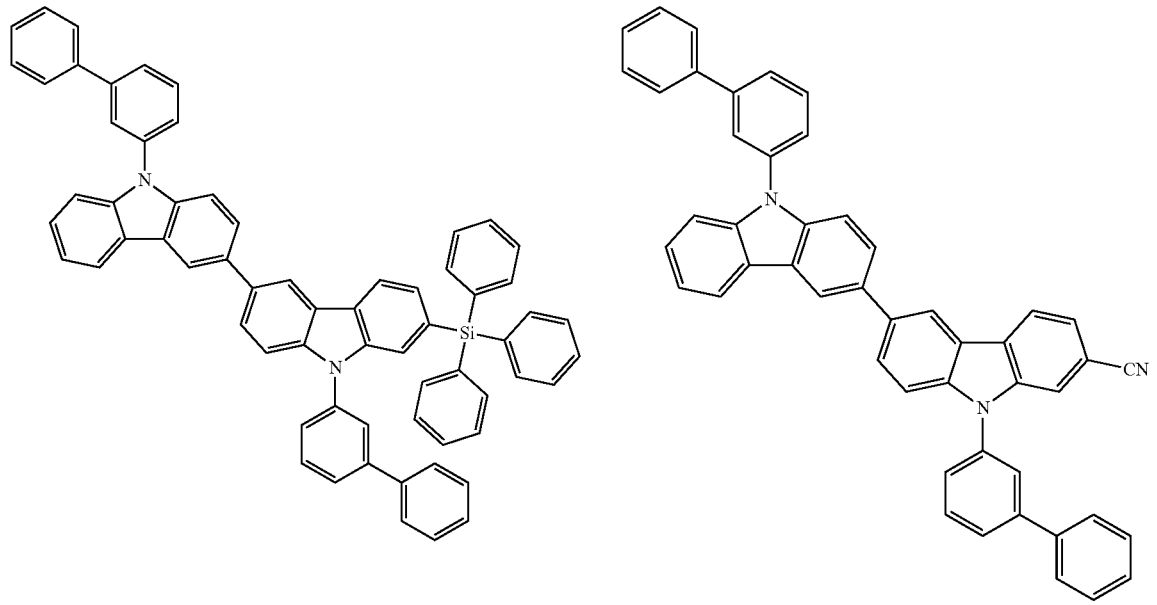
H1-238
H1-239
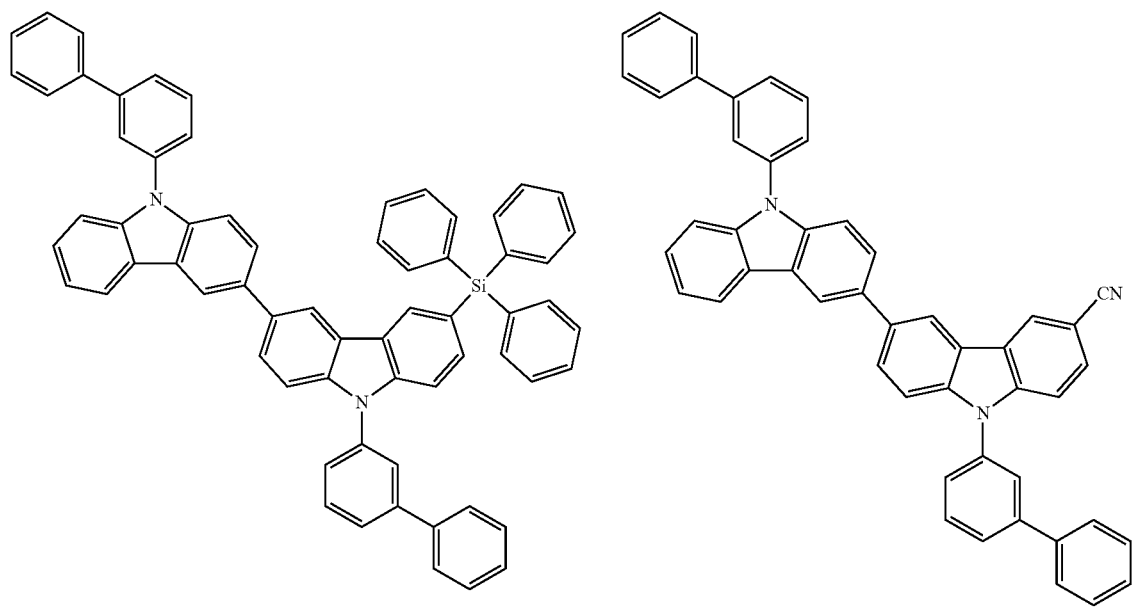
H1-240

-continued
H1-241
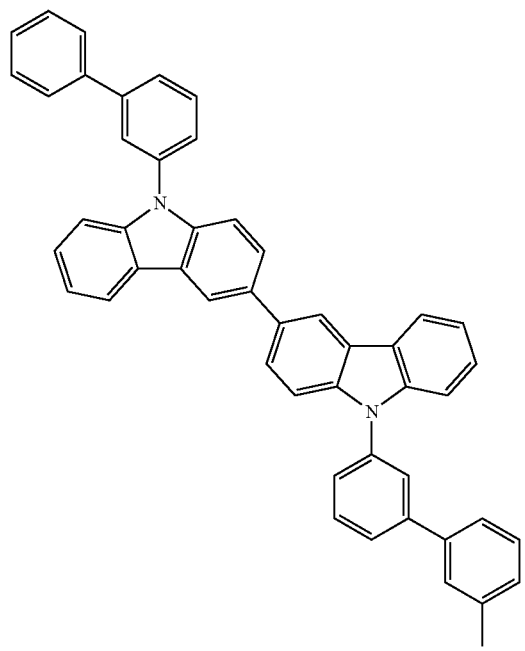
H1-242
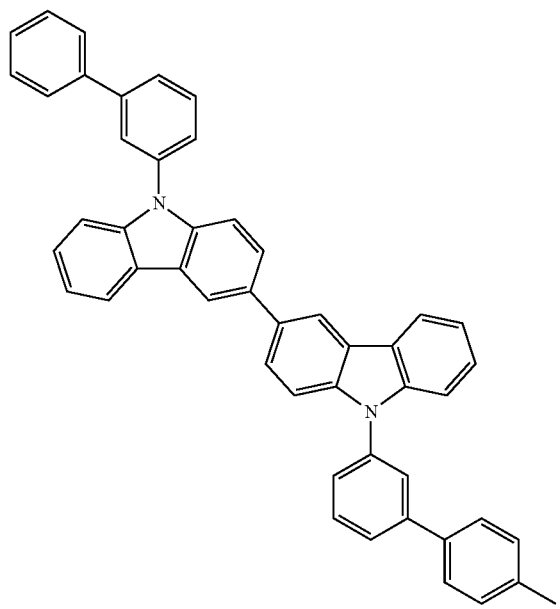
H1-243
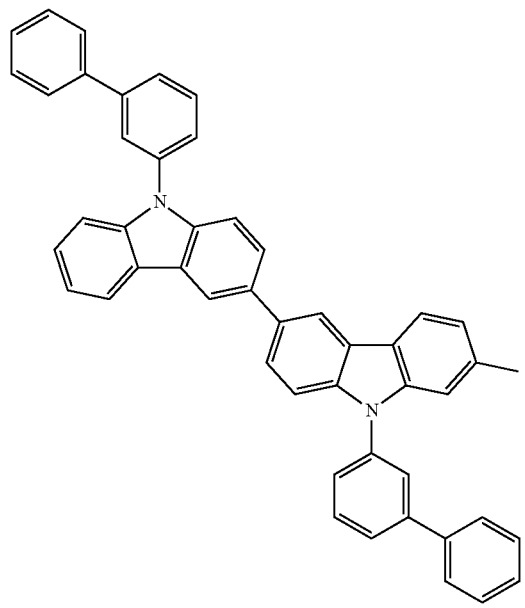
H1-244
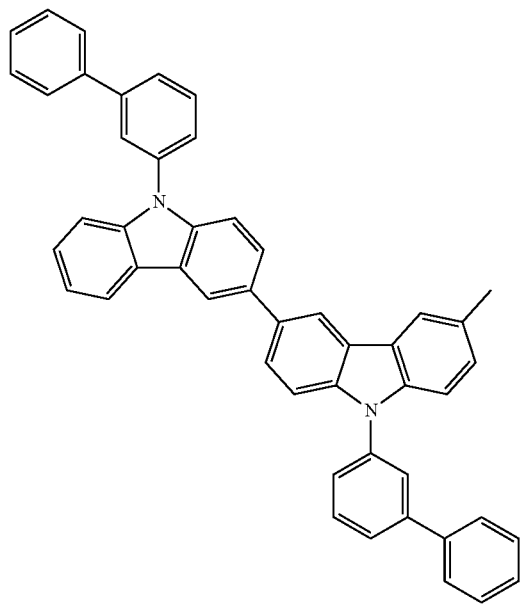

H1-245
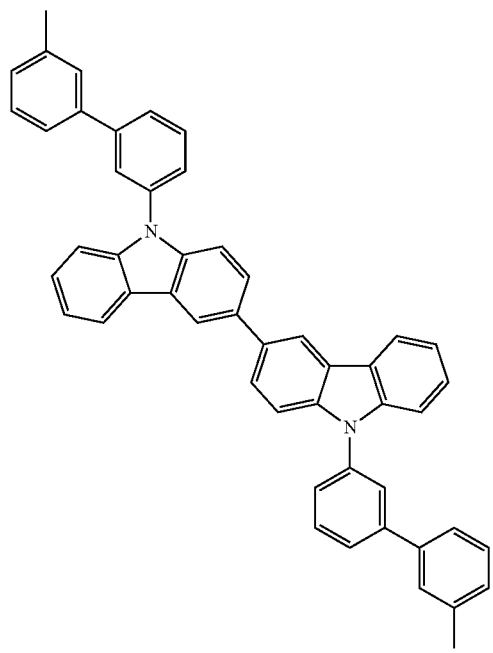
H1-246
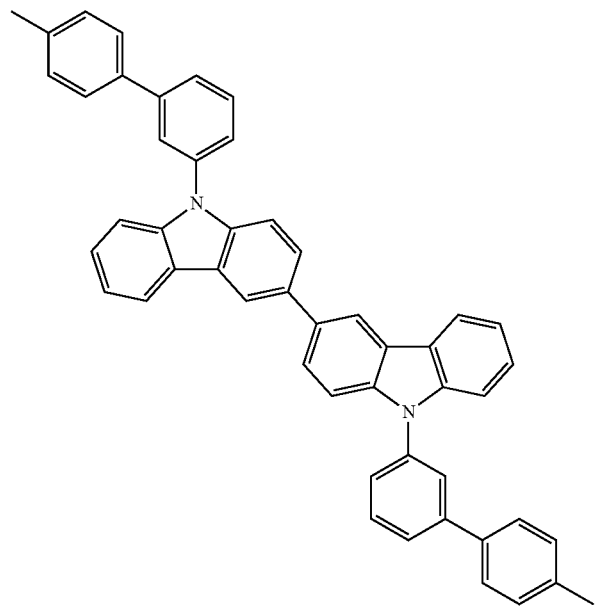
H1-247
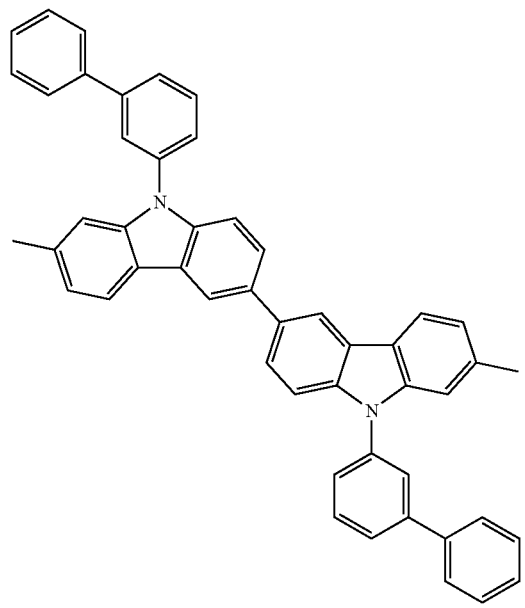
H1-248
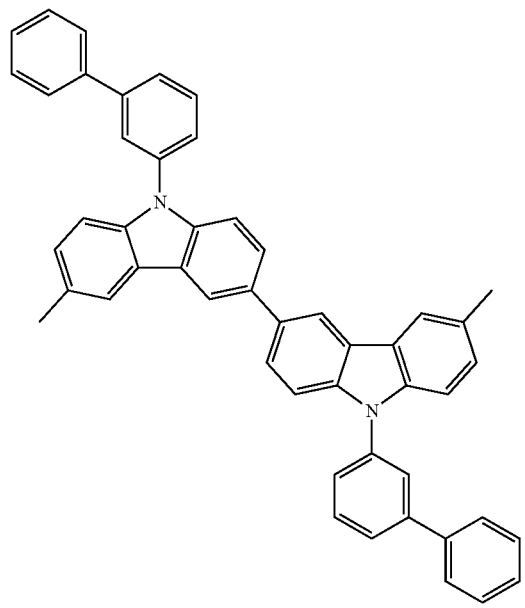

-continued
H1-249
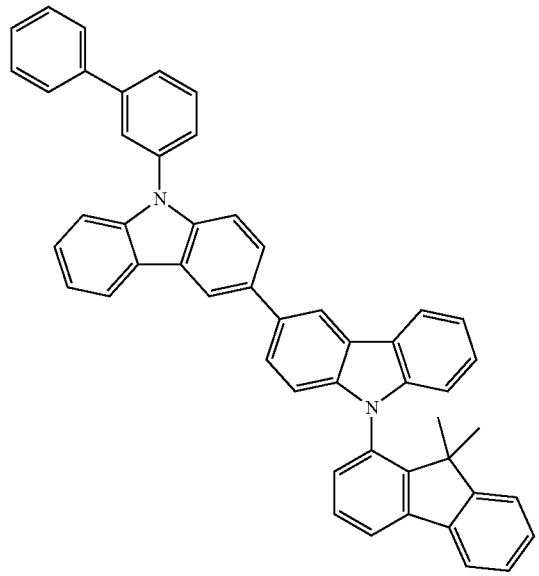
H1-250
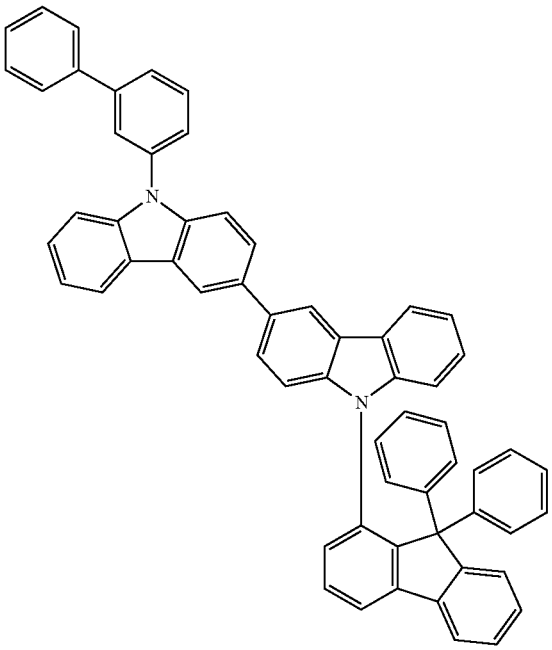
H1-251
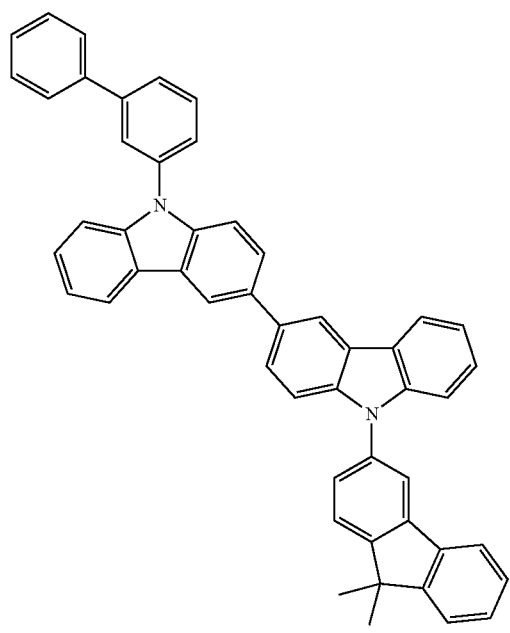
H1-252
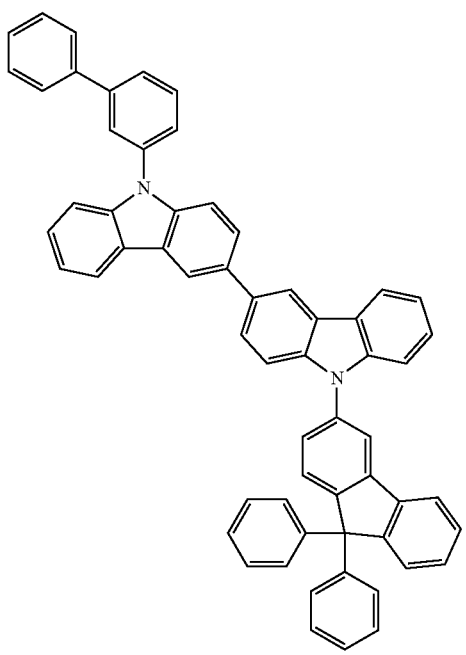

H1-253
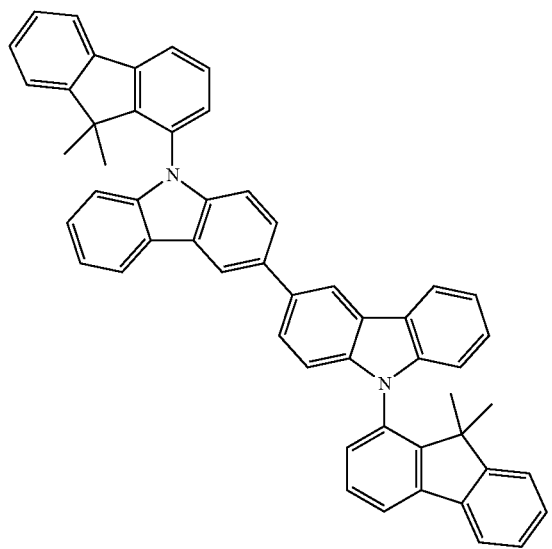
H1-254
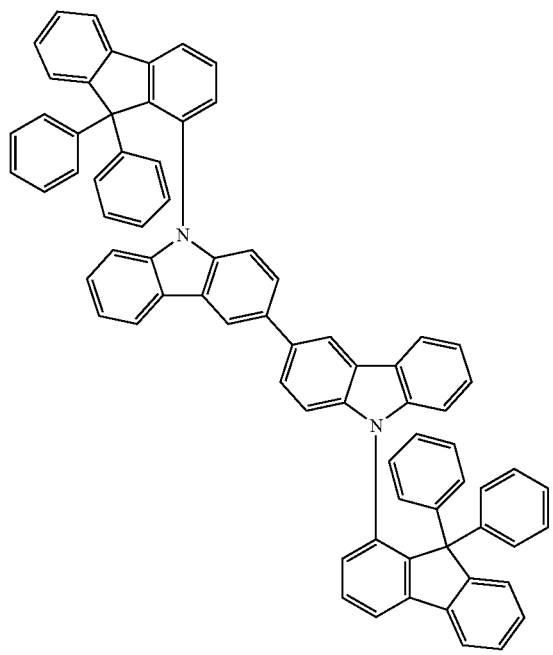
H1-255
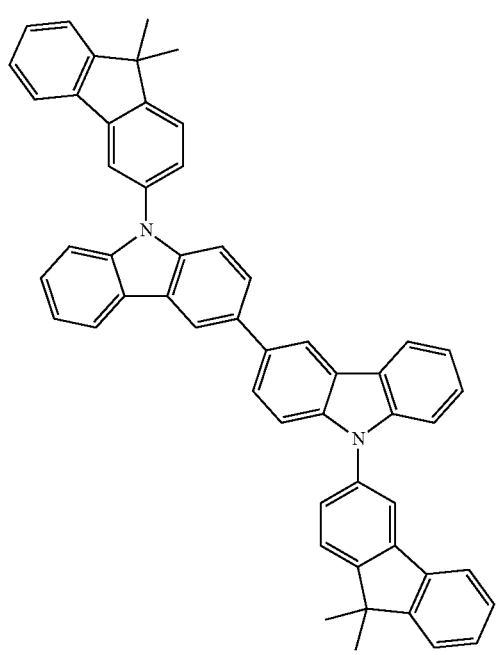
H1-256
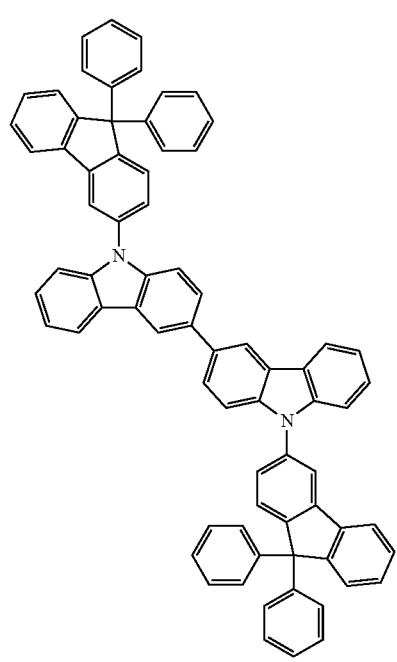

-continued
H1-257
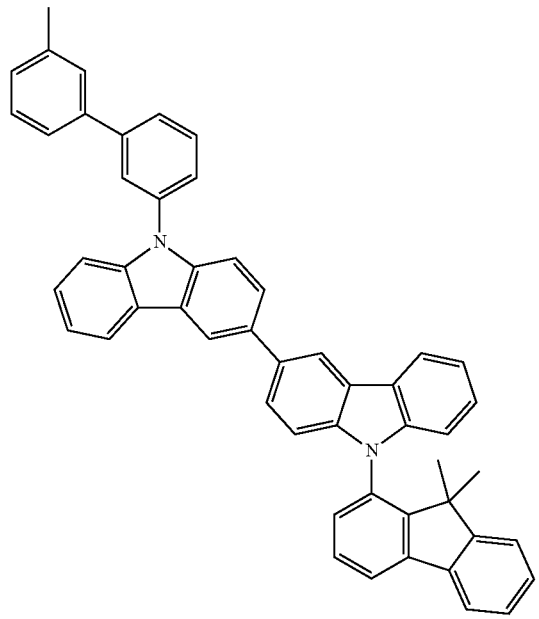
H1-258
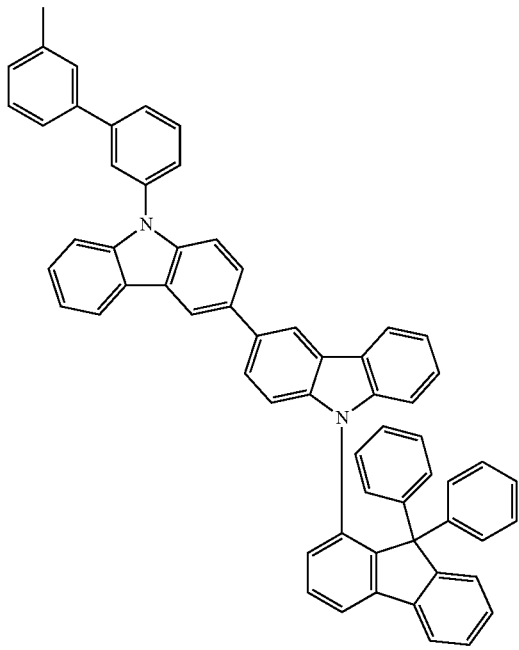
H1-259
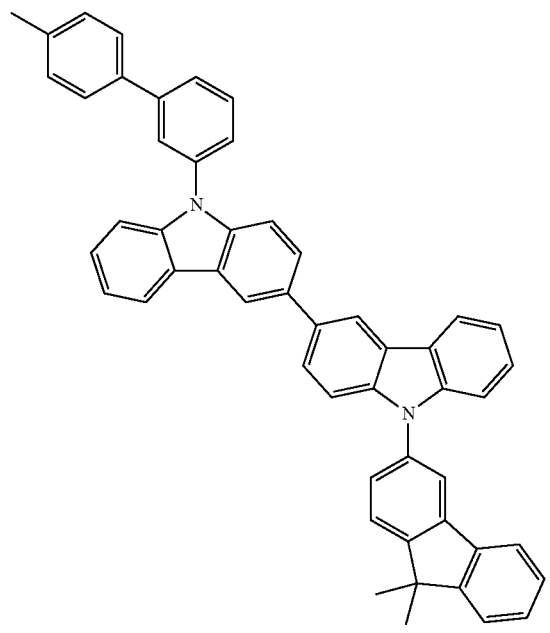
H1-260
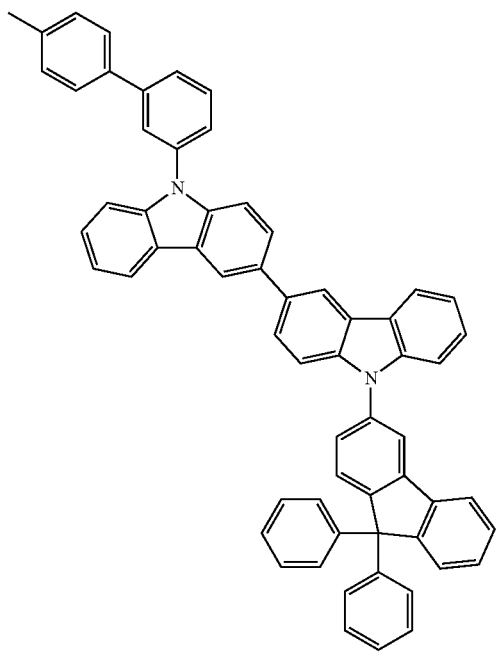

-continued
H1-261
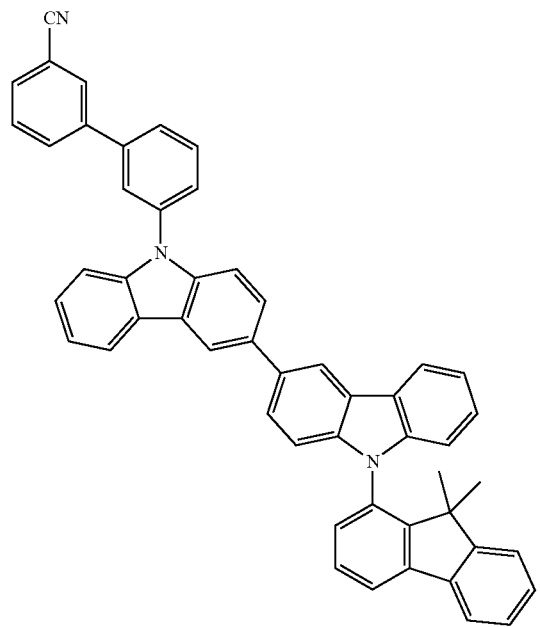
H1-262
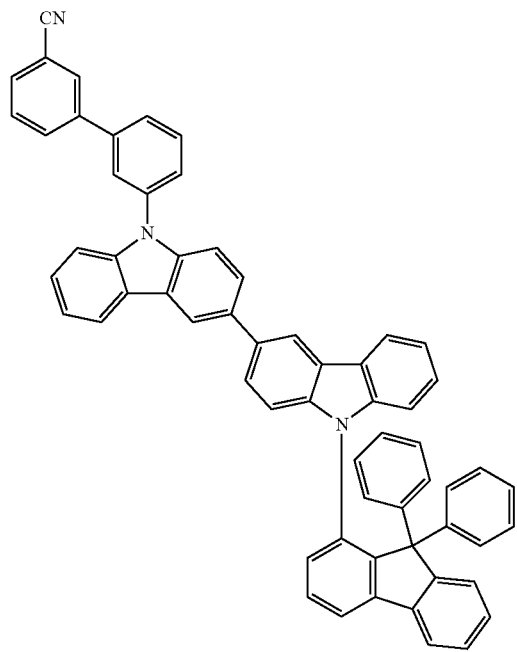
H1-263
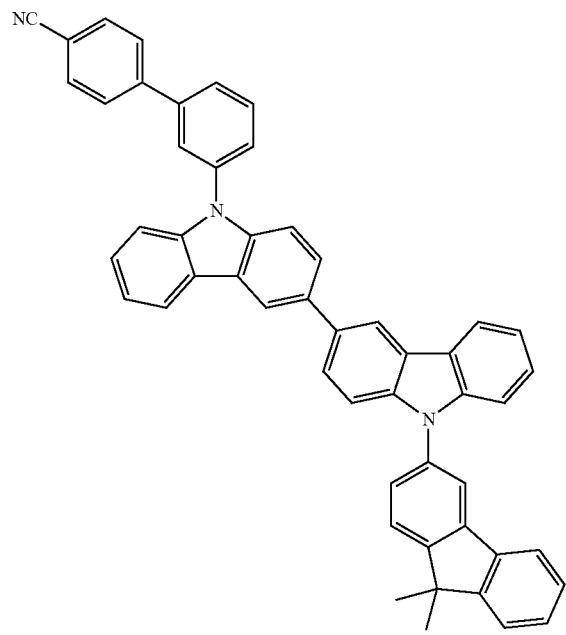
H1-264
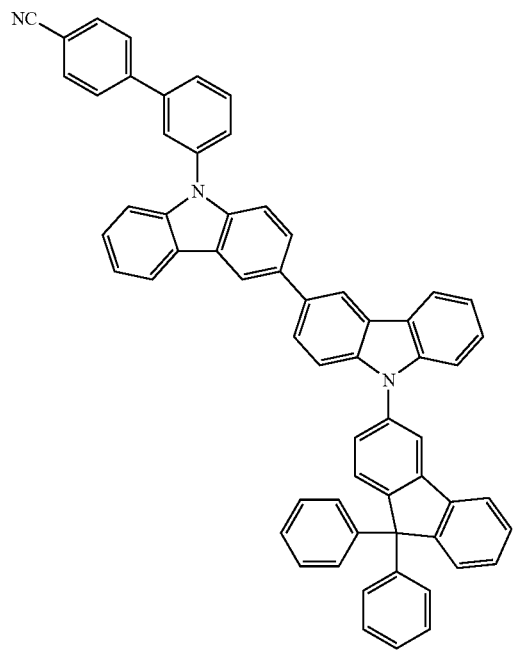

-continued
H1-265
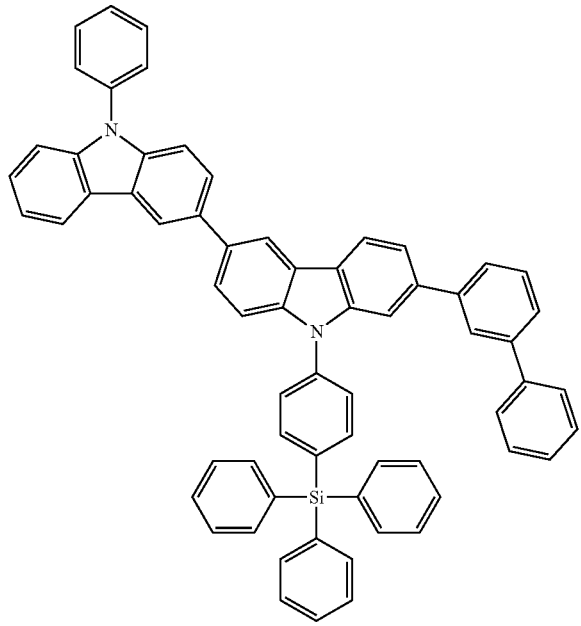
H1-266
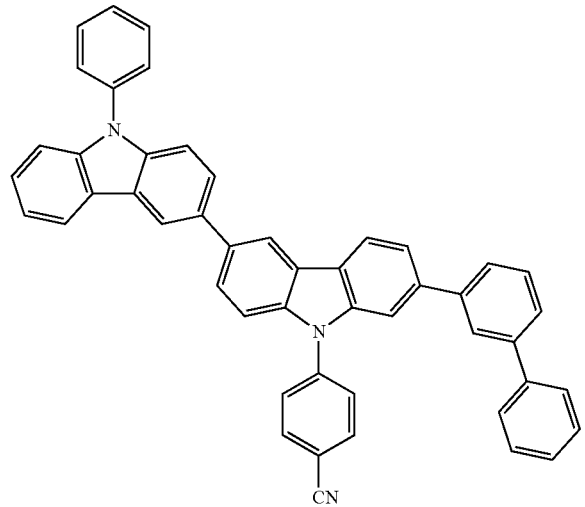
H1-267
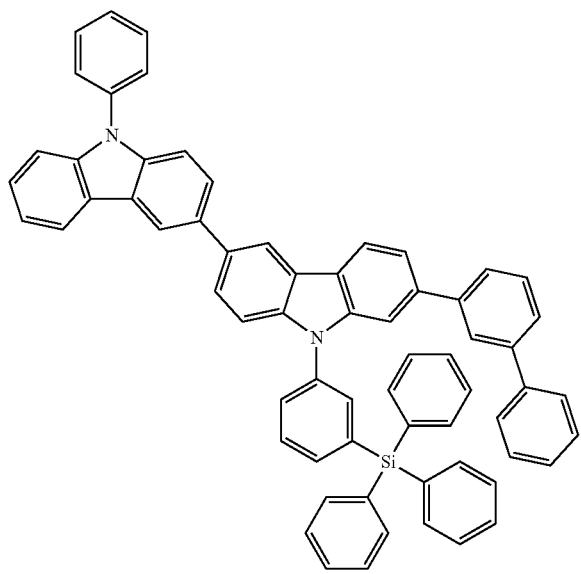
H1-268
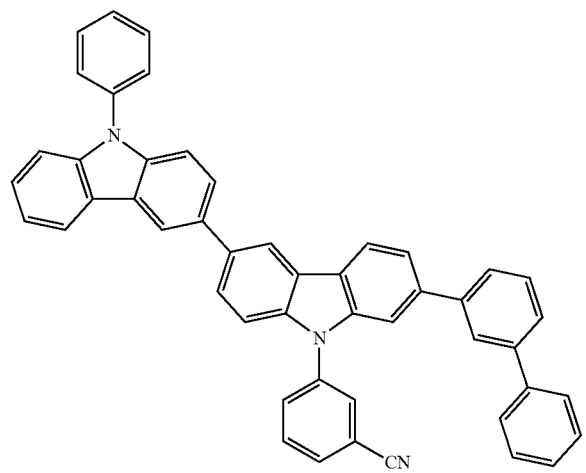

H1-269
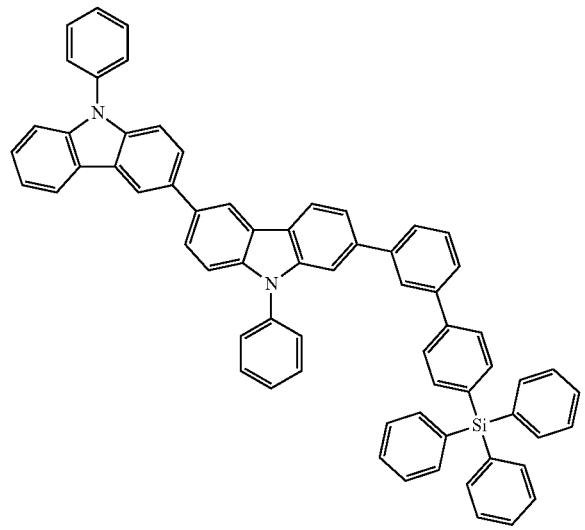
H1-270
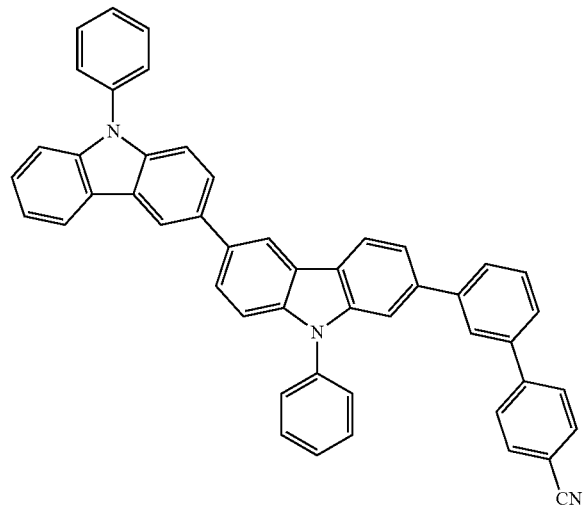
H1-271
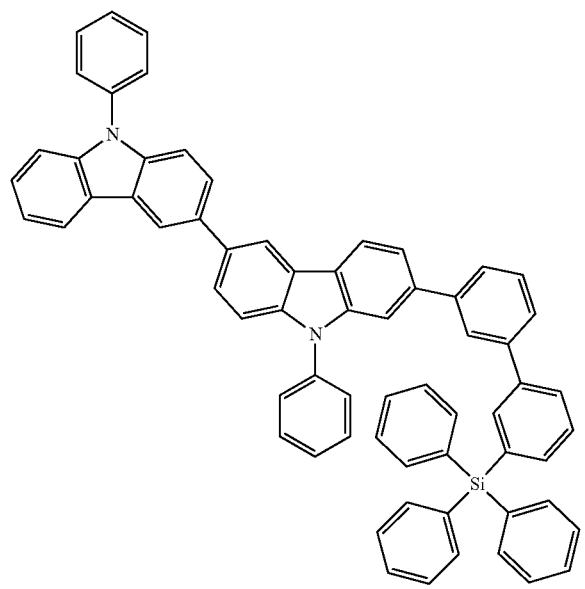
H1-272
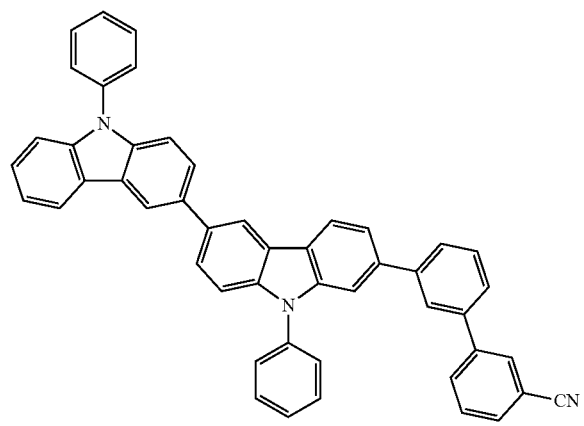

-continued
H1-273
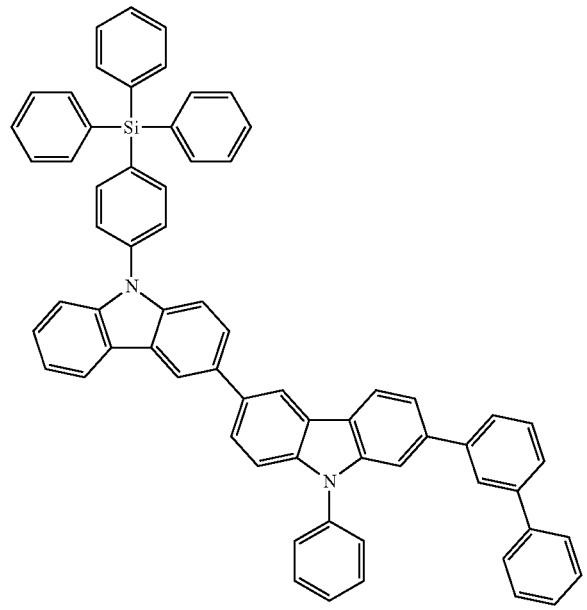
H1-274
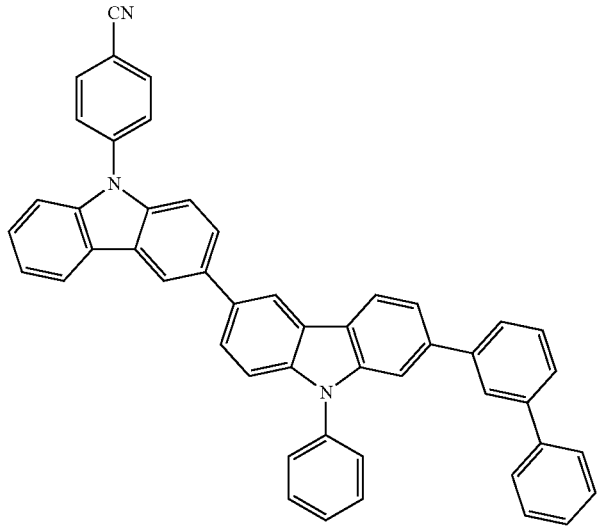
H1-275
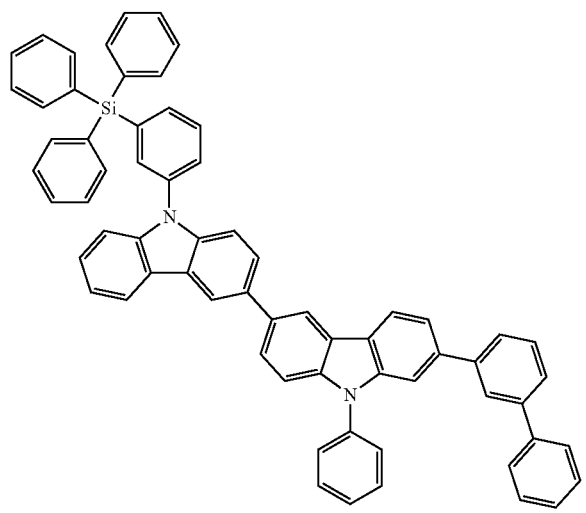
H1-276
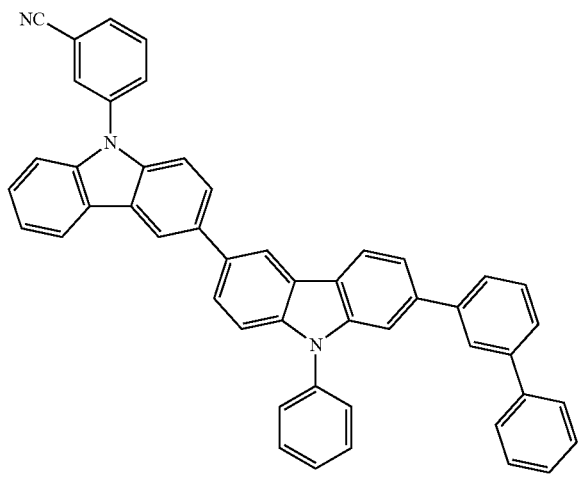
H1-277
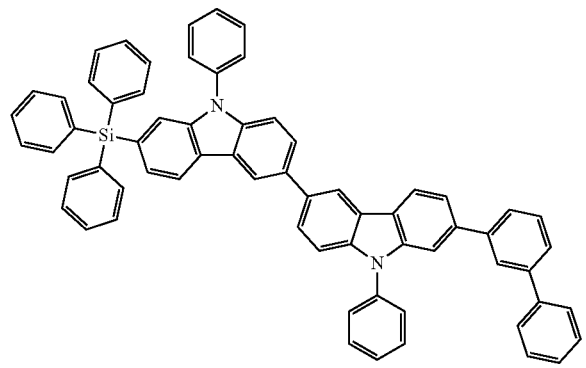
H1-278
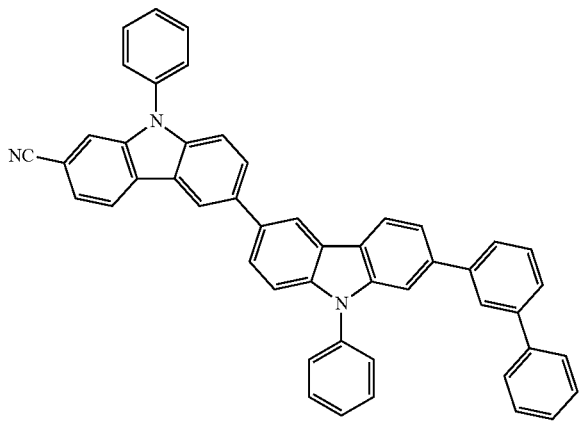

-continued
H1-279
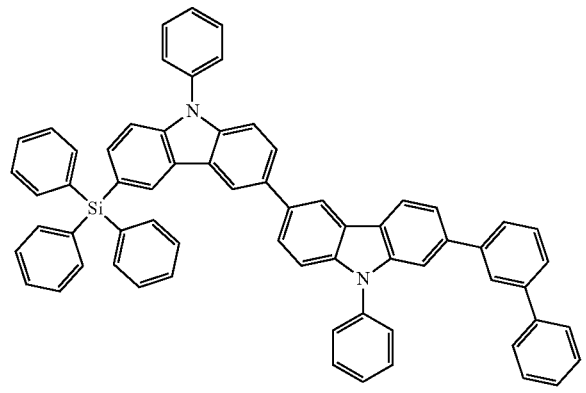
H1-280
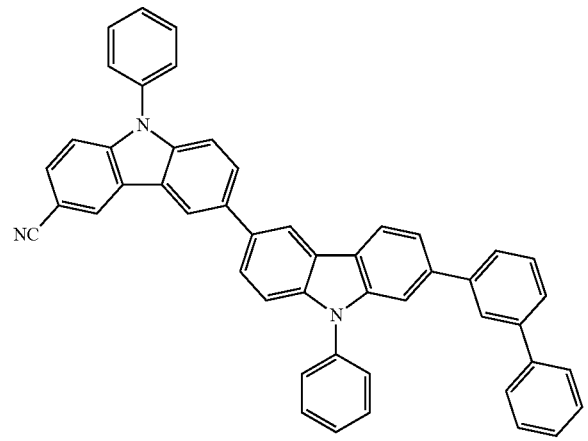
H1-281
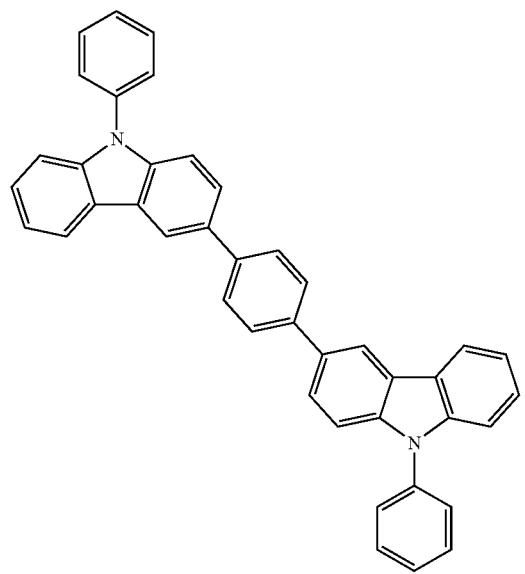
H1-282
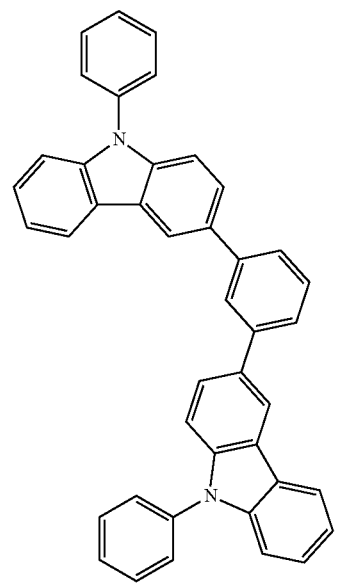

-continued
H1-283
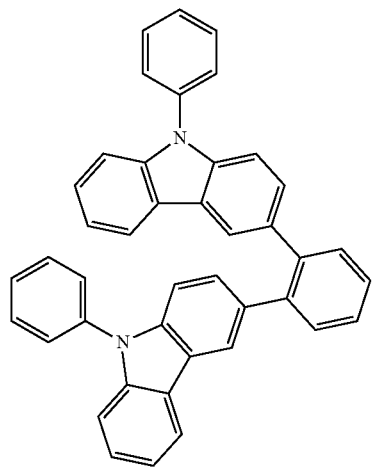
H1-284
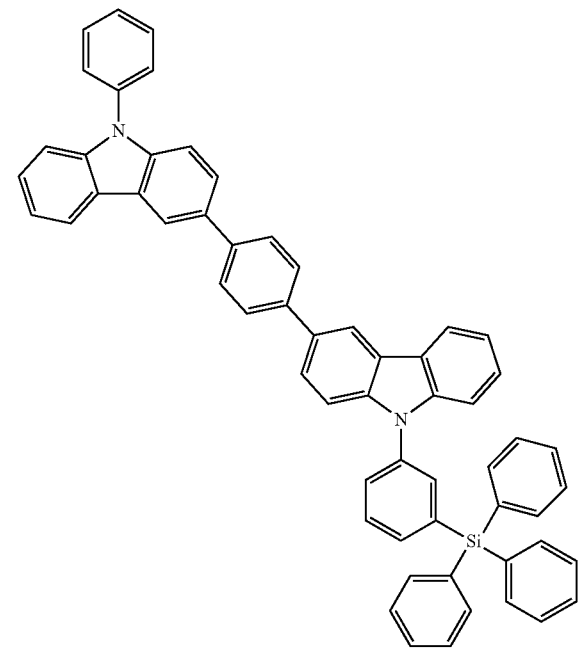
H1-285
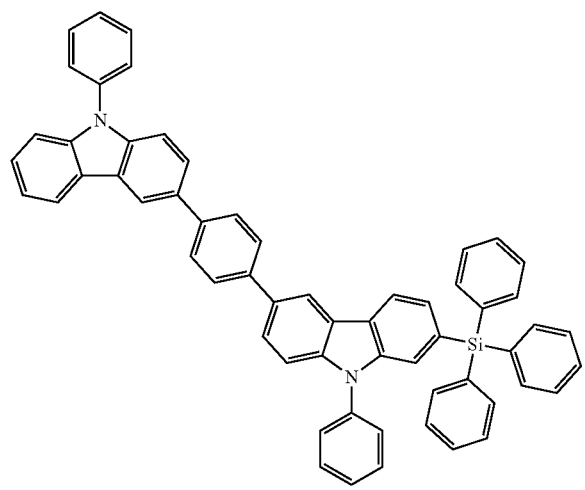
H1-286
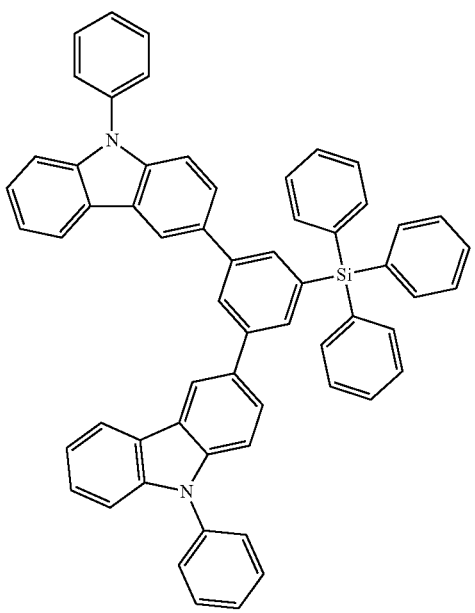

H1-287
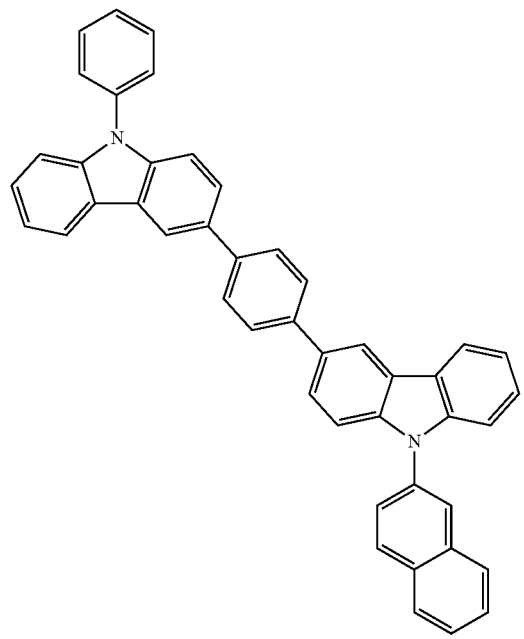
H1-288
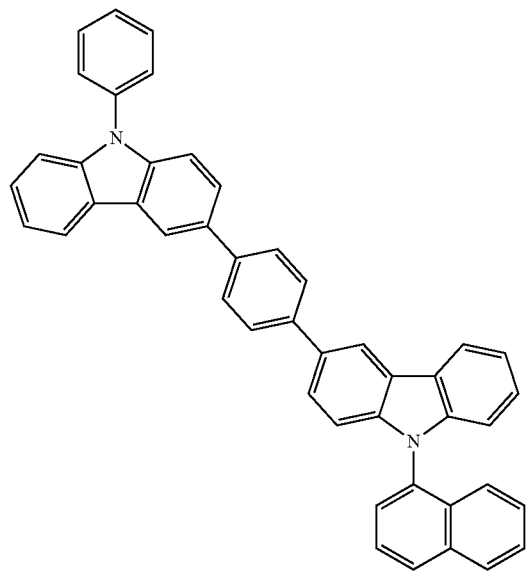
H1-289
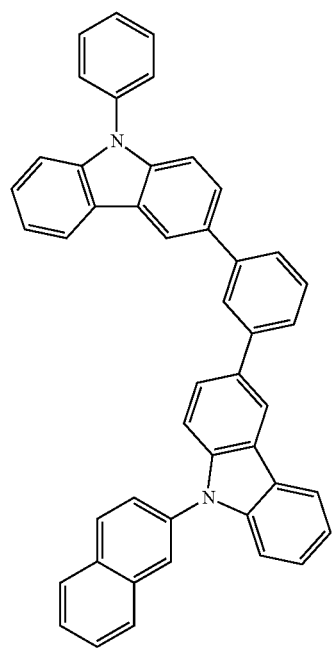
H1-290
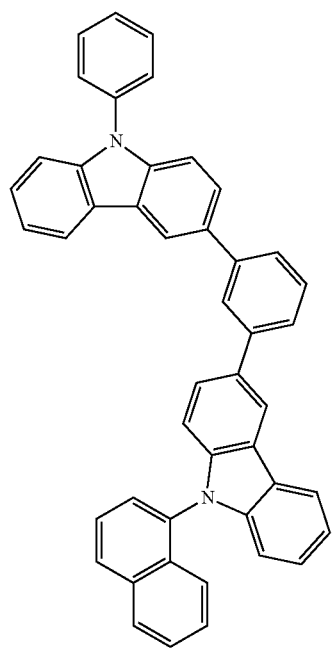

H1-291
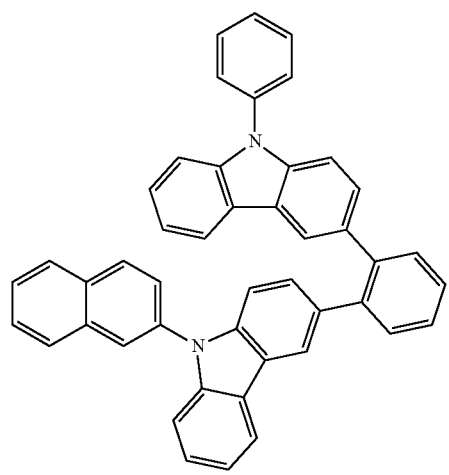
H1-292
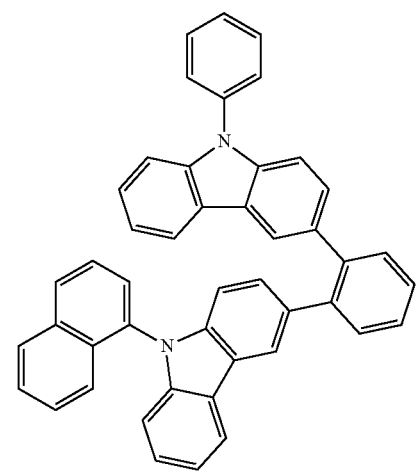
H1-293
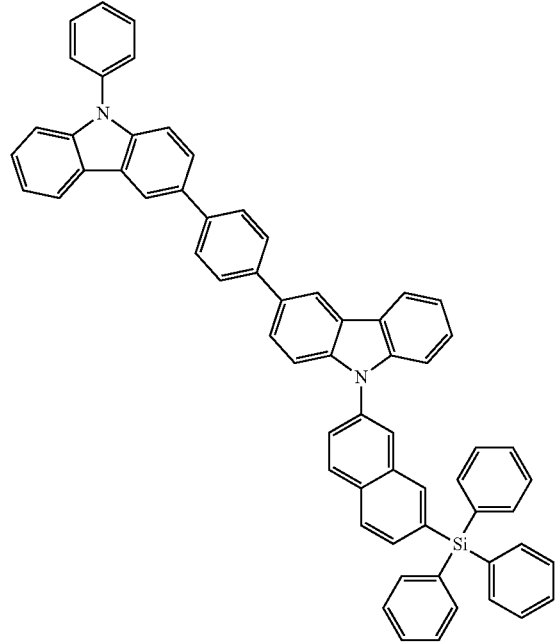
H1-294
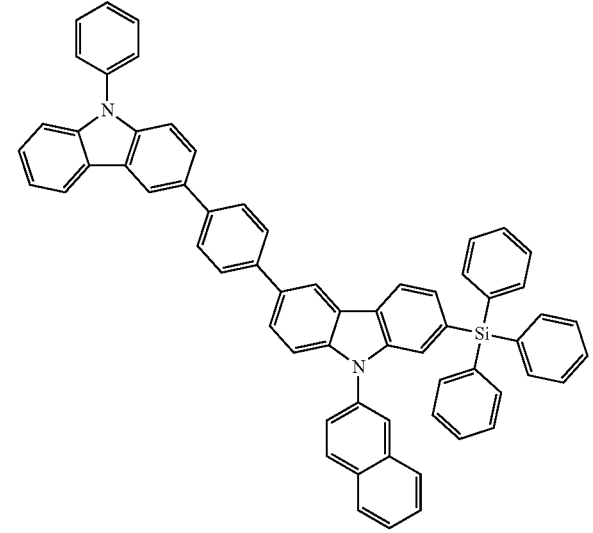

-continued
H1-295
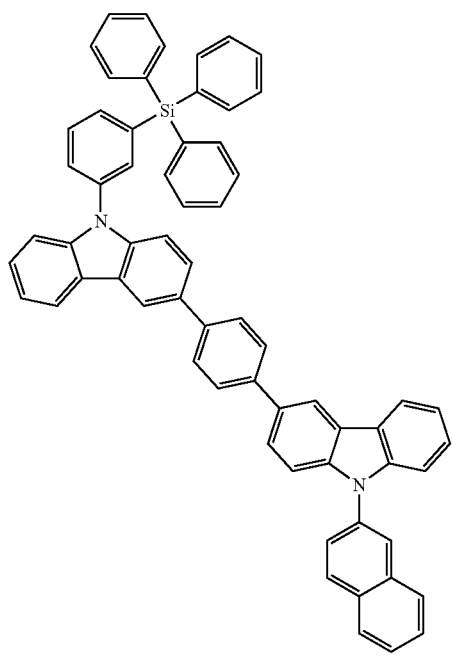
H1-296
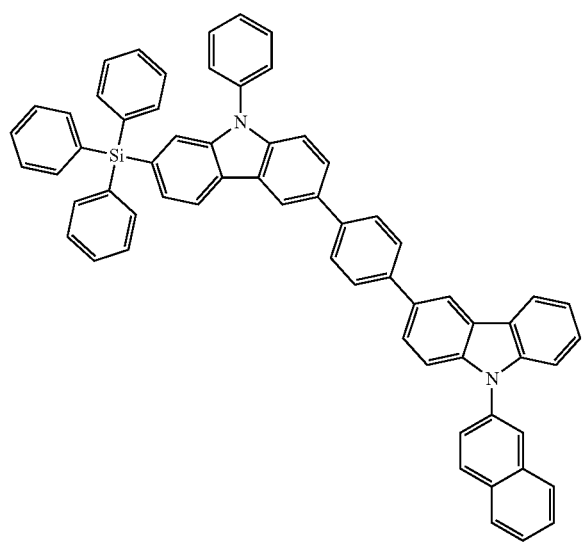
H1-297
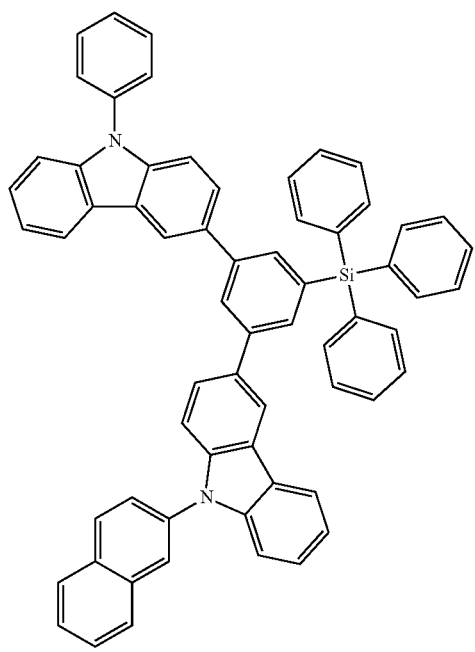
H1-298
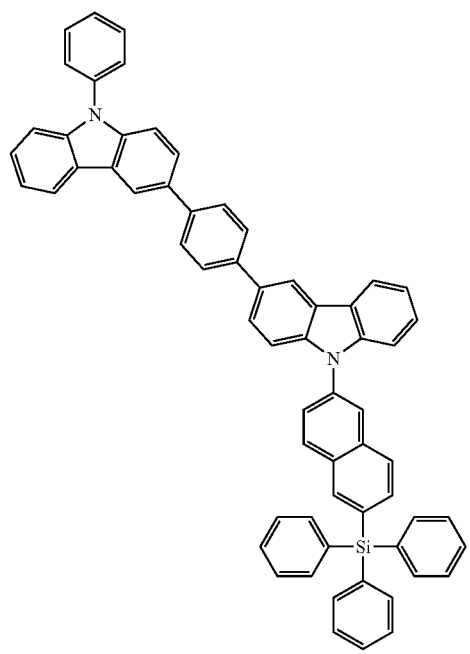

H1-299
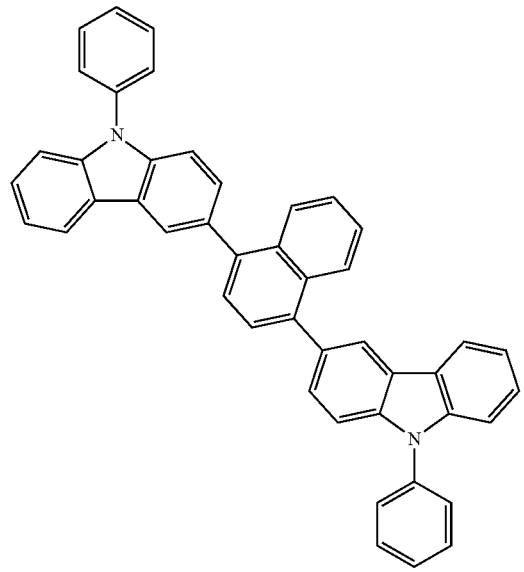
H1-300
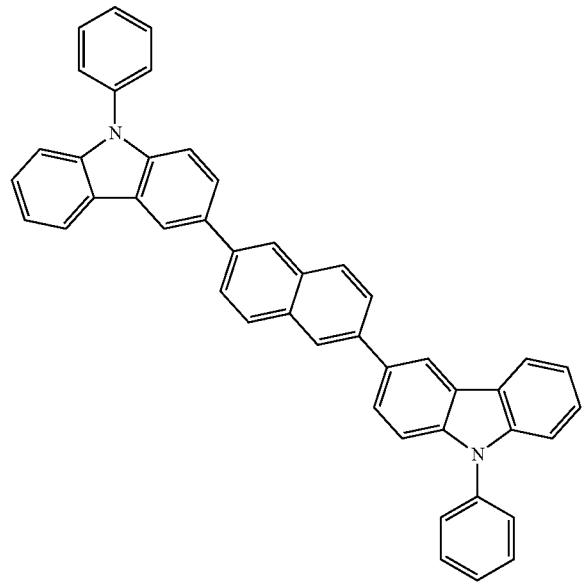
H1-301
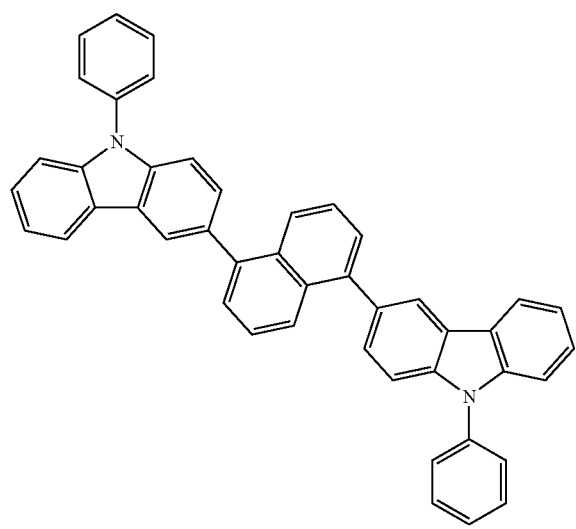
H1-302
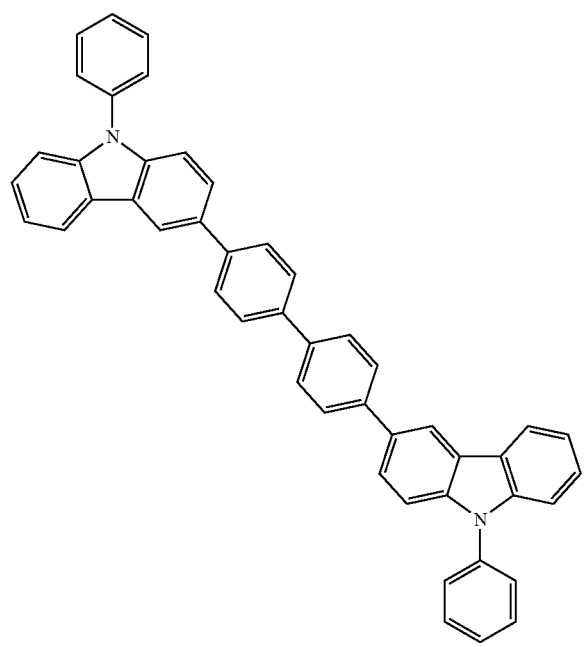

-continued
H1-303
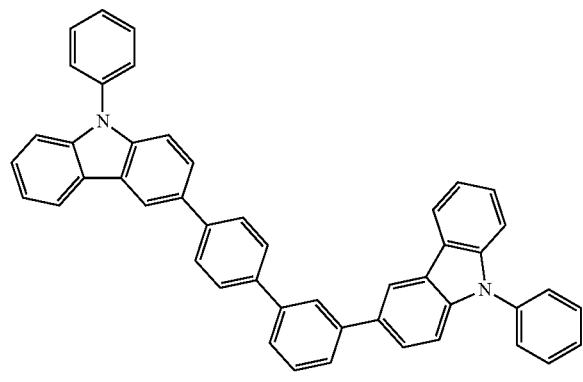
H1-304
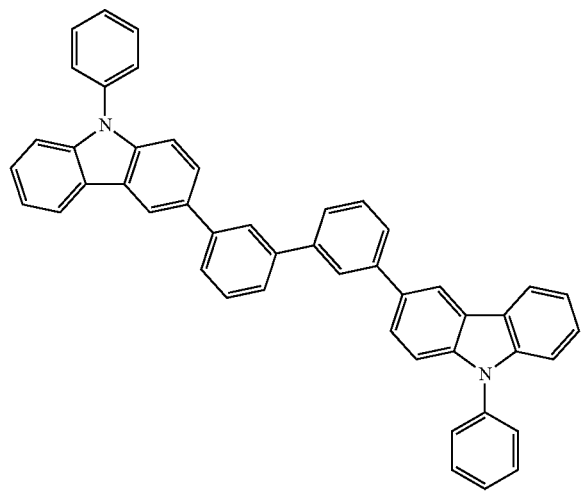
H1-305
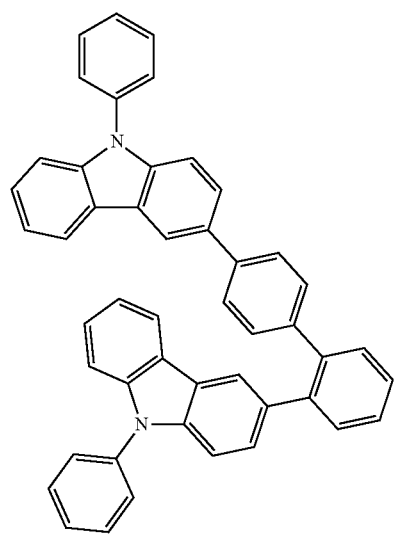
H1-306
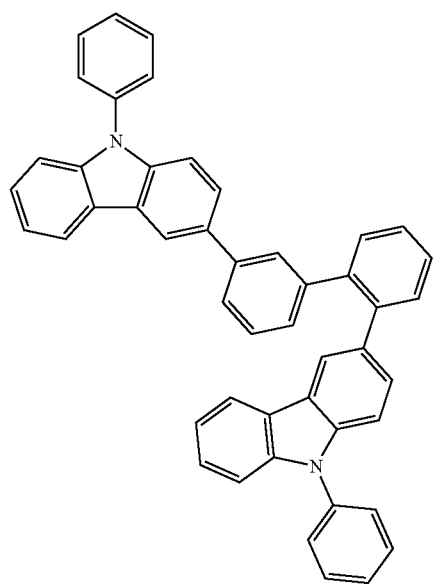

H1-307
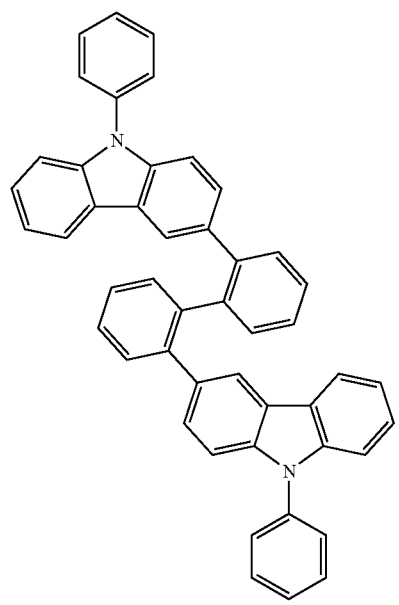
H1-308
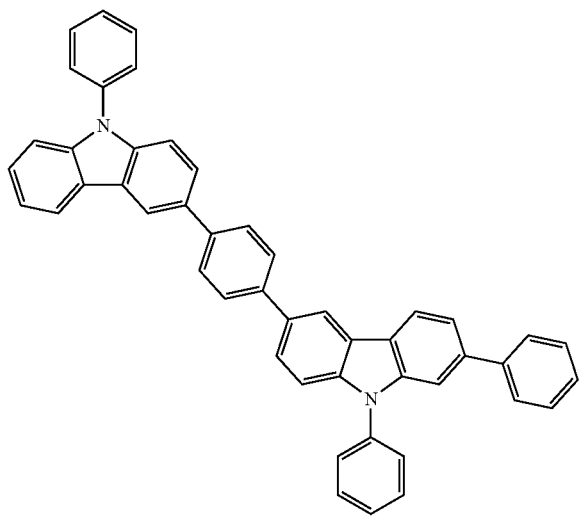
H1-309
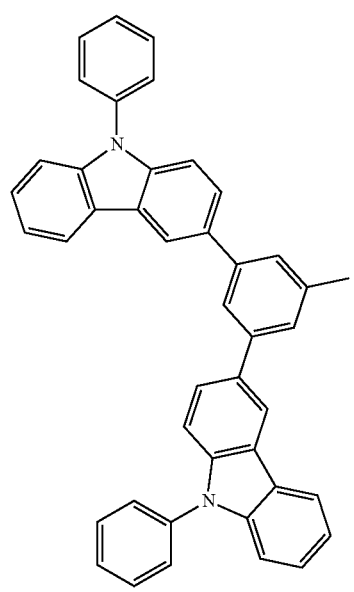

H1-310
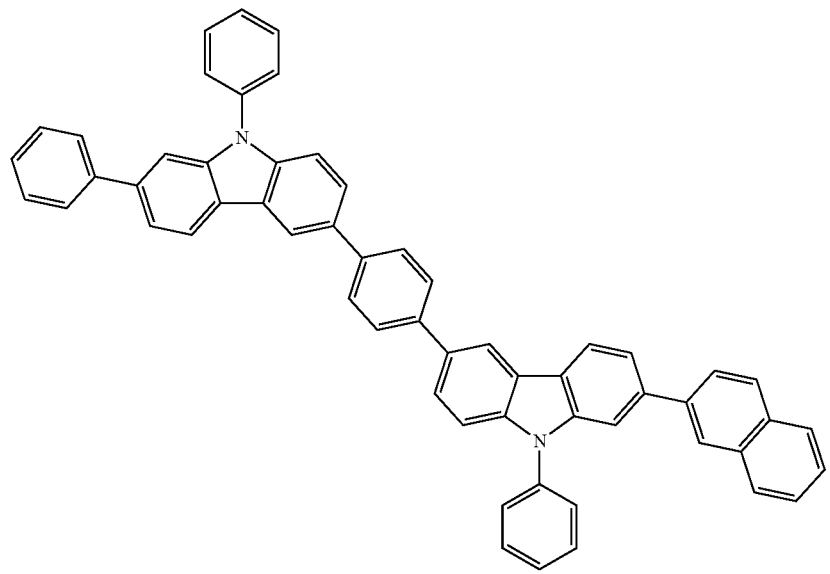
H1-311
H1-312
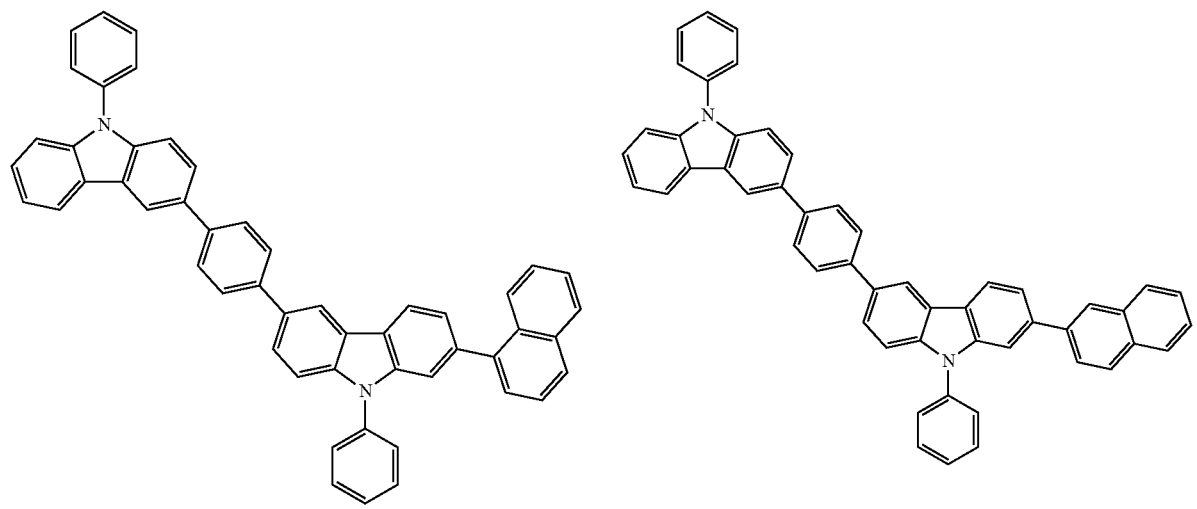

H1-313
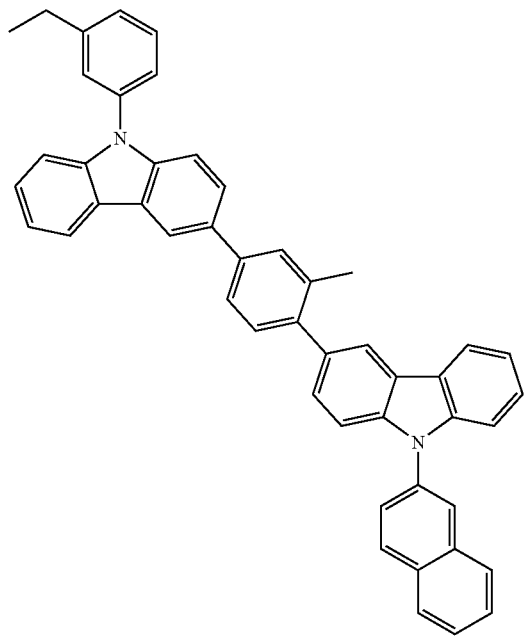
H1-314
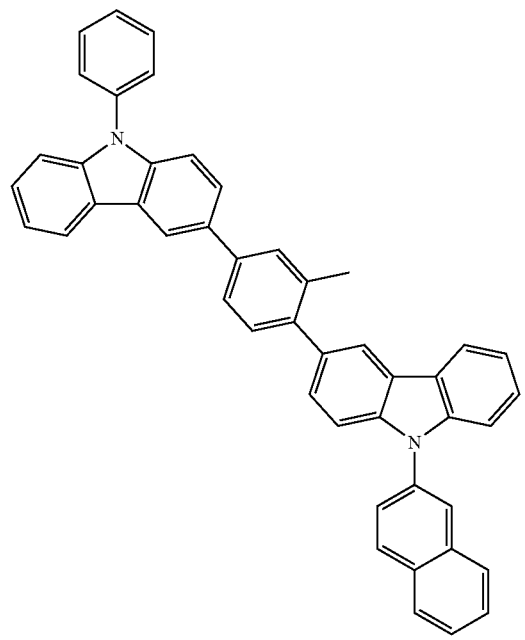
H1-315
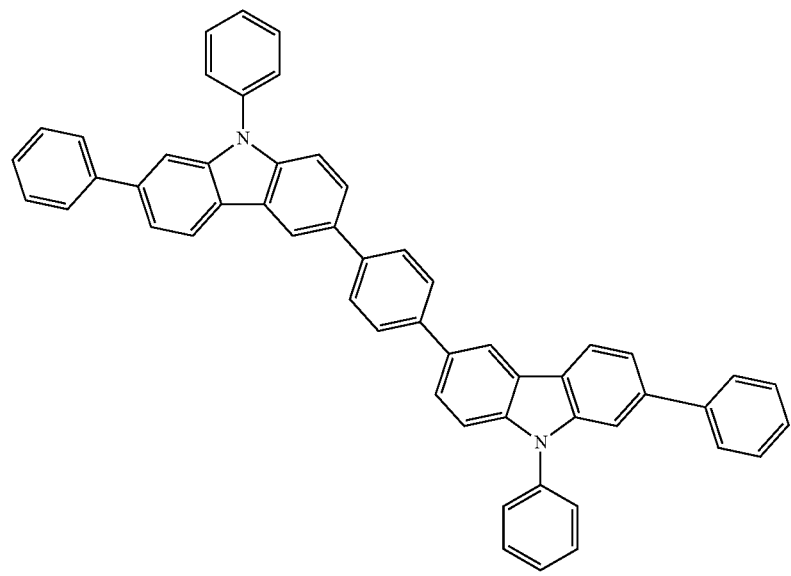

-continued
H1-316
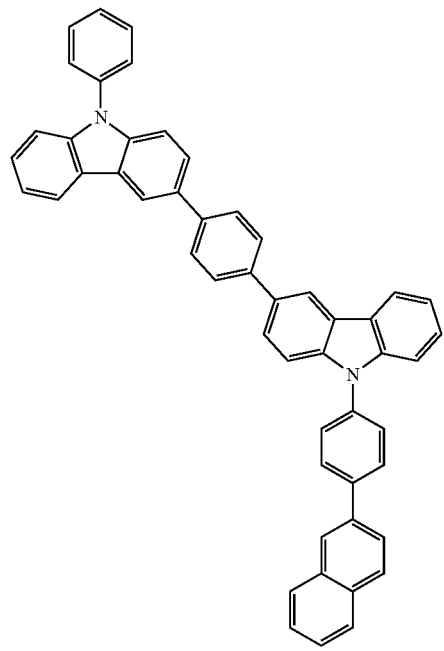
H1-317
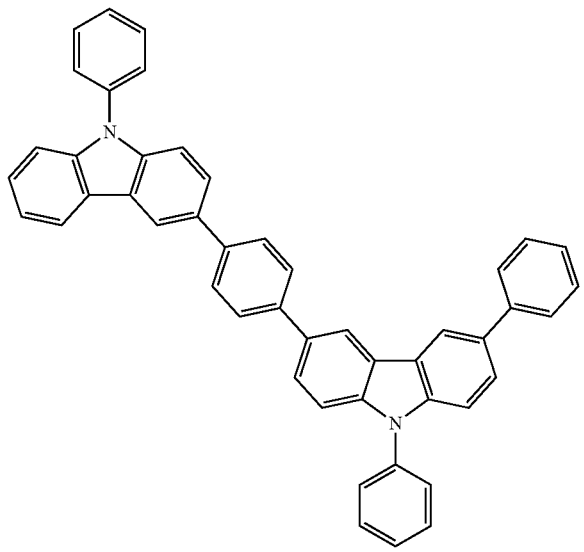
H1-318
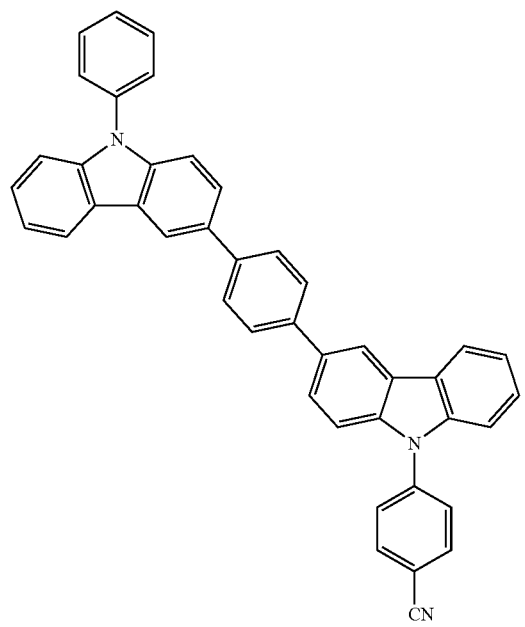
H1-319
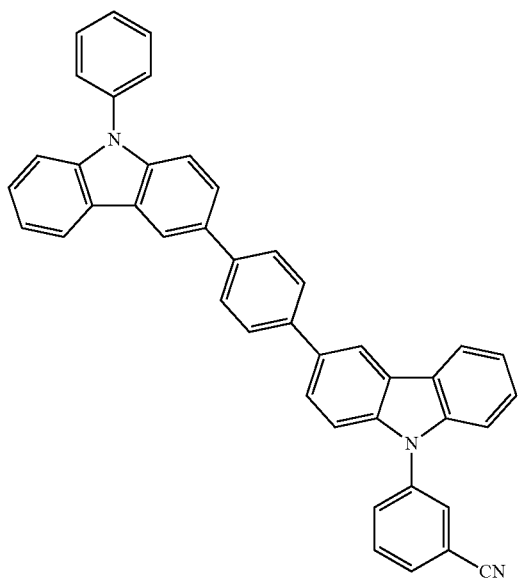

H1-320
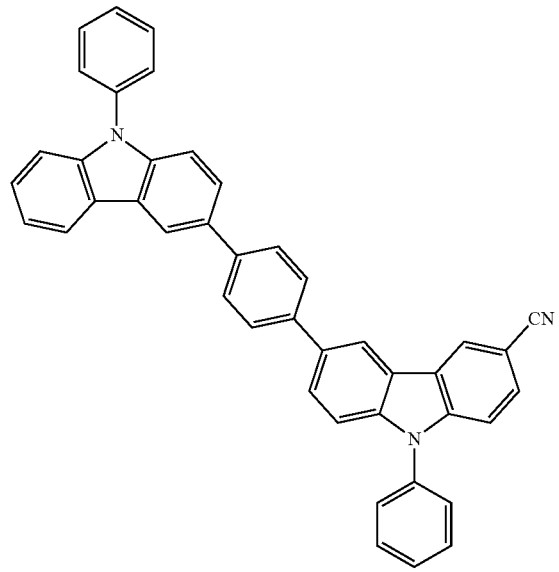
H1-321
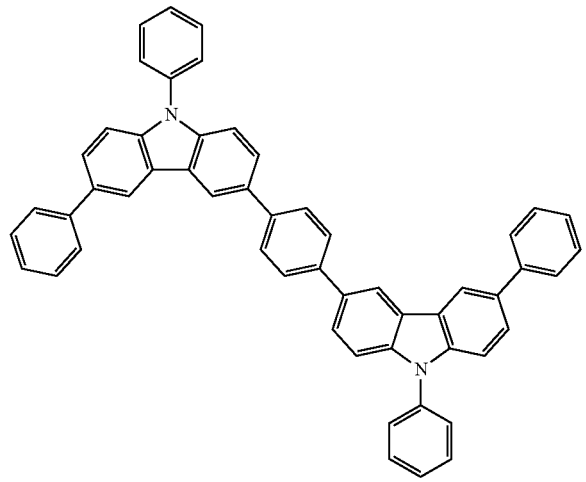
H1-322
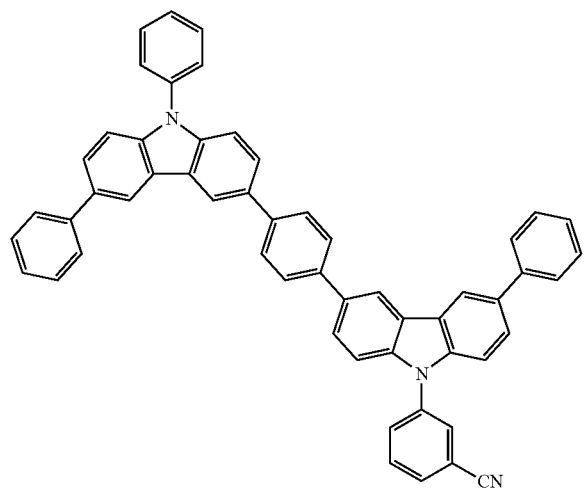
H1-323
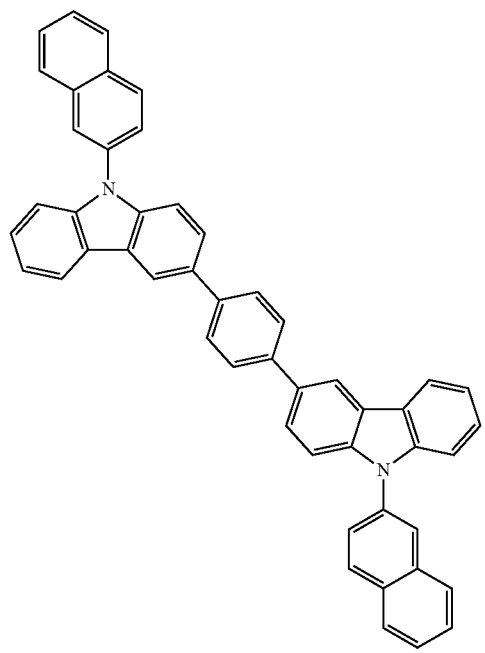

-continued
H1-324
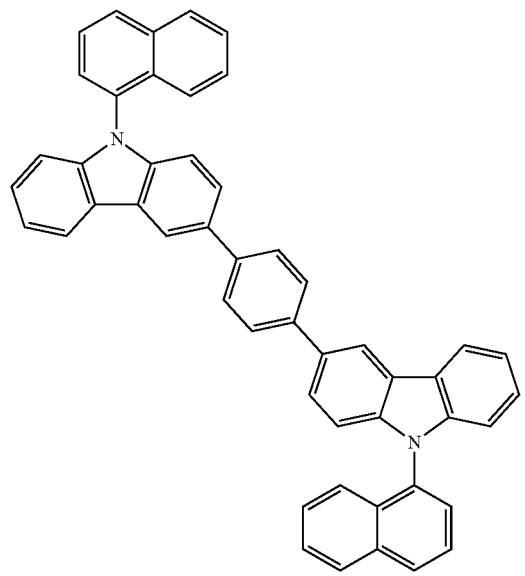
H1-325
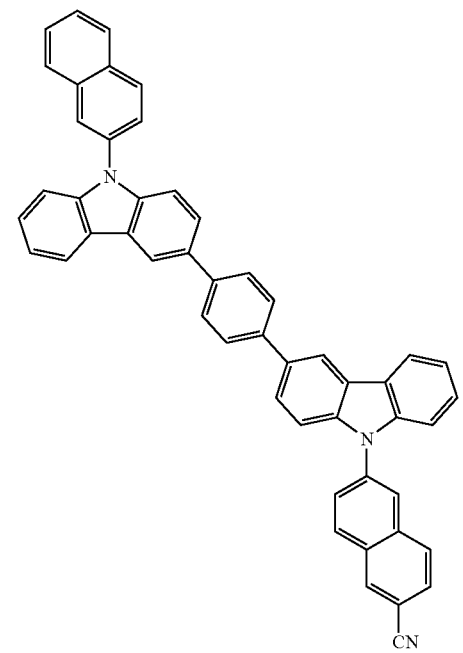
H1-326
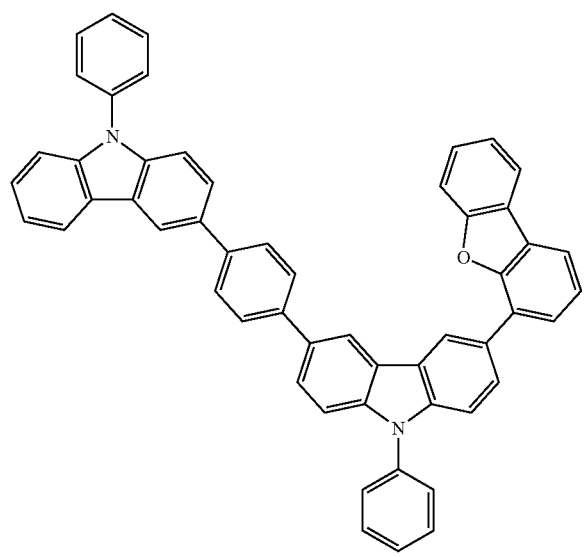
H1-327
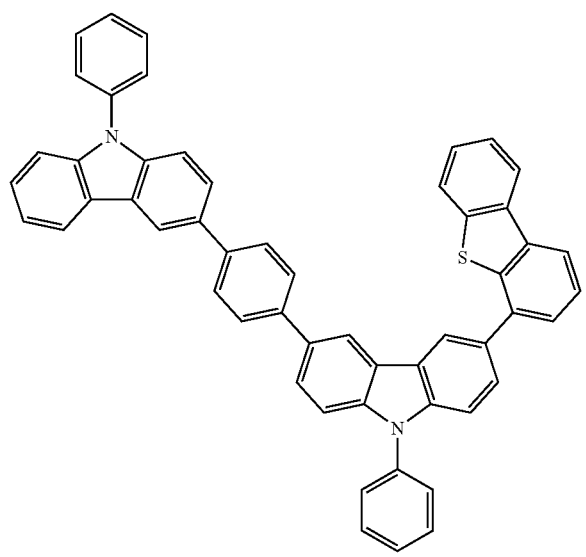

-continued
H1-328
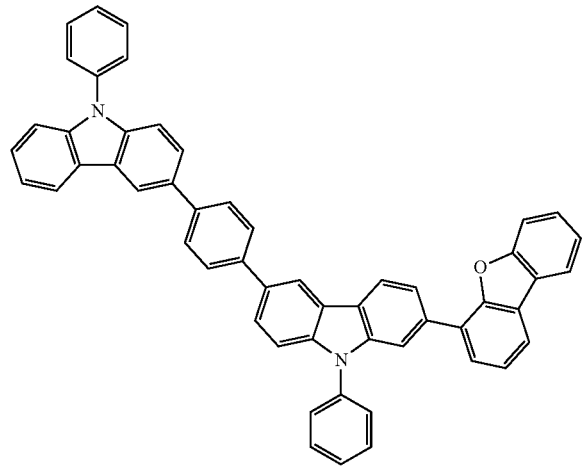
H1-329
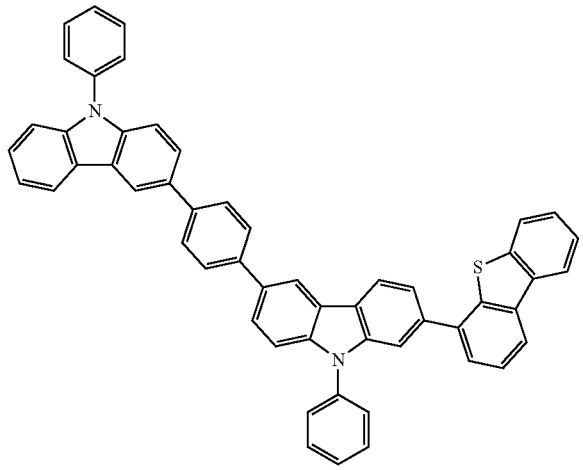
H1-330
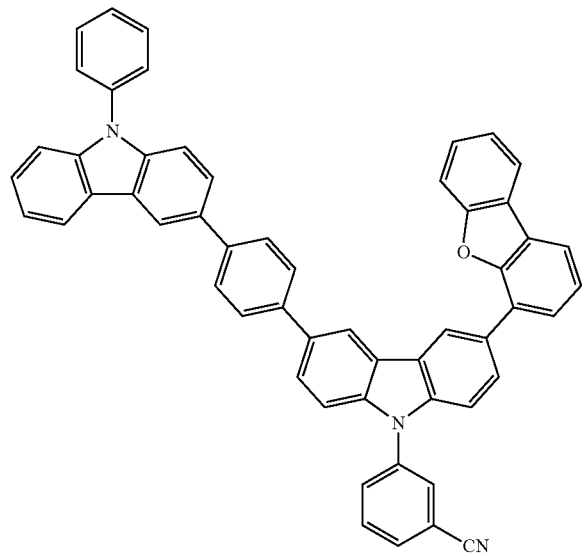
H1-331
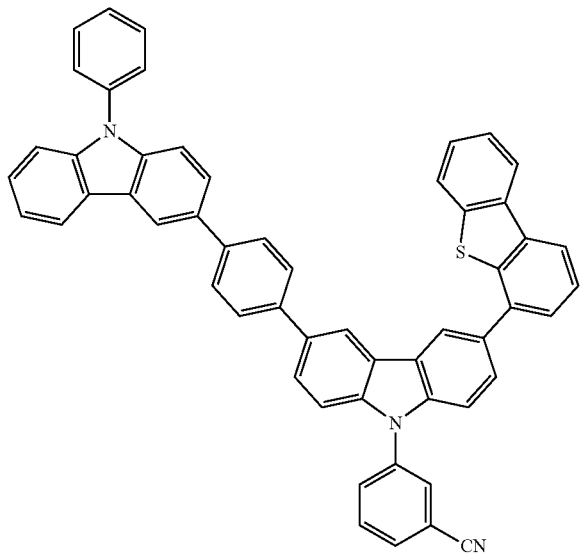
H1-332
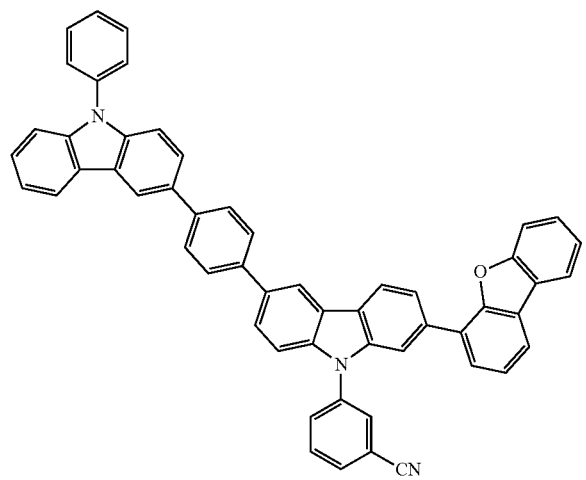
H1-333
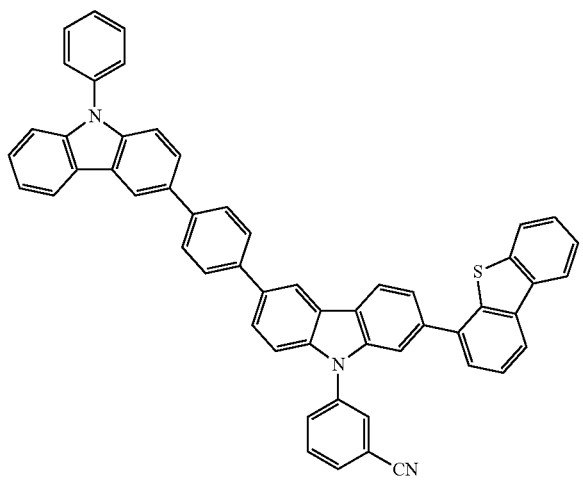

-continued
H1-334
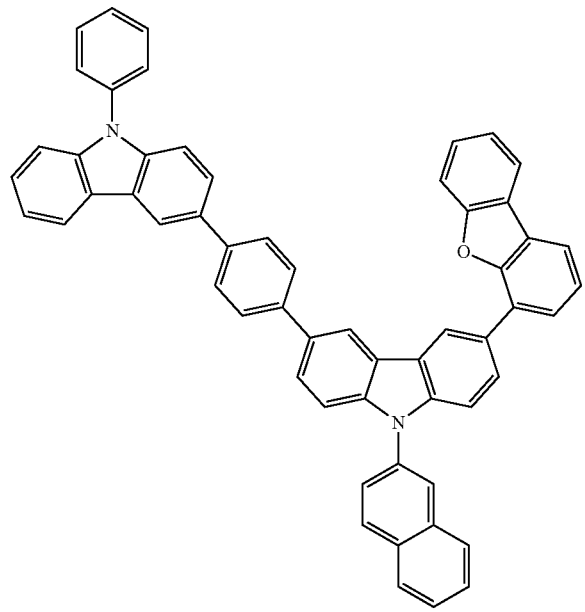
H1-335
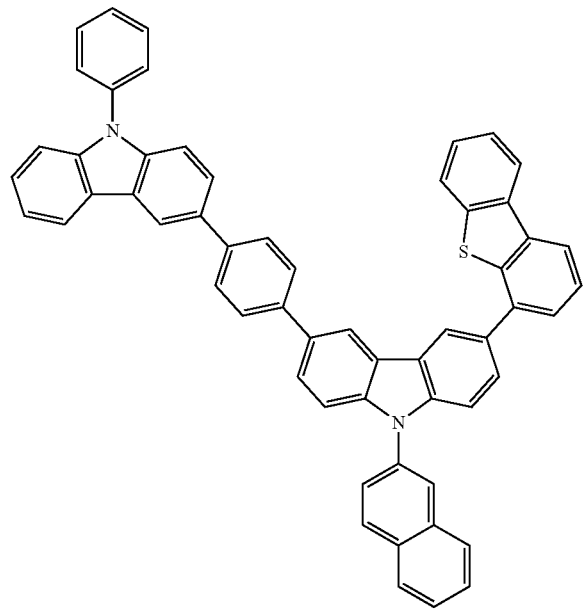
H1-336
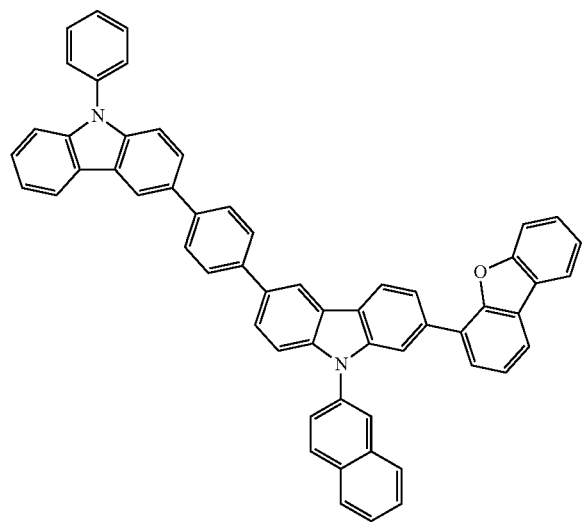
H1-337
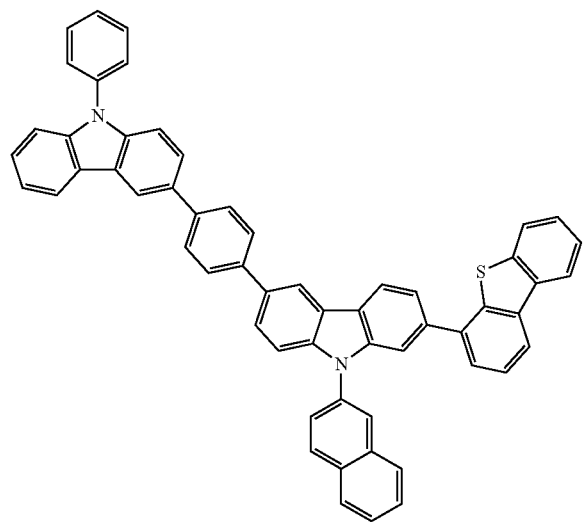

H1-338
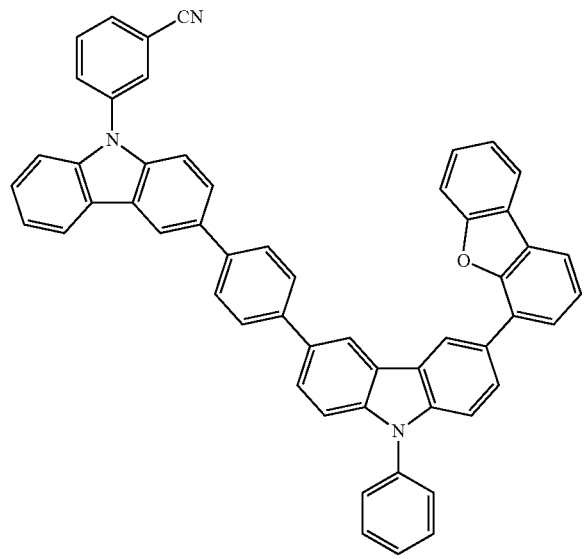
H1-339
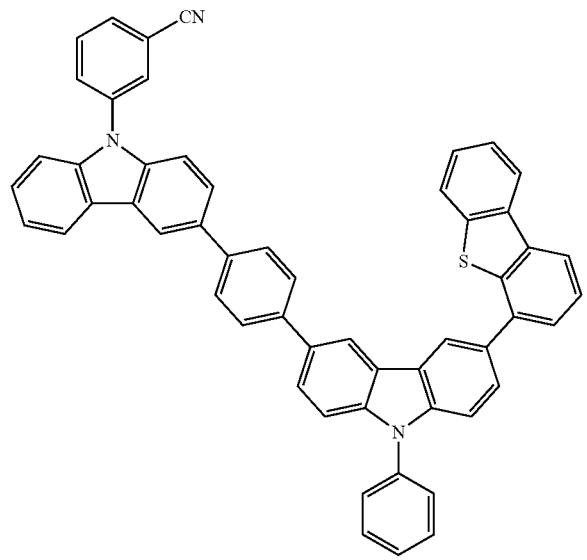
H1-340
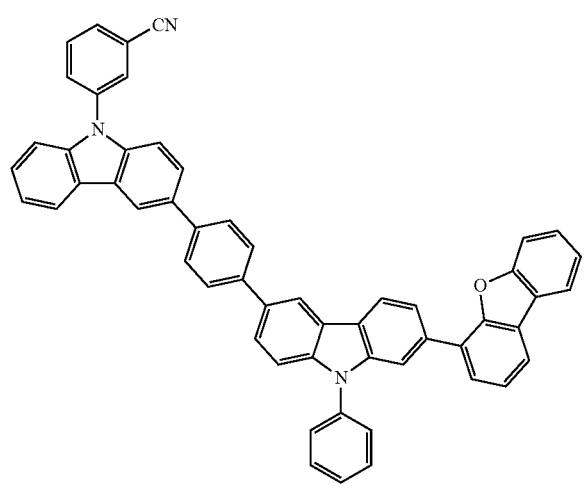
H1-341
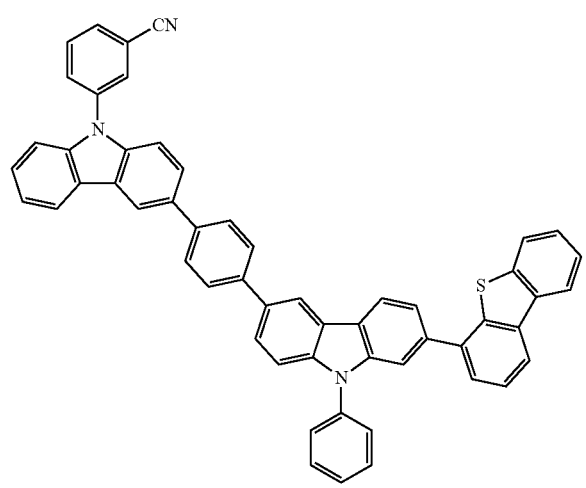

-continued
H1-342
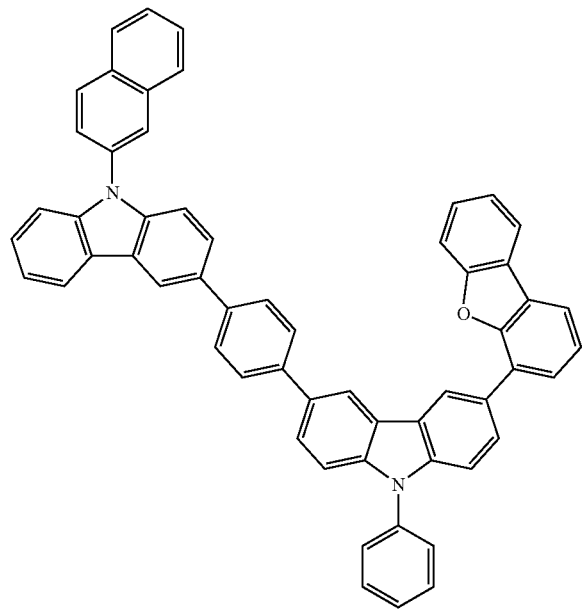
H1-343
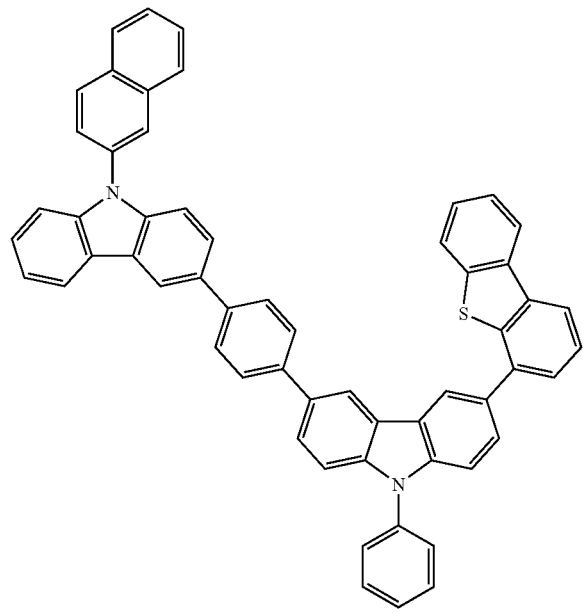
H1-344
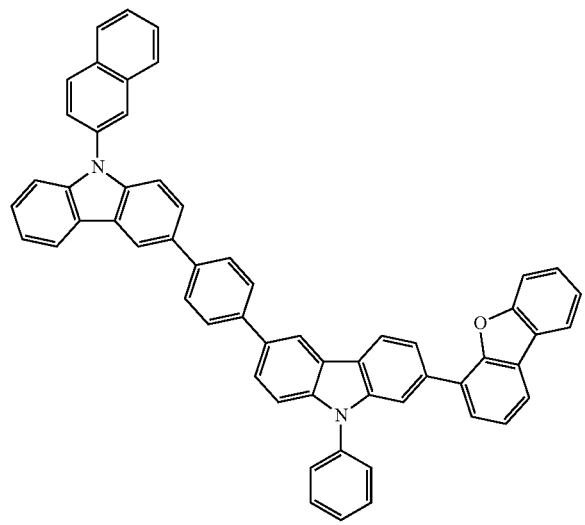
H1-345
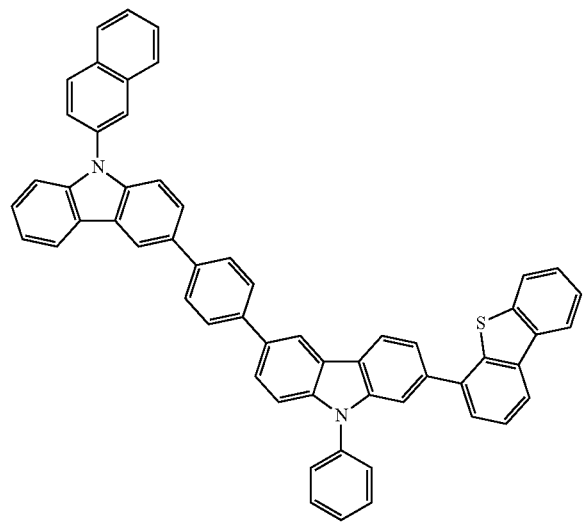

-continued
H1-346
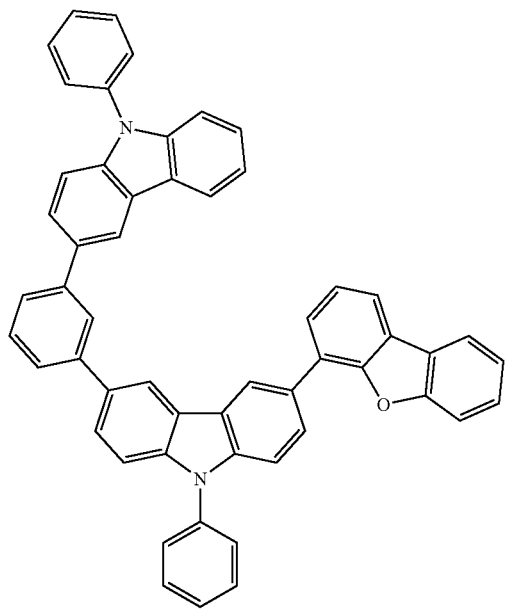
H1-347
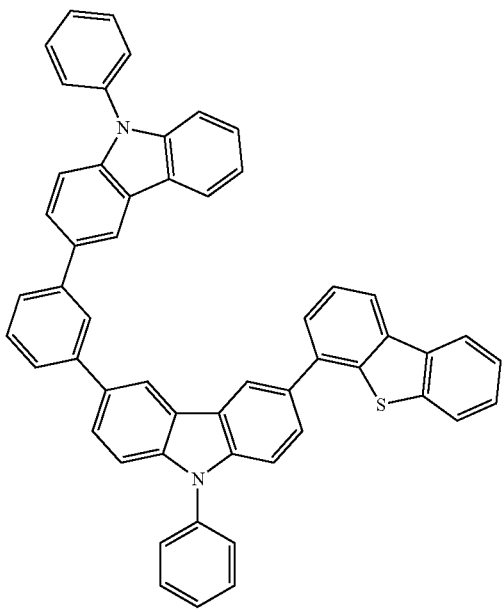
H1-348
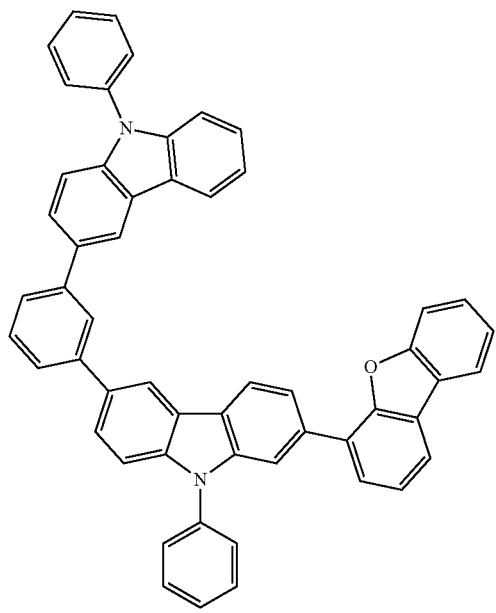
H1-349
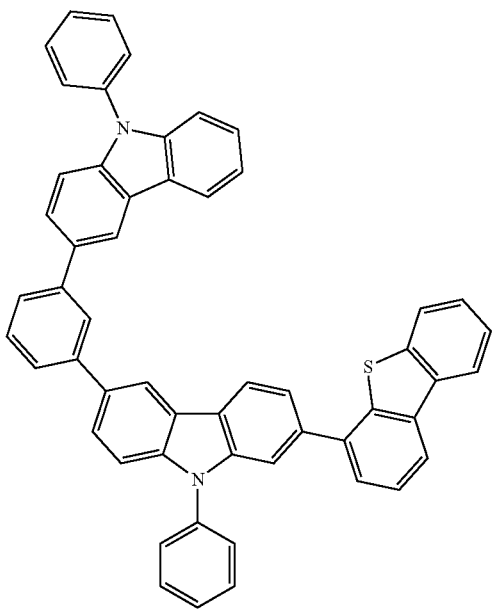

-continued
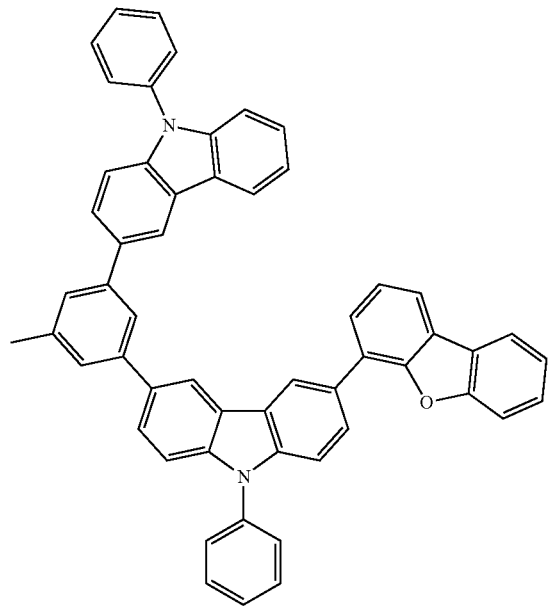

-continued
H1-354
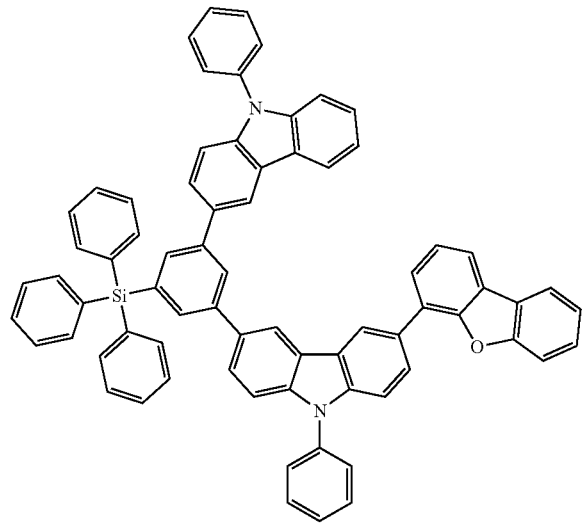
H1-355
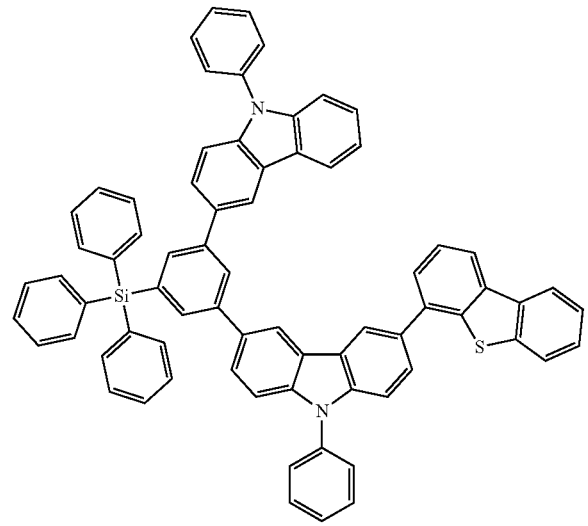
H1-356
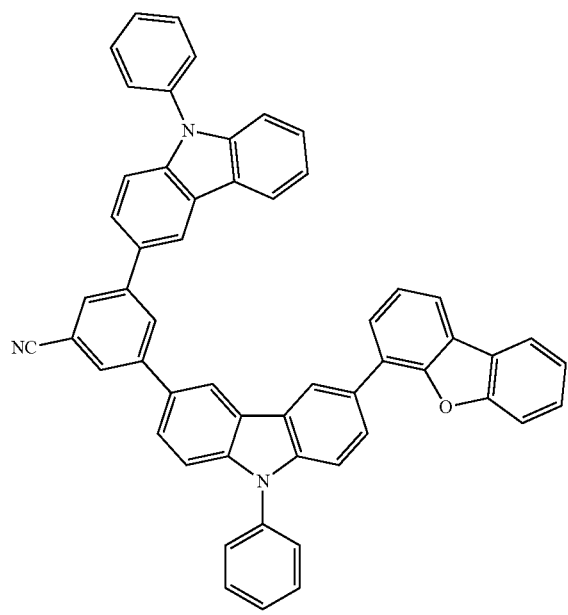
H1-357
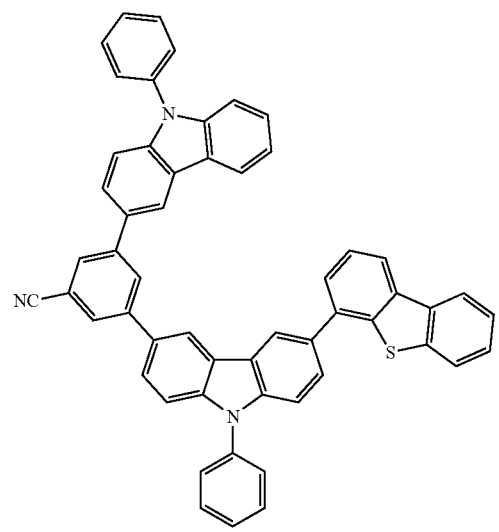

-continued
H1-358
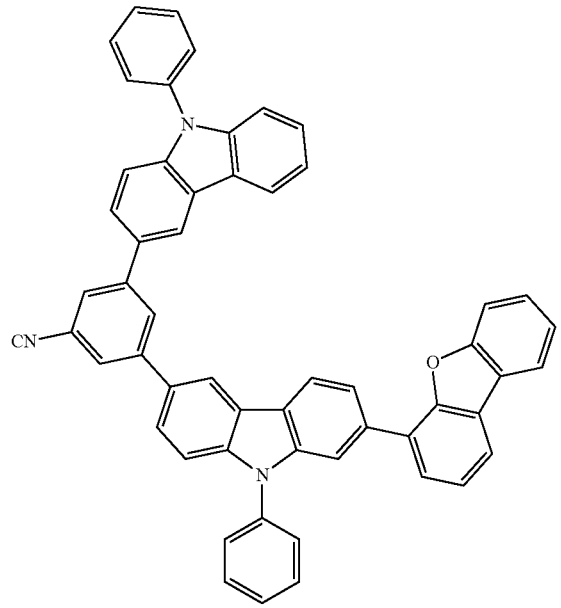
H1-359
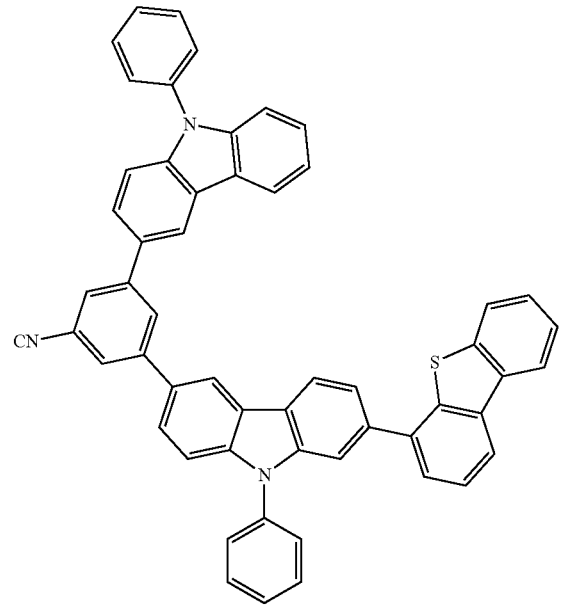
H1-360
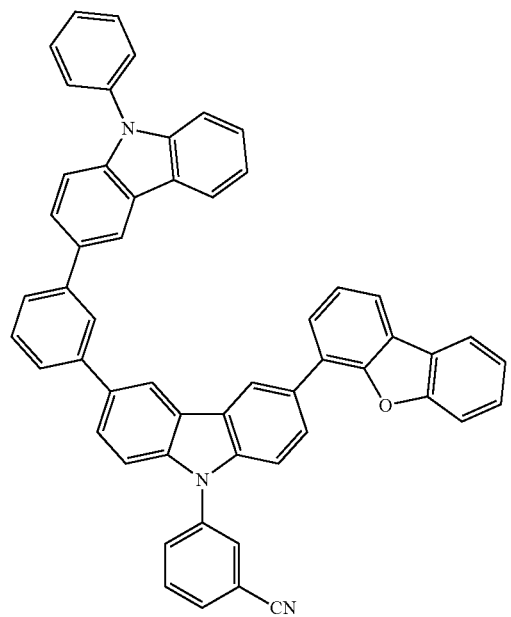
H1-361

-continued
H1-362
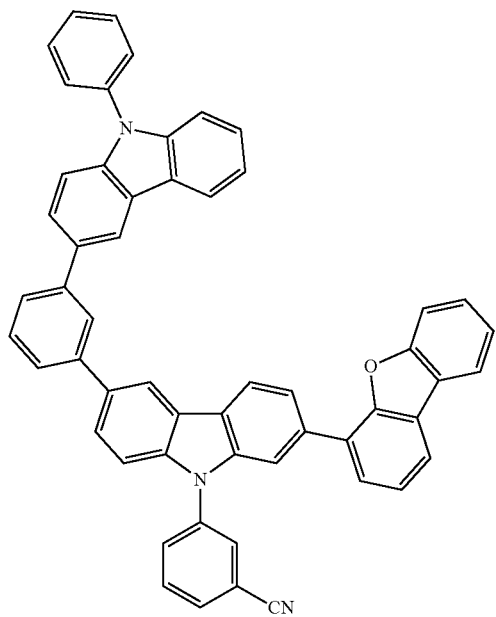
H1-363
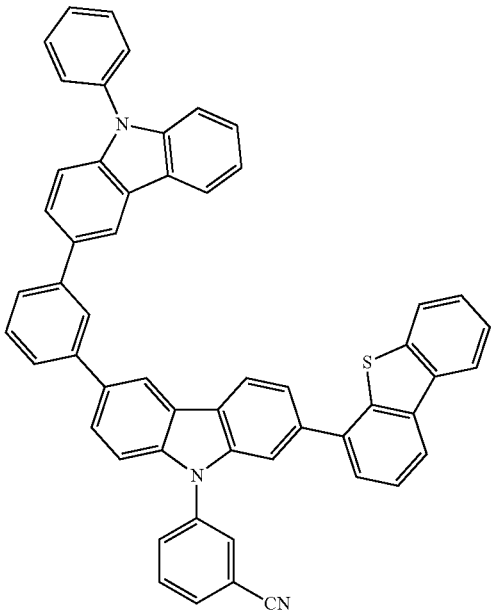
H1-364
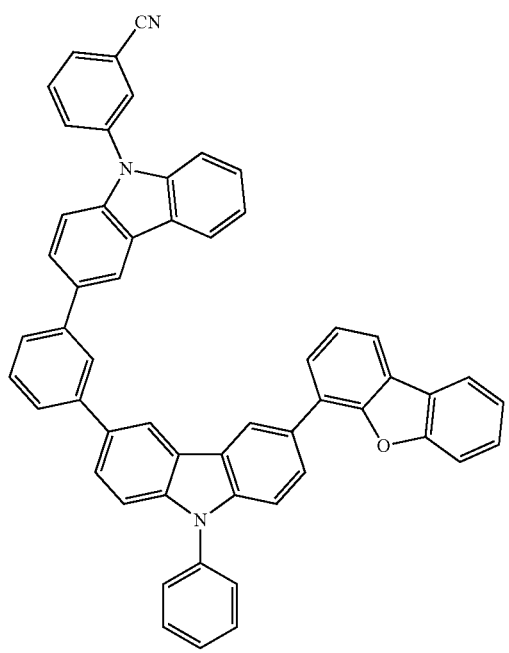
H1-365
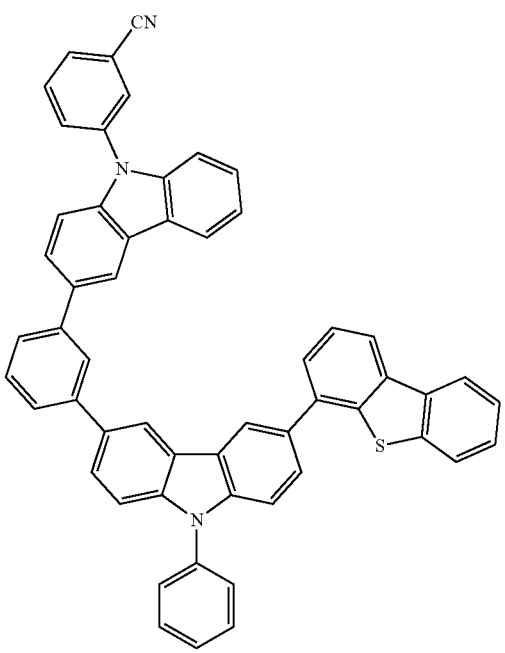

-continued
H1-366
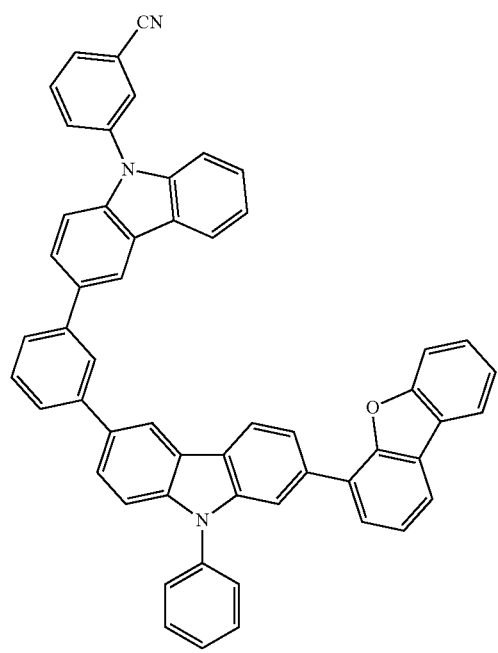
H1-367
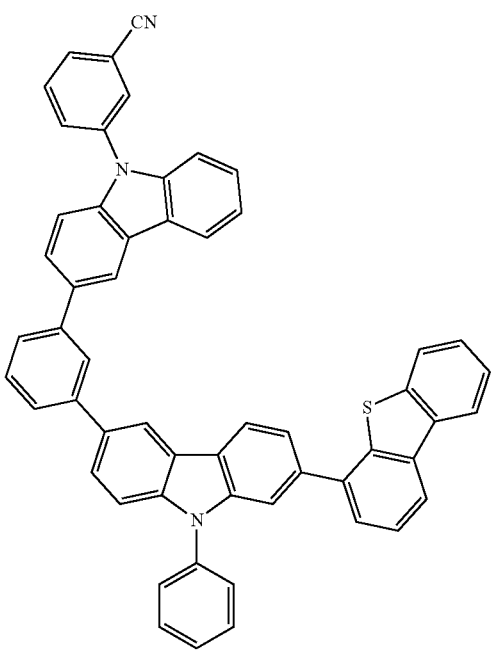
H1-368
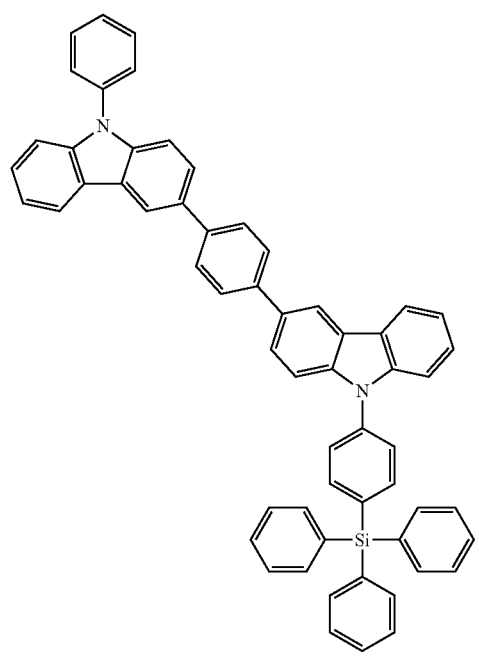
H1-369
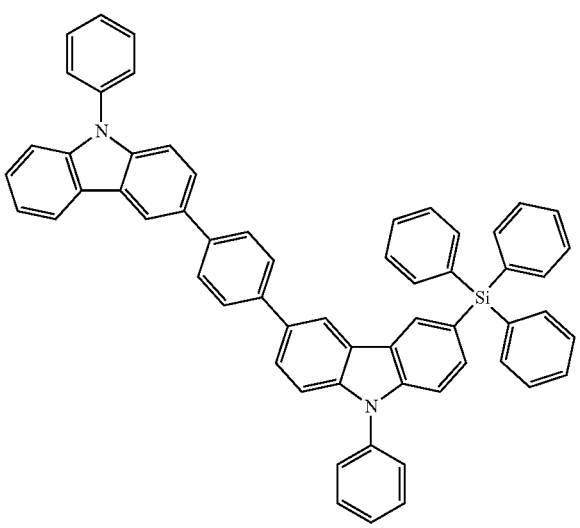

-continued
H1-370
H1-371
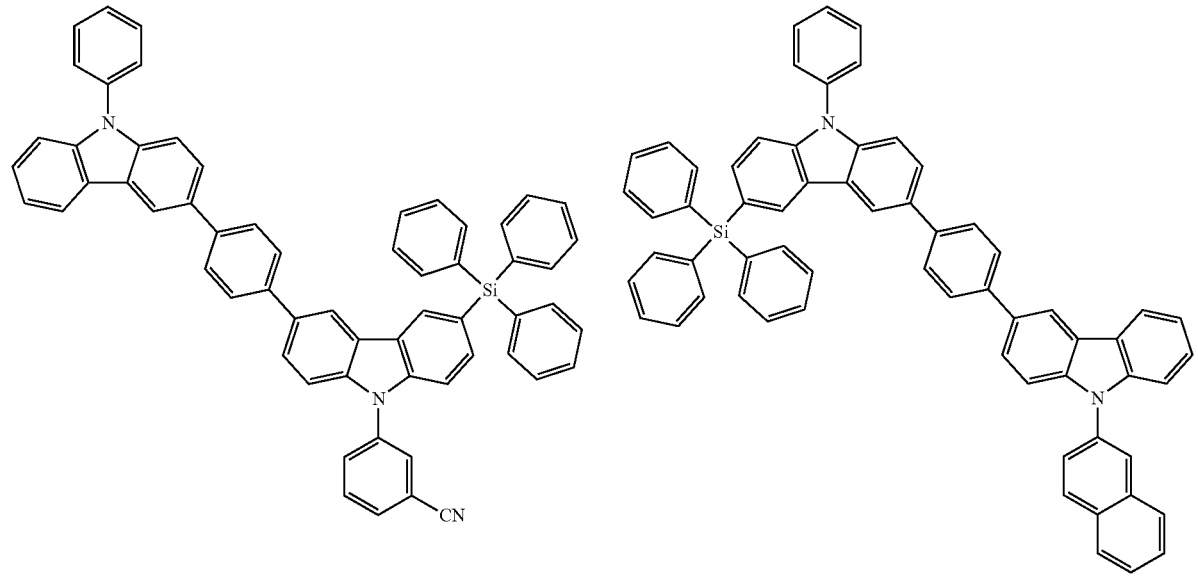
H1-372
H1-373
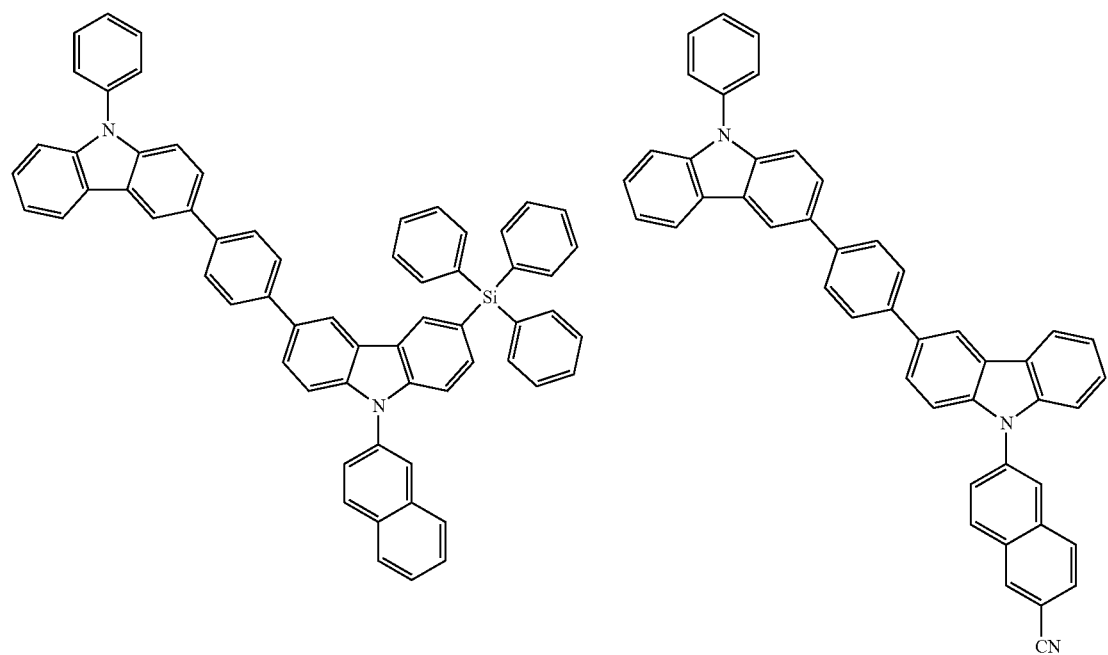

-continued
H1-374
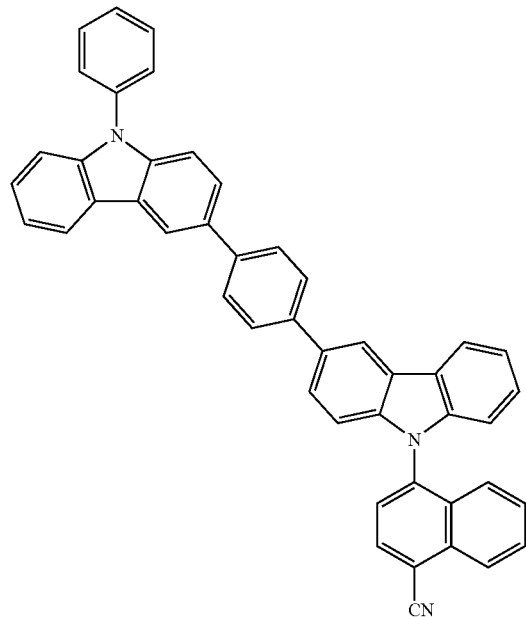
H1-375
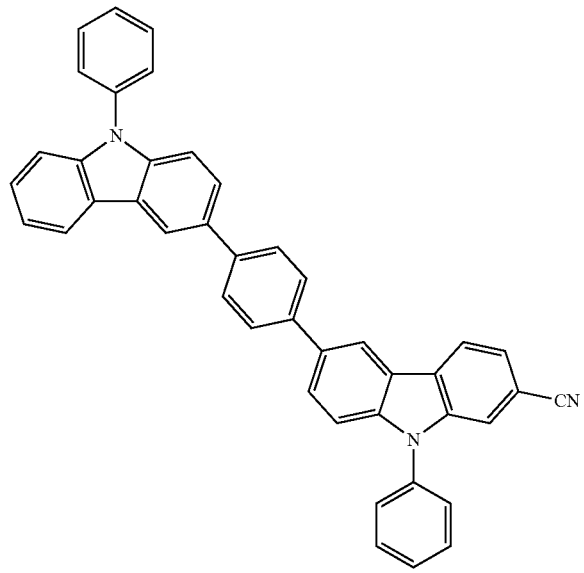
H1-376
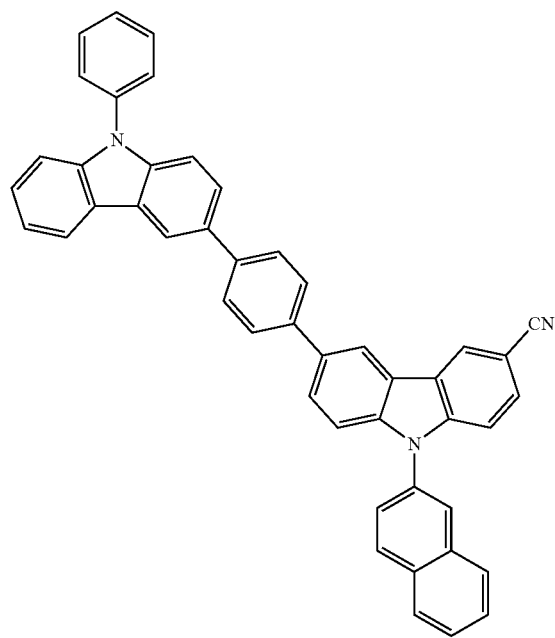
H1-377
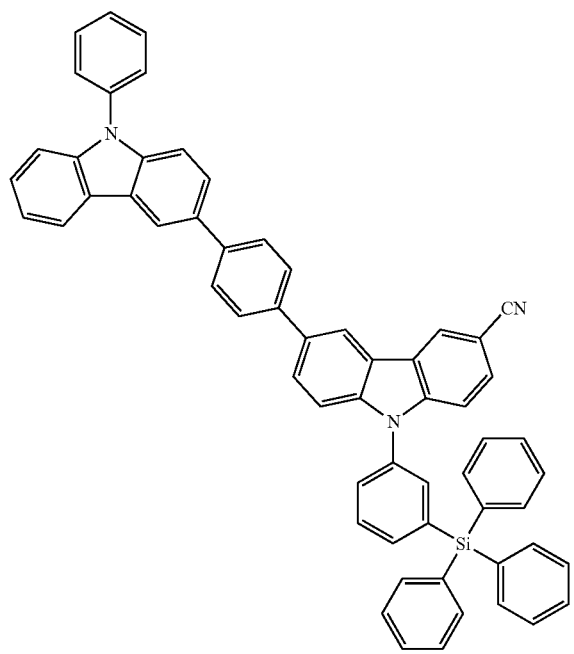

-continued
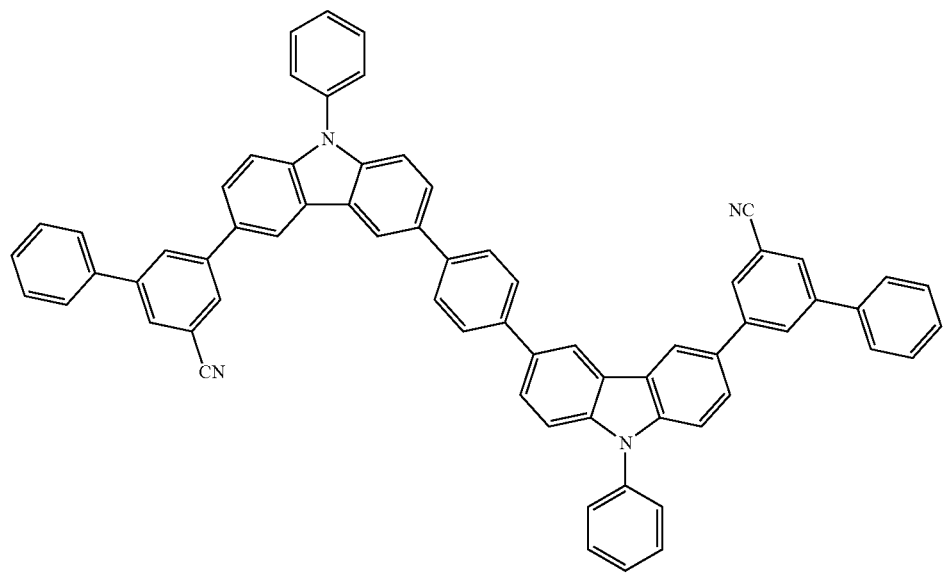
H1-378
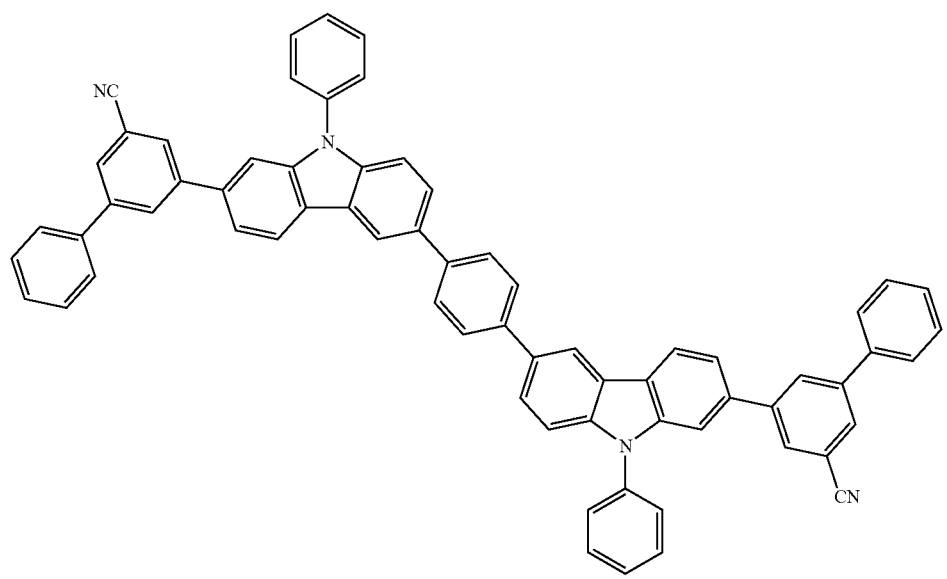
H1-379
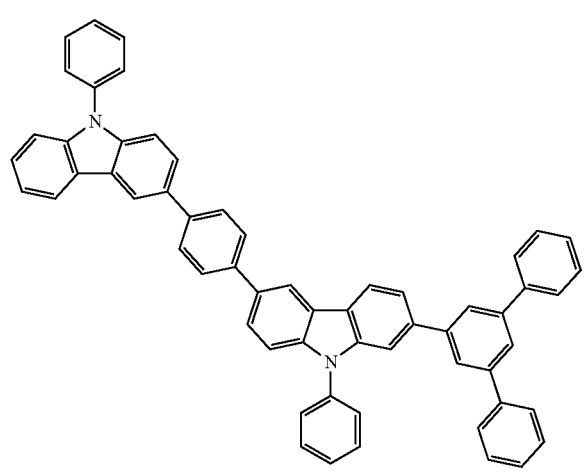
H1-380
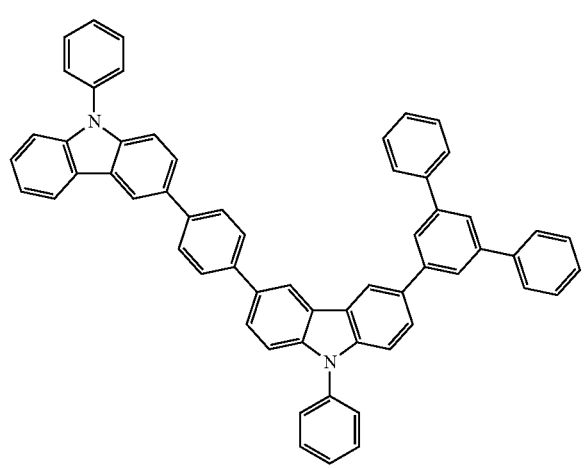
H1-381

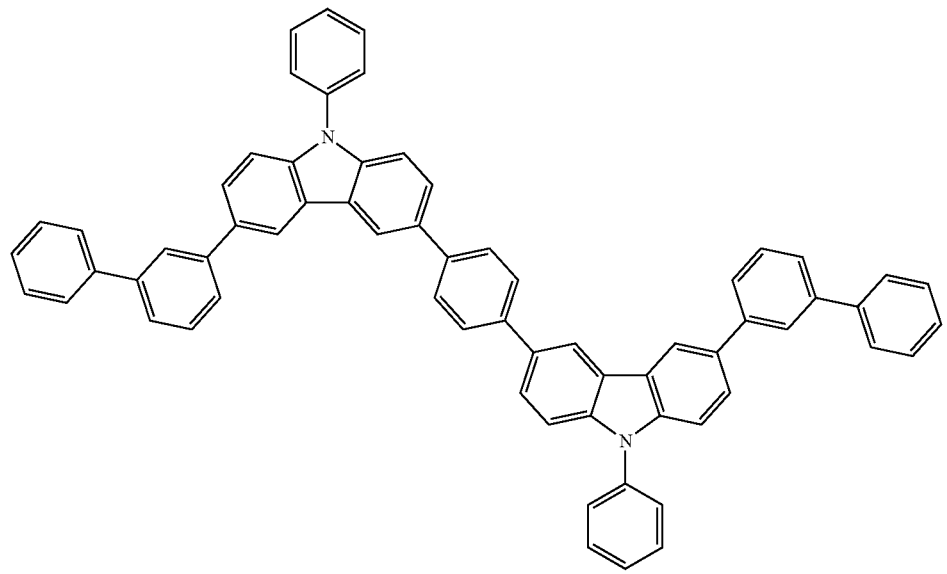
H1-382
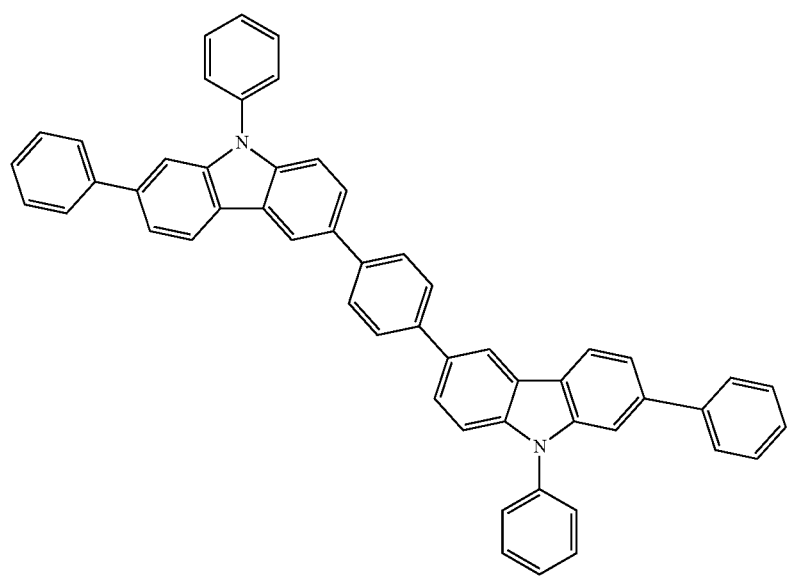
H1-383

H1-384
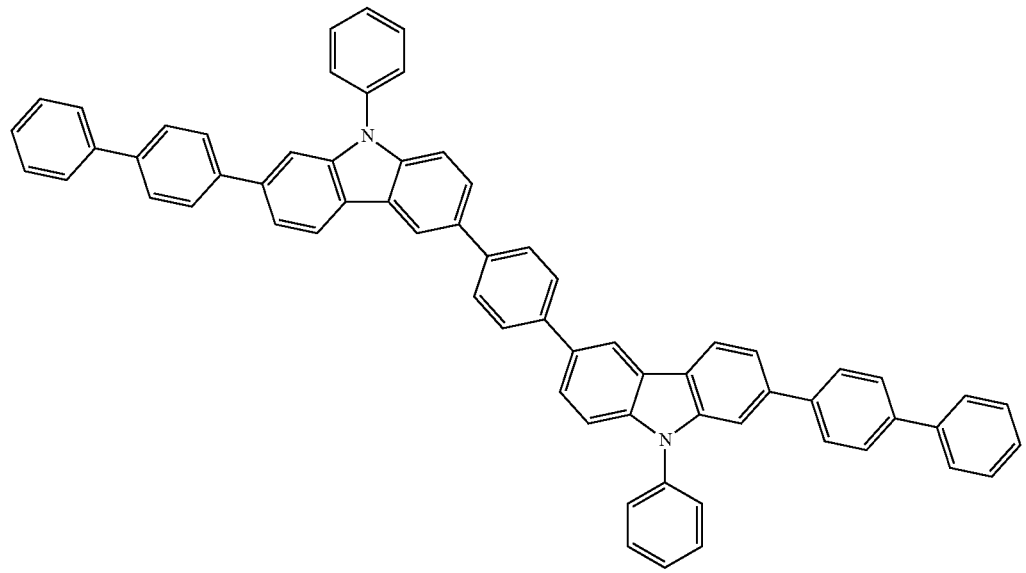
H1-385
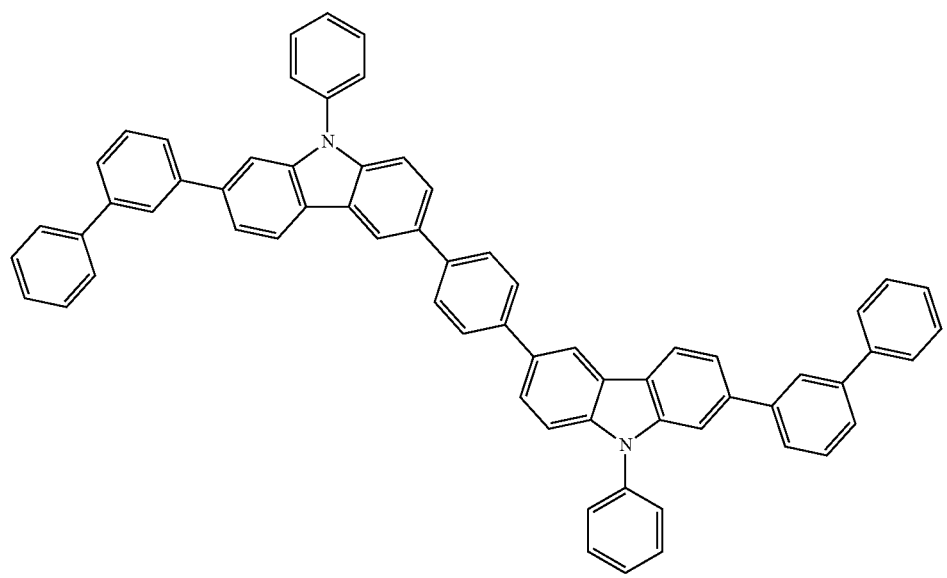
H1-386    H1-387
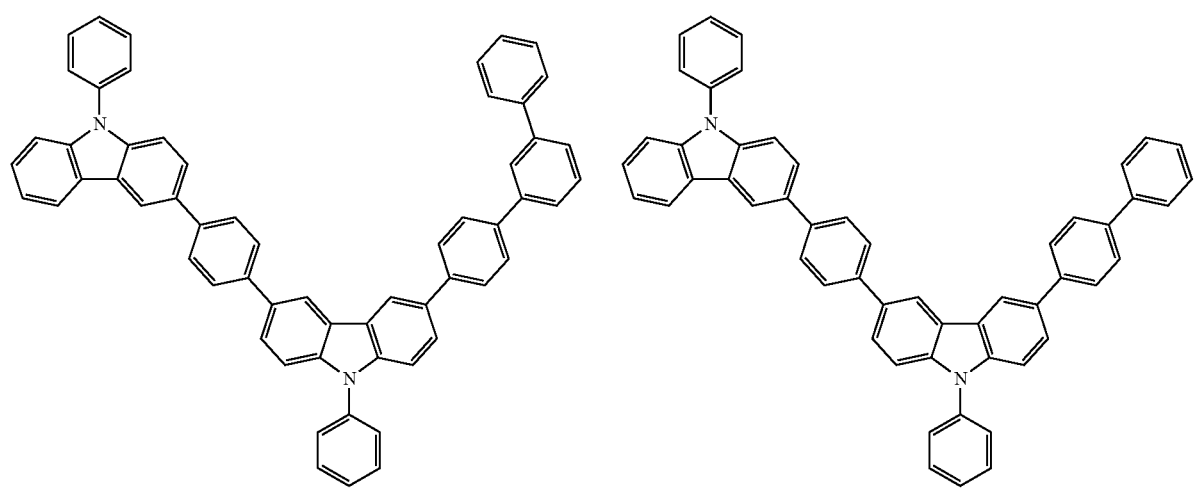

H1-388
H1-389
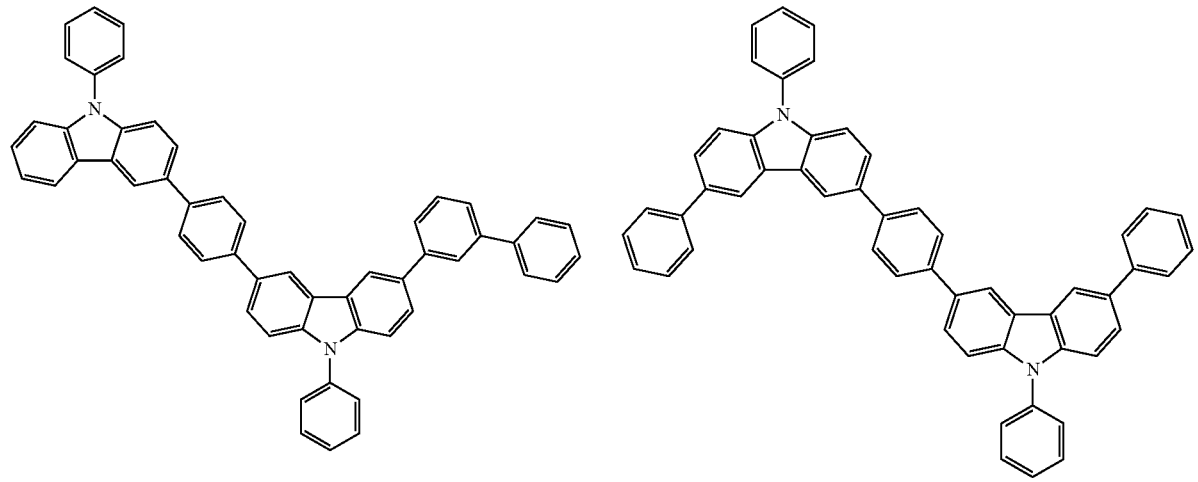
H1-390
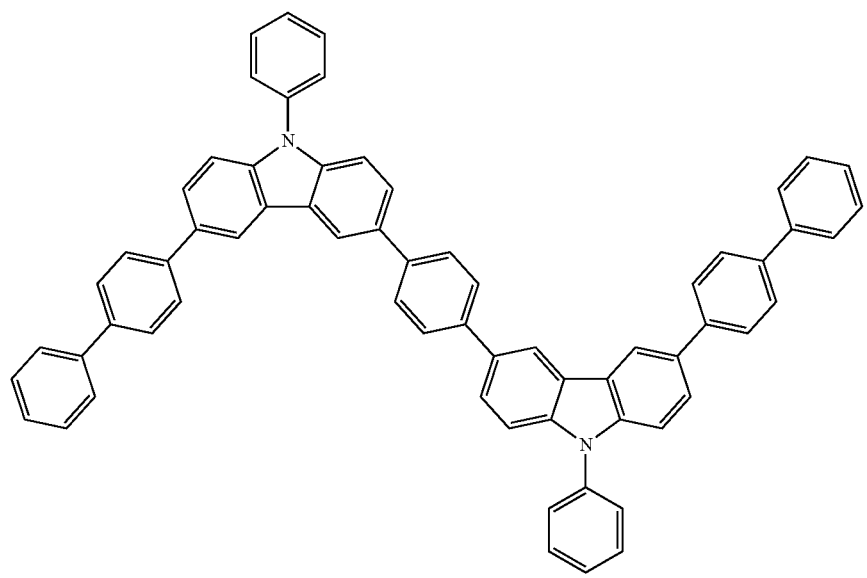

-continued
H1-391
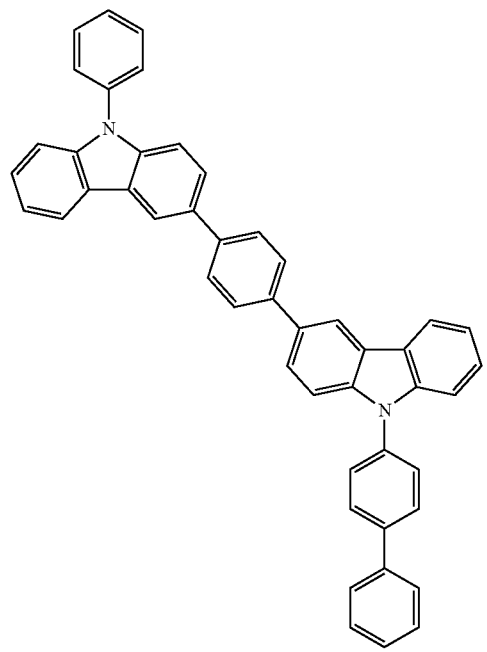
H1-392
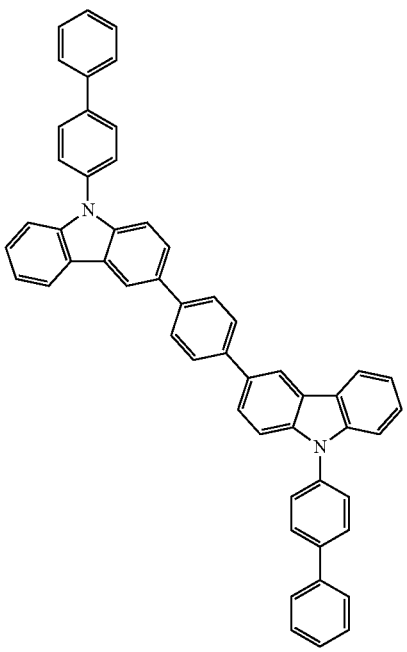
H1-393
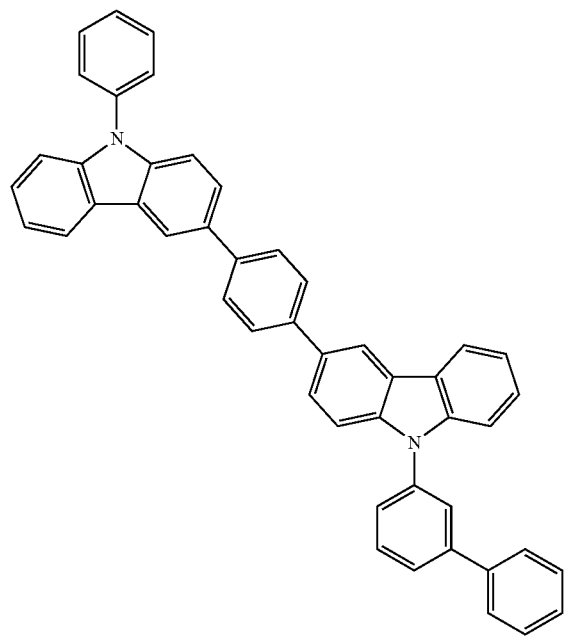
H1-394
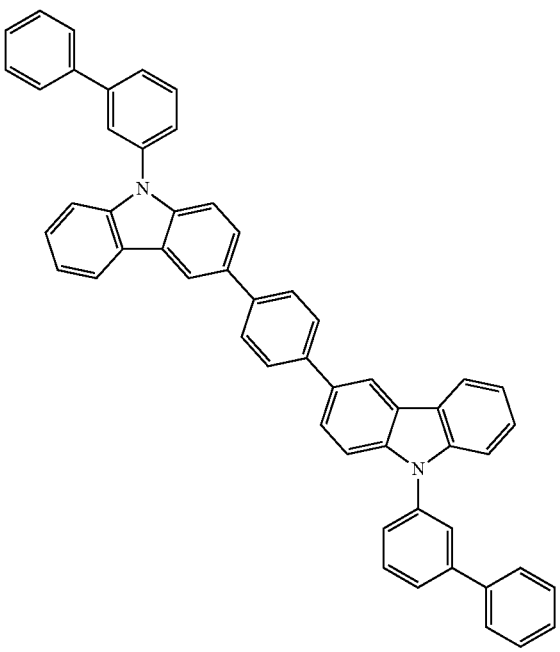

-continued
H1-395
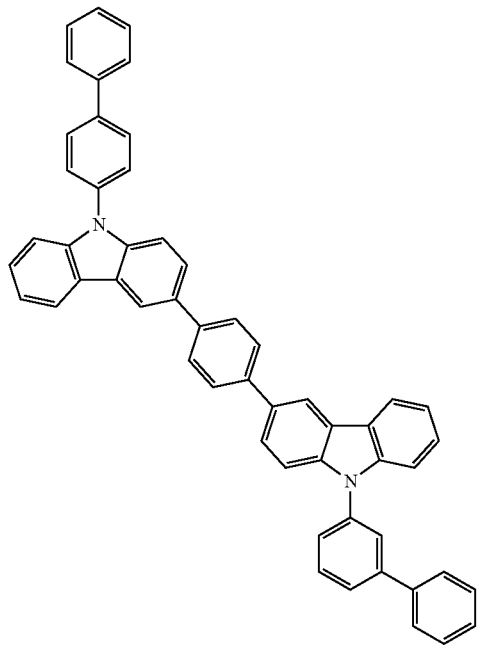
H1-396
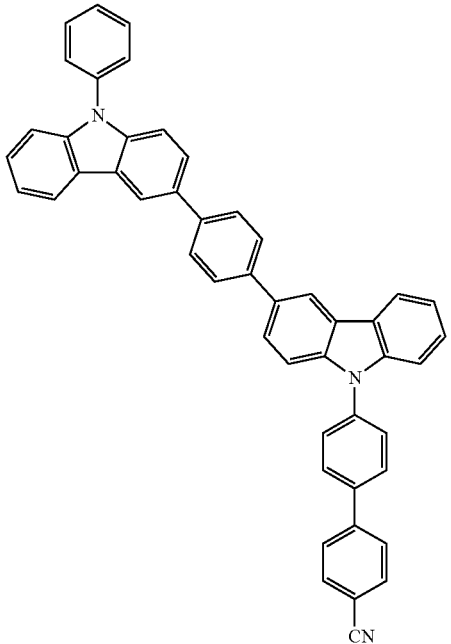
H1-397
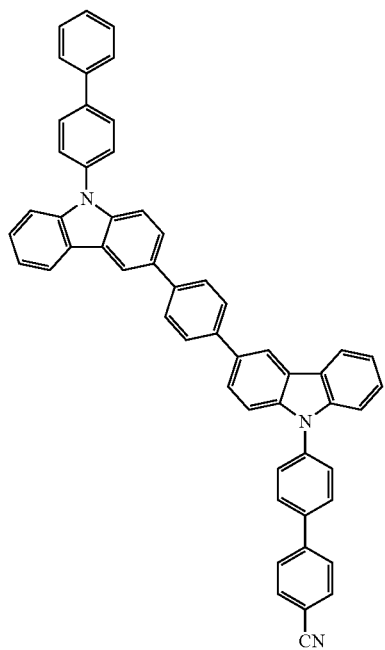
H1-398
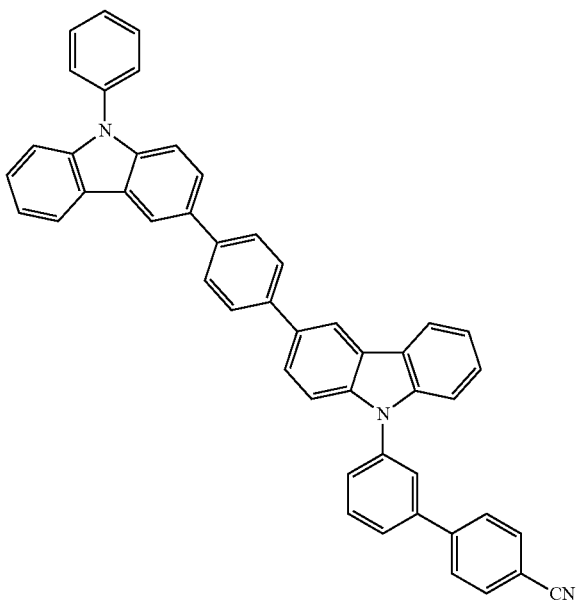

H1-399
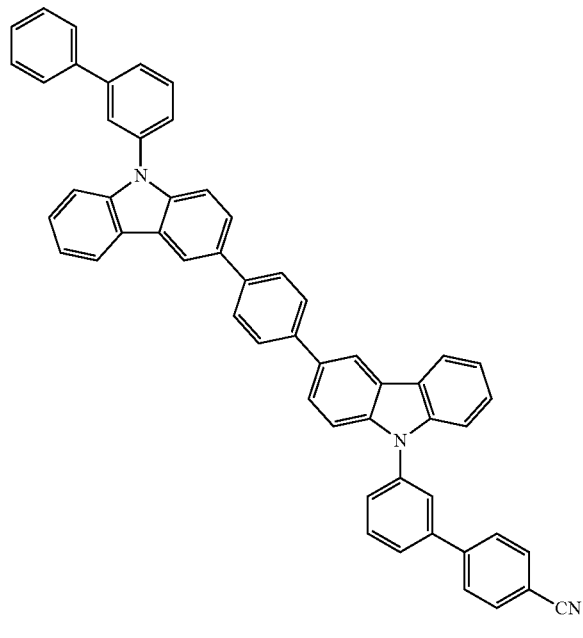
H1-400
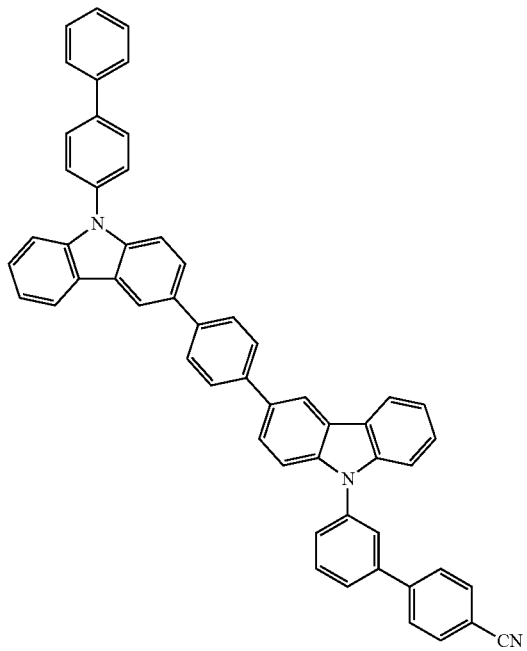
H1-401
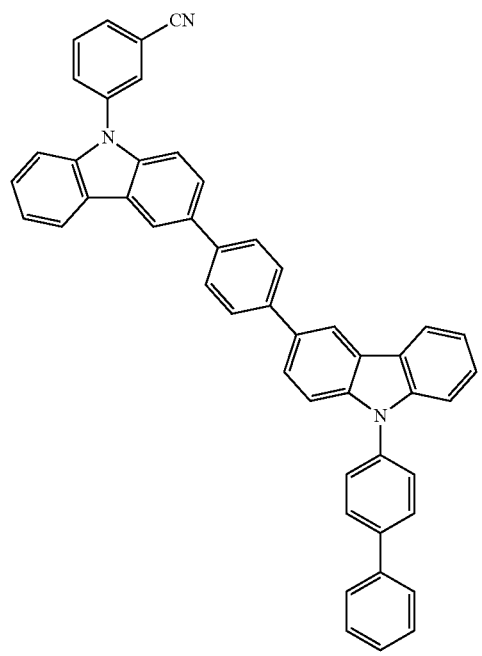
H1-402
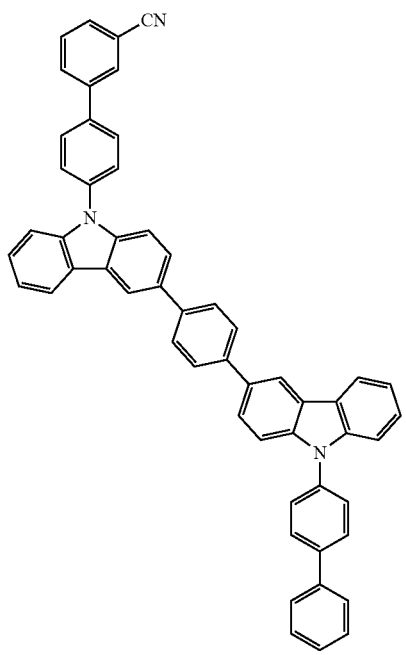

-continued
H1-403
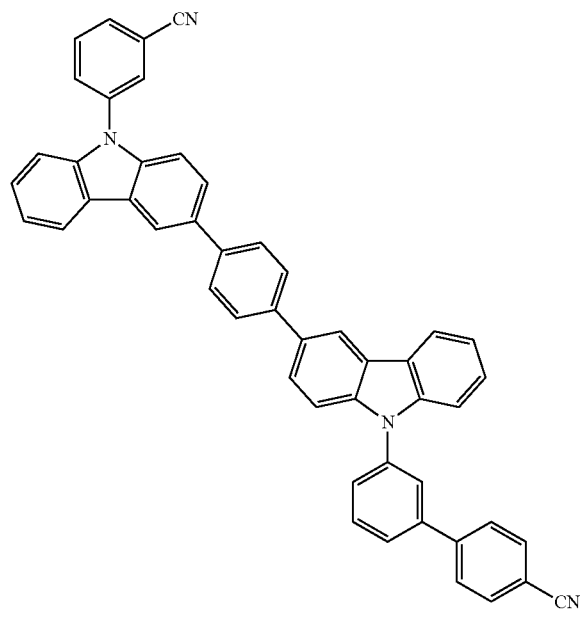
H1-404
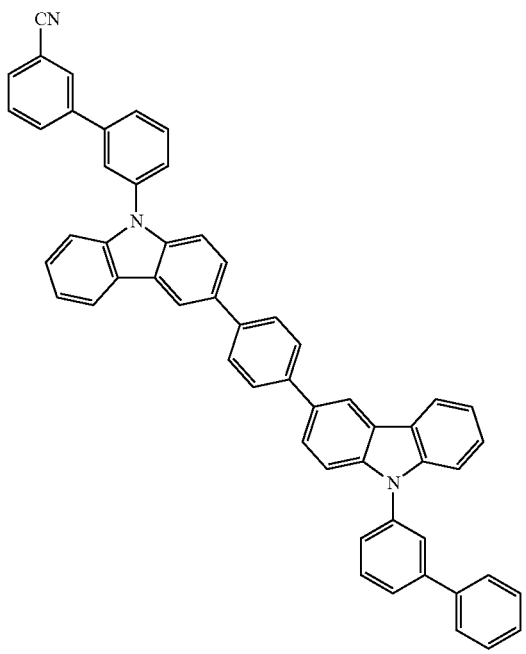
H1-405
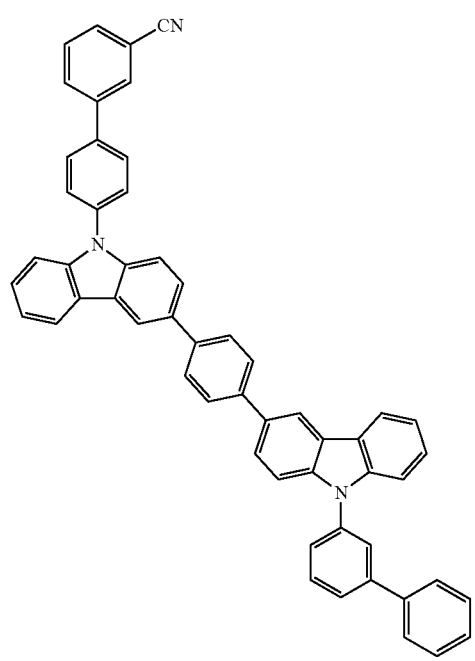
H1-406
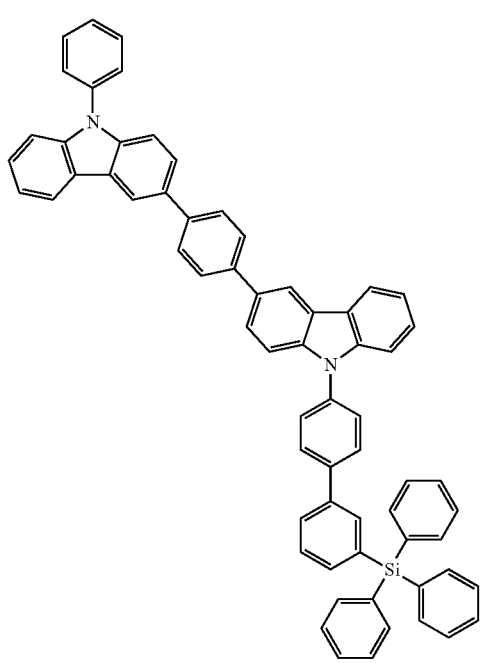

-continued
H1-407
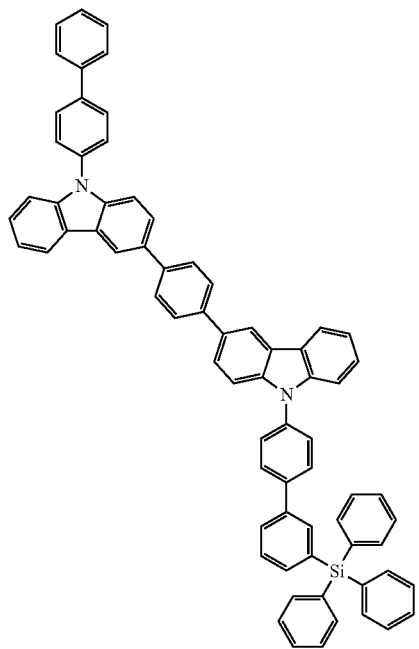
H1-408
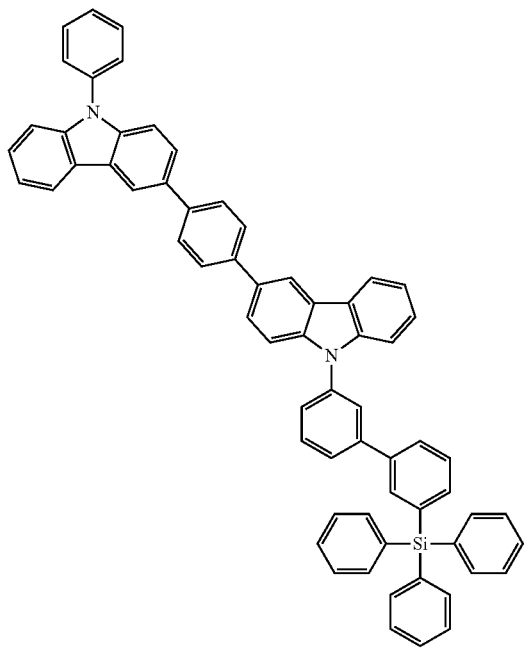
H1-409
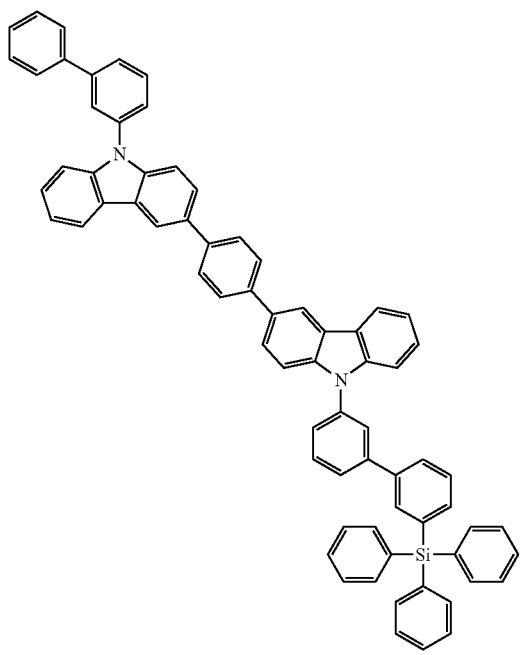
H1-410
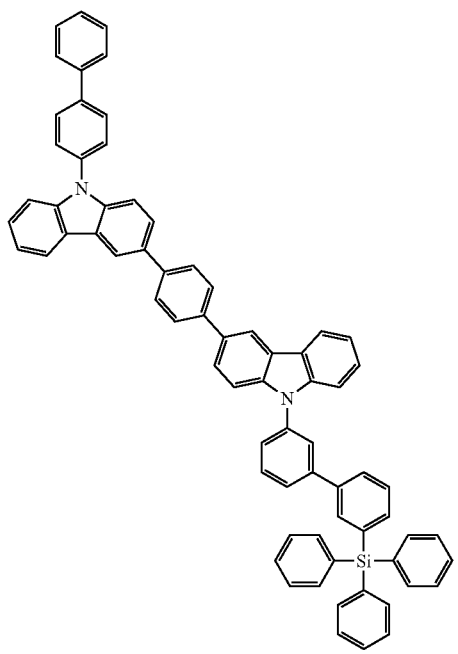

H1-411
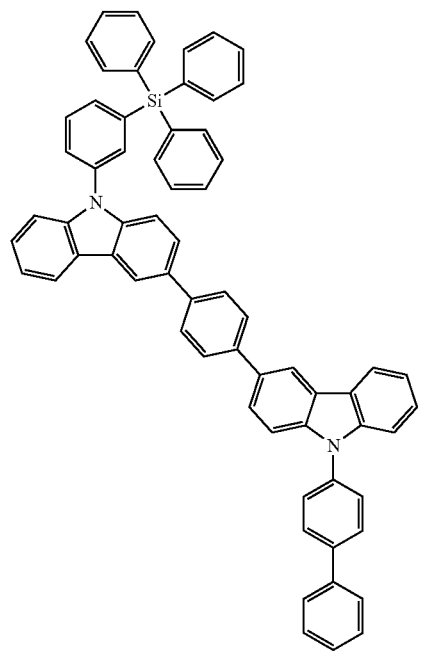
H1-412
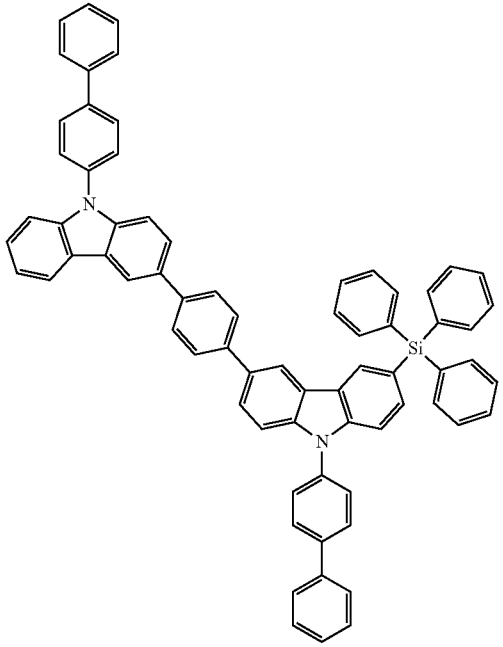
H1-413
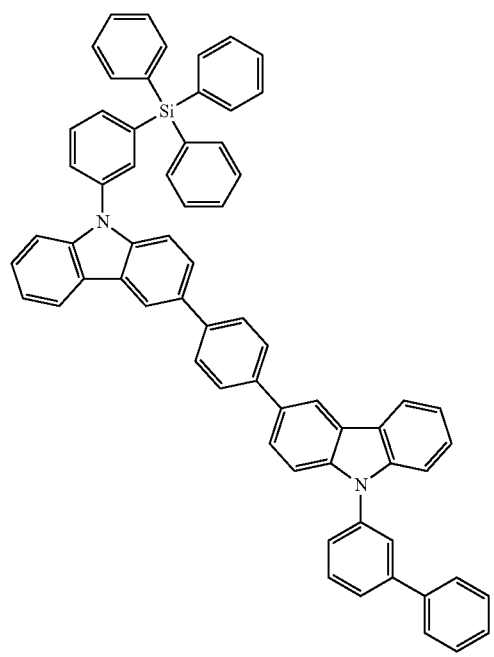
H1-414
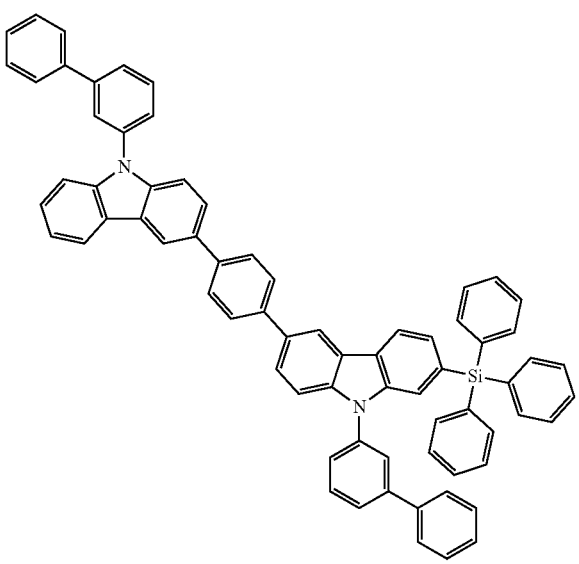

-continued
H1-415
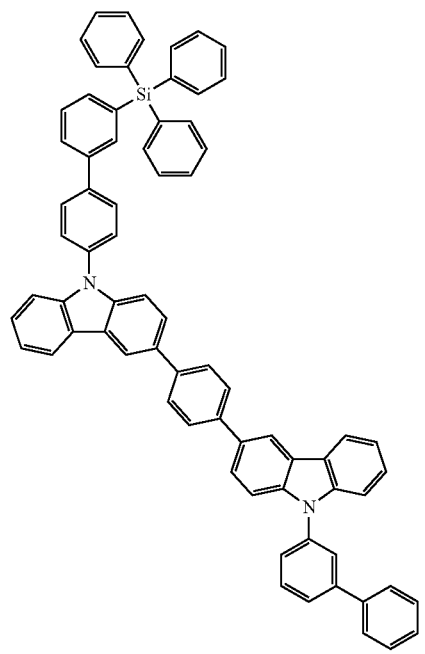
H1-416
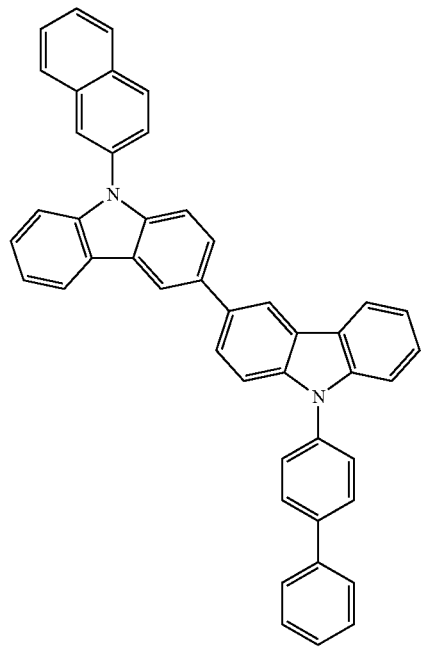
H1-417
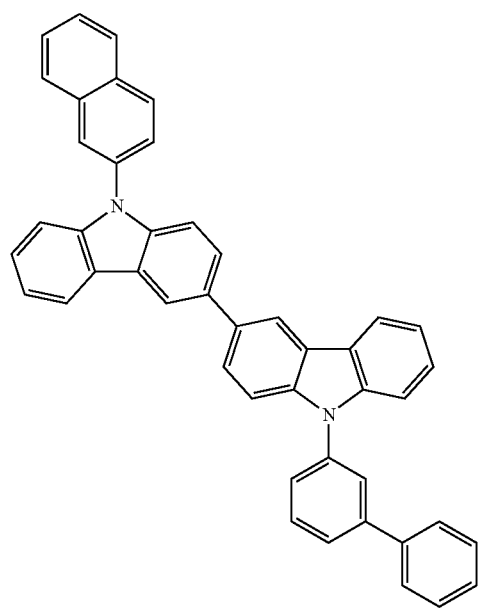
H1-418
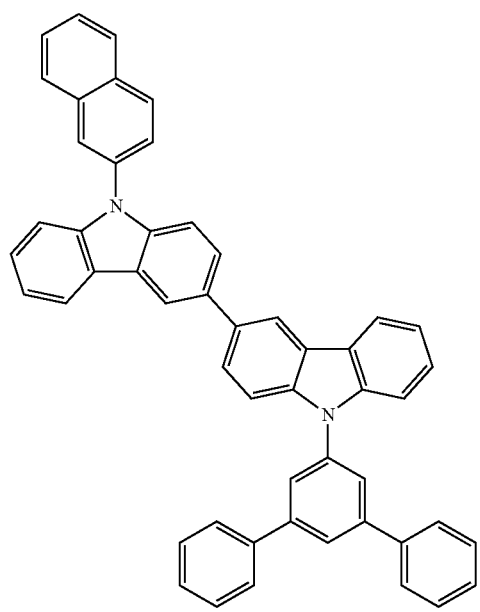

-continued
H1-419
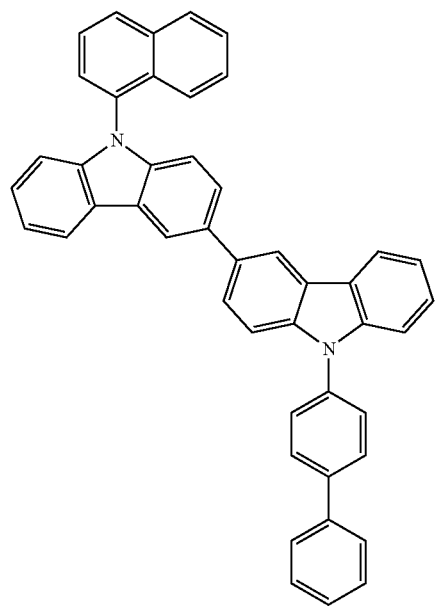
H1-420
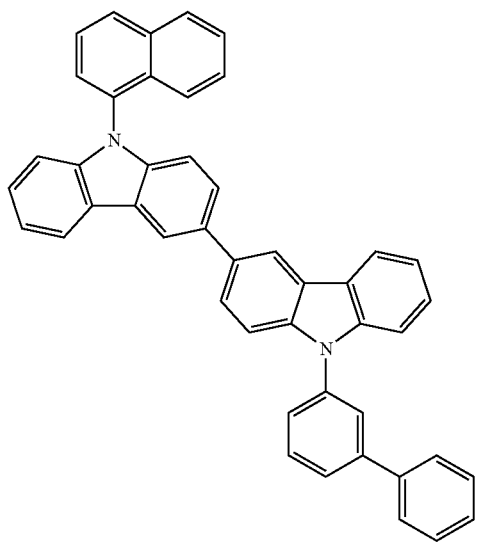
H1-421
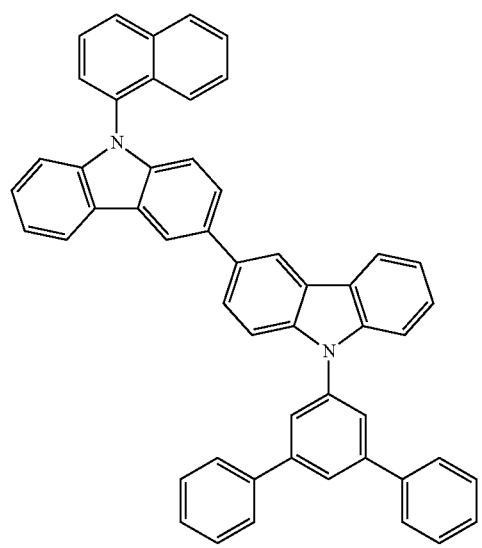
H1-422
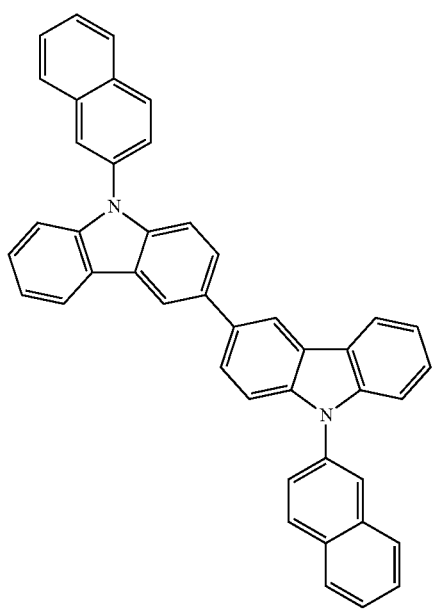

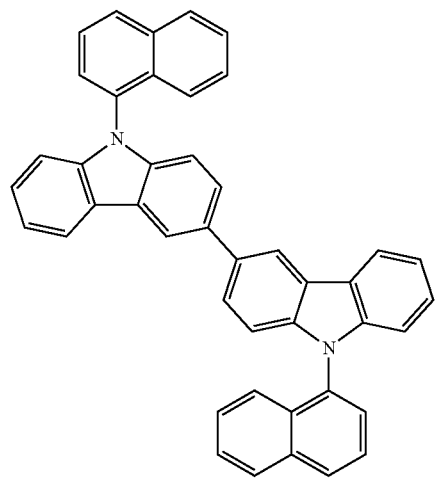

H1-423

When using the compound of the present disclosure as a host, at least one phosphorescent dopant may be used as a dopont. The phosphorescent dopant material used for the OLED of the present disclosure is not particularly limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant to be comprised in the OLED of the present disclosure may be selected from the group consisting of the compounds represented by the following formulas 100 to 102.

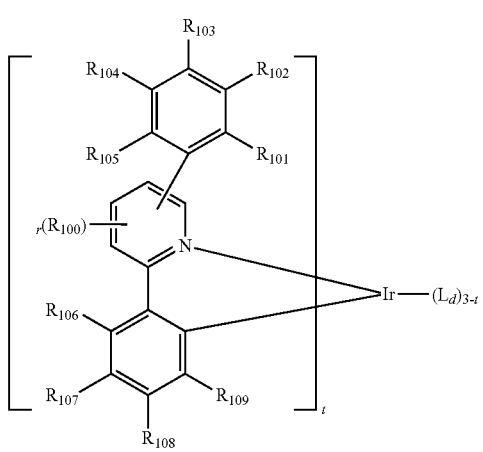

(100)

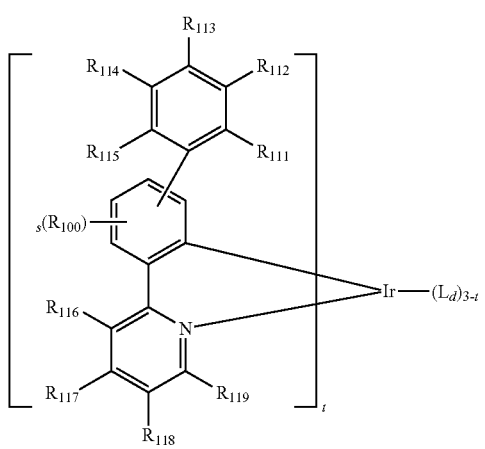

(101)

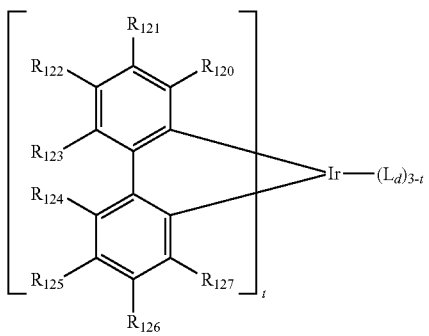

(102)

wherein $L_d$ is selected from the following structures:

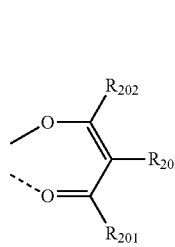 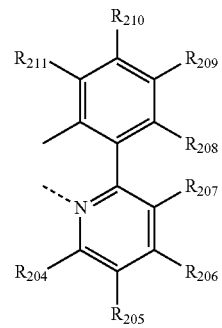

$R_{100}$ represents hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a substituted or unsubstituted (C1-C30)alkyl, a substituted or unsubstituted (C3-C30)cycloalkyl, a cyano, or a substituted or unsubstituted (C1-C30)alkoxy; adjacent substituents of $R_{106}$ to $R_{109}$ may be linked to each other to form a substituted or unsubstituted fused ring, e.g., a substituted or unsubstituted dibenzofuran; and adjacent substituents of $R_{120}$ to $R_{123}$ may be linked to each other to form a substituted or unsubstituted fused ring, e.g., a substituted or unsubstituted quinoline;

$R_{124}$ to $R_{127}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a substituted or unsubstituted fluorene, a substituted or unsubstituted dibenzothiophene, or a substituted or unsubstituted dibenzofuran;

$R_{201}$ to $R_{211}$, each independently, represent hydrogen, deuterium, a halogen, a substituted or unsubstituted (C1-C30)alkyl, a substituted or unsubstituted (C3-C30)cycloalkyl, or a substituted or unsubstituted (C6-C30)aryl; and adjacent substituents of $R_{208}$ to $R_{211}$ may be linked to each other to form a substituted or unsubstituted fused ring, e.g., a substituted or unsubstituted dibenzofuran, or a substituted or unsubstituted dibenzothiophene;

r and s, each independently, represent an integer of 1 to 3; where r or s is an integer of 2 or more, each of $R_{100}$ may be the same or different; and t represents an integer of 1 to 3.

Specifically, the phosphorescent dopant materials include the following:

D-1

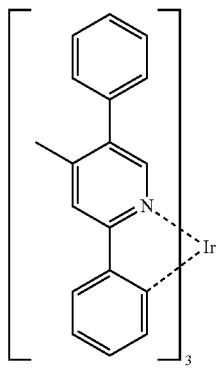

D-2

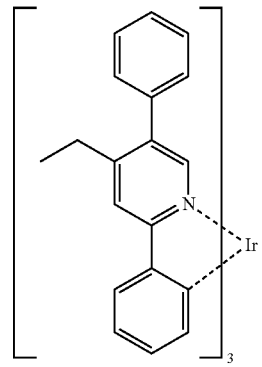

D-3

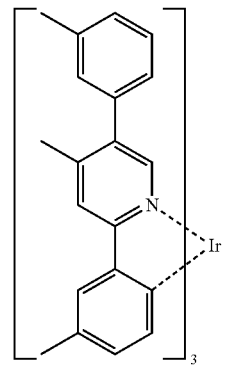

D-4

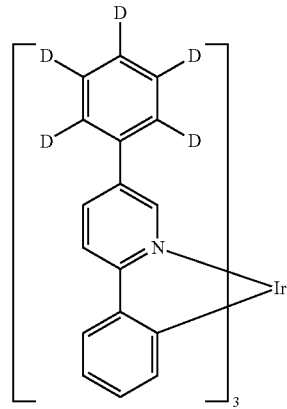

D-5

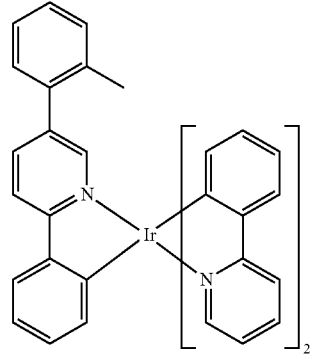

D-6 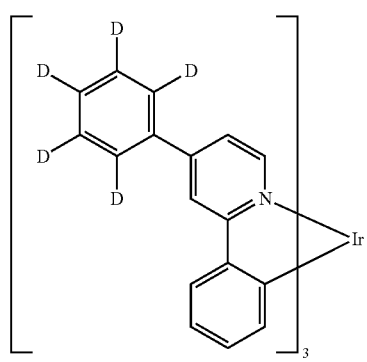
D-7 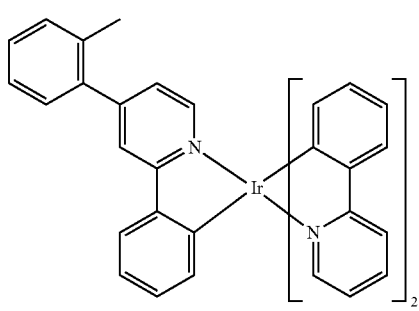
D-8 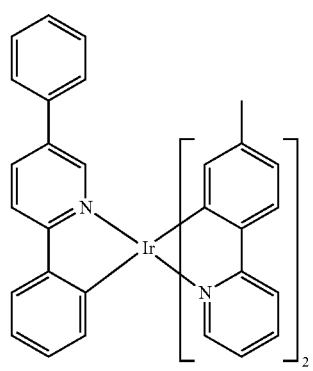
D-9 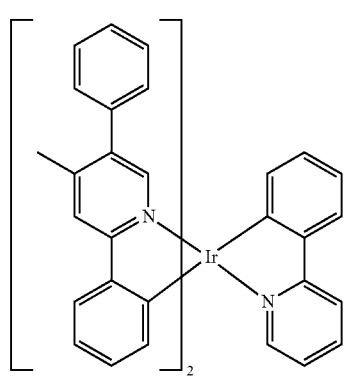
D-10 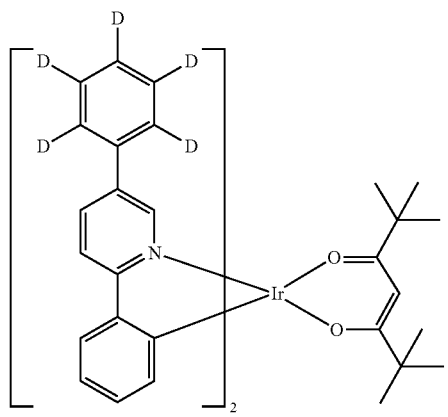
D-11 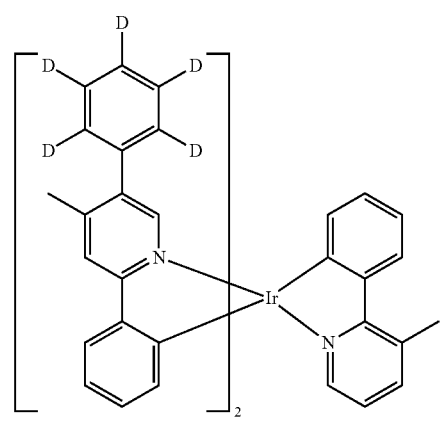
D-12 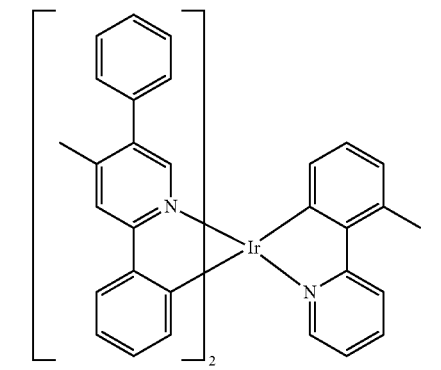
D-13 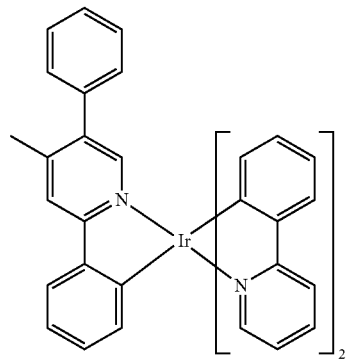

D-14
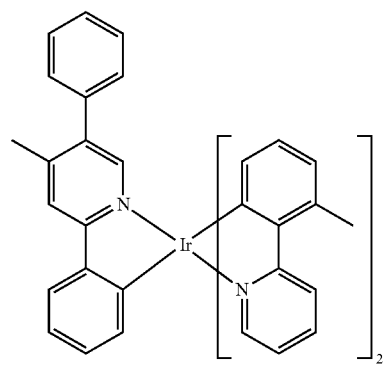
D-15
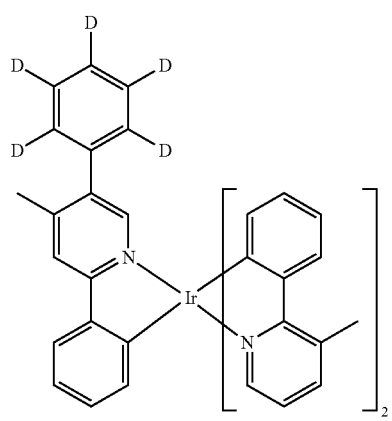
D-16
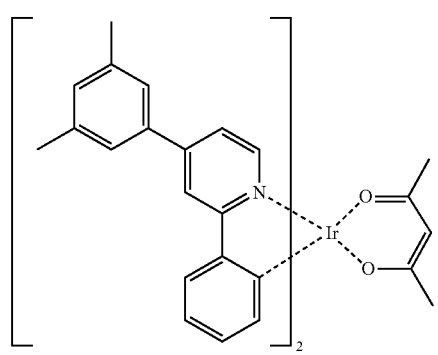
D-17
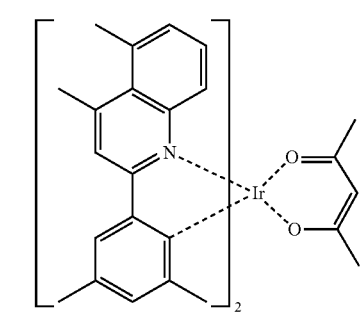
D-18
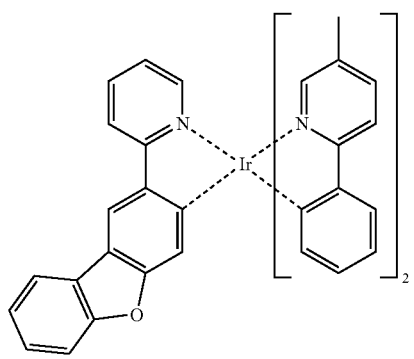
D-19
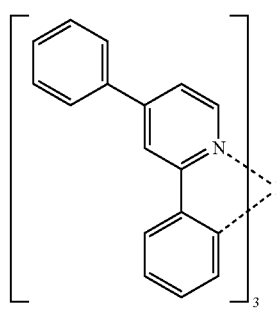
D-20
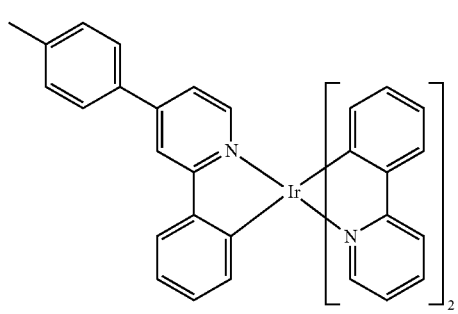
D-21
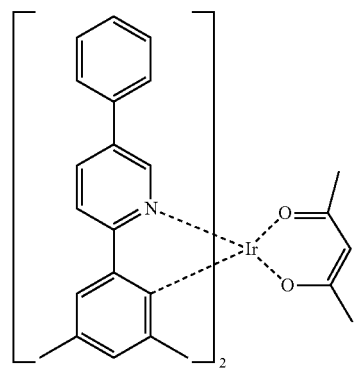

D-22
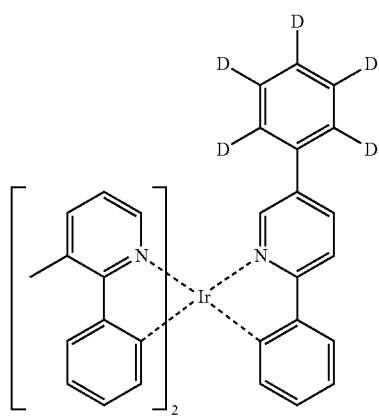
D-26
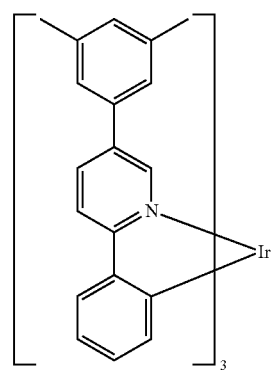
D-23
D-27
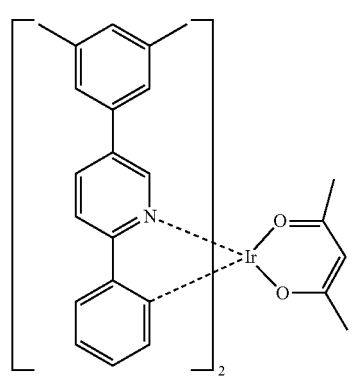
D-24
D-28
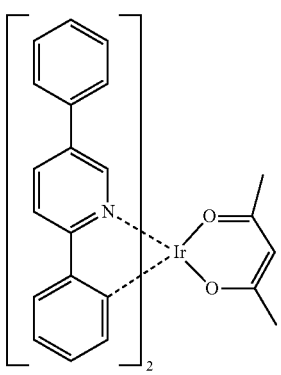
D-25
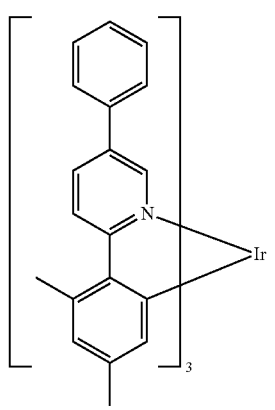
D-29

D-30
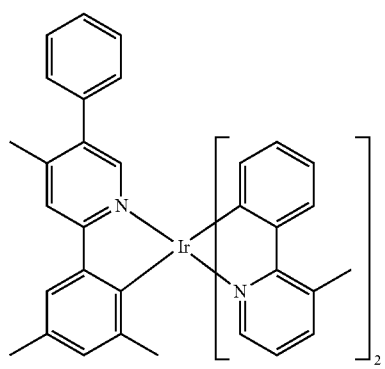
D-31
D-34
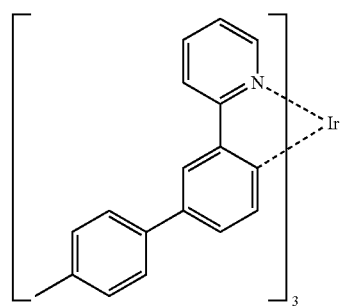
D-35
D-32
D-36
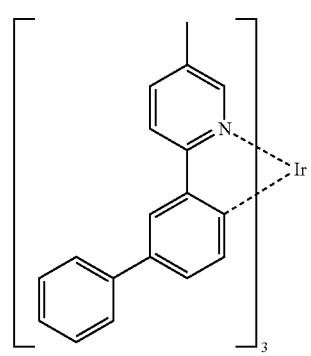
D-33
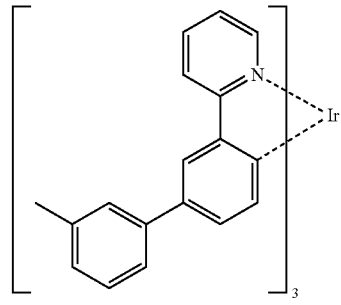
D-37
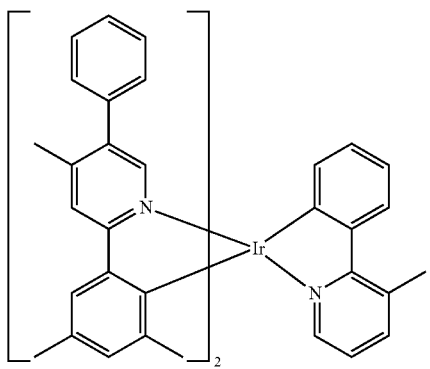

D-38
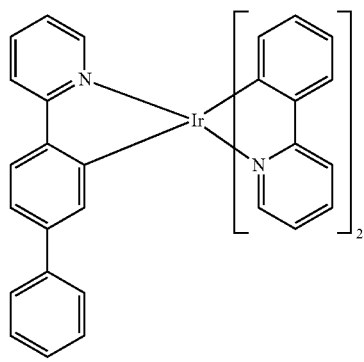
D-39
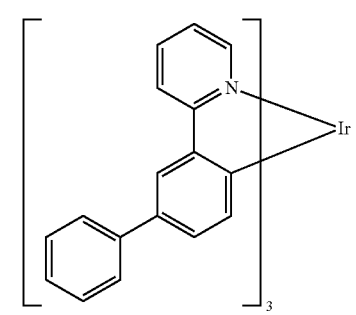
D-40
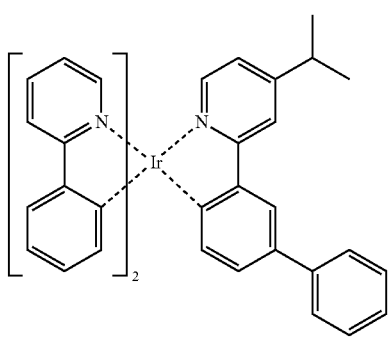
D-41
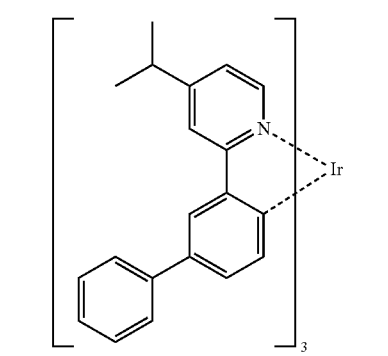
D-42
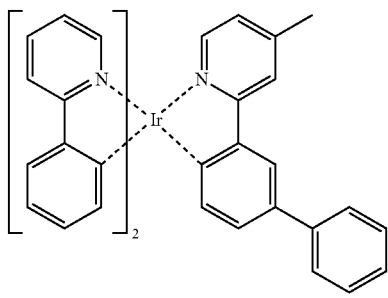
D-43
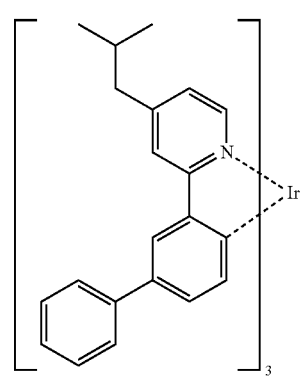
D-44
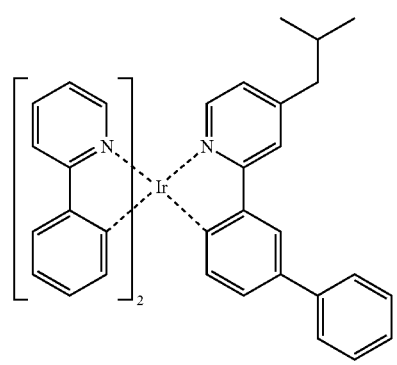
D-45
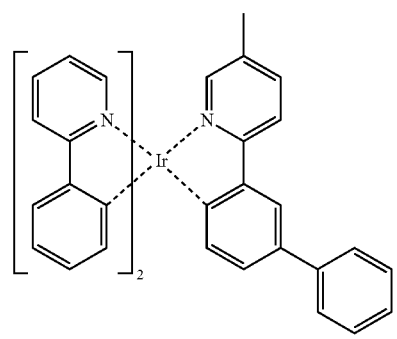
D-46
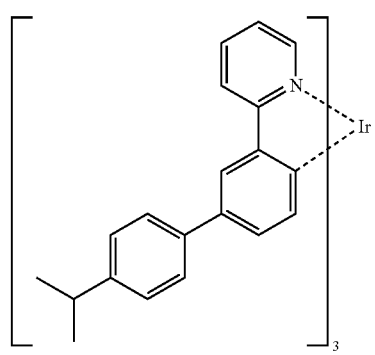

D-47
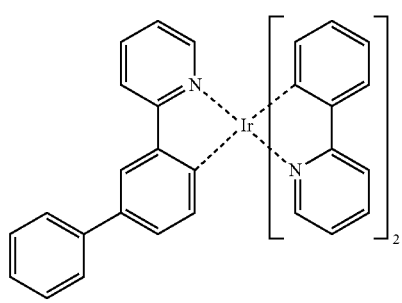
D-48
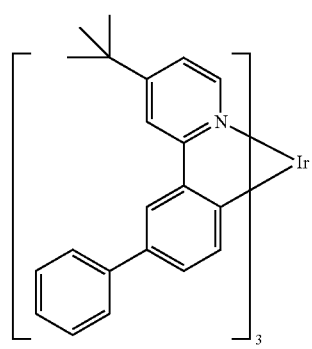
D-49
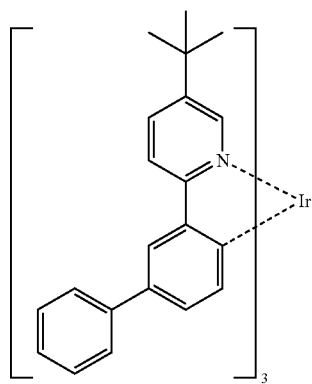
D-50
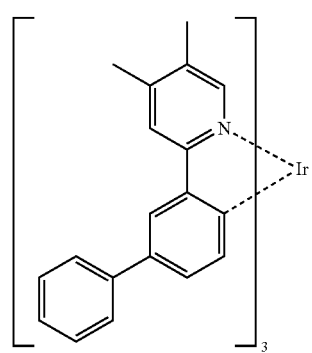
D-51
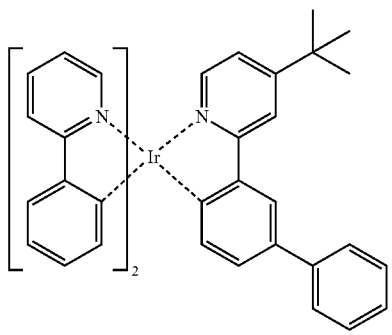
D-52
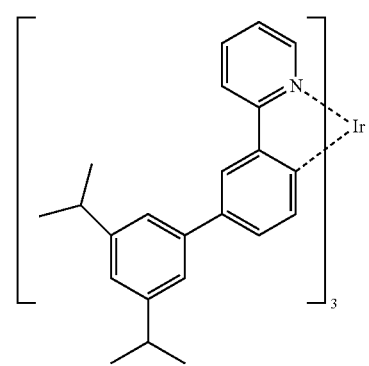
D-53
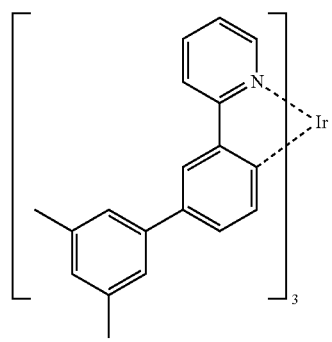
D-54
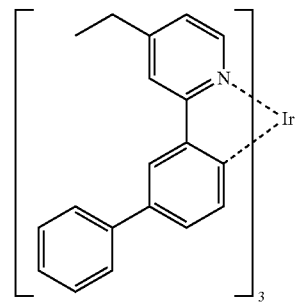

-continued
D-55
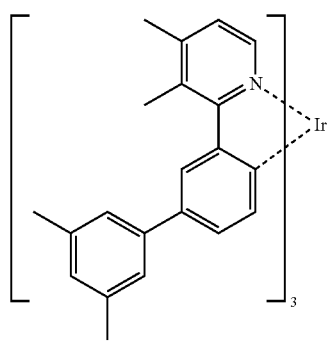
D-56
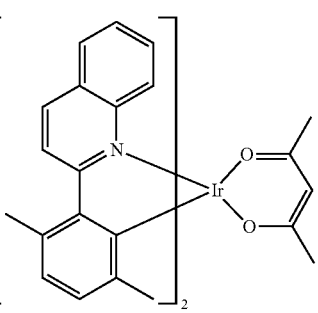
D-57
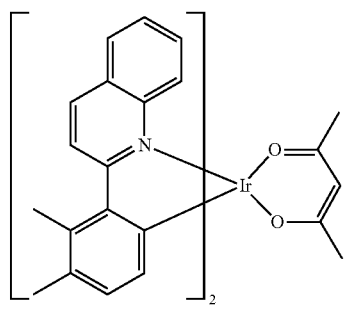
D-58
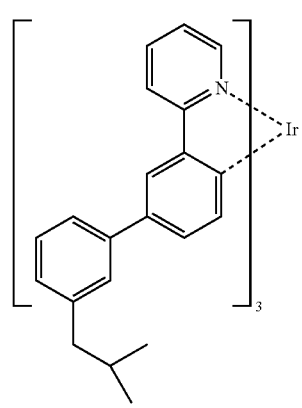
-continued
D-59
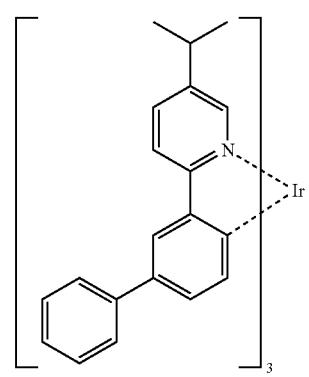
D-60
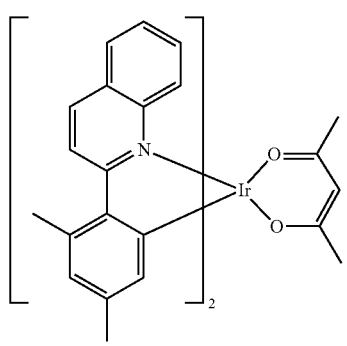
D-61
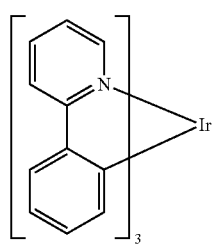
D-62
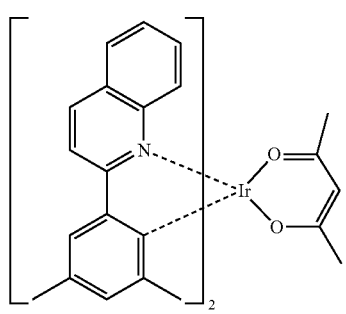

D-63
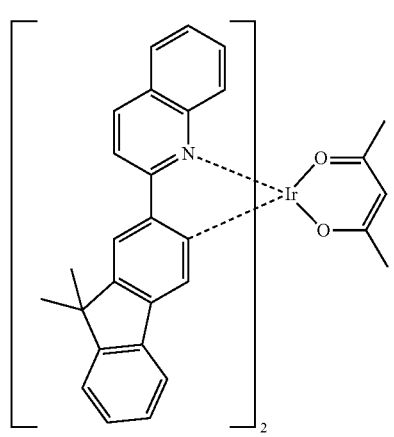
D-64
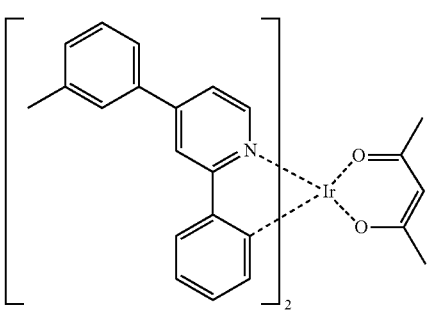
D-65
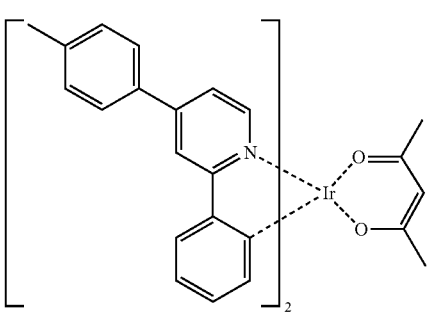
D-66
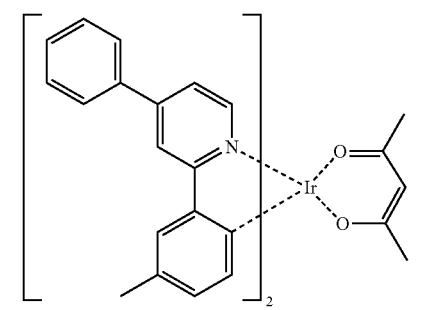
D-67
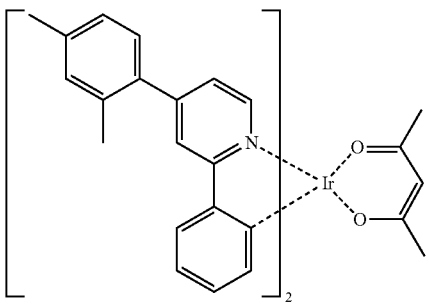
D-68
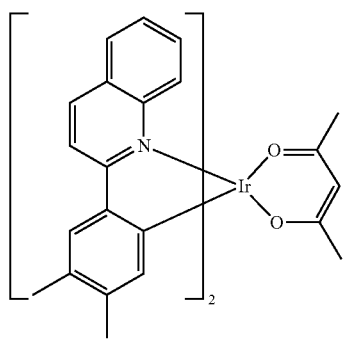
D-69
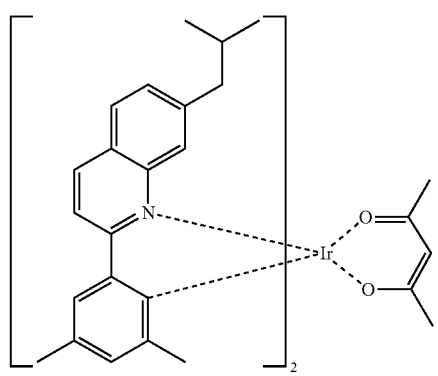
D-70
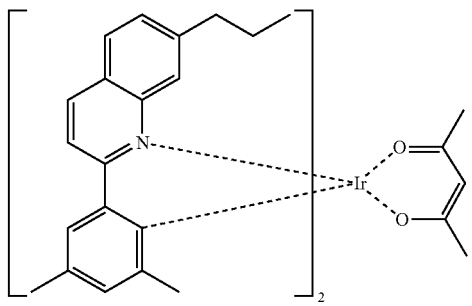
D-71
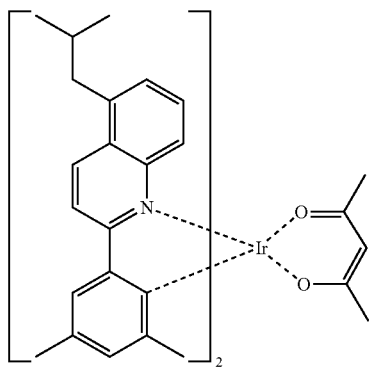

-continued
D-72
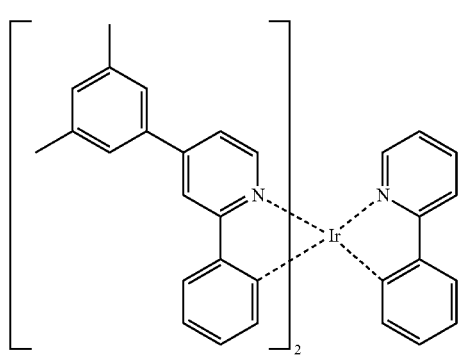
D-73
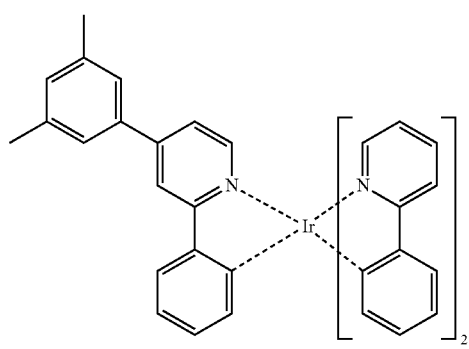
D-74
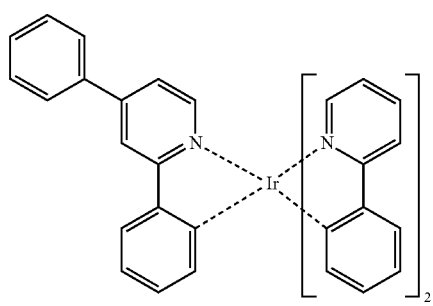
D-75
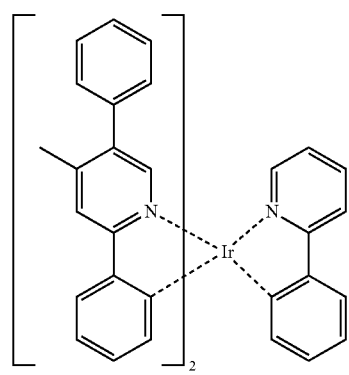
-continued
D-76
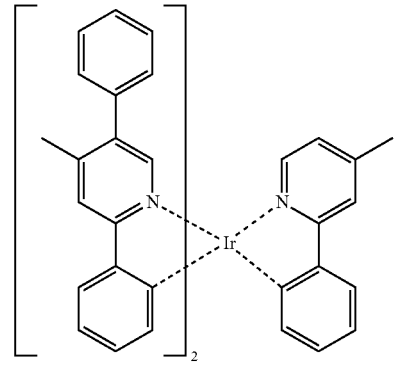
D-77
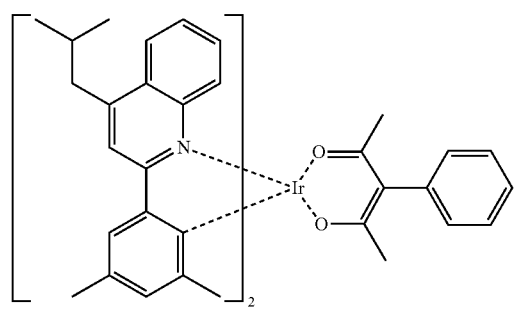
D-78
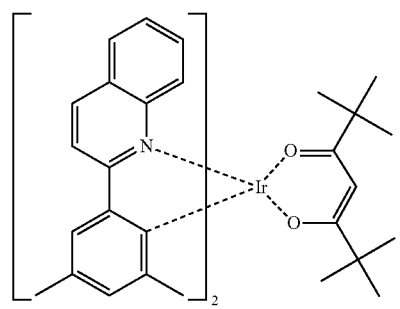
D-79
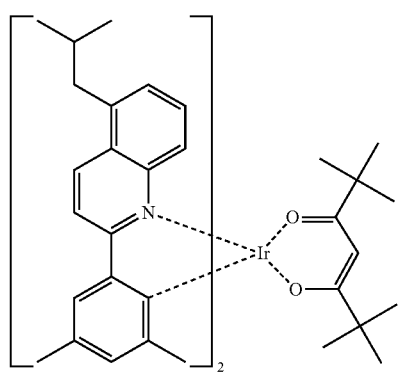

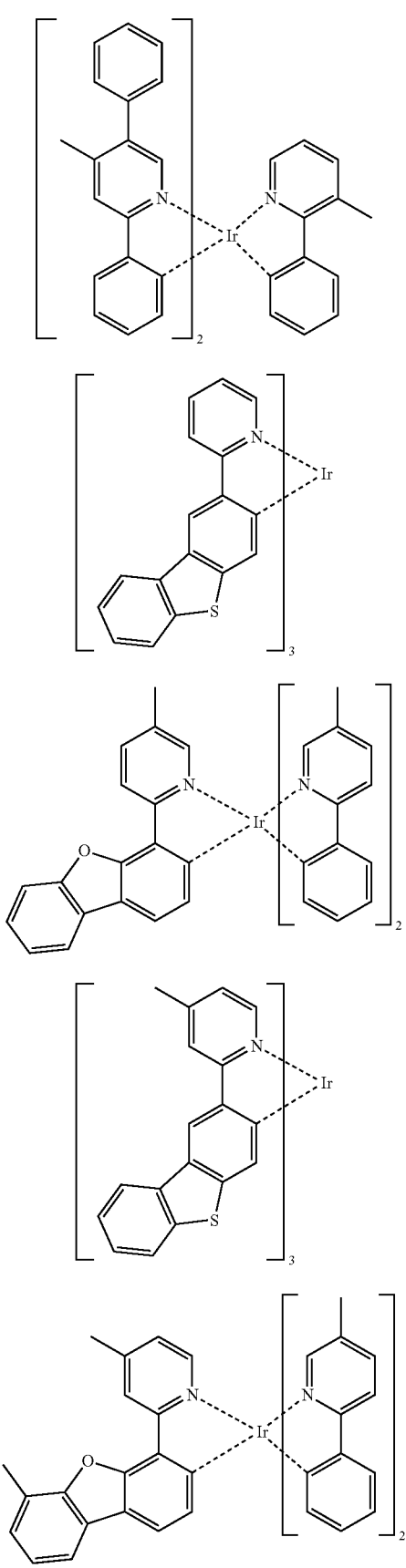
D-80
D-81
D-82
D-83
D-84
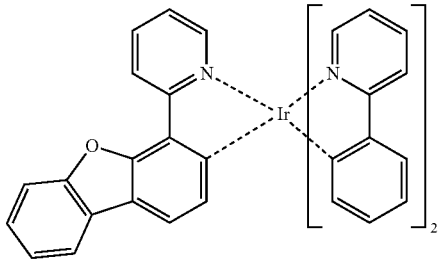
D-85
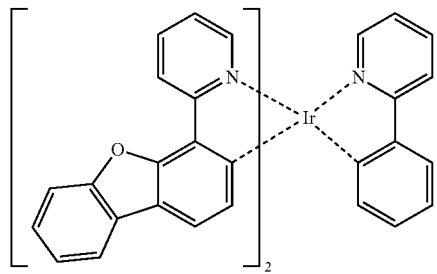
D-86
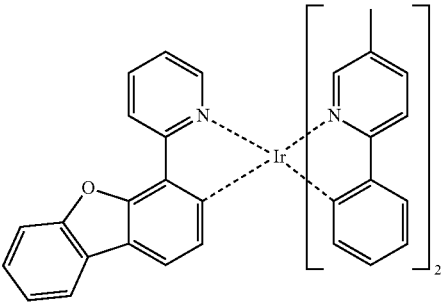
D-87
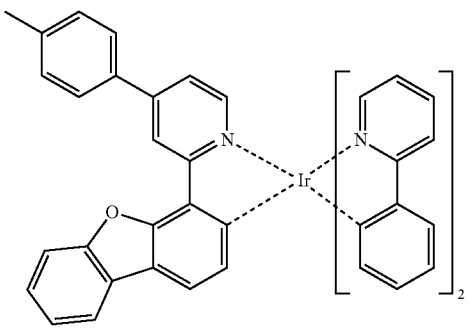
D-88
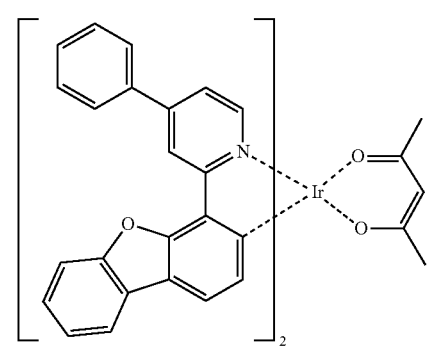
D-89

D-90
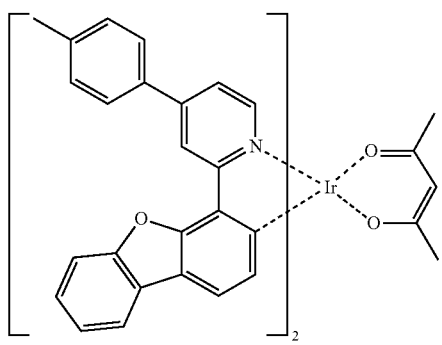
D-91
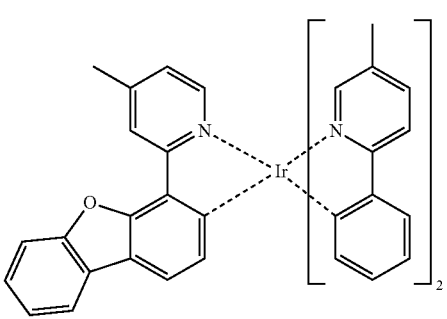
D-92
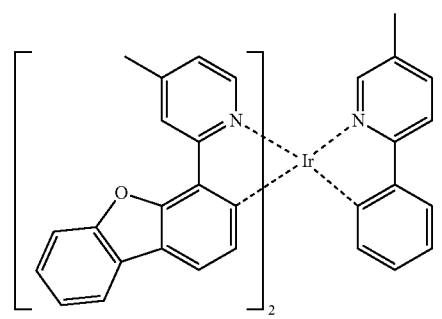
D-93
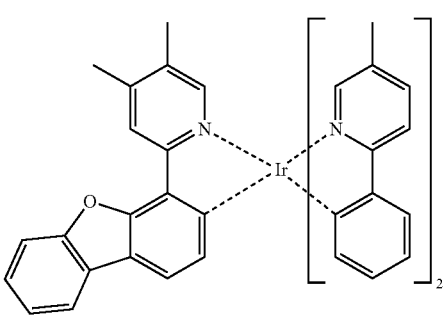
D-94
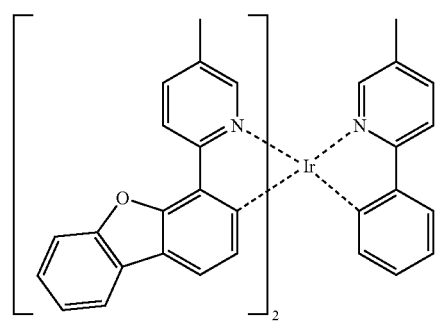
D-95
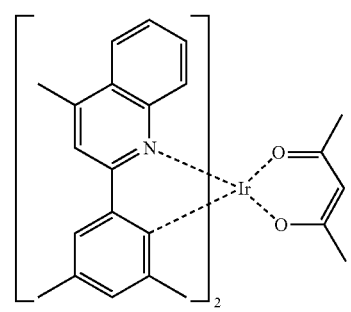
D-96
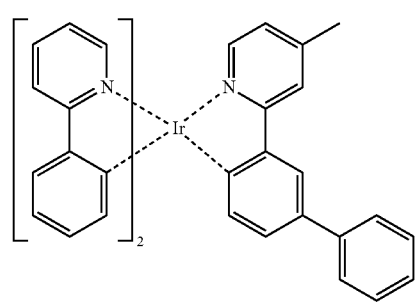
D-97
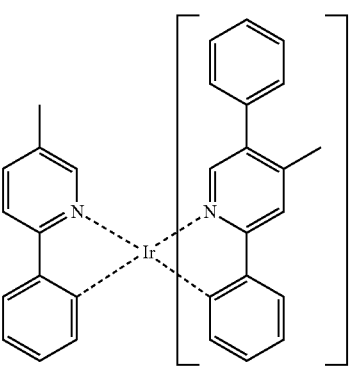
D-98
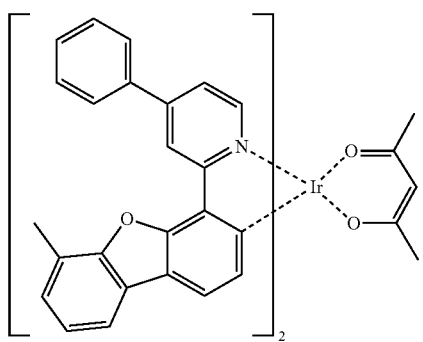

D-99
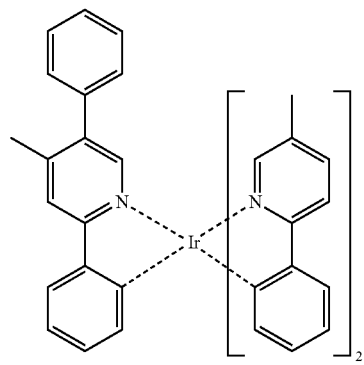
D-100
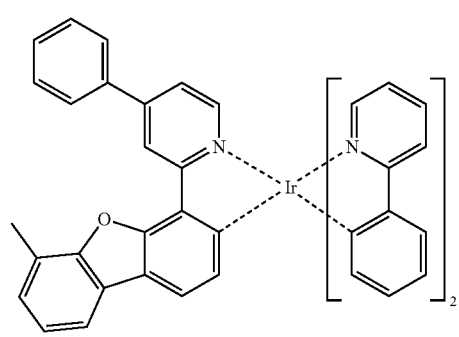
D-101
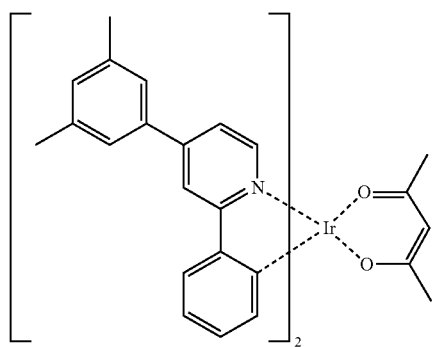
D-102
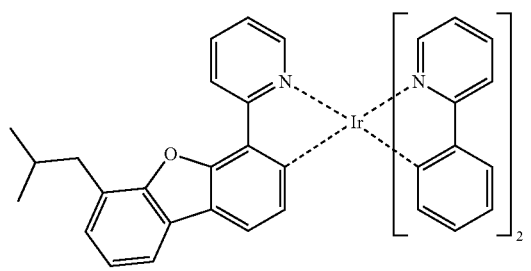
D-103
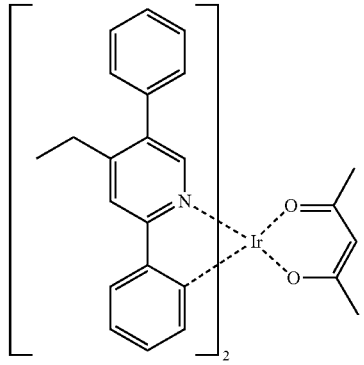
D-104
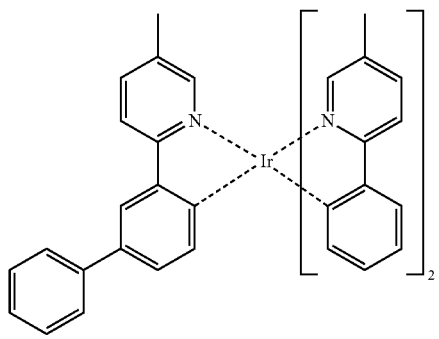
D-105
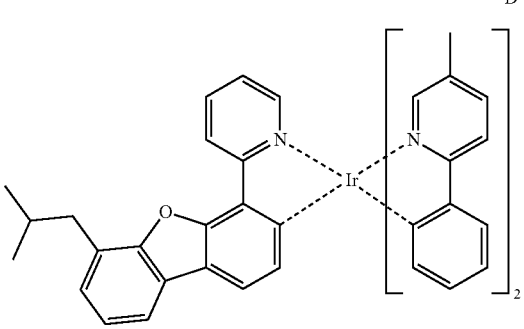
D-106
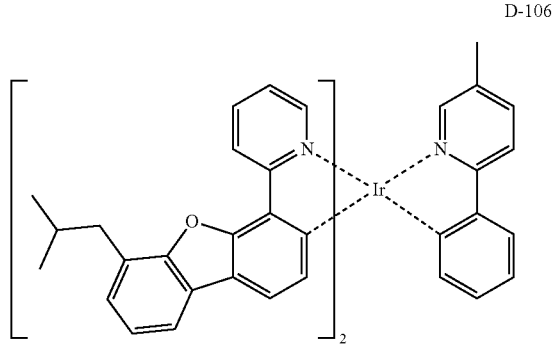

D-107 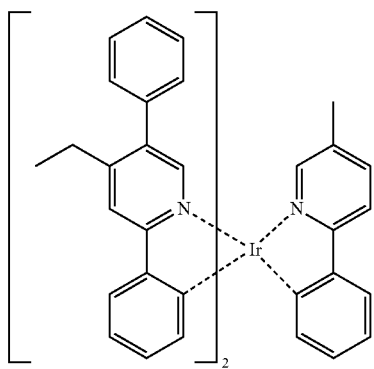
D-111 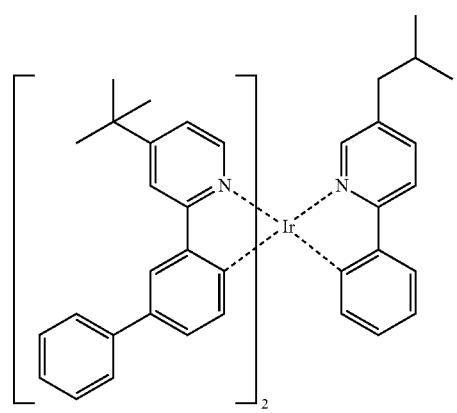
D-108 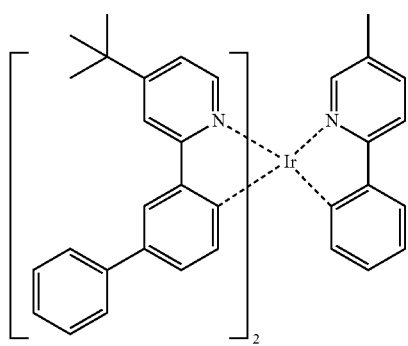
D-112 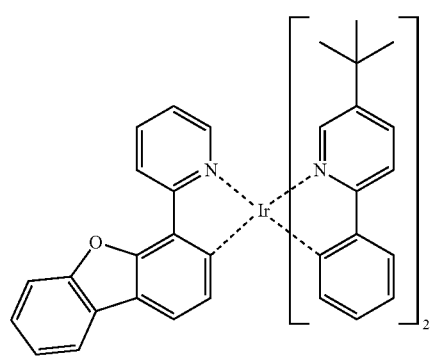
D-109 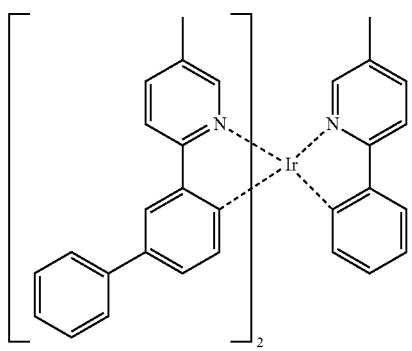
D-113 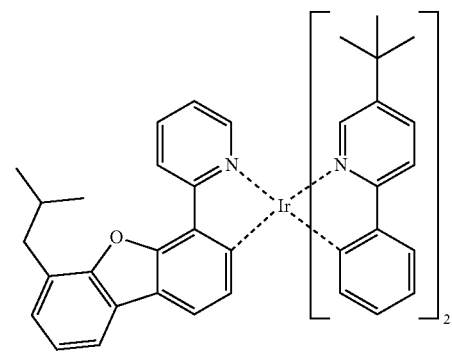
D-110 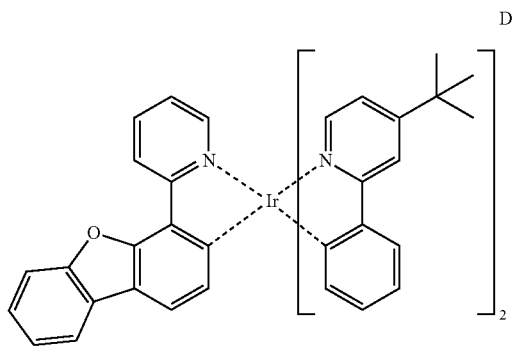
D-114 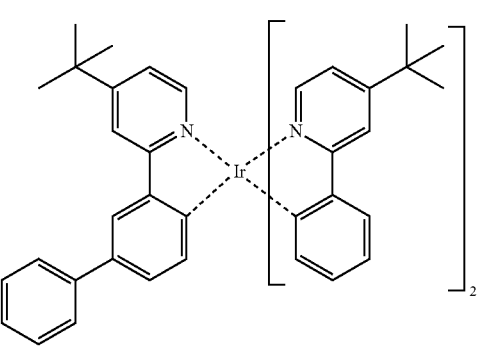

D-115
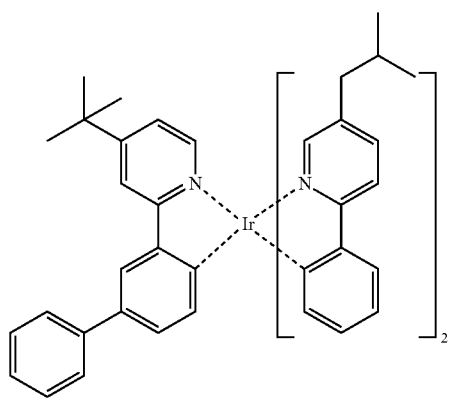
D-116
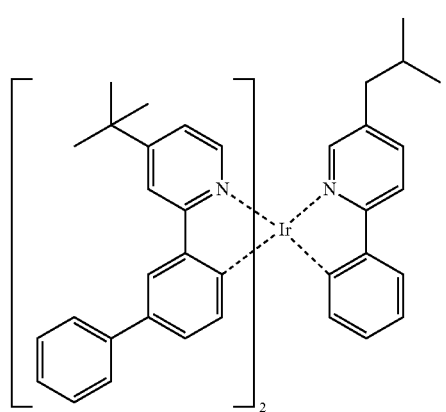
D-117
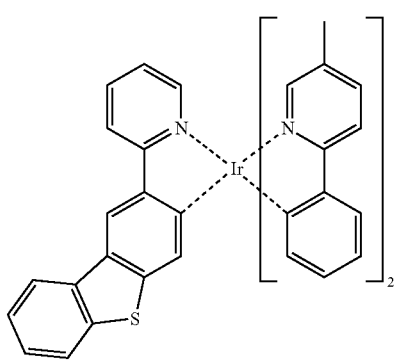
D-118
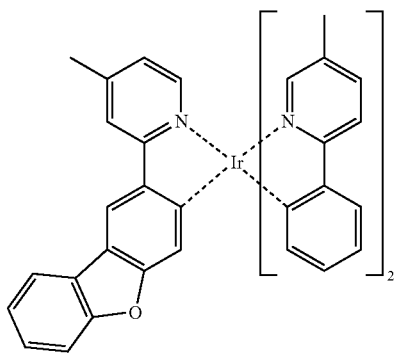
D-119
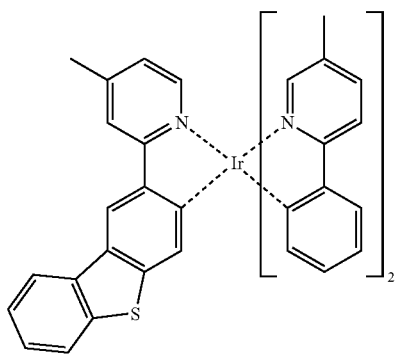
D-120
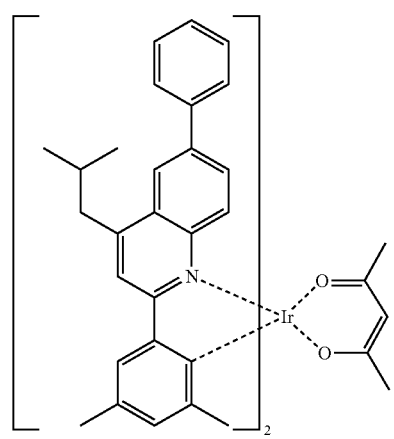
D-121
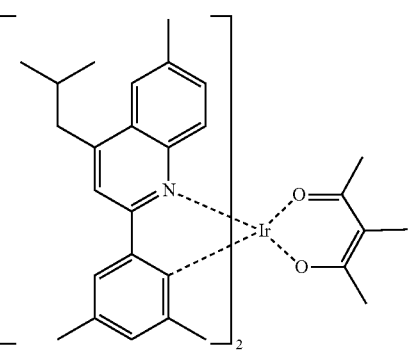
D-122
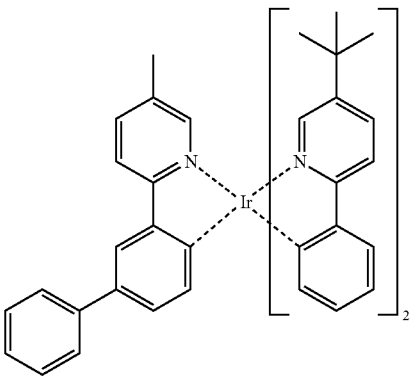

D-123
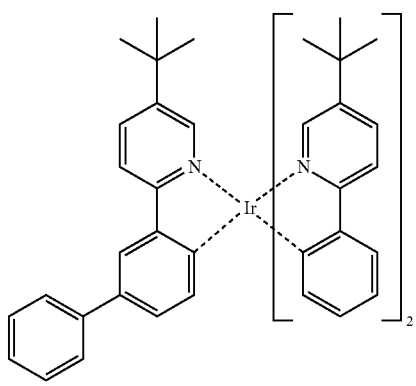
D-124
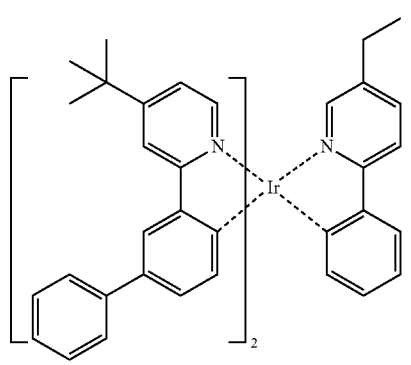
D-125
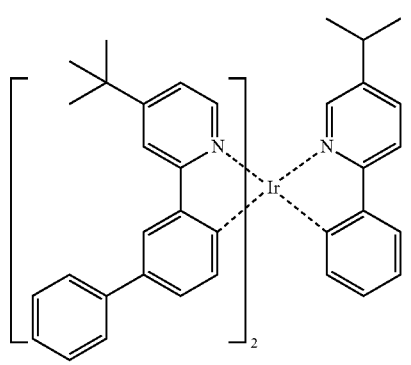
D-126
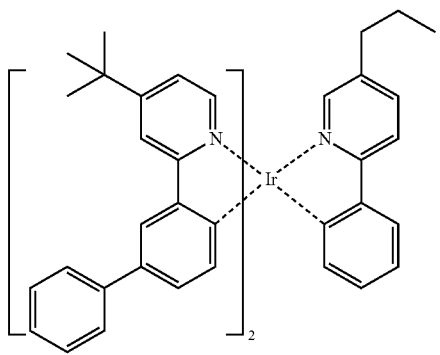
D-127
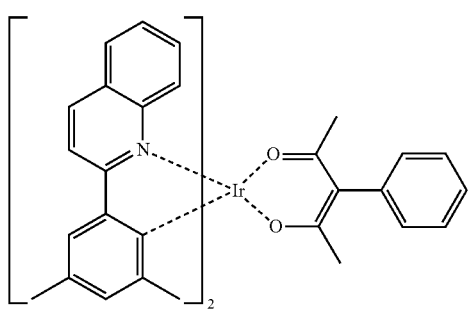
D-128
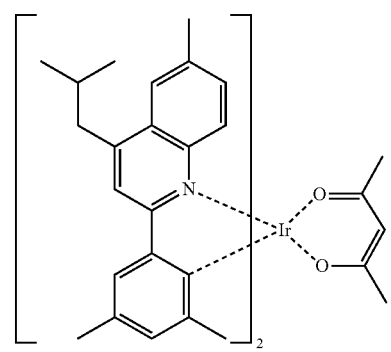
D-129
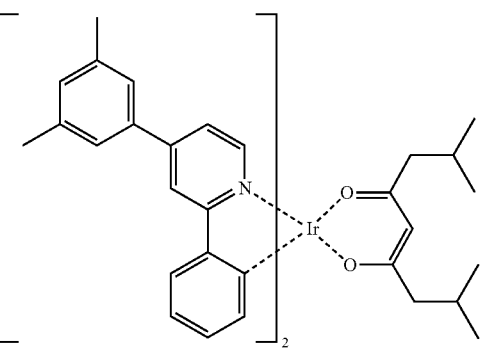
D-130
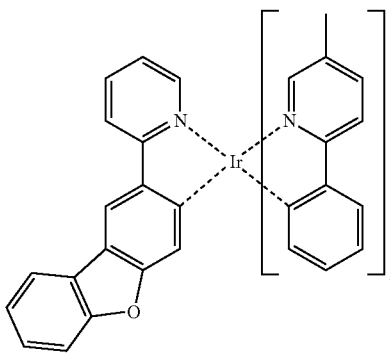

D-131
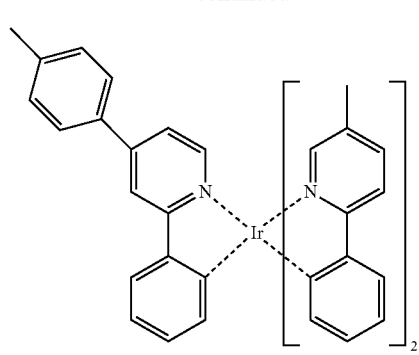
D-132
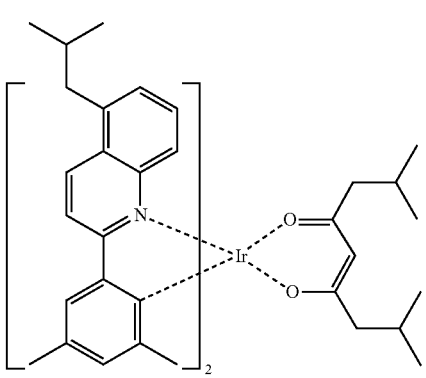
D-133
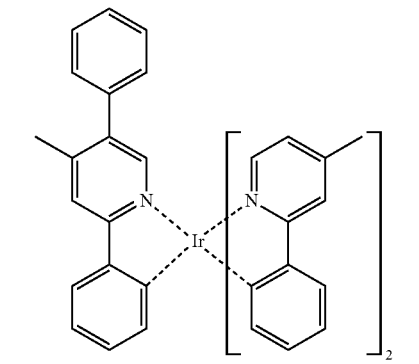
D-134
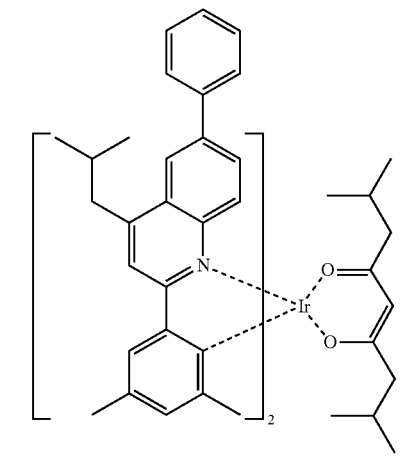
D-135
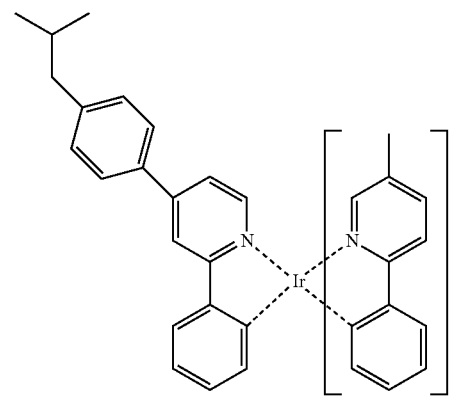
D-136
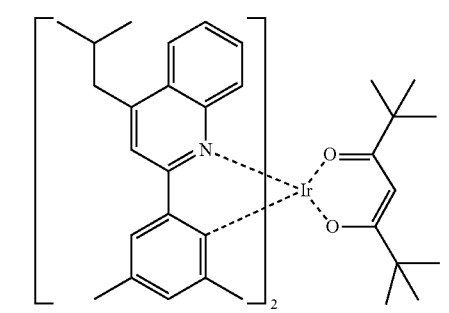
D-137
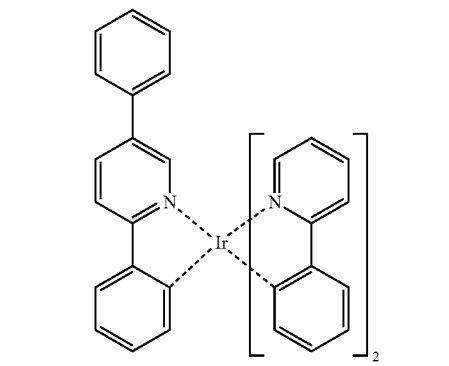
D-138

D-139
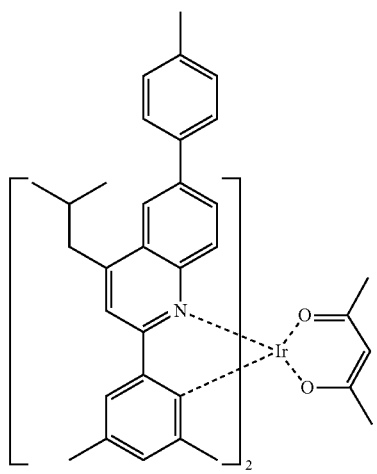
D-140
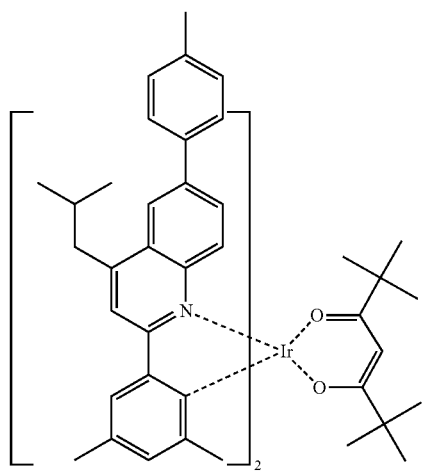
D-141
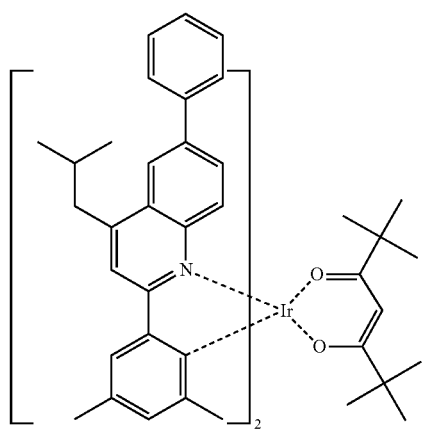
D-142
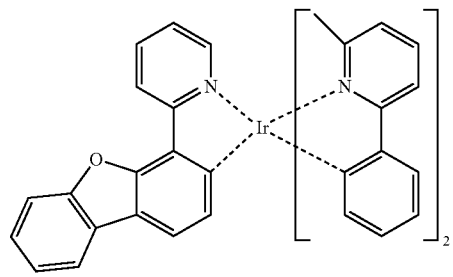
D-143
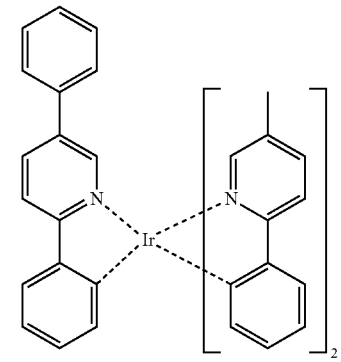
D-144
D-145
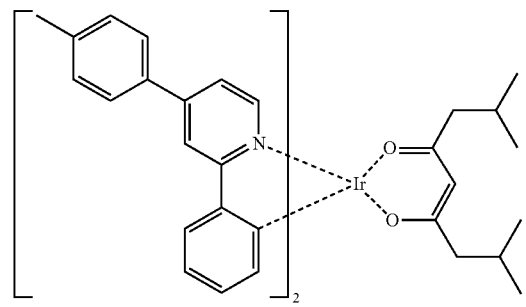

-continued

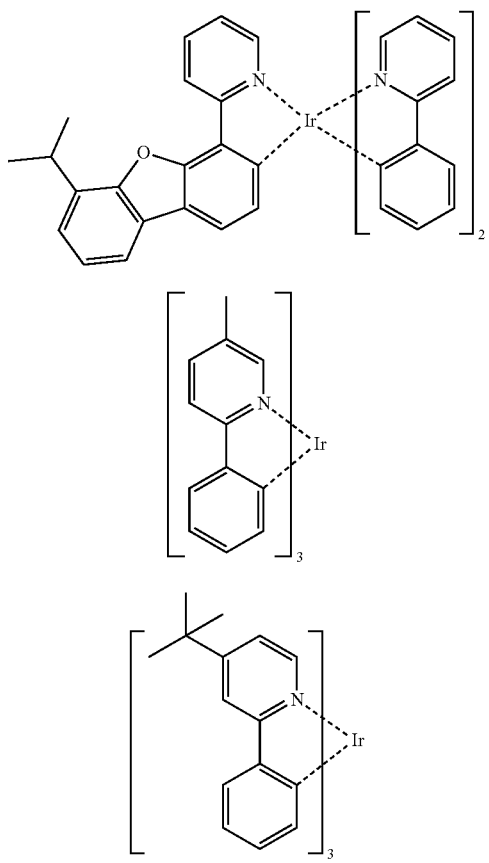

D-146

D-147

D-148

The organic electroluminescent compound of the present disclosure may be produced by a synthetic method known to a person skilled in the art, for example, the following reaction scheme 1:

[Reation Scheme 1]

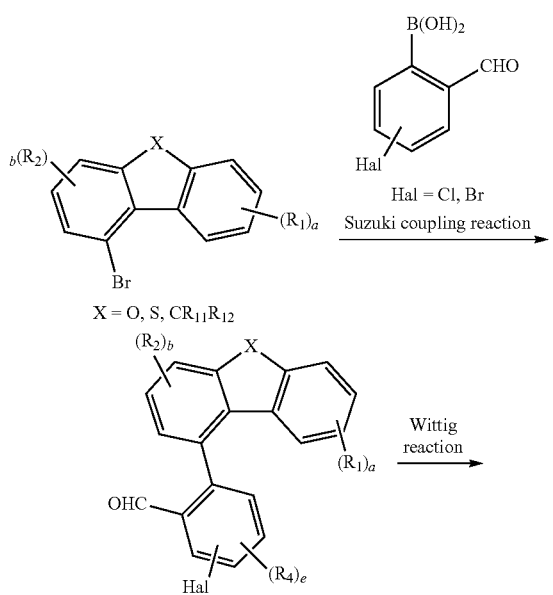

-continued

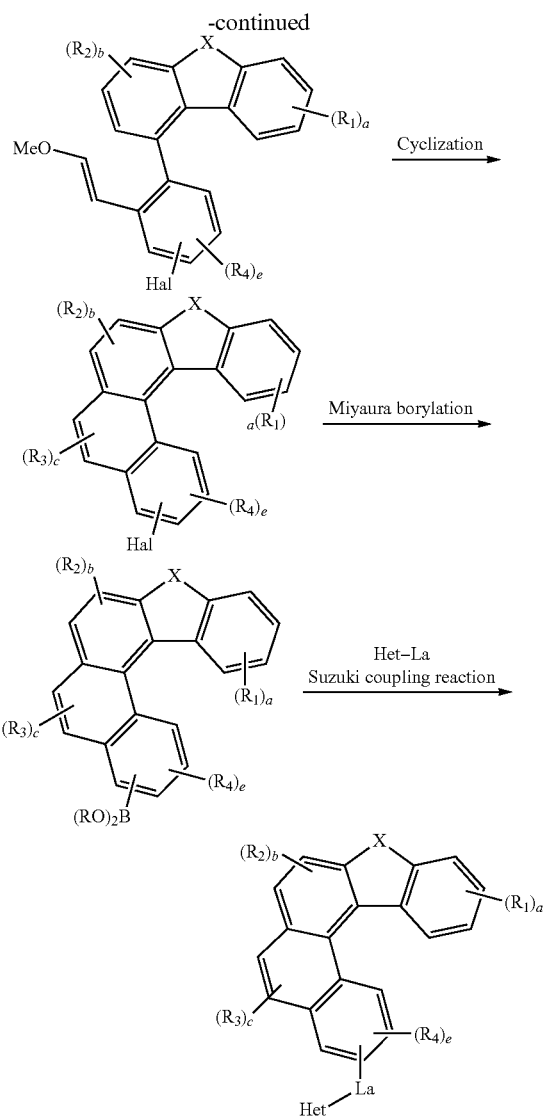

wherein X represents O, S, or $CR_{11}R_{12}$; Het-La is as defined in $R_4$ of formula 1; $R_1$, $R_2$, $R_3$, $R_4$, a, b, c and e are as defined in formulas 1 to 4; and Hal represents halogen, for example Cl or Br.

According to one embodiment of the present disclosure, the present disclosure provides an electron buffer material comprising the compound represented by formula 1. The electron buffer material indicates a material to control flow properties of an electron. For example, the electron buffer material may trap an electron, block an electron, or lower an energy barrier between an electron transport zone and a light-emitting layer. Specifically, the electron buffer material may be an electron buffer material of an OLED. The electron buffer material in an OLED may be used in the electron buffer layer, or may also be simultaneously used in other zones such as an electron transport zone or a light-emitting layer. The electron buffer material may be a mixture or a composition further comprising conventional materials generally used in producing an OLED.

According to another embodiment of the present disclosure, the present disclosure provides an electron transport material comprising the compound represented by formula 1. The electron transport material performs a role to increase the chance of recombining the holes and electrons in a light-emitting layer, by transporting an electron from a cathode to a light-emitting layer smoothly and blocking the mobility of holes uncombined in a light-emitting layer, and thus the electron transport material indicates a material having excellent electron affinity. Specifically, the electron transport material may be an electron transport material of an OLED. The electron transport material in an OLED may be used in the electron transport layer, or may also be simultaneously used in other zones such as an electron injection layer, a light-emitting layer, or an electron buffer layer. The electron transport material may be a mixture or a composition further comprising conventional materials generally used in producing an OLED.

According to another embodiment of the present disclosure, the OLED of the present disclosure may comprise a first electrode, a second electrode opposing the first electrode, and at least one organic electroluminescent compound represented by formula 1 between the first and second electrodes. Also, the OLED may comprise a light-emitting layer between the first and second electrodes; and an electron transport zone between the light-emitting layer and the second electrode, wherein the compound represented by formula 1 may be comprised in the electron transport zone. Further, the OLED may further comprise an electron buffer layer between the light-emitting layer and the second electrode, wherein the compound represented by formula 1 may be comprised in the electron buffer layer.

In an OLED comprising first and second electrodes and a light-emitting layer, an electron buffer layer can be disposed between the light-emitting layer and the second electrode to focus on obtaining high efficiency and long lifespan due to electron injection controlled by the LUMO energy level of the electron buffer layer.

An electron buffer layer and an electron transport zone may be disposed between the light-emitting layer and the second electrode, wherein the electron buffer layer may be disposed between the light-emitting layer and the electron transport zone, or between the electron transport zone and the second electrode.

Herein, an electron transport zone indicates a zone in which electrons are transported from the second electrode to the light-emitting layer in the device. The electron transport zone may comprise an electron transport compound, a reducing dopant, or the combination thereof. The electron transport compound may be at least one selected from the group consisting of oxazole-based compounds, isoxazole-based compounds, triazole-based compounds, isothiazole-based compounds, oxadiazole-based compounds, thiadiazole-based compounds, perylene-based compounds, and anthracene-based compounds, aluminum complexes, and gallium complexes. The reductive dopant may be at least one selected from the group consisting of alkali metals, alkali metal compounds, alkaline-earth metals, rare-earth metals, halides thereof, oxides thereof, and complexes thereof. In addition, the electron transport zone may comprise an electron transport layer, an electron injection layer, or both of them. Each of the electron transport layer and the electron injection layer may be comprised of two or more layers.

FIG. 1 illustrates a schematic section view of an OLED according to one embodiment of the present disclosure. Hereinafter, the structure and preparation method of an OLED will be explained with reference to FIG. 1.

Referring to FIG. 1, an OLED 100 comprises a substrate 101, a first electrode 110 formed on the substrate 101, an organic layer 120 formed on the first electrode 110, and a second electrode 130 opposing the first electrode 110 and formed on the organic layer 120.

The organic layer 120 comprises a hole injection layer 122, a hole transport layer 123 formed on the hole injection layer 122, a light-emitting layer 125 formed on the hole transport layer 123, an electron buffer layer 126 formed on the light-emitting layer 125, and an electron transport zone 129 formed on the electron buffer layer 126, wherein the electron transport zone 129 comprises an electron transport layer 127 formed on the electron buffer layer 126 and the electron injection layer 128 formed on the electron transport layer 127.

The substrate 101 may be a glass substrate, a plastic substrate, or a metal substrate generally used in an OLED.

The first electrode 110 may be an anode, and may be formed by a material having high work function. An example of the material for the first electrode 110 may be indium tin oxide (ITO), tin oxide (TO), indium zinc oxide (IZO), indium tin zinc oxide (ITZO), or the mixture thereof. The first electrode 110 may be formed by various known methods such as a deposition method, a sputtering method, etc.

Figure 2:
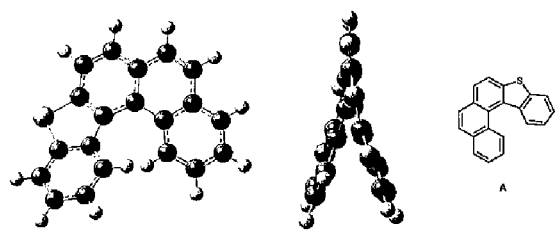
FIG. 2 illustrates a view representing a computational modeling result of core structure A.

FIG. 2 illustrates a computational modeling result of core structure A of the present disclosure.

By disposing the electron buffer layer in the OLED, injection and transport of electrons can be controlled due to the difference of affinities between the light-emitting layer and the electron transport zone in accordance with LUMO energy levels.

The thickness of the electron buffer layer 126 may be 1 nm or more, but is not particularly limited thereto. Specifically, the thickness of the electron buffer layer 126 may be from 2 to 100 nm. The electron buffer layer 126 may be formed on the light-emitting layer 125 by various known methods such as a vacuum vapor deposition method, a wet film-forming method, a laser induced thermal imaging method, etc.

When the compound of the present disclosure is used as an electron transport material or an electron buffer material, a light-emitting layer comprised in an OLED may comprise a host and a dopant. The host compound may be a phosphorescent host compound or a fluorescent host compound. The dopant compound may be a phosphorescent dopant compound or a fluorescent dopant compound.

A fluorescent host material may be an anthracene derivative, an aluminum complex, a rubrene derivative, an arylamine derivative, etc., and preferably, an anthracene derivative.

Specifically, the fluorescent host material of the present disclosure may include the following compounds, but is not limited thereto:

BH-1

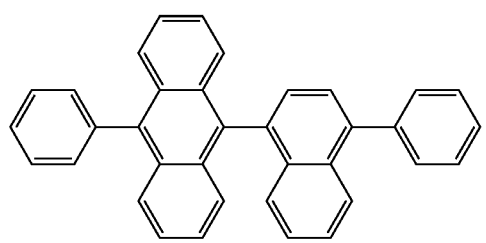

-continued
BH-2
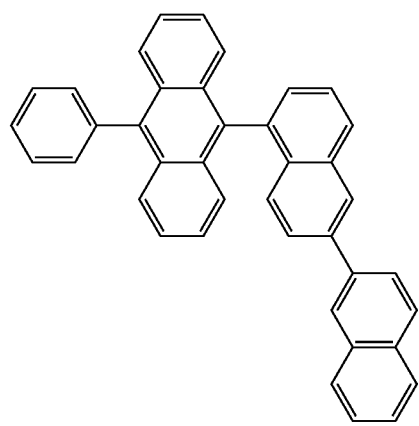
BH-3
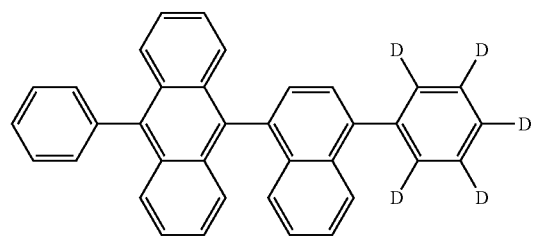
BH-4
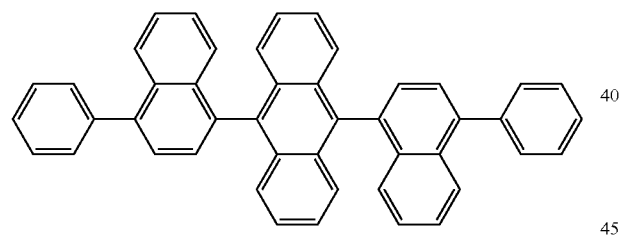
BH-5
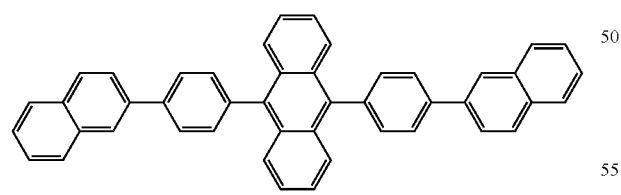
BH-6
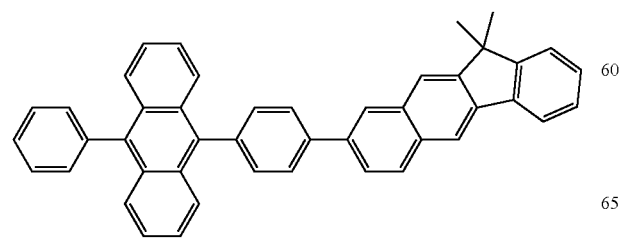
-continued
BH-7
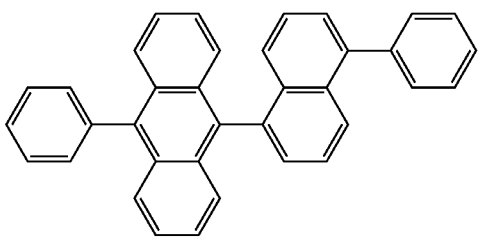
BH-8
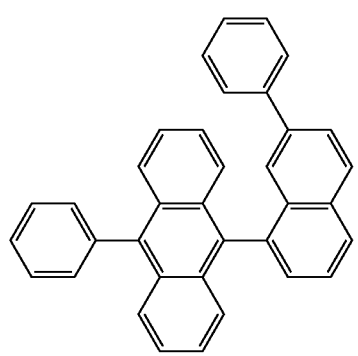
BH-9
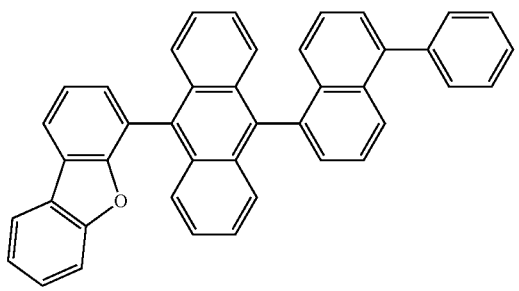
BH-10
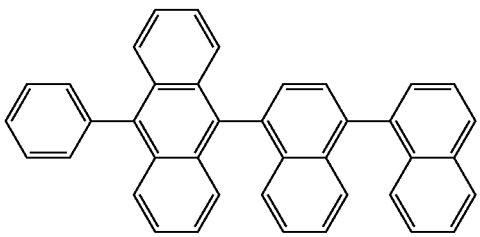
BH-11
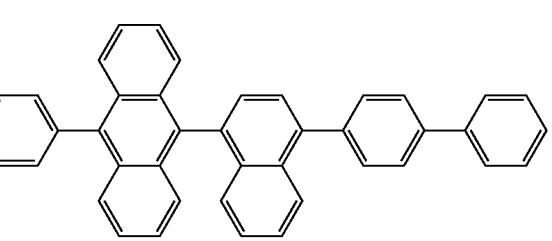

BH-12
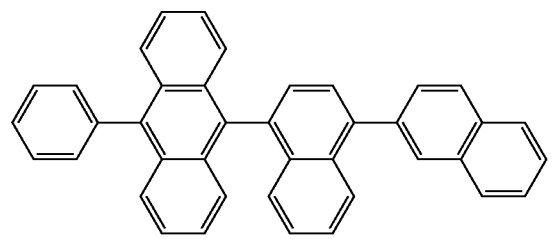
BH-13
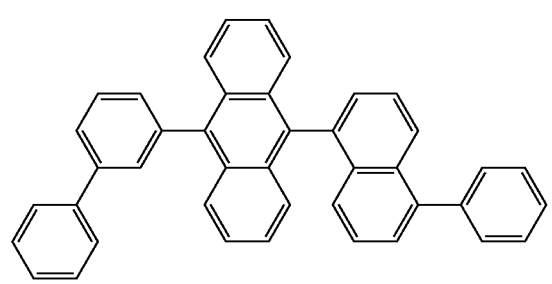
BH-14
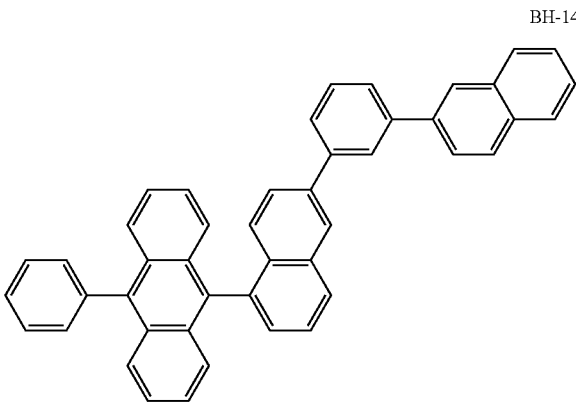
BH-15
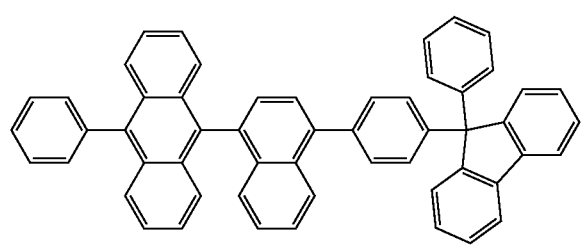
BH-16
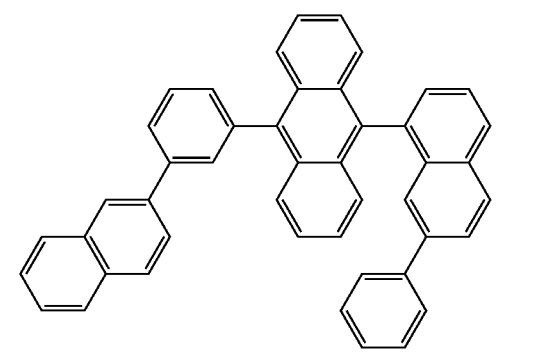
BH-17
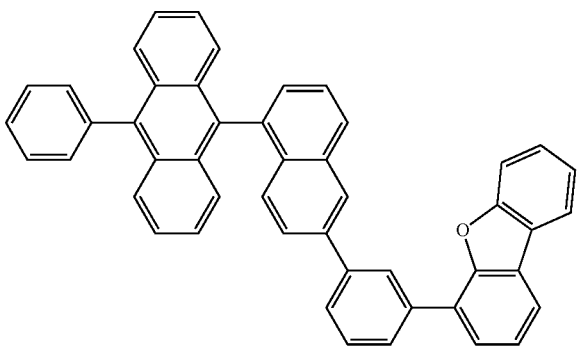
BH-18
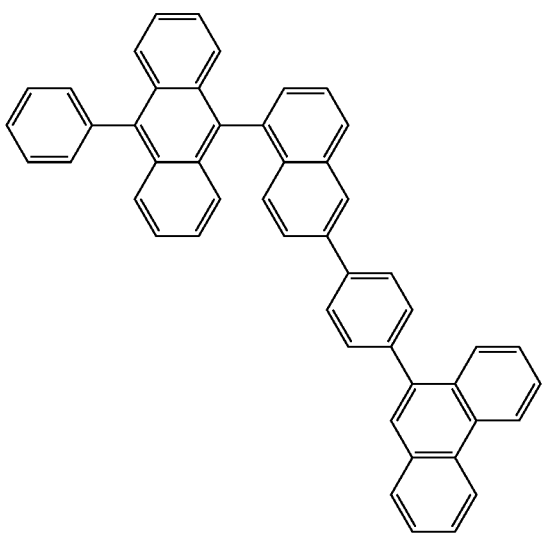
BH-19
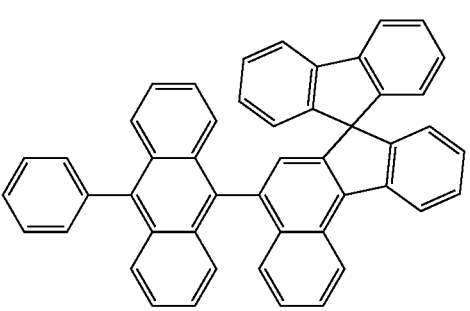

BH-20

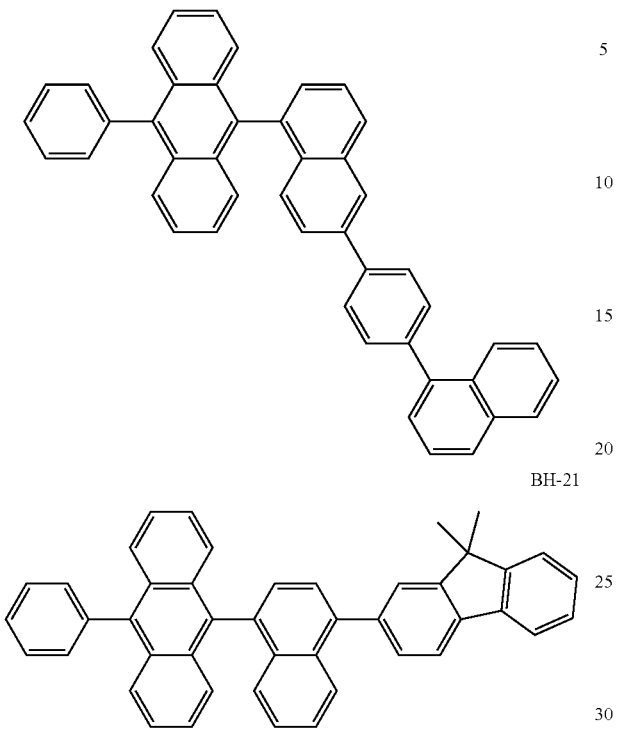

BH-21

BH-22

BH-23

BH-24

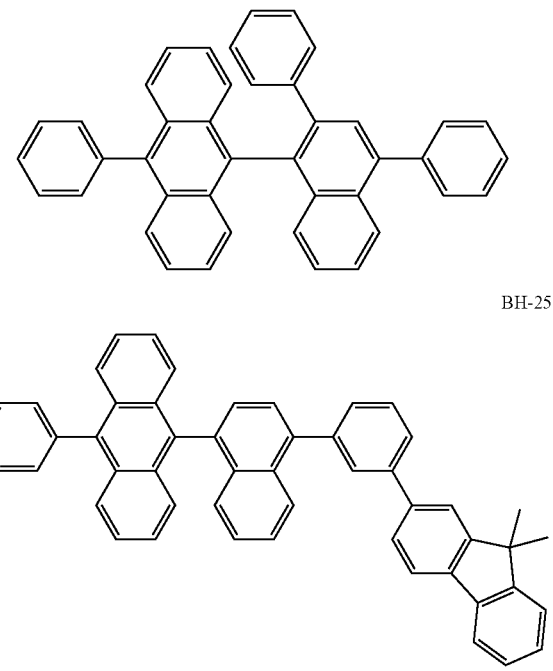

BH-25

A fluorescent dopant material may be a pyrene-based derivative, an aminofluorene-based derivative, an aminoanthracene-based derivative, an aminochrysene-based derivative, etc., and preferably, a pyrene-based derivative.

Specifically, the fluorescent dopant material of the present disclosure may include the following compounds, but is not limited thereto:

BD-1

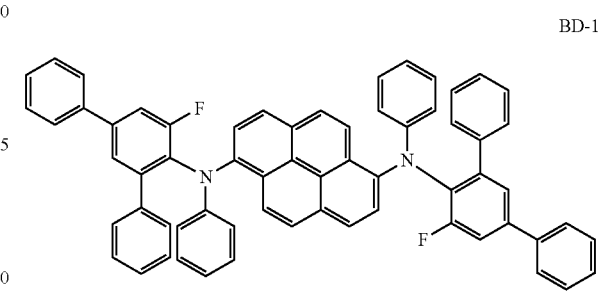

BD-2

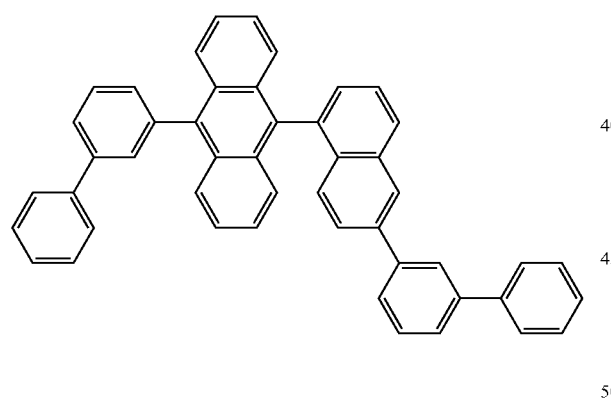

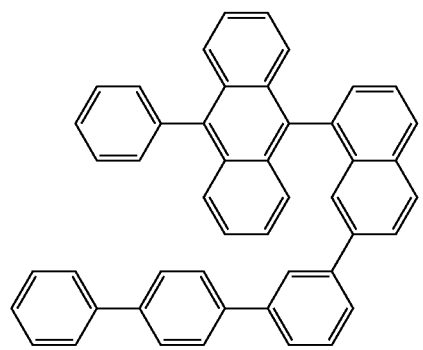

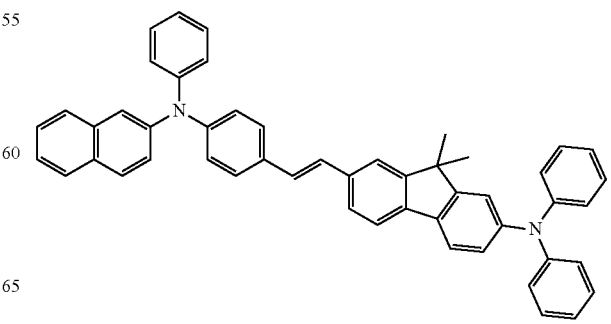

-continued
BD-3
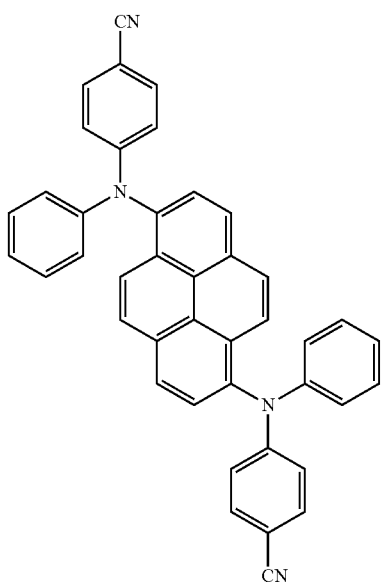
BD-7
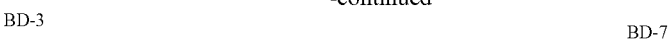
BD-8
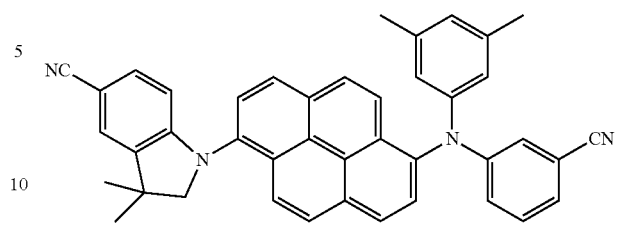
BD-4
BD-9
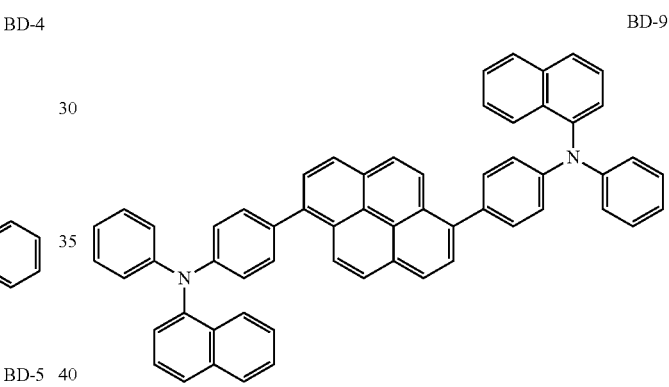
BD-5
BD-10
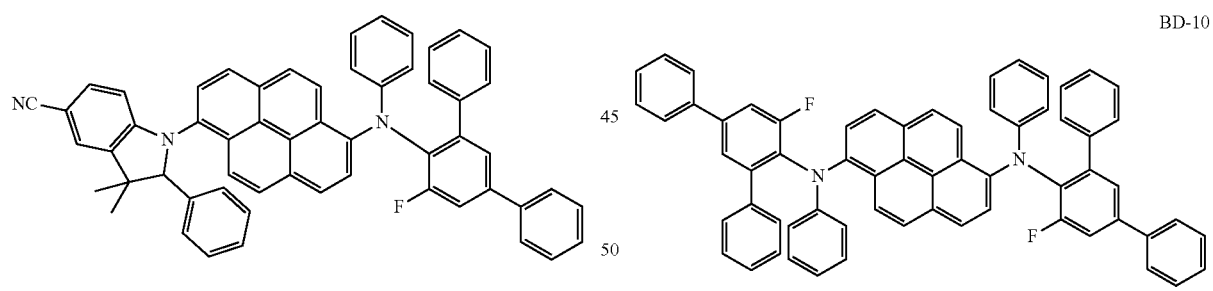
BD-6
BD-11
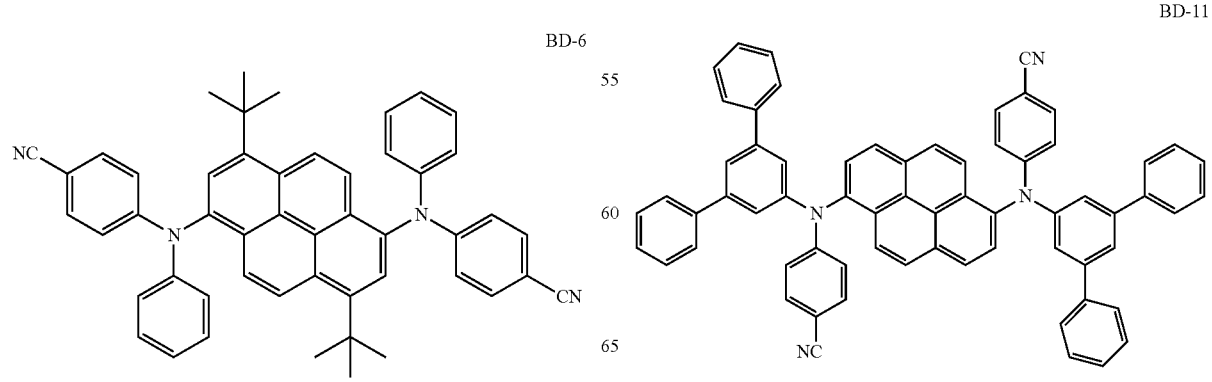

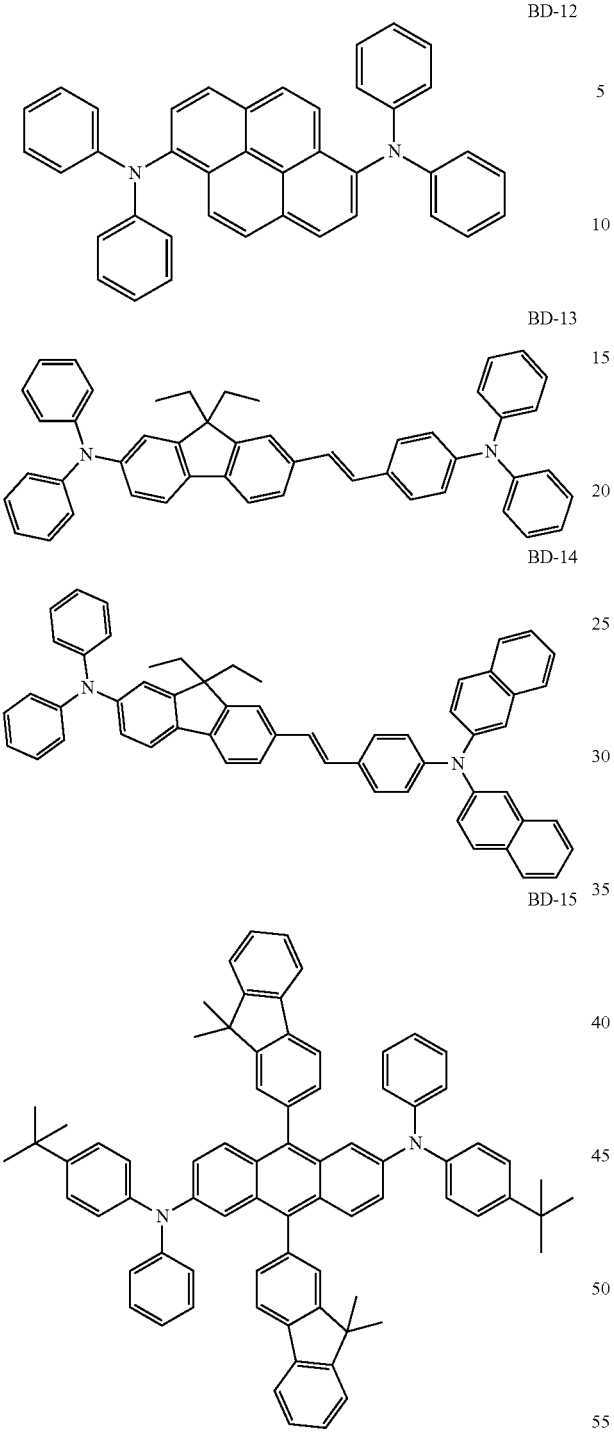

BD-12

BD-13

BD-14

BD-15

When the light-emitting layer 125 comprise a host and a dopant, the dopant may be doped in an amount of less than about 25 wt %, preferably, less than 17 wt %, based on the total amount of the host and dopant of the light-emitting layer. The thickness of the light-emitting layer 125 may be from about 5 nm to about 100 nm, preferably, from about 10 nm to about 60 nm. The light-emitting layer 125 is a layer in which light emission occurs, and may be a single layer or multiple layers of two or more layers. When the light-emitting layer 125 is multiple layers of two or more layers, each light-emitting layer may emit different colors of light. For example, a white light-emitting device may be produced by forming three light-emitting layers 125, which emit the light with blue, red and green, respectively. The light-emitting layer 125 may be formed on the hole transport layer 123 by various known methods such as a vacuum vapor deposition method, a wet film-forming method, a laser induced thermal imaging method, etc.

The OLED of the present disclosure may further comprise a hole injection layer or a hole transport layer between the first electrode and the light-emitting layer.

The material used in the hole injection layer 122 may be the known hole injection material, for example, a phthalocyanine compound such as a copper phthalocyanine, MTDATA (4,4',4''-tris[(3-methylphenyl)phenylamino]triphenylamine), 2-TNATA (4,4',4''-tris[2-naphthyl(phenyl)amino]triphenylamine), $N^1,N^1$-([1,1'-biphenyl]-4,4'-diyl)bis($N^1$-(naphthalene-1-yl)-$N^4,N^4$-diphenylbenzene-1,4-diamine), Pani/DBSA (polyaniline/dodecylbenzenesulfonic acid), PEDOT/PSS (poly(3,4-ethylenedioxythiophene)/poly(4-styrenesulfonate)), Pani/CSA (polyaniline/camphorsulfonic acid), or Pani/PSS (polyaniline)/poly(4-styrenesulfonate)), etc., but is not limited thereto.

In addition, the hole injection layer 122 may be formed by using the following compound of formula 200:

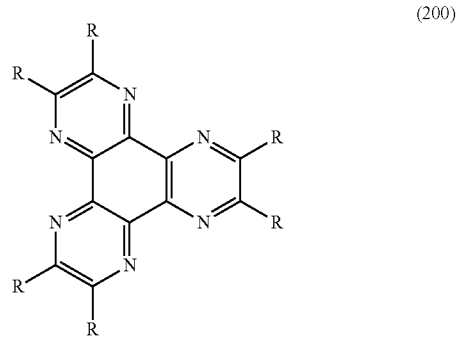

(200)

Wherein, R may be selected from the group consisting of a cyano (—CN), a nitro (—$NO_2$), a phenylsulfonyl (—$SO_2$($C_6H_5$)), a (C2-C5)alkenyl substituted with cyano or nitro, and a phenyl substituted with a cyano or a nitro.

The compound of the formula 200 has properties of being crystallized, and thus the hole injection layer 122 may obtain strength by comprising the compound.

The hole injection layer 122 may be a single layer or multiple layers of two or more layers. When the hole injection layer 122 is multiple layers of two or more layers, the compound of the formula 200 may be used at one of them. The thickness of the hole injection layer 122 may be from about 1 nm to about 1,000 nm, preferably, about 5 nm to about 100 nm. The hole injection layer 122 may be formed on the first electrode 110 by various known methods such as a vacuum vapor deposition method, a wet film-forming method, a laser induced thermal imaging method, etc.

Specifically, a hole injection material comprised in the hole injection layer includes the following compounds, but is not limited thereto:

HI-1

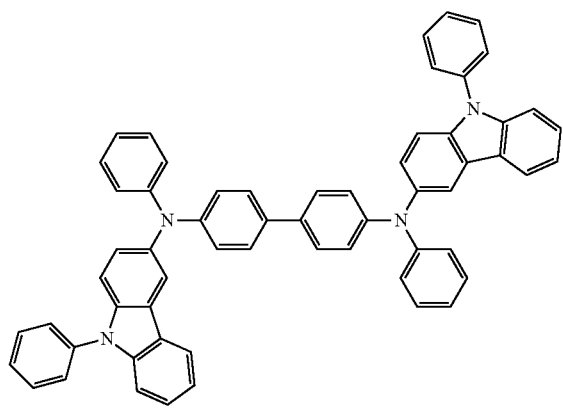

HT-2

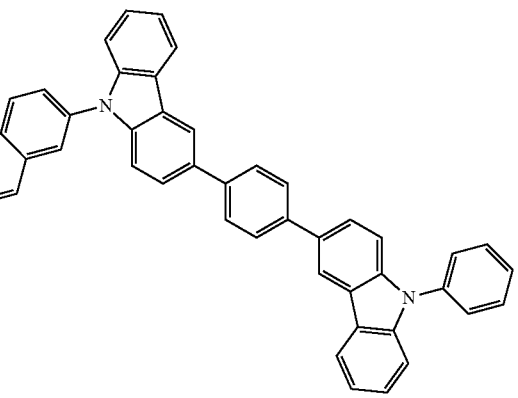

HI-2

HT-3

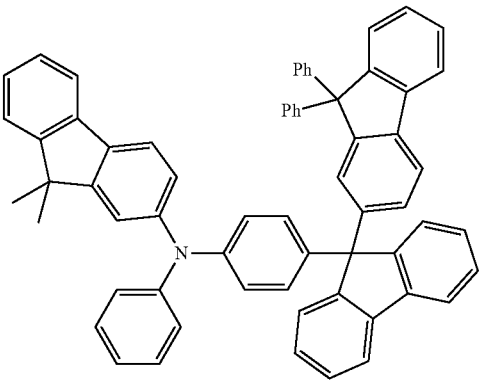

The material used in the hole transport layer 123 may be the known hole transport material, for example, an aromatic amine-based derivative, especially, a biphenyldiamine-based derivative such as TPD (N,N'-bis-(3-methylphenyl)-N,N'-diphenylbenzidine), $N^4,N^4,N^{4'},N^{4'}$-tetra([1,1'-biphenyl]-4-yl)-[1,1'-biphenyl]-4,4'-diamine, etc., but is not limited thereto.

Specifically, a hole transport material comprised in the hole transport layer includes the following compounds, but is not limited thereto:

HT-1

HT-4

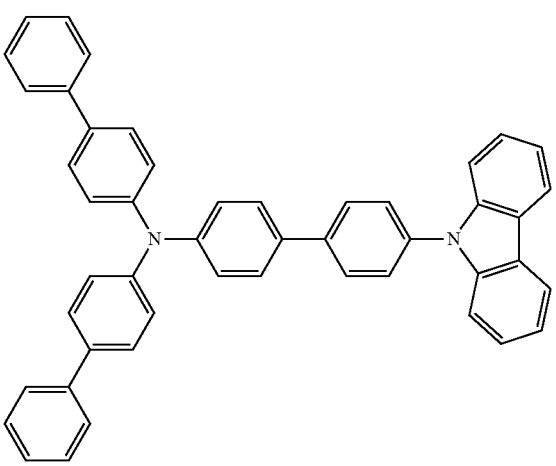

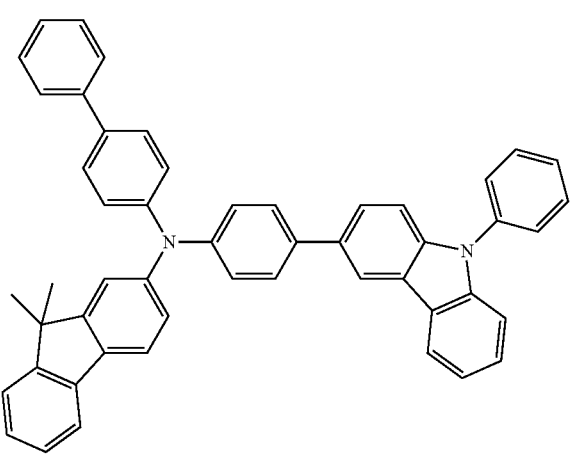

The hole transport layer 123 may be a single layer or multiple layers. The thickness of the hole transport layer 123 may be from about 1 nm to about 100 nm, preferably, from about 5 nm to about 80 nm. The hole transport layer 123 may be formed on the hole injection layer 122 by various known methods such as a vacuum vapor deposition method, a wet film-forming method, a laser induced thermal imaging method, etc.

When a material having improved HOMO characteristics and anion stability is used as a hole transport material, the lifespan properties of the device is also improved as the hole transport layer stabilized, even for OLEDs comprising an electron buffer layer of which lifespan is relatively short. In other words, upon comparing using a material having improved HOMO characteristics and anion stability with using a material having vulnerable HOMO characteristics and anion stability as a hole transport material of the hole transport layer, lifespan properties can be prevented from being decreased by using a material having improved HOMO characteristics and anion stability even for a device comprising an electron buffer layer of which lifespan is relatively short, due to relatively low deviation of lifespan according to the material groups consisting of the electron buffer layer.

The electron transport layer 127 may comprise the known electron transport material besides the compound of the present disclosure. For example, the electron transport material may be oxazole-based compounds, isoxazole-based compounds, triazole-based compounds, isothiazole-based compounds, oxadiazole-based compounds, thiadiazole-based compounds, perylene-based compounds, and anthracene-based compounds, aluminum complexes, gallium complexes, etc., but is not limited thereto.

Specifically, an electron transport material comprised in the electron transport layer includes the following compounds, but is not limited thereto:

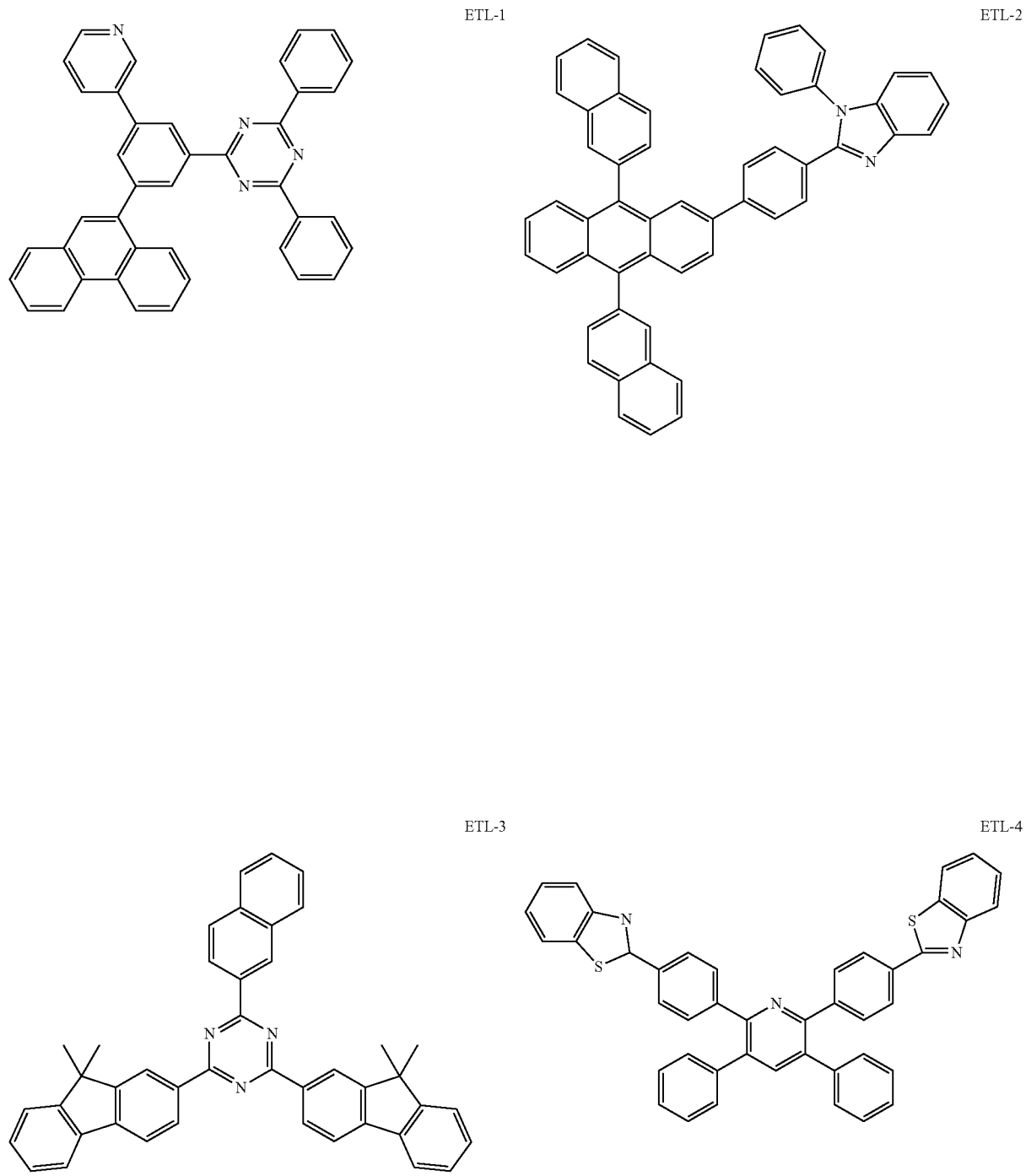

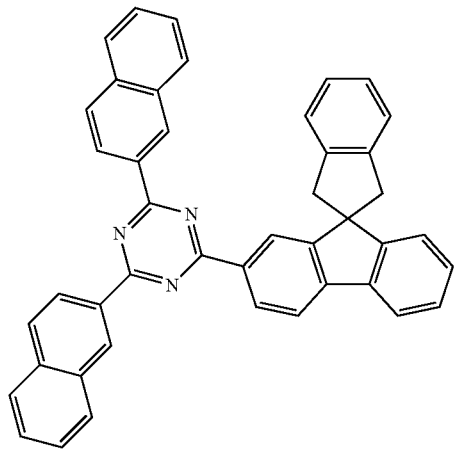

ETL-5

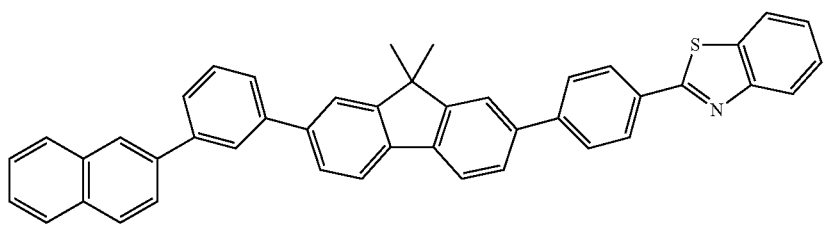

ETL-6

Preferably, the electron transport layer 127 may be a mixed layer comprising an electron transport compound and a reductive dopant. When formed as a mixed layer, electrons can be easily injected and transported to a light-emitting medium since the electron transport compound is reduced to an anion.

When the electron transport layer 127 is formed as a mixed layer, the electron transport compound is not specifically limited, and the known electron transport material may be used.

The reductive dopant may be alkali metals, alkali metal compounds, alkaline-earth metals, rare-earth metals, halides thereof, oxides thereof, and complexes thereof. Specifically, the reductive dopant includes lithium quinolate, sodium quinolate, cesium quinolate, potassium quinolate, LiF, NaCl, CsF, $Li_2O$, BaO, and $BaF_2$, but is not limited thereto.

The thickness of the electron transport layer 127 may be from about 5 nm to about 100 nm, and preferably from about 10 nm to about 60 nm. The electron transport layer 127 may be formed on the electron buffer layer 126 by various known methods such as a vacuum vapor deposition method, a wet film-forming method, a laser induced thermal imaging method, etc.

The material used in the electron injection layer 128 may be the known electron injection materials, for example, lithium quinolate, sodium quinolate, cesium quinolate, potassium quinolate, LiF, NaCl, CsF, $Li_2O$, BaO, $BaF_2$, etc., but are not limited thereto.

The thickness of the electron injection layer 128 may be from about 0.1 nm to about 10 nm, and preferably from about 0.3 nm to about 9 nm. The electron injection layer 128 may be formed on the electron transport layer 127 by various known methods such as a vacuum vapor deposition method, a wet film-forming method, a laser induced thermal imaging method, etc.

The electron injection material comprised in the electron injection layer may be a lithium quinoline complex metal, and specifically, includes the following compound, but is not limited thereto:

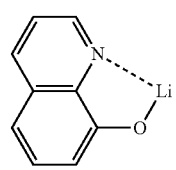

EIL-1

The second electrode 130 may be a cathode, and may be formed by a material having low work function. The material for the second electrode 130 may be aluminum (Al), calcium (Ca), magnesium (Mg), silver (Ag), cesium (Cs), lithium (Li), or a combination thereof. The second electrode 130 may be formed by various known methods such as a deposition method, a sputtering method, etc.

The OLED of FIG. 1 is only one embodiment to be explained clearly, and the present invention should not be limited to the embodiment but may be varied to another mode. For example, an optional component of the OLED of FIG. 1 besides a light-emitting layer and an electron buffer layer, such as the hole injection layer may be omitted. In addition, an optional component may be further added. Examples of the further added optional component are impurity layers such as n-doping layer and p-doping layer. Moreover, the OLED may emit light from both sides by placing a light-emitting layer each in both sides in between the impurity layers. The light-emitting layers of both sides may emit different colors. In addition, the first electrode may be a transparent electrode and the second electrode may be a reflective electrode so that the OLED may be a bottom emission type, and the first electrode may be a reflective electrode and the second electrode may be a transparent electrode so that the OLED may be a top emission type. Also, a cathode, an electron transport layer, a light-emitting layer, a hole transport layer, a hole injection layer, and an anode may be sequentially deposited on a substrate to be an inverted OLED.

LUMO (lowest unoccupied molecular orbital) energy level and HOMO (highest occupied molecular orbital) energy level have inherently negative numbers, but the LUMO energy level and the HOMO energy level in the present disclosure are conveniently expressed as their absolute values. Furthermore, the comparison between LUMO energy levels is based on their absolute values.

The LUMO energy levels of the present disclosure may be easily measured by the various known methods. Generally, LUMO energy levels are measured by cyclic voltammetry or ultraviolet photoelectron spectroscopy (UPS). Thus, a person skilled in the art may easily comprehend the electron buffer layer, host material, and electron transport zone that satisfy the equational relationship of the LUMO energy levels of the present disclosure to practice the present disclosure. HOMO energy levels may be easily measured by the same as the method of measuring LUMO energy levels.

Values measured by density functional theory (DFT) are used for the LUMO energy level of the electron buffer layer. The results according to the relationship of the LUMO energy level of the electron buffer layer (Ab) and the LUMO energy level of the host (Ah) are to explain the general tendency of the device in accordance with the overall LUMO energy groups of the electron buffer layer, and thus results other than the above may appear according to the inherent properties of the specific derivatives and the stability of the materials.

The electron buffer layer may be comprised in an OLED emitting every color including blue, red, and green, preferably, a blue light-emitting OLED (i.e. the main peak wavelength is from 430 to 470 nm, preferably, in the 450's nm).

Hereinafter, the preparation method of the compounds of the present disclosure, and the properties of the device comprising the compounds will be explained in detail with reference to the representative compounds of the present disclosure. However, the present invention is not limited by the following examples.

Example 1: Preparation of Compound C-1

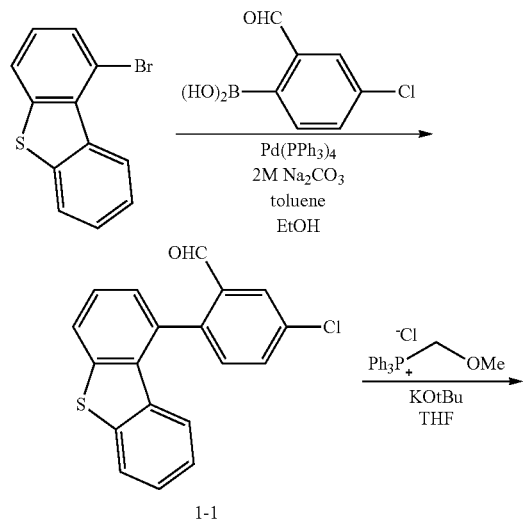

1-1

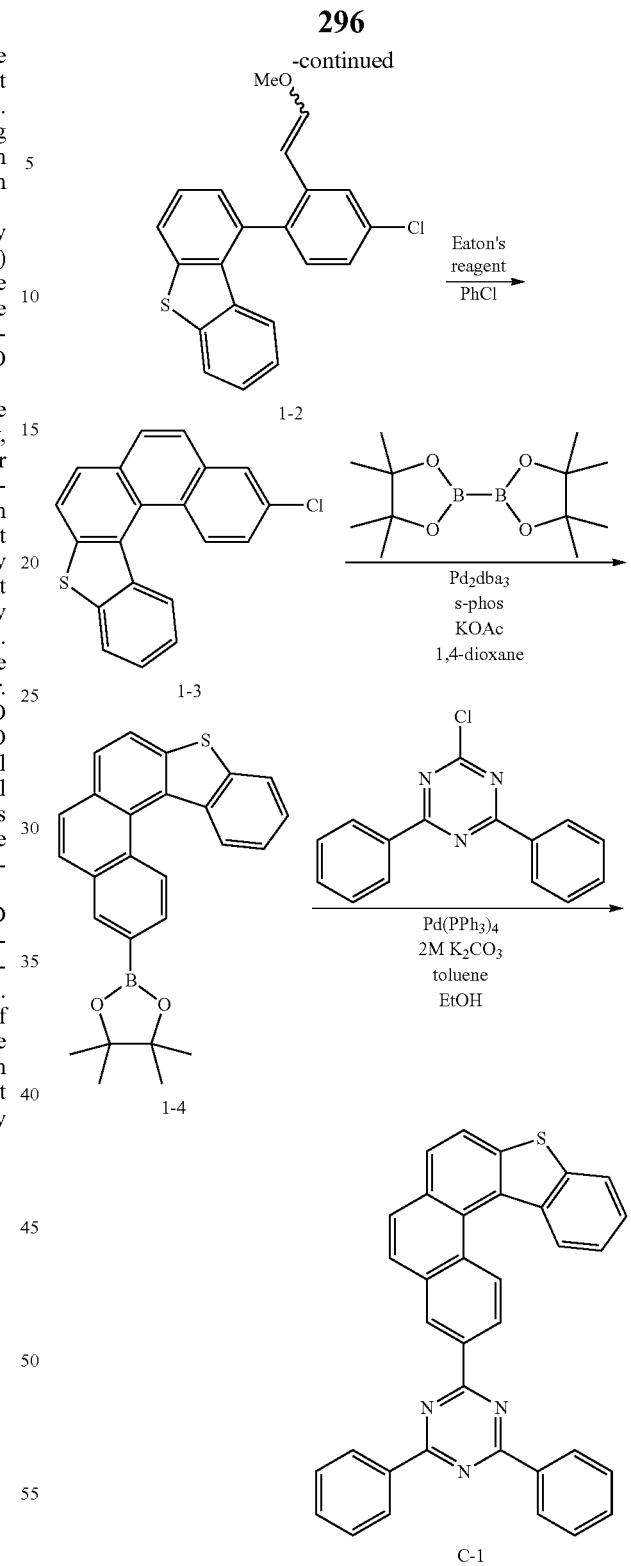

1) Preparation of Compound 1-1

After introducing 1-bromodibenzothiophene (CAS: 65642-94-6, 19.4 g, 73.7 mmol), 4-chloro-2-formylbenzene boronic acid (15 g, 81.7 mmol), tetrakis(triphenylphosphine) palladium (3.4 g, 3.0 mmol), sodium carbonate (19.5 g, 184 mmol), toluene (400 mL), ethanol (100 mL), and distilled water (100 mL) into a reaction vessel, the mixture was stirred for 3 hours at 140° C. After completing the reaction by adding distilled water to the reaction solution, an organic layer was extracted with ethyl acetate. The extracted organic layer was dried with magnesium sulfate, and the solvent was removed therefrom using a rotary evaporator. After dissolving the product into chloroform, the product was filtered with silica gel to obtain compound 1-1. The obtained compound 1-1 was used in the next reaction without any further purification.

2) Preparation of Compound 1-2

After introducing compound 1-1 (24 g, 74 mmol), (methoxymethyl)triphenylphosphonium chloride (38 g, 111 mmol) and tetrahydrofuran (500 mL) into a reaction vessel, the mixture was stirred for 5 hours. Potassium tert-butoxide (1M in THF, 111 mL) was then slowly added dropwise to the mixture at 0° C. The temperature of the mixture was slowly raised, and the mixture was stirred at room temperature for 3 hours. After completing the reaction by adding distilled water to the reaction solution, an organic layer was extracted with ethyl acetate. The extracted organic layer was dried with magnesium sulfate, and the solvent was removed therefrom using a rotary evaporator. After dissolving the product into chloroform, the product was filtered with silica gel to obtain compound 1-2. The obtained compound 1-2 was used in the next reaction without any further purification.

3) Preparation of Compound 1-3

After introducing compound 1-2 (26 g, 74 mmol), Eaton's reagent (4 mL) and chlorobenzene (400 mL) into a reaction vessel, the mixture was refluxed for 2 hours. After completing the reaction, the mixture was cooled to room temperature, and an organic layer was extracted with methylene chloride (MC). After drying the extracted organic layer with magnesium sulfate, the solvent was removed by using a rotary evaporator. Thereafter, the obtained product was purified by column chromatography to obtain compound 1-3 (16.3 g, 66%).

4) Preparation of Compound 1-4

After introducing compound 1-3 (10.5 g, 33 mmol), bis(pinacolato)diborane (10 g, 39.6 mmol), tris(dibenzylideneacetone)dipalladium (1.3 g, 1.65 mmol), 2-dicyclohexylphosphino-2',6'-dimethoxybiphenyl (s-phos) (1.4 g, 3.3 mmol), potassium acetate (9.7 g, 99 mmol) and 1,4-dioxane (150 mL) into a reaction vessel, the mixture was stirred for 3 hours at 140° C. After completing the reaction, the mixture was cooled to room temperature, and an organic layer was extracted with ethyl acetate. After drying the extracted organic layer with magnesium sulfate, the solvent was removed by using a rotary evaporator. Thereafter, the obtained product was purified by column chromatography to obtain compound 1-4 (14.3 g, 99%).

5) Preparation of Compound C-1

After introducing compound 1-4 (7.2 g, 17.6 mmol), 2-chloro-4,6-diphenyl-1,3,5-triazine (CAS: 3842-55-5, 4.7 g, 17.6 mmol), tetrakis(triphenylphosphine)palladium (1.0 g, 0.88 mmol), potassium carbonate (6 g, 44 mmol), toluene (60 mL), ethanol (20 mL), and distilled water (20 mL) into a reaction vessel, the mixture was stirred for 3 hours at 140° C. After completing the reaction, the mixture was added dropwise to methanol, and the obtained solid was filtered. The obtained solid was purified by column chromatography and recrystallization to obtain compound C-1 (7 g, 77%).

Example 2: Preparation of Compound C-21

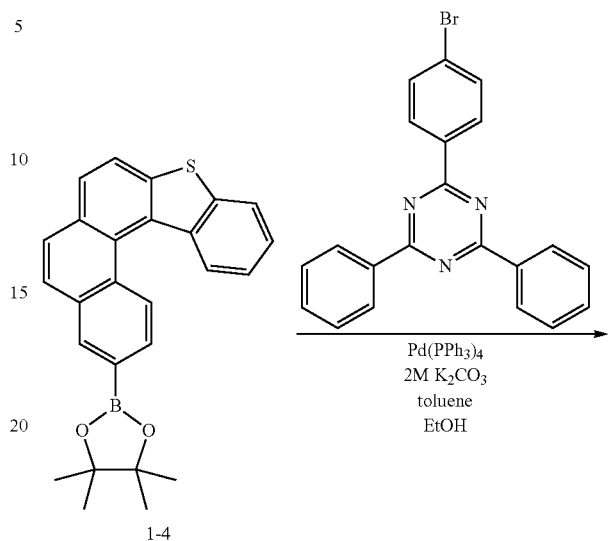

1-4

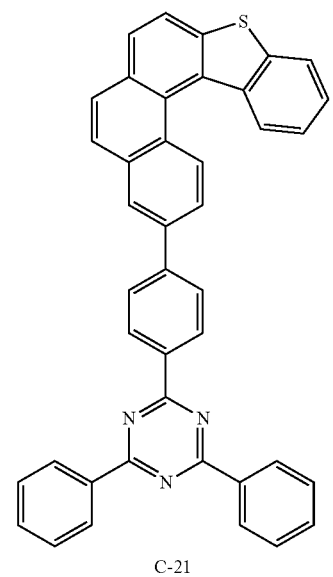

C-21

After introducing compound 1-4 (6.0 g, 14.6 mmol), 2-(4-bromophenyl)-4,6-diphenyl-1,3,5-triazine (CAS: 23449-08-3, 5.2 g, 13.3 mmol), tetrakis(triphenylphosphine) palladium (0.77 g, 0.67 mmol), potassium carbonate (4.6 g, 36.5 mmol), toluene (60 mL), ethanol (20 mL), and distilled water (20 mL) into a reaction vessel, the mixture was stirred for 3 hours at 140° C. After completing the reaction, the precipitated solid was washed with distilled water and methanol. The obtained compound was purified by column chromatography and recrystallization to obtain compound C-21 (4.4 g, 56%).

Example 3: Preparation of Compound C-31

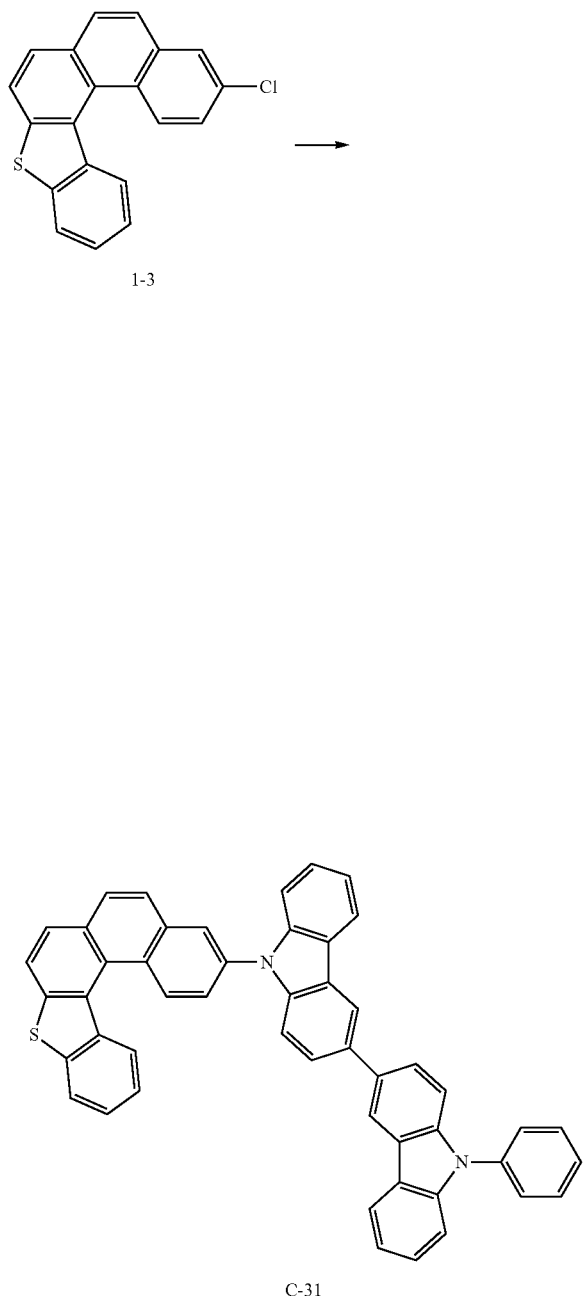

After introducing compound 1-3 (4 g, 12.5 mmol), 9-phenyl-9H,9'H-[3,31']bicarbazolyl (CAS: 1060735-14-9, 5.1 g, 23 mmol), tris(dibenzylideneacetone)dipalladium (0.46 g, 0.50 mmol), 2-dicyclohexylphosphino-2',6'-dimethoxybiphenyl (s-phos) (0.41 g, 1.00 mmol), sodium tert-butoxide (2.4 g, 25.1 mmol) and o-xylene (70 mL) into a reaction vessel, the mixture was stirred for 3 hours at 170° C. After completing the reaction, the mixture was added dropwise to methanol, and the obtained solid was filtered. The obtained solid was purified by column chromatography and recrystallization to obtain compound C-31 (6.9 g, 80%).

Example 4: Preparation of Compound C-42

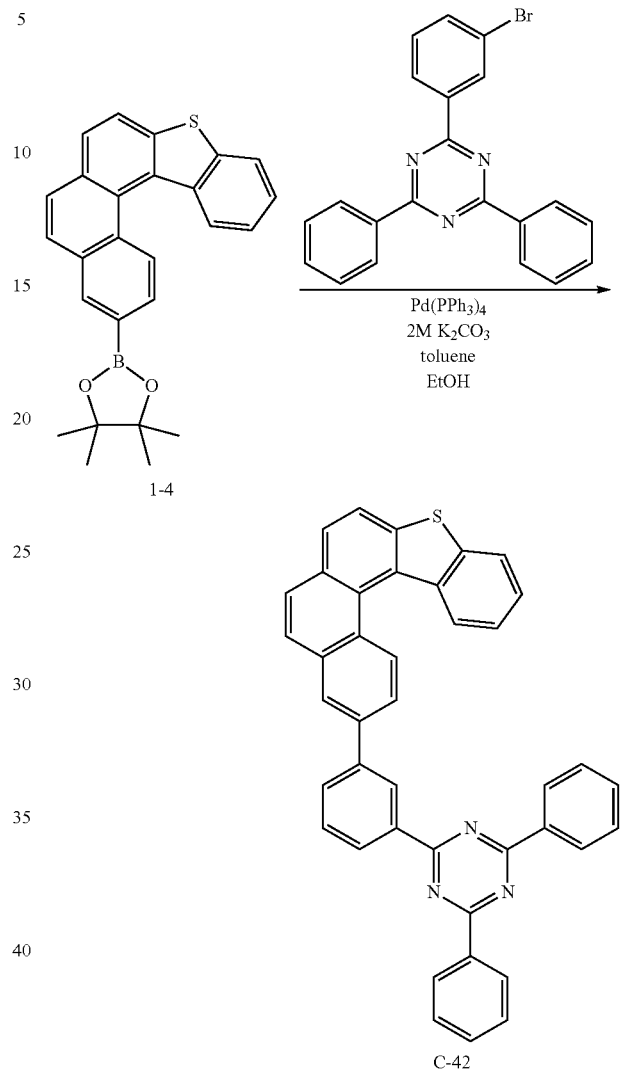

After introducing compound 1-4 (7.2 g, 17.6 mmol), 2-(3-bromophenyl)-4,6-diphenyl-1,3,5-triazine (CAS: 864377-31-1, 4.7 g, 17.6 mmol), tetrakis(triphenylphosphine)palladium (1.0 g, 0.88 mmol), potassium carbonate (6.0 g, 44 mmol), toluene (60 mL), ethanol (20 mL), and distilled water (20 mL) into a reaction vessel, the mixture was stirred for 3 hours at 140° C. After completing the reaction, the precipitated solid was washed with distilled water and methanol. The obtained compound was purified by column chromatography and recrystallization to obtain compound C-42 (5.7 g, 84%).

The properties of compounds C-1, C-21, C-31 and C-42 synthesized as described above are shown in Table 1 below.

TABLE 1

| Compound | MW | UV Spectrum (in toluene, nm) | PL Spectrum (in toluene, nm) | M.P. (° C.) |
|---|---|---|---|---|
| C-1 | 516 | 280 | 431 | 301 |
| C-21 | 591.72 | 258 | 427 | 278 |

TABLE 1-continued

| Compound | MW | UV Spectrum (in toluene, nm) | PL Spectrum (in toluene, nm) | M.P. (° C.) |
|---|---|---|---|---|
| C-31 | 691.0 | 302 | 406 | 299 |
| C-42 | 592 | 258 | 399 | 257 |

Hereinafter, the luminescent properties of the OLED comprising the organic electroluminescent compound of the present disclosure will be explained in detail.

Comparative Example 1: Producing a Blue Light-Emitting OLED Device not Comprising an Electron Buffer Layer An OLED device was produced as follows: A transparent electrode indium tin oxide (ITO) thin film (10 Ω/sq) on a glass substrate for an OLED (GEOMATEC CO., LTD., Japan) was subjected to an ultrasonic washing by sequentially using acetone, ethanol, and distilled water, and was then stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming the first hole injection layer having a thickness of 60 nm on the ITO substrate. Compound HI-2 was then introduced into another cell of the vacuum vapor deposition apparatus, and an electric current was applied to the cell to evaporate the introduced material, thereby forming the second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming the first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming the second hole transport layer having a thickness of 5 nm on the first hole transport layer. After forming the hole injection layers and the hole transport layers, a light-emitting layer was then deposited as follows. Compound BH-1 as a host was introduced into one cell of the vacuum vapor deposition apparatus and compound BD-1 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, compound ETL-1 as an electron transport material was introduced into one cell of the vacuum vapor deposition apparatus, and compound EIL-1 was introduced into another cell of the vacuum vapor deposition apparatus. The two materials were evaporated at the same rate and doped in a doping amount of 50 wt %, respectively, to form an electron transport layer having a thickness of 35 nm on the light-emitting layer. After depositing compound EIL-1 having a thickness of 2 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr.

The driving voltage at the luminance of 1,000 nits, the luminous efficiency, the CIE color coordinate, the External Quantum Efficiency, and the time taken to be reduced to 90% of the luminance, where the early luminance is 100%, at 2,000 nits and a constant current (T90 lifespan) of the OLED device produced as described above are provided in Table 2 below.

Device Example 1: Producing a Blue Light-Emitting OLED Device Comprising the Compound of the Present Disclosure as an Electron Buffer Material An OLED device was produced in the same manner as in Comparative Example 1, that except the thickness of an electron transport layer was reduced to 25 nm, and an electron buffer layer having a thickness of 5 nm was inserted between the light-emitting layer and the electron transport layer. Evaluation results of the OLED device produced in Device Example 1 are provided in Table 2 below.

TABLE 2

| | Electron Buffer Material | Driving Voltage (V) | Luminous Efficiency (cd/A) | Color Coordinate (x) | Color Coordinate (y) | External Quantum Efficiency (%) | Lifespan T90 (hr) |
|---|---|---|---|---|---|---|---|
| Comparative Example 1 | — | 4.3 | 6.0 | 139 | 88 | 8.7 | 40.3 |
| Device Example 1 | C-42 | 4.2 | 6.4 | 139 | 87 | 9.4 | 44.2 |

From Table 2 above, it can be seen that the electron buffer material of the present disclosure has fast electron current properties, and thus Device Example 1 provides high efficiency and long lifespan compared to Comparative Example 1 which does not have an electron buffer material.

Comparative Example 2: Producing a Blue Light-Emitting OLED Device Comprising a Conventional Electron Transport Material An OLED device was produced in the same manner as in Comparative Example 1, except for changing the electron transport layer and the electron injection layer as follows: Compound ETL-2 as an electron transport material was introduced into one cell of the vacuum vapor deposition apparatus and was then evaporated to form an electron transport layer having a thickness of 33 nm. After depositing compound EIL-1 having a thickness of 4 nm as an electron injection layer, an Al cathode having a thickness of 80 nm was then deposited by another vacuum vapor deposition apparatus. Thus, an OLED device was produced. Each of the materials used for producing the OLED device was purified by vacuum sublimation at $10^{-6}$ torr.

The driving voltage at the luminance of 1,000 nits, the luminous efficiency, the CIE color coordinate, and the External Quantum Efficiency of the OLED device produced as described above are provided in Table 3 below.

Device Example 2: Producing a Blue Light-Emitting OLED Device Comprising the Compound of the Present Disclosure as an Electron Transport Material An OLED device was produced in the same manner as in Comparative Example 2, except for changing the electron transport material as shown in Table 3 below. Evaluation results of the OLED device produced in Device Example 2 are provided in Table 3 below.

TABLE 3

|  | Electron Transport Material | Driving Voltage (V) | Luminous Efficiency (cd/A) | Color Coordinate (x) | Color Coordinate (y) | External Quantum Efficiency (%) |
|---|---|---|---|---|---|---|
| Comparative Example 2 | ETL-2 | 4.6 | 4.6 | 144 | 115 | 4.8 |
| Device Example 2 | C-42 | 3.9 | 6.4 | 139 | 88 | 8.0 |

Comparative Example 3: Producing a Blue Light-Emitting OLED Device Comprising a Conventional Electron Transport Material An OLED device was produced in the same manner as in Comparative Example 2, except for changing the electron transport layer and the electron injection layer as follows: Compound ETL-2 as an electron transport material was introduced into one cell of the apparatus and compound EIL-1 as an electron transport material was introduced into another cell of the apparatus. The two materials were evaporated at the same rate and doped in a doping amount of 50 wt %, respectively, to deposit an electron transport layer having a thickness of 35 nm. Next, compound EIL-1 was deposited in the electron injection layer having a thickness of 2 nm.

The driving voltage at the luminance of 1,000 nits, the luminous efficiency, the CIE color coordinate, and the External Quantum Efficiency of the OLED device produced as described above are provided in Table 4 below.

Device Example 3: Producing a Blue Light-Emitting OLED Device Comprising the Compound of the Present Disclosure as an Electron Transport Material An OLED device was produced in the same manner as in Comparative Example 3, except for changing the electron transport material as shown in Table 4 below. Evaluation results of the OLED device produced in Device Example 3 are provided in Table 4 below.

TABLE 4

|  | Electron Transport Material | Driving Voltage (V) | Luminous Efficiency (cd/A) | Color Coordinate (x) | Color Coordinate (y) | External Quantum Efficiency (%) |
|---|---|---|---|---|---|---|
| Comparative Example 3 | ETL-2:EIL-1 | 4.2 | 5.5 | 140 | 92 | 7.6 |
| Device Example 3 | C-42 | 4.3 | 6.5 | 139 | 85 | 9.6 |

From Tables 3 and 4 above, it can be seen that the electron transport material of the present disclosure has fast electron current property, and thus Device Examples 2 and 3 provide high efficiency compared to Comparative Examples 2 and 3.

Device Example 4: Producing a Blue Light-Emitting OLED Device Comprising the Compound of the Present Disclosure as an Electron Transport Material and not Comprising an Electron Buffer Layer An OLED device was produced in the same manner as in Comparative Example 1, except for changing the electron transport material to compound C-42.

The driving voltage at the luminance of 1,000 nits, the luminous efficiency, the CIE color coordinate, the External Quantum Efficiency, and the time taken to be reduced to 90% of the luminance, where the early luminance is 100%, at 2,000 nits and a constant current (T90 lifespan) of the OLED device produced as described above are provided in Table 5 below.

Device Examples 5 to 7: Producing a Blue Light-Emitting OLED Device Comprising the Compound of the Present Disclosure as an Electron Transport Material, and Further Comprising an Electron Buffer Layer An OLED device was produced in the same manner as in Device Example 4, except that the thickness of an electron transport layer was reduced to 25 nm, and an electron buffer layer having a thickness of 5 nm was inserted between the light-emitting layer and the electron transport layer. Evaluation results of the OLED device produced in Device Examples 5 to 7 are provided in Table 5 below.

TABLE 5

| | Electron Transport Material | Electron Buffer Material | Driving Voltage (V) | Luminous Efficiency (cd/A) | Color Coordinate (x) | Color Coordinate (y) | External Quantum Efficiency (%) | Lifespan T90 (hr) |
|---|---|---|---|---|---|---|---|---|
| Device Example 4 | C-42 | — | 4.1 | 6.5 | 139 | 86 | 9.2 | 37.1 |
| Device Example 5 | C-42 | BF-1 | 4.1 | 6.7 | 139 | 87 | 9.7 | 42.5 |
| Device Example 6 | C-42 | BF-2 | 4.3 | 6.3 | 139 | 87 | 9.1 | 62.1 |
| Device Example 7 | C-42 | C-42 | 4.3 | 6.3 | 139 | 87 | 9.1 | 49.0 |

In Device Examples 5 to 7, the properties of the OLED device according to different electron buffer materials were evaluated by fixing compound C-42 as an electron transport material. As shown in Table 5 above, an OLED device (Device Example 4) having excellent properties was obtained by using the compound of the present disclosure as an electron transport material, despite not comprising an electron buffer layer. Furthermore, the luminous efficiencies and the lifespan properties of the OLED devices (Device Examples 5 to 7), in which the compound of the present disclosure was used as an electron transport material and an electron buffer material was further comprised, were improved compared to those of the OLED device (Device Example 4), in which the compound of the present disclosure was used as an electron transport material but an electron buffer layer was not comprised. The difference of the efficiency and the performance of the OLED are due to the different HOMO orbital characteristics change of the electron buffer material used in Device Examples 5 to 7. Specifically, it can be seen that when the electron buffer layer comprises a diphenylfluorene and the electron transport layer comprises a benzophenanthrothiophene as shown in Device Example 5, the OLED may show relatively high efficiency properties while maintaining a proper lifespan compared to Device Example 4. Also, it can be seen that when the electron buffer layer comprises a diphenylindenocarbazole and a benzophenanthrothiophene, respectively, and the electron transport layer comprises a benzophenanthrothiophene as shown in Device Examples 6 and 7, the OLED may show improved lifespan properties while maintaining proper efficiency properties compared to Device Example 4. From Table 5 above, it can be seen that the efficiencies and lifespan properties of a OLED device may be improved not only by using the compound of the present disclosure as an electron transport material as a sole compound, but also by using the compound of the present disclosure as an electron transport material with a conventional electron buffer material or an electron buffer material of the present disclosure.

Device Example 8: Producing an OLED Device Comprising the Organic Electroluminescent Compounds of the Present Disclosure as a Host An OLED device was produced as follows: A transparent electrode indium tin oxide (ITO) thin film (10 Ω/sq) on a glass substrate for an OLED device (GEOMATEC CO., LTD., Japan) was subjected to an ultrasonic washing by sequentially using acetone, ethanol, and distilled water, and was then stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-6}$ torr. Thereafter, an electric current was applied to the cell to evaporate the introduced material, thereby forming the first hole injection layer having a thickness of 80 nm on the ITO substrate. Compound HI-2 was then introduced into another cell of the vacuum vapor deposition apparatus, and an electric current was applied to the cell to evaporate the introduced material, thereby forming the second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming the first hole transport layer having a thickness of 10 nm on the second hole injection layer. Compound HT-3 was then introduced into another cell of the vacuum vapor deposition apparatus, and an electric current was applied to the cell to evaporate the introduced material, thereby forming the second hole transport layer having a thickness of 60 nm on the first hole transport layer. After forming the hole injection layers and the hole transport layers, a light-emitting layer was then deposited as follows. Compound C-42 as a host was introduced into one cell of the vacuum vapor deposition apparatus and compound D-71 as a dopant was introduced into another cell of the apparatus. The two materials were evaporated at a different rate and the dopant was deposited in a doping amount of 3 wt %, based on the total weight of the host and dopant, to form a light-emitting layer having a thickness of 40 nm on the second hole transport layer. Next, compound ETL-3 and compound EIL-1 were then introduced into another two cells, and evaporated at a rate of 1:1 to form an electron transport layer having a thickness of 30 nm on the light-emitting layer. After depositing compound EIL-1 as an electron injection layer having a thickness of 2 nm on the electron transport layer, an Al cathode having a thickness of 80 nm was deposited by another vacuum vapor deposition apparatus. Thus, an OLED device was produced.

As a result, the produced OLED device showed a luminous efficiency of 28.2 cd/A at a driving voltage of 4.1 V, and a red light-emission having a luminance of 1,000 nits.

Device Example 9: Producing an OLED Device Comprising Organic Electroluminescent Compounds of the Present Disclosure as a Host and the Second Host Compound An OLED device was produced in the same manner as in Device Example 8, except for co-depositing compound C-42 and compound H1-12 as a host.

As a result, the produced OLED device showed a luminous efficiency of 27.7 cd/A at a driving voltage 3.6 V, and a red light-emission having a luminance of 1,000 nits.

Comparative Example 4: Producing an OLED Device Comprising a Conventional Compound as a Host An OLED device was produced in the same manner as in Device Example 8, except for using compound X as a host.

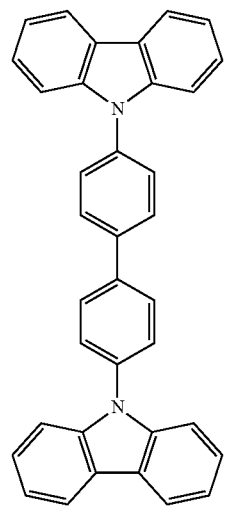

Compound X

As a result, the produced OLED device showed a luminous efficiency of 14.3 cd/A at a driving voltage of 10 V, and a red light-emission having a luminance of 1,000 nits.

TABLE 6

Compounds used in the Comparative Examples and Device Examples

Hole Injection Layer/Hole Transport Layer

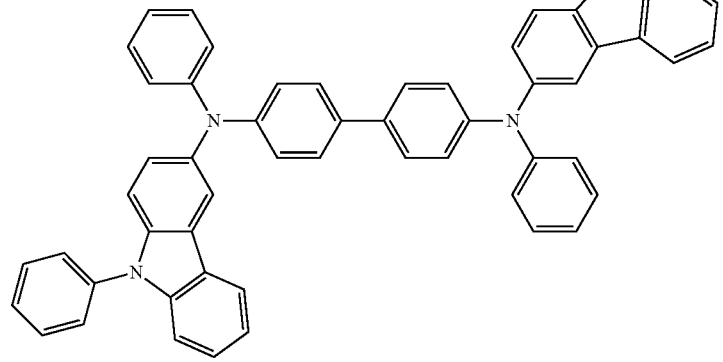

HI-1

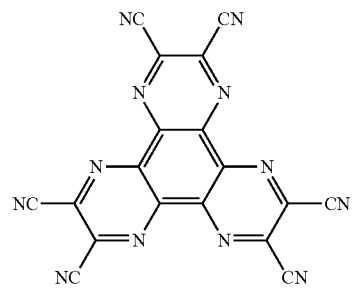

HI-2

TABLE 6-continued
Compounds used in the Comparative Examples and Device Examples
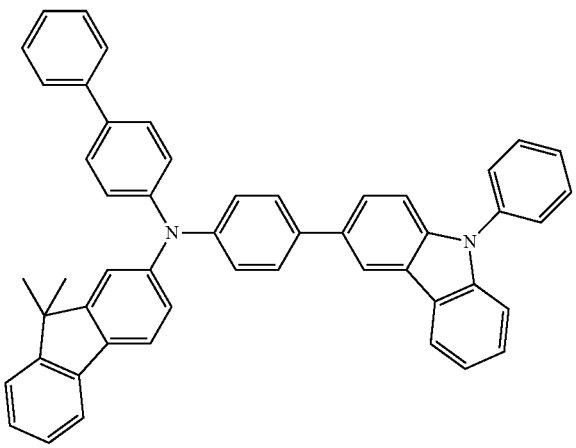
HT-1
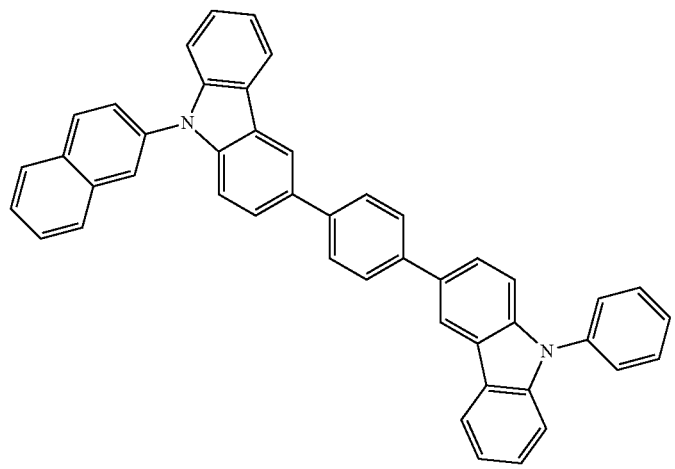
HT-2
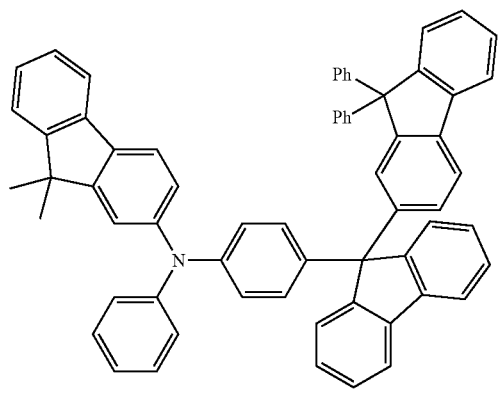
HT-3

TABLE 6-continued
Compounds used in the Comparative Examples and Device Examples
Light-
Emitting
Layer
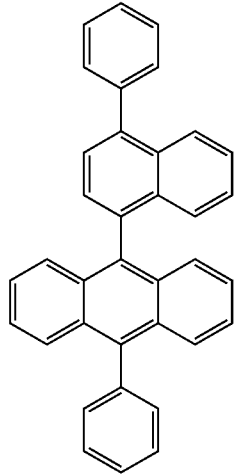
BH-1
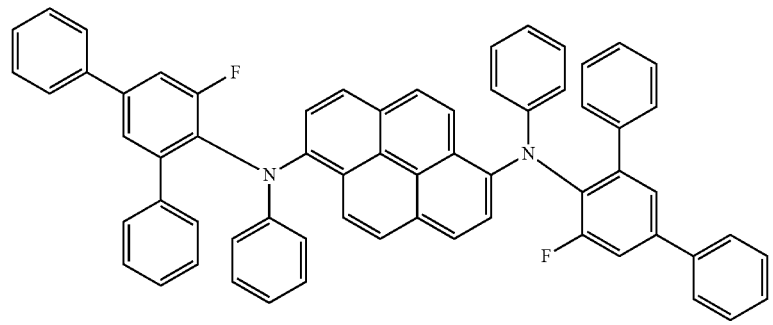
BD-1
Electron
Buffer
layer
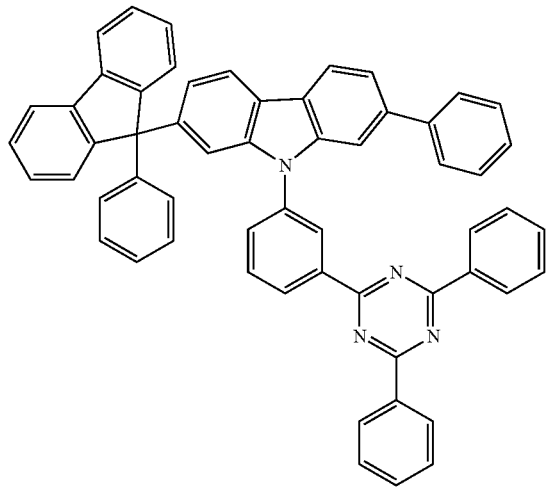
BF-1

TABLE 6-continued
Compounds used in the Comparative Examples and Device Examples
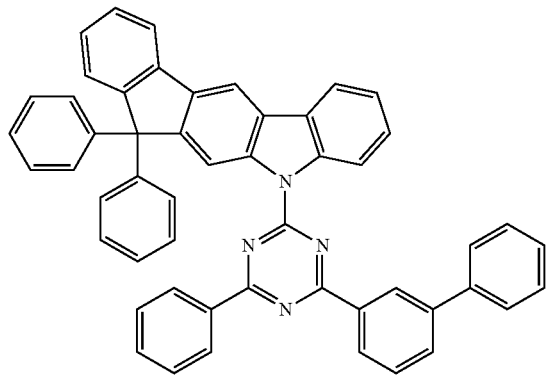
BF-2
Electron Transport Layer/ Electron Injection Layer
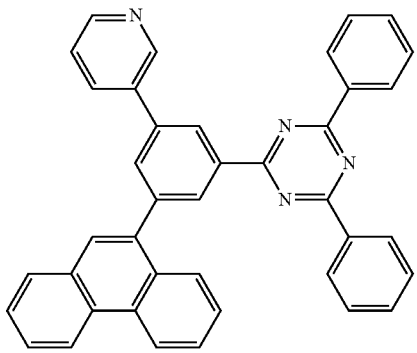
ETL-1
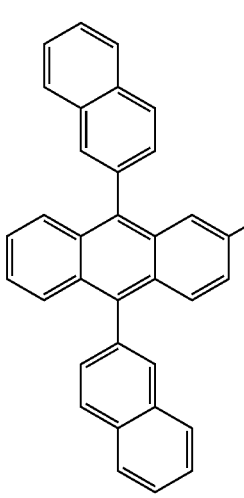
ETL-2
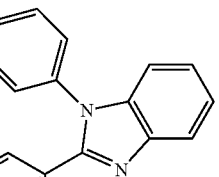
EIL-1
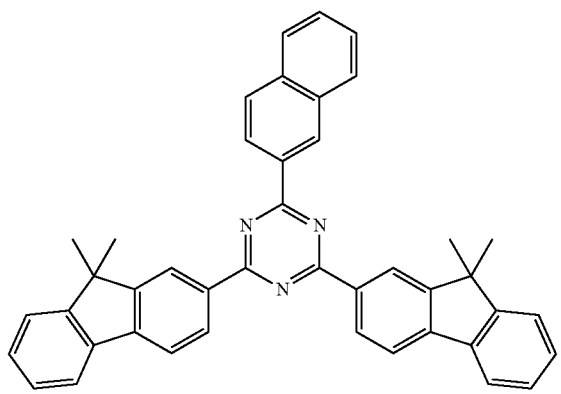
ETL-3

The invention claimed is:
1. An organic electroluminescent compound represented by any one of the following formulas 2 to 4:

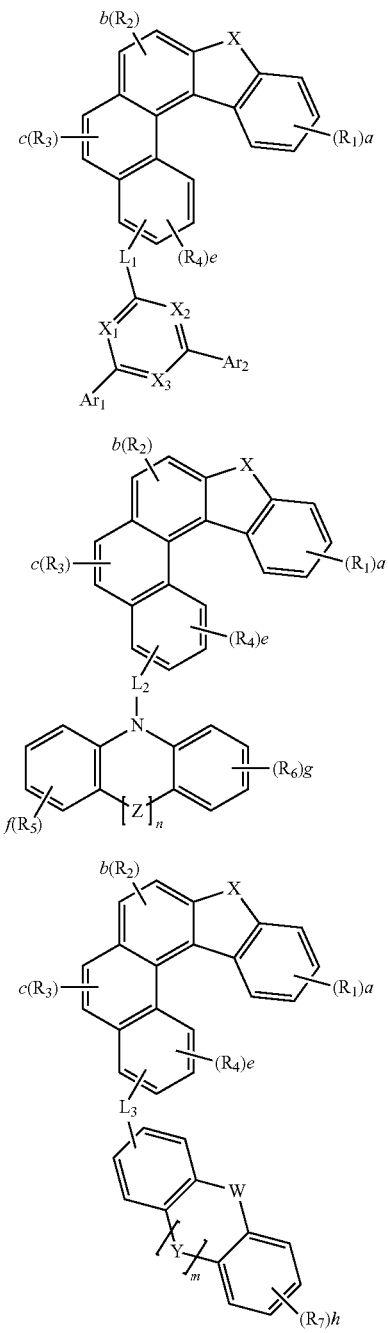

wherein
X represents O, S, or CR$_{11}$R$_{12}$;
R$_1$ to R$_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; wherein, at least one of R$_1$ to R$_4$ represents a substituted or unsubstituted (C6-C30)aryl, a substituted or unsubstituted (3- to 30-membered)heteroaryl, or a substituted or unsubstituted mono- or di-(C6-C30)arylamino, with the proviso that at least one of R$_1$ to R$_4$ does not represent a triphenylenyl;
a represents an integer from 1 to 4;
b and c each independently represent an integer of 1 or 2;
L$_1$ to L$_3$, each independently, represent a single bond, a substituted or unsubstituted (C6-C30)arylene, or a substituted or unsubstituted (3- to 30-membered)heteroarylene;
X$_1$ to X$_3$, each independently, represent N or CH; with the proviso that at least one of them represents N;
Ar$_1$ and Ar$_2$, each independently, represent a substituted or unsubstituted (C6-C30)aryl, or a substituted or unsubstituted (3- to 30-membered)heteroaryl;
W, Y, and Z, each independently, represent a single bond, O, S, NR$_{13}$, or CR$_{14}$R$_{15}$;
n and m, each independently, represent an integer of 0 or 1;
e represents an integer of 1 to 3; f, g, and h, each independently represent an integer of 1 to 4;
R$_5$ to R$_7$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one heteroatom selected from nitrogen, oxygen, and sulfur; and
R$_{13}$ to R$_{15}$, each independently, represent a substituted or unsubstituted (C1-C30)alkyl, a substituted or unsubstituted (C6-C30)aryl, or a substituted or unsubstituted (3- to 30-membered)heteroaryl; or R$_{14}$ and R$_{15}$ may be linked to each other to form a substituted or unsubstituted, mono- or polycyclic, (C3-C30) alicyclic or aromatic ring, whose carbon atom(s) may be replaced with at least one heteroatom selected from nitrogen, oxygen, and sulfur.

2. The organic electroluminescent compound according to claim 1, wherein the substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring in R₁ to R₇, R₁₁ to R₁₅, Ar₁, Ar₂, and L₁ to L₃, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C1-C30)alkyl or a (C6-C30)aryl; a (C6-C30)aryl unsubstituted or substituted with a (C6-C30)aryl, a (5- to 30-membered)heteroaryl, or mono- or di-(C6-C30)arylamino; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein the compound represented by formula 1 is selected from the group consisting of:

C-1

C-2

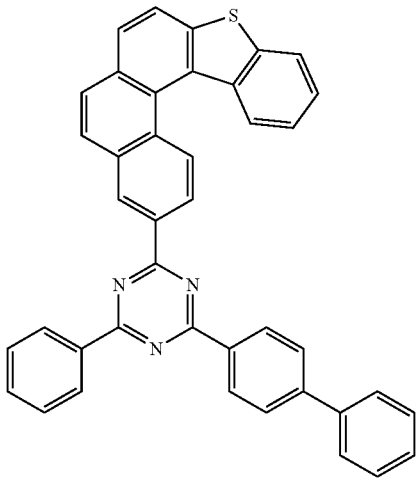

C-3

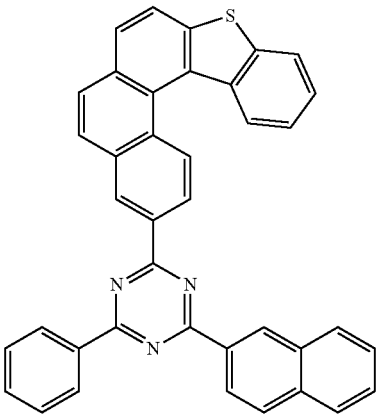

C-4

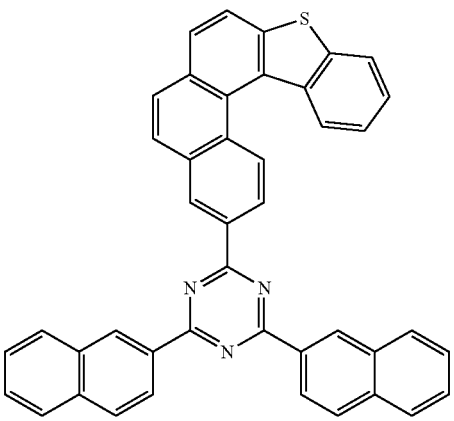

C-5

C-6
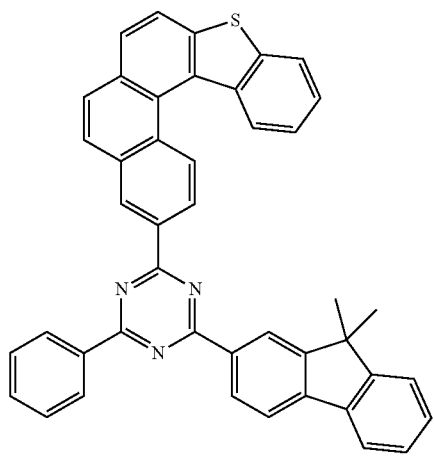
C-7
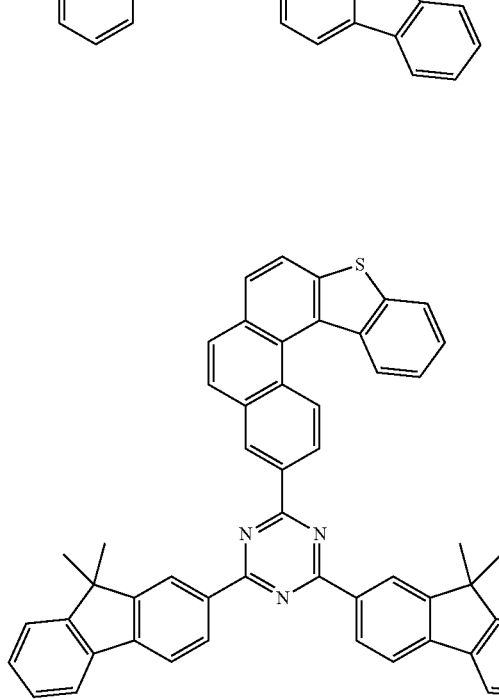
C-9
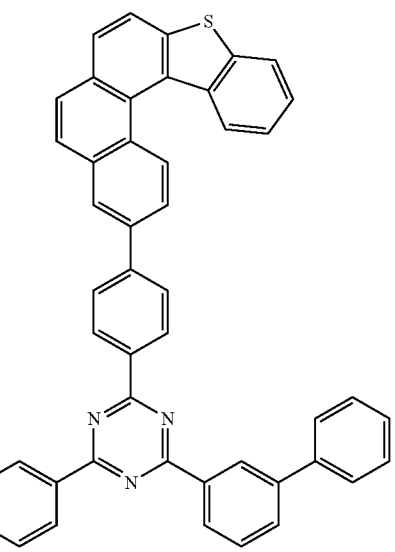
C-8
C-10
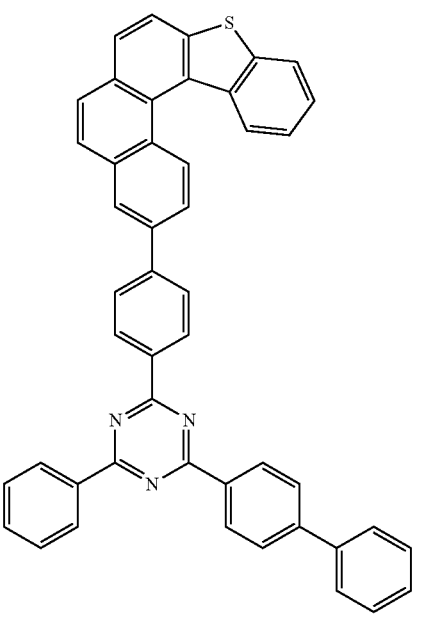

-continued
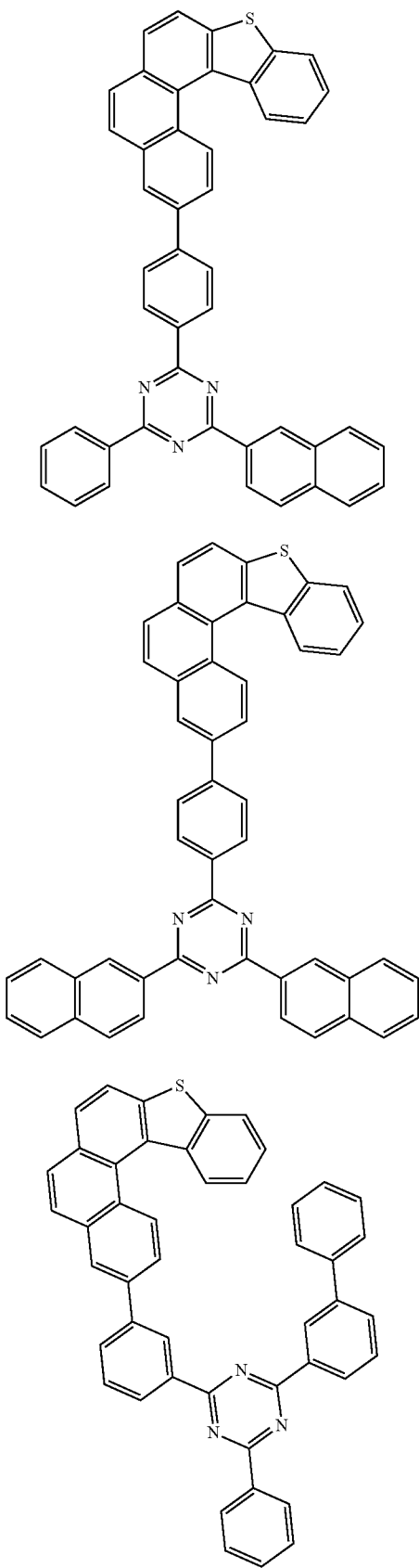
C-11
C-12
C-13
-continued
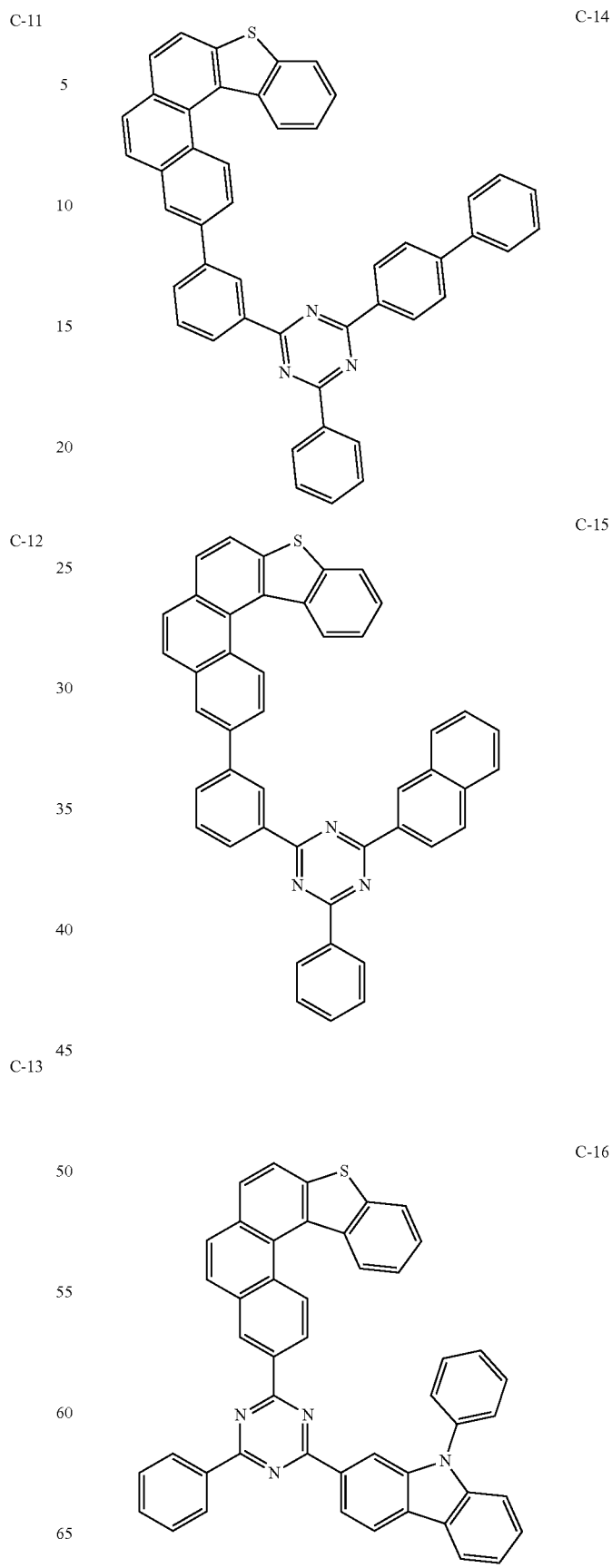
C-14
C-15
C-16

C-17
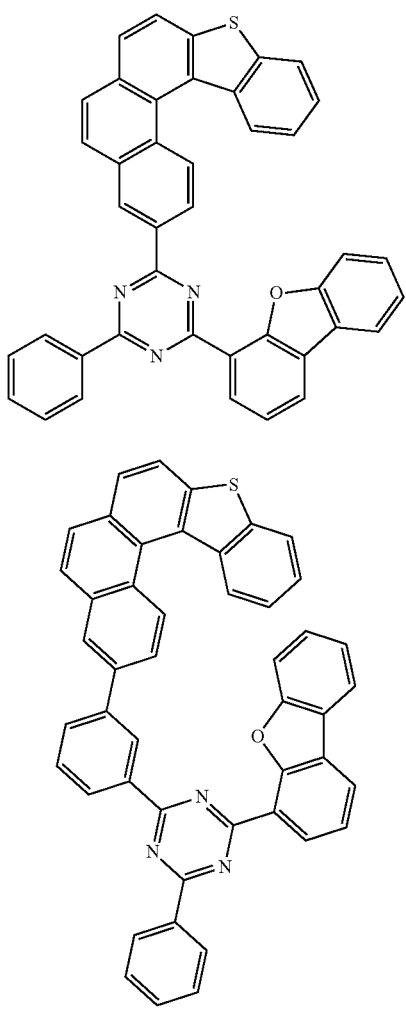
C-18
C-20
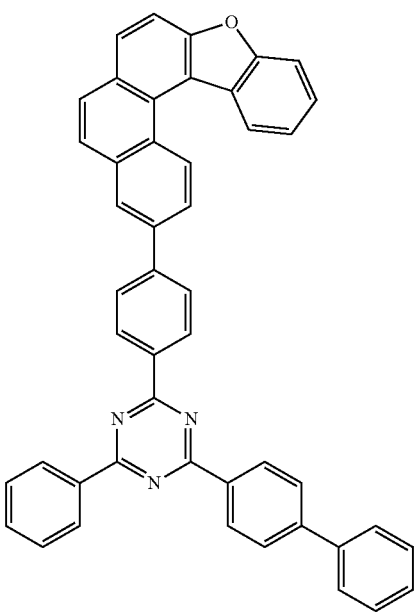
C-19
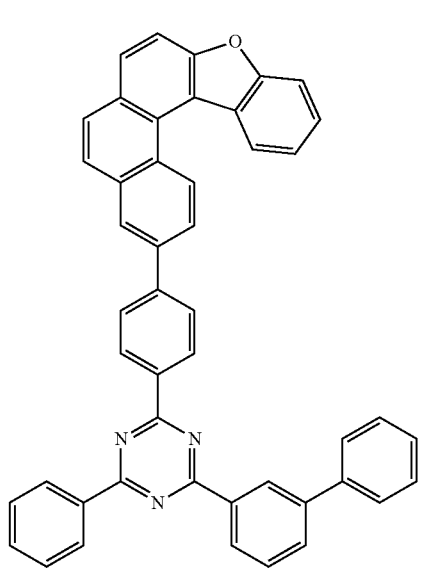
C-21
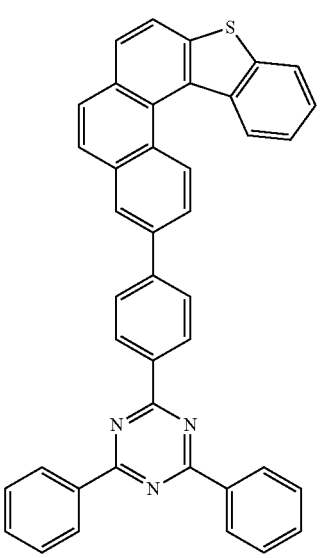

C-22
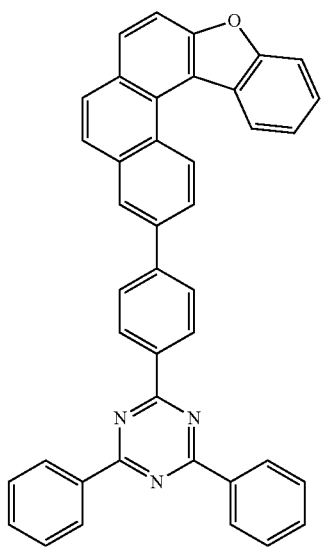
C-24
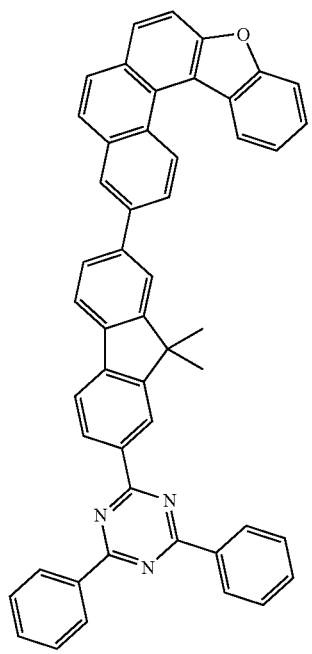
C-23
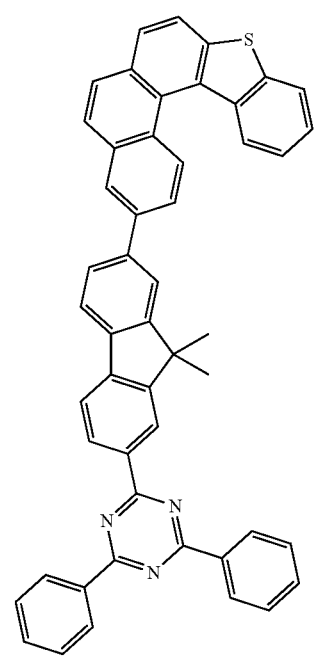
C-25
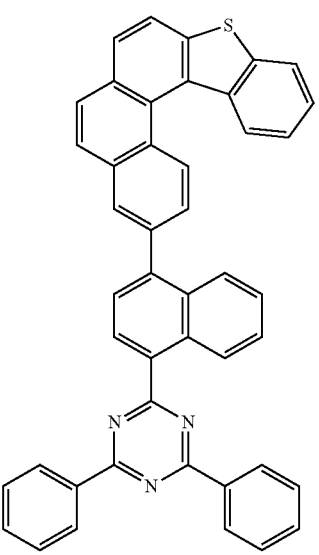

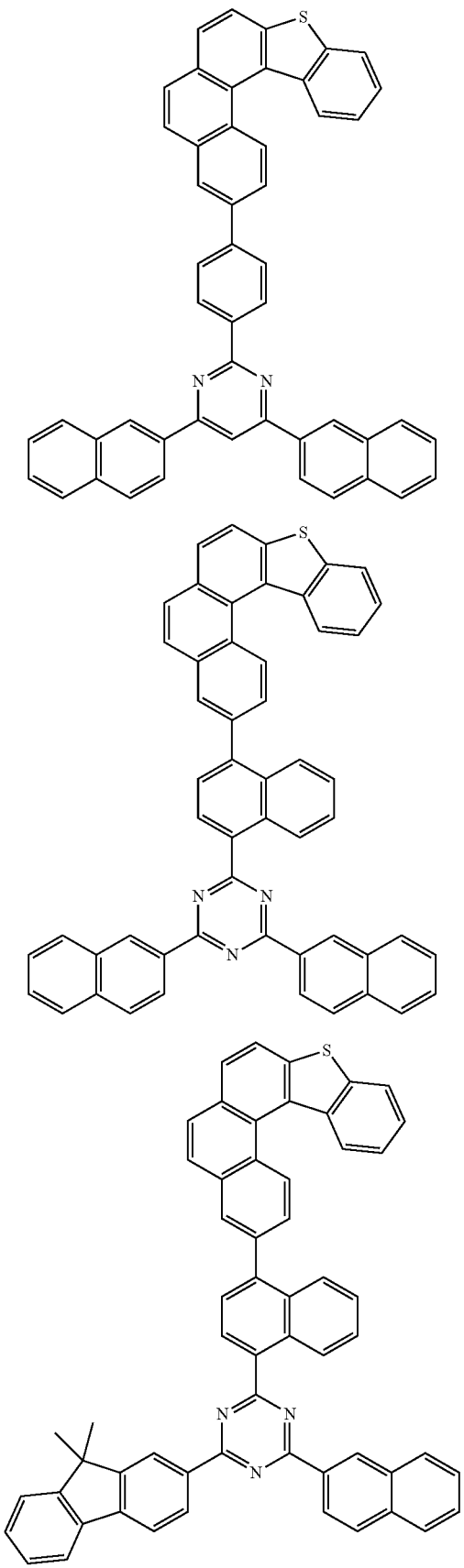
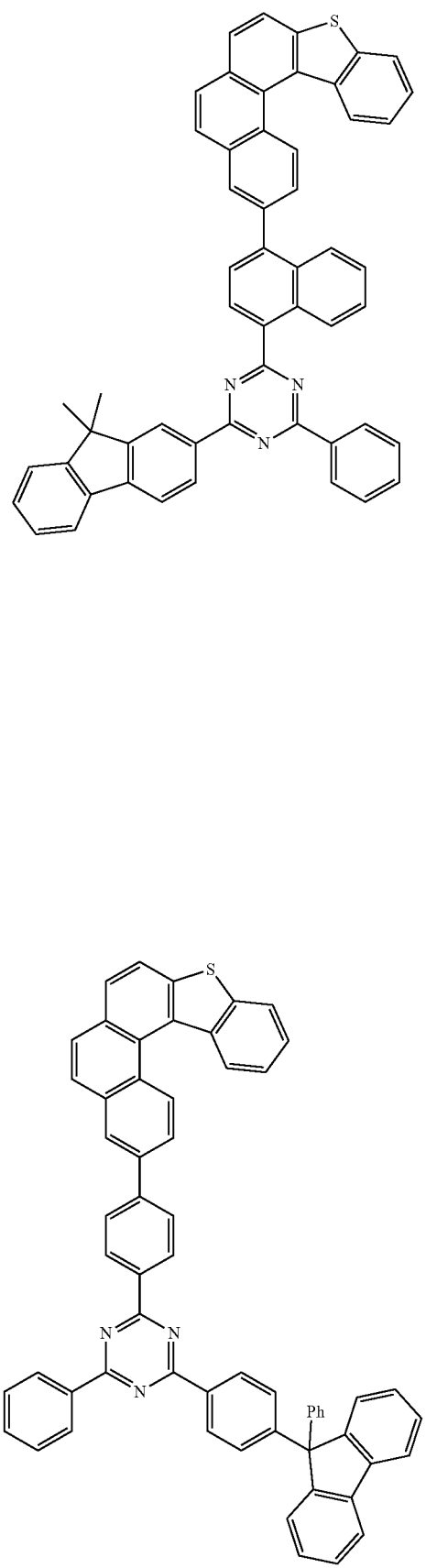

C-31
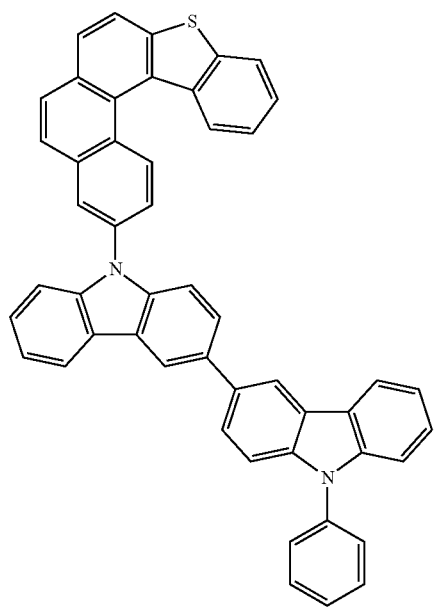
C-32
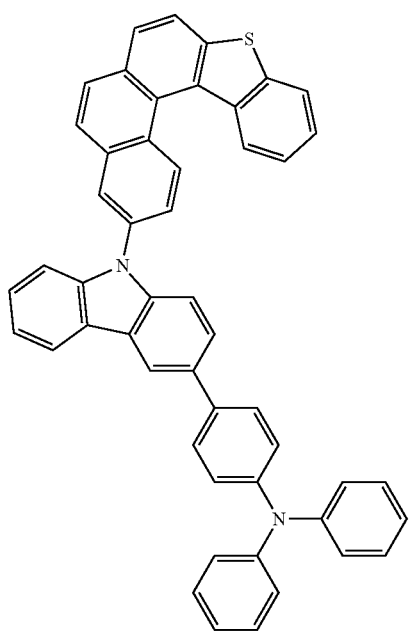
C-33
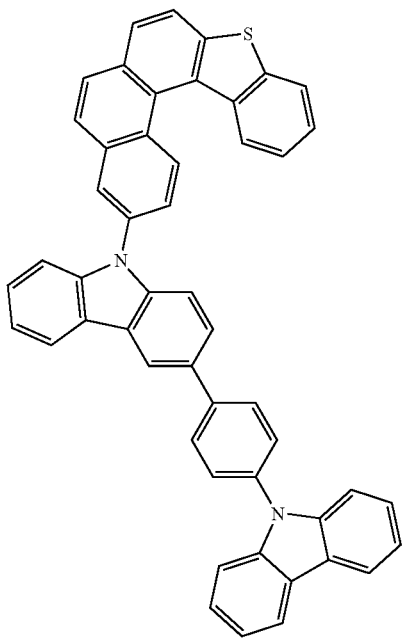
C-34
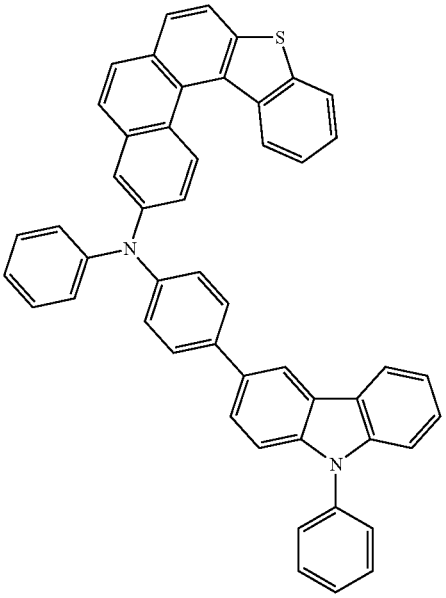

C-35
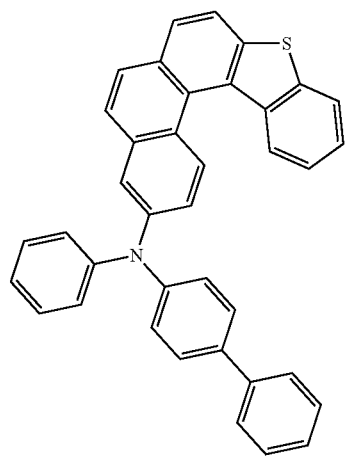
C-36
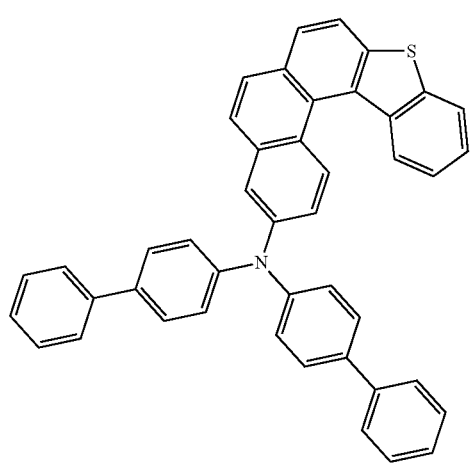
C-37
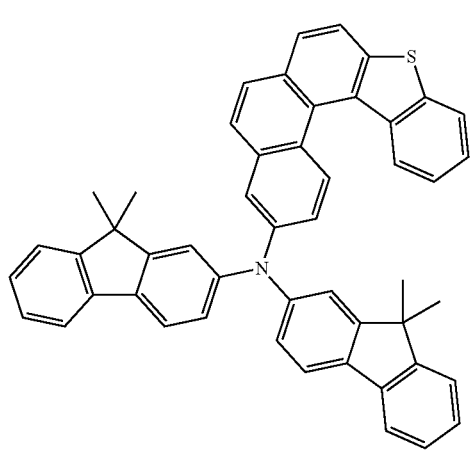
C-38
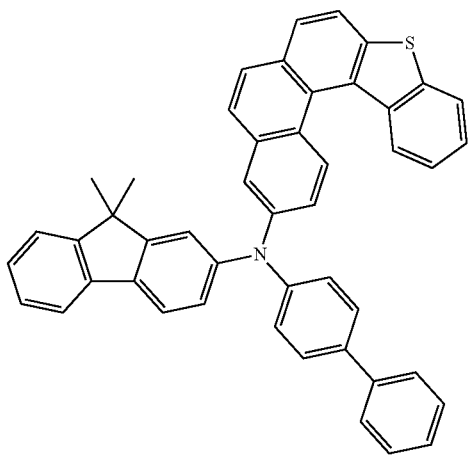
C-39
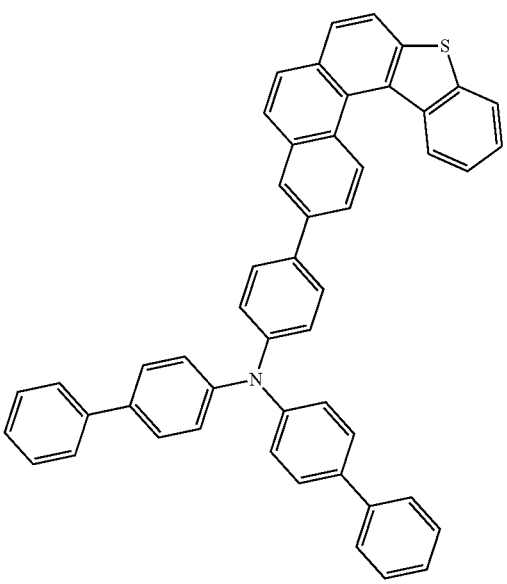
C-40
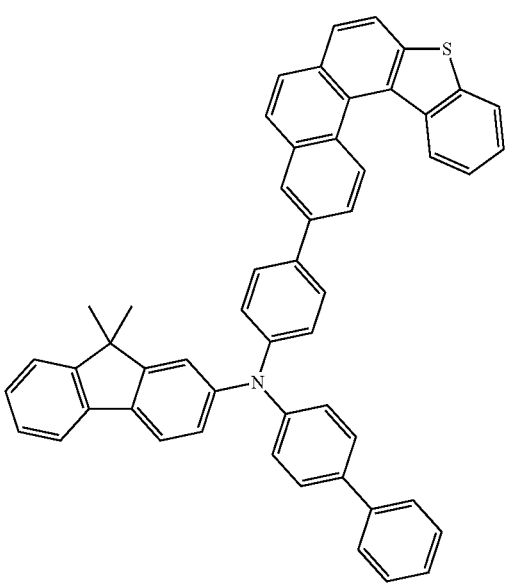

333
-continued
C-41
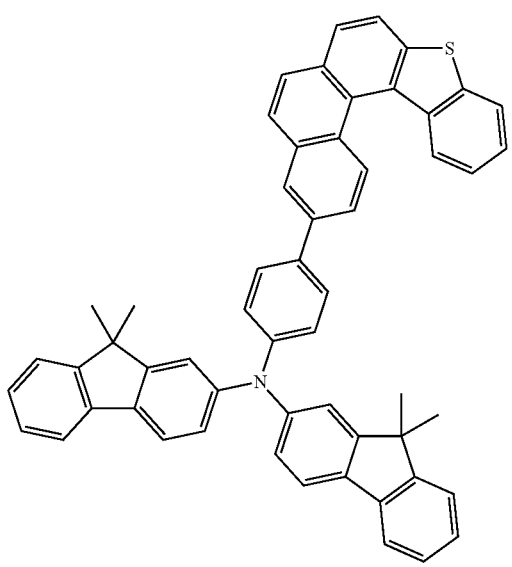
C-42
C-43
334
-continued
C-44
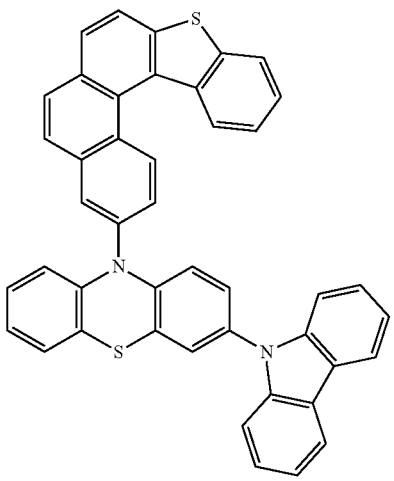
C-45
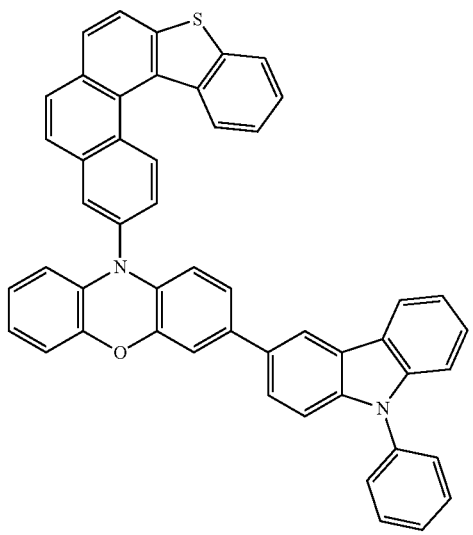
C-46
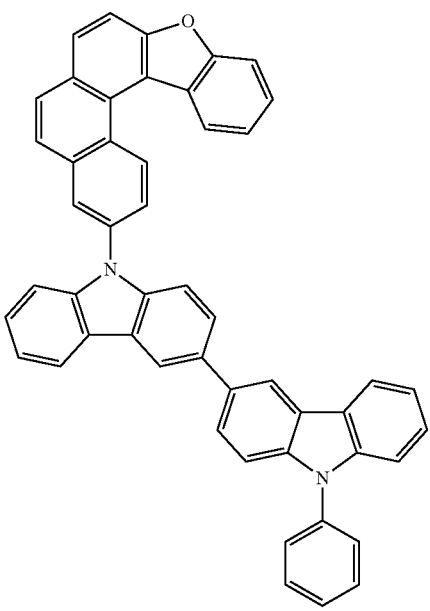

C-47

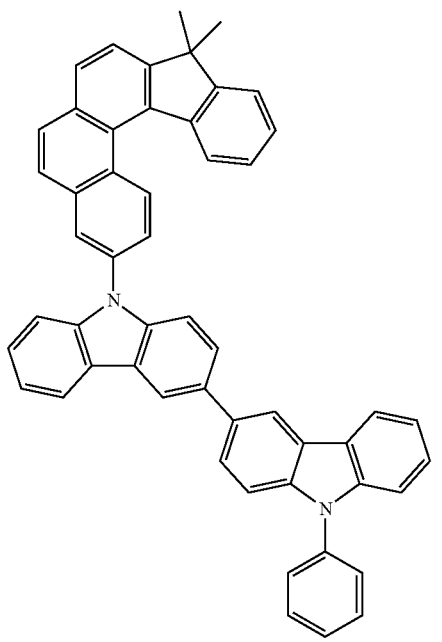

C-48

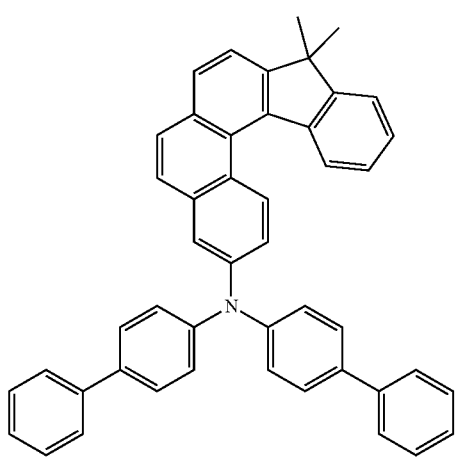

C-49

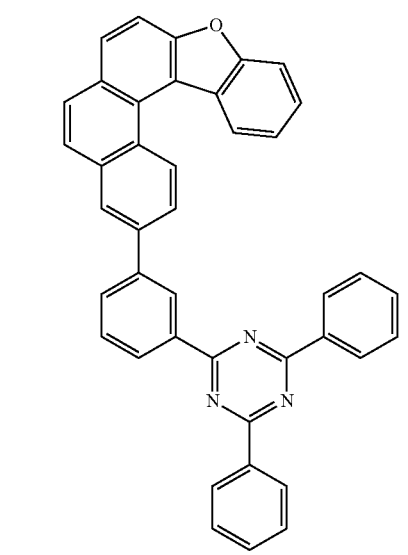

C-50

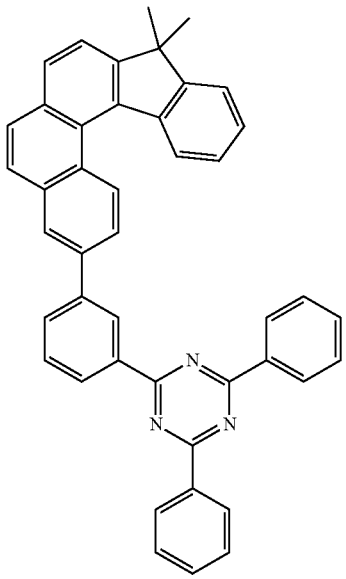

4. A host material comprising the organic electroluminescent compound according to claim 1.

5. An electron buffer material comprising the organic electroluminescent compound according to claim 1.

6. An electron transport material comprising the organic electroluminescent compound according to claim 1.

7. An organic electroluminescent device comprising the organic electroluminescent compound according to claim 1.

8. The organic electroluminescent device according to claim 7, comprising the organic electroluminescent compound as an electron transport material, and further comprising an electron buffer material.

9. The organic electroluminescent device according to claim 7, wherein the organic electroluminescent device comprises at least one light-emitting layer disposed between a first electrode and a second electrode, wherein the light-emitting layer comprises a host and a phosphorescent dopant, wherein the host comprises a plurality of host compounds, and wherein at least a first host compound of the plurality of host compounds is the organic electroluminescent compound, and at least a second host compound of the plurality of host compounds is represented by the following formula 5:

(5)

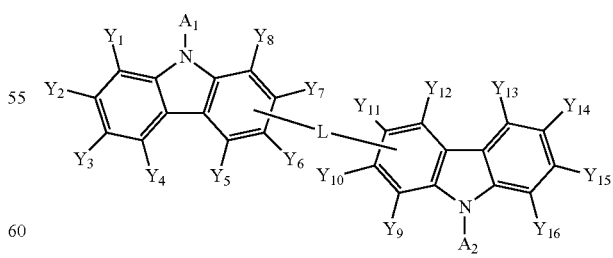

wherein $A_1$ and $A_2$, each independently, represent a substituted or unsubstituted (C6-C30)aryl; with the proviso that a substituent for neither $A_1$ nor $A_2$ is a nitrogen-containing heteroaryl;

L represents a single bond, or a substituted or unsubstituted (C6-C30)arylene; and $Y_1$ to $Y_{16}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered) heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one heteroatom selected from nitrogen, oxygen, and sulfur.

* * * * *